(12) United States Patent
Gilbert et al.

(10) Patent No.: US 7,632,515 B2
(45) Date of Patent: Dec. 15, 2009

(54) STREPTOCOCCUS PNEUMONIAE PROTEINS AND NUCLEIC ACID MOLECULES

(75) Inventors: Christophe Francois Guy Gilbert, Villeurbanne cedex (FR); Philip Michael Hansbro, Newcastle (AU)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 11/785,503

(22) Filed: Apr. 18, 2007

(65) Prior Publication Data

US 2008/0175857 A1 Jul. 24, 2008

Related U.S. Application Data

(60) Division of application No. 10/873,528, filed on Jun. 23, 2004, now abandoned, which is a division of application No. 09/769,787, filed on Jan. 26, 2001, now Pat. No. 6,936,252, which is a continuation of application No. PCT/GB99/02451, filed on Jul. 27, 1999.

(60) Provisional application No. 60/125,164, filed on Mar. 19, 1999.

(30) Foreign Application Priority Data

Jul. 27, 1998 (GB) ................................. 9816337.1

(51) Int. Cl.
| | |
|---|---|
| A61K 39/09 | (2006.01) |
| C07H 21/04 | (2006.01) |
| C12P 21/04 | (2006.01) |
| C12N 1/20 | (2006.01) |
| C07K 14/315 | (2006.01) |

(52) U.S. Cl. .............. 424/244.1; 424/184.1; 424/190.1; 435/69.7; 435/252.3; 435/320.1; 536/23.7; 530/350

(58) Field of Classification Search ........................ None
See application file for complete search history.

(56) References Cited

U.S. PATENT DOCUMENTS

| 6,420,135 B1 | 7/2002 | Kunsch et al. |
| 6,573,082 B1 | 6/2003 | Choi et al. |
| 6,699,703 B1 | 3/2004 | Doucette-Stamm et al. |
| 6,800,744 B1 | 10/2004 | Doucette-Stamm et al. |
| 6,936,252 B2 | 8/2005 | Gilbert et al. |

FOREIGN PATENT DOCUMENTS

| EP | 0622081 | 11/1994 |
| EP | 1 785 486 A | 5/2007 |
| WO | WO 95/06732 | 3/1995 |
| WO | WO 97/09994 | 3/1997 |
| WO | WO 97/37026 | 10/1997 |
| WO | WO 97/43303 | 11/1997 |
| WO | WO 98/06734 | 2/1998 |
| WO | WO 98/18930 | 5/1998 |
| WO | WO 98/18931 | 5/1998 |
| WO | WO 98/26072 | 6/1998 |
| WO | WO 98/31786 | 7/1998 |
| WO | WO 99/15675 | 4/1999 |

OTHER PUBLICATIONS

Lederman et al (Molecular Immunology 28:1171-1181, 1991.*
Li et al (Proc. Natl. Acad. Sci. USA 77:3211-3214, 1980).*
Boslego et al, Chapter 17 in Vaccines and Immunotherapy 1991.*
Houghten et al. (Vaccines, 1986, Edited by Fred Brown: Cold Spring Harbor Laboratory).*
Anderson et al. (1996) "Immune Response in mice following immunization with DNA encoding fragment C of tetanus toxin." Infection and Immunity 64: 3168-3173.
Angel, et al. (1994) "Degradation of C3 by *Streptococcus pneumoniae*." Journal of Infectious Disease 170(3): 600-608.
Alonsodevelasco, et al. (Dec. 1995) "*Streptococcus pneumoniae*: Virulence Factors, Pathogenesis, and Vaccines." Microbiological Reviews 59(4): 591-603.
Breiman et al. (1990) Arch. Intern. Med. 150: 1401.
Breiman et al. (1994) J. Am. Med. Assoc. 271: 1831.
Bowie (1990) Science 257: 1306-1310.
Burgess, et al. (1990) The Journal of Cell Biology 111: 2129-2136.
Donnelly et al. (1997) Ann. Rev. Immunol. 15: 617-648.
Dougall et al. (Sep. 1994) Tibtech 12: 372-379.
Ellis (1988) Vaccines Chapter 29: 568-575.
Greenspan, et al. (1999) Nature Biotechnology 7: 936-937.
Herbert, et al. (1985) The Dictionary of Immunology (Academic Press) 3$^{rd}$ Ed. pp. 58-59.
Holmes, et al. (2001) Exp. Opin. Invest. Drugs 10(3): 511-519.
Jobling et al. (1991) Mol. Microbiol 5(7): 1755-67.
Kohler & Milstein (1975) Nature 256.
Kolkman et al. (1996) 178: 3736-3741.
Kovacevic et al. (1985) J. Bacteriol. 162: 521-528.
Kurar and Splitter (1997) Vaccine 15: 1851-57.
Lange et al. (Sep. 3, 1999) Gene 237(1): 223-234.
Lazar et al. (1988) Molecular and Cellular Biology 8(3): 1247-1252.
Le Loir et al. (1994) J. Bacteriol. 176: 5135-5139.
LeBlanc et al. (1978) PNAS USA 75: 3484-3487.
Li et al. (1997) PNAS 94: 13251-13256.
Liebl et al. (1992) J. Bacteriol. 174: 1854-1861.
Marck (1988) Nucleic Acids Research 16: 1829-1836.
Miller et al. (1987) J. Bacteriol. 169: 3508-3514.
Morrison et al. (1984) PNAS 81: 6851-6855.
Nanidwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).

(Continued)

*Primary Examiner*—Robert B Mondesi
*Assistant Examiner*—Padma V Baskar
(74) *Attorney, Agent, or Firm*—Hunton & Williams LLP

(57) ABSTRACT

Protein antigens from *Streptococcus pneumoniae* are disclosed, together with nucleic acid sequences encoding them. Their use in vaccines and in screening methods is also described.

5 Claims, 2 Drawing Sheets

OTHER PUBLICATIONS

Oultram and Klaenhammer (1985) FEMS Microbiological Letters 27: 129-134.
Pearson et al. (1988) "Improved tools for biological sequence comparison," Proc. Natl. Acad. Sci. USA, vol. 85, 2444-2448.
Poquet et al. (1998) J. Bacteriol. 180: 1904-1912.
Roitt, et al. (1993) Immunology p. 7.7-7.8.
Rudinger et al. (Jun. 1976) "Peptide Hormones" p. 6.
Schappert (1992) Vital and Health Statistics of the Centres for Disease Control/National Centre for Health Statistics 214: 1.
Shortle (1983) Gene 22: 181-189.
Siber (Sep. 1994) "Pneumococcal Disease: Prospects for a New Generation of Vaccines" Science vol. 265, pp. 1385-1387.
Simon and Chopin (1988) Biochimie 70: 559-567.
Stansfield (1987) "Acute respiratory infections in the developing world: strategies for prevention, treatment and control," Pediatric Infect Dis. Journal, vol. 6, 622-629.

Takeda et al. (1985) Nature 314: 452-454.
Taber's Cyclopedic Medical Dictionary (1985) $16^{th}$ Ed. p. 1354.
van der Vossen, et al. (1985) Applied and Environmental Microbiology 50: 540-542.
Waterfield et al. (1995) Gene 165: 9-15.
Wells and Schoefield (1996) In Current advances in metabolism, genetics, and applications-NATO ASI Series H 98: 37-62.
Wells et al. (1993) J. Appl. Bacteriol. 74: 629-636.
Zhang et al. (1997) Infection and Immunity 176: 1035-1040.
Nandiwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).

\* cited by examiner

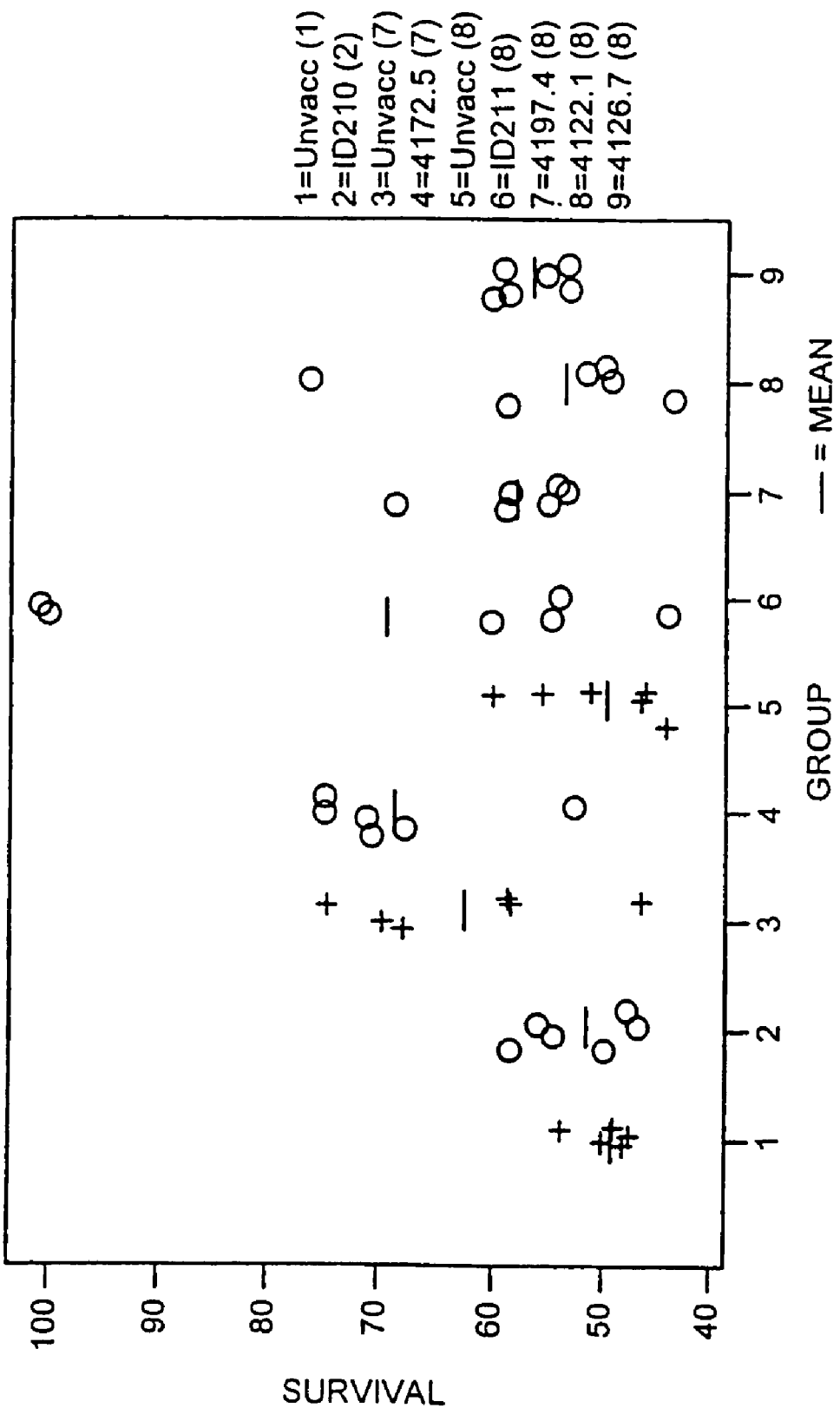

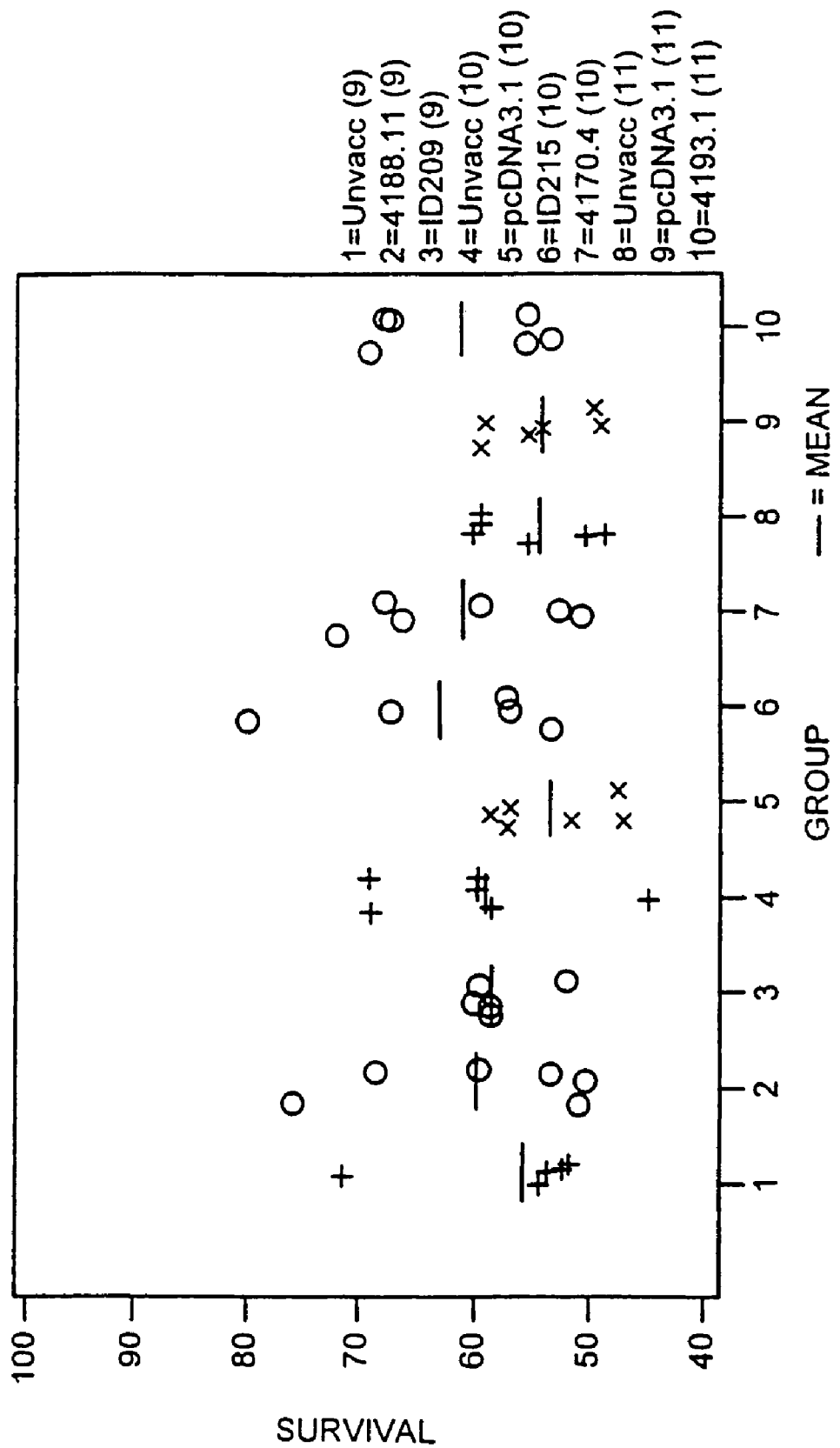

STREPTOCOCCUS PNEUMONIAE PROTEINS AND NUCLEIC ACID MOLECULES

This application is a divisional of U.S. patent application Ser. No. 10/873,528, filed Jun. 23, 2004, now abandoned, which is a divisional of U.S. patent application Ser. No. 09/769,787, filed Jan. 26, 2001, now U.S. Pat. No. 6,936,252, which is a continuation of PCT/GB99/02451, filed Jul. 27, 1999, which claims benefit of U.S. Provisional Application No. 60/125,164, filed Mar. 19, 1999, and which also claims benefit of United Kingdom 9816337.1, filed Jul. 27, 1998, the disclosures of which are all hereby incorporated by reference.

The present invention relates to proteins derived from *Streptococcus pneumoniae*, nucleic acid molecules encoding such proteins, the use of the nucleic acid and/or proteins as antigens/immunogens and in detection/diagnosis, as well as methods for screening the proteins/nucleic acid sequences as potential anti-microbial targets.

*Streptococcus pneumoniae*, commonly referred to as the pneumococcus, is an important pathogenic organism. The continuing significance of *Streptococcus pneumoniae* infections in relation to human disease in developing and developed countries has been authoritatively reviewed (Fiber, G. R., *Science*, 265:1385-1387 (1994)). That indicates that on a global scale this organism is believed to be the most common bacterial cause of acute respiratory infections, and is estimated to result in 1 million childhood deaths each year, mostly in developing countries (Stansfield, S. K., *Pediatr. Infect. Dis.*, 6:622 (1987)). In the USA it has been suggested (Breiman et al., *Arch. Intern. Med.*, 150:1401 (1990)) that the pneumococcus is still the most common cause of bacterial pneumoniae, and that disease rates are particularly high in young children, in the elderly, and in patients with predisposing conditions such as asplenia, heart, lung, and kidney disease, diabetes, alcoholism, or with immunosuppressive disorders, especially AIDS. These groups are at higher risk of pneumococcal septicaemia and hence meningitis and therefore have a greater risk of dying from pneumococcal infection. The pneumococcus is also the leading cause of otitis media and sinusitis, which remain prevalent infections in children in developed countries, and which incur substantial costs.

The need for effective preventative strategies against pneumococcal infection is highlighted by the recent emergence of penicillin-resistant pneumococci. It has been reported that 6.6% of pneumococcal isolates in 13 US hospitals in 12 states were found to be resistant to penicillin and some isolates were also resistant to other antibiotics including third generation cyclosporins (Schappert, S. M., *Vital and Health Statistics of the Centres for Disease Control/National Centre for Health Statistics*, 214:1 (1992)). The rates of penicillin resistance can be higher (up to 20%) in some hospitals (Breiman et al, *J. Am. Med. Assoc.*, 271: 1831 (1994)). Since the development of penicillin resistance among pneumococci is both recent and sudden, coming after decades during which penicillin remained an effective treatment, these findings are regarded as alarming.

For the reasons given above, there are therefore compelling grounds for considering improvements in the means of preventing, controlling, diagnosing or treating pneumococcal diseases.

Various approaches have been taken in order to provide vaccines for the prevention of pneumococcal infections. Difficulties arise for instance in view of the variety of serotypes (at least 90) based on the structure of the polysaccharide capsule surrounding the organism. Vaccines against individual serotypes are not effective against other serotypes and this means that vaccines must include polysaccharide antigens from a whole range of serotypes in order to be effective in a majority of cases. An additional problem arises because it has been found that the capsular polysaccharides (each of which determines the serotype and is the major protective antigen) when purified and used as a vaccine do not reliably induce protective antibody responses in children under two years of age, the age group which suffers the highest incidence of invasive pneumococcal infection and meningitis.

A modification of the approach using capsule antigens relies on conjugating the polysaccharide to a protein in order to derive an enhanced immune response, particularly by giving the response T-cell dependent character. This approach has been used in the development of a vaccine against *Haemophilus influenzae*. There are issues of cost concerning both the multi-polysaccharide vaccines and those based on conjugates.

A third approach is to look for other antigenic components which offer the potential to be vaccine candidates.

BACKGROUND OF THE INVENTION

In the present application we provide a group of proteins antigens which are secreted/exported proteins.

BRIEF SUMMARY OF THE INVENTION

Thus, in a first aspect the present invention provides a *Streptococcus pneumoniae* protein or polypeptide having a sequence selected from those shown in Table 2 herein.

A protein or polypeptide of the present invention may be provided in substantially pure form. For example, it may be provided in a form which is substantially free of other proteins.

In a preferred embodiment, a protein or polypeptide having an amino acid sequence as shown in Table 3 is provided.

The invention encompasses any protein coded for by a nucleic acid sequence as shown in Table 1 herein.

DETAILED DESCRIPTION OF THE INVENTION

As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject.

Thus, in the latter case, the protein or polypeptide may be capable of not only generating an antibody response and in addition non-antibody based immune responses.

The skilled person will appreciate that homologues or derivatives of the proteins or polypeptides of the invention will also find use in the context of the present invention, i.e. as antigenic/immunogenic material. Thus, for instance proteins or polypeptides which include one or more additions, deletions, substitutions or the like are encompassed by the present invention.

In addition, it may be possible to replace one amino acid with another of similar "type". For instance replacing one hydrophobic amino acid with another. One can use a program such as the CLUSTAL program to compare amino acid sequences. This program compares amino acid sequences and finds the optimal alignment by inserting spaces in either sequence as appropriate.

It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein or polypeptide as described herein is less important than that the homologue or derivative should retain its antigenicity or immunogenicity to Streptoccocus_pneumoniae. However, suitably, homologues or derivatives having at least 60% similarity (as discussed above) with the proteins or polypeptides described herein are provided.

Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

In an additional aspect of the invention there are provided antigenic fragments of the proteins or polypeptides of the invention, or of homologues or derivatives thereof.

For fragments of the proteins or polypeptides described herein, or of homologues or derivatives thereof, the situation is slightly different. It is well known that is possible to screen an antigenic protein or polypeptide to identify epitopic regions, i.e., those regions which are responsible for the protein or polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for homologues, derivatives and fragments is that they possess at least a degree of the antigenicity/immunogenicity of the protein or polypeptide from which they are derived.

Gene cloning techniques may be used to provide a protein of the invention in substantially pure form, These techniques are disclosed, for example, in J. Sambrook et al *Molecular Cloning* 2nd Edition, Cold Spring Harbor Laboratory Press (1989). Thus, in a fourth aspect, the present invention provides a nucleic acid molecule comprising or consisting of a sequence which is:

(i) any of the DNA sequences set out in Table 1 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 1.

In a fifth aspect the present invention provides a nucleic acid molecule comprising or consisting of a sequence which is:

(i) any of the DNA sequences set out in Table 4 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 4.

The nucleic acid molecules of the invention may include a plurality of such sequences, and/or fragments. The skilled person will appreciate that the present invention can include, novel variants of those particular novel nucleic acid molecules which are exemplified herein. Such variants are encompassed by the present invention. These may occur in nature, for example because of strain variation. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention compare when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes based upon the nucleic acid sequences provided herein, genes in *Streptococcus pneumoniae* can be identified. They can then be excised using restriction enzymes and cloned into a vector. The vector can be introduced into a suitable host for expression.

Nucleic acid molecules of the present invention may be obtained from *S. pneumoniae* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree. One primer will normally show a high degree of specificity for a first sequence located on one strand of a DNA molecule, and the other primer will normally show a high degree of specificity for a second sequence located on the complementary strand of the DNA sequence and being spaced from the complementary sequence to the first sequence.

Typically primers will be at least 15-25 nucleotides long.

As a further alternative chemical synthesis may be used. This may be automated. Relatively short sequences may be chemically synthesised and ligated together to provide a longer sequence.

In yet a further aspect the present invention provides an immunogenic/antigenic composition comprising one or more proteins or polypeptides selected from those whose sequences are shown in Tables 24, or homologues or derivatives thereof, and/or fragments of any of these. In preferred embodiments, the immunogenic/antigenic composition is a vaccine or is for use in a diagnostic assay.

In the case of vaccines suitable additional excipients, diluents, adjuvants or the like may be included. Numerous examples of these are well known in the art.

It is also possible to utilise the nucleic acid sequences shown in Table 1 in the preparation of so-called DNA vaccines. Thus, the invention also provides a vaccine composition comprising one or more nucleic acid sequences as defined herein. The use of such DNA vaccines is described in the art. See for instance, Donnelly et al, *Ann. Rev. Immunol.*, 15:617-648 (1997).

As already discussed herein the proteins or polypeptides described herein, their homologues or derivatives, and/or fragments of any of these, can be used in methods of detecting/diagnosing *S. pneumoniae*. Such methods can be based on the detection of antibodies against such proteins which may be present in a subject. Therefore the present invention provides a method for the detection/diagnosis of *S. pneumoniae* which comprises the step of bringing into contact a sample to be tested with at least one protein, or homologue, derivative or fragment thereof, as described herein. Suitably, the sample is a biological sample, such as a tissue sample or a sample of blood or saliva obtained from a subject to be tested.

In an alternative approach, the proteins described herein, or homologues, derivatives and/or fragments thereof, can be used to raise antibodies, which in turn can be used to detect the antigens, and hence *S. pneumoniae*. Such antibodies form another aspect of the invention. Antibodies within the scope of the present invention may be monoclonal or polyclonal.

Polyclonal antibodies can be raised by stimulating their production in a suitable animal host (e.g. a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall et al in *Tibtech* 12 372-379 (September 1994).

Antibody fragments include, for example, Fab, $F(ab')_2$ and Fv fragments. Fab fragments (These are discussed in Roitt et al [supra]). Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison et al in PNAS, 81, 6851-6855 (1984) and by Takeda et al in Nature. 314, 452454 (1985).

Synthetic constructs also include molecules comprising an additional moiety that provides the molecule with some desirable property in addition to antigen binding. For example the moiety may be a label (e.g., a fluorescent or radioactive label). Alternatively, it may be a pharmaceutically active agent.

Antibodies, or derivatives thereof, find use in detection/diagnosis of *S. pneumoniae*. Thus, in another aspect the present invention provides a method for the detection/diagnosis of *S. pneumoniae* which comprises the step of bringing into contact a sample to be tested and antibodies capable of binding to one or more proteins described herein, or to homologues, derivatives and/or fragments thereof.

In addition, so-called AFFIBODIES may be utilised. These are binding proteins selected from combinatorial libraries of an alpha-helical bacterial receptor domain (Nord et al) Thus, Small protein domains, capable of specific binding to different target proteins can be selected using combinatorial approaches.

It will also be clear that the nucleic acid sequences described herein may be used to detect/diagnose *S. pneumoniae*. Thus, in yet a further aspect, the present invention provides a method for the detection/diagnosis of *S. pneumoniae* which comprises the step of bringing into contact a sample to be tested with at least one nucleic acid sequence as described herein. Suitably, the sample is a biological sample, such as a tissue sample or a sample of blood or saliva obtained from a subject to be tested. Such samples may be pre-treated before being used in the methods of the invention. Thus, for example, a sample may be treated to extract DNA. Then, DNA probes based on the nucleic acid sequences described herein (i.e., usually fragments of such sequences) may be used to detect nucleic acid from S. pneumoniae.

In additional aspects, the present invention provides:

(a) a method of vaccinating a subject against S. pneumoniae which comprises the step of administering to a subject a protein or polypeptide of the invention, or a derivative, homologue or fragment thereof, or an immunogenic composition of the invention;

(b) a method of vaccinating a subject against S. pneumoniae which comprises the step of administering to a subject a nucleic acid molecule as defined herein;

(c) a method for the prophylaxis or treatment of S. pneumoniae infection which comprises the step of administering to a subject a protein or polypeptide of the invention, or a derivative, homologue or fragment thereof, or an immunogenic composition of the invention;

(d) a method for the prophylaxis or treatment of S. pneumoniae infection which comprises the step of administering to a subject a nucleic acid molecule as defined herein;

(e) a kit for use in detecting/diagnosing S. pneumoniae infection comprising one or more proteins or polypeptides of the invention, or homologues, derivatives or fragments thereof, or an antigenic composition of the invention; and (f) a kit for use in detecting/diagnosing S. pneumoniae infection comprising one or more nucleic acid molecules as defined herein.

Given that we have identified a group of important proteins, such proteins are potential targets for anti-microbial therapy. It is necessary, however, to determine whether each individual protein is essential for the organism's viability. Thus, the present invention also provides a method of determining whether a protein or polypeptide as described herein represents a potential anti-microbial target which comprises inactivating said protein and determining whether S. pneumoniae is still viable, in vitro or in vivo.

A suitable method for inactivating the protein is to effect selected gene knockouts, i.e. prevent expression of the protein and determine whether this results in a lethal change. Suitable methods for carrying out such gene knockouts are described in Li et al, P.N.A.S., 94:13251-13256 (1997).

In a final aspect the present invention provides the use of an agent capable of antagonising, inhibiting or otherwise interfering with the function or expression of a protein or polypeptide of the invention in the manufacture of a medicament for use in the treatment or prophylaxis of S. pneumoniae infection.

The invention will now be described with reference to the following examples, which should not be construed as in any way limiting the invention. The examples refer to the figures in which:

BRIEF DESCRIPTION OF THE FIGURES

FIG. 1: shows the results of various DNA vaccine trials; and

FIG. 2: shows the results of further DNA vaccine trials.

EXAMPLE 1

The Genome sequencing of Streptococcus pneumoniae type 4 is in progress at the Institute for Genomic Research (TIGR, Rockville, Md., USA). Up to now, the whole sequence has not been completed or published. On Nov. 21, 1997, the TIGR centre released some DNA sequences as contigs which are not accurate reflections of the finished sequence. These contigs can be downloaded from their website. We downloaded these contigs and created a local database using the application GCGToBLAST (Wisconsin Package Version 9.1, Genetics Computer Group (GCG), Madison, USA). This database can be searched with the FastA and TfastA procedures (using the method of Pearson and Lipman (PNAS USA, 85:2444-2448 (1988)).

Using FastA and TfastA procedures, the local pneumococcus database was searched for putative leader sequence or anchor sequence features. Relevant sequences were used to interrogate for comparative novel sequences. These were:

(i) already described leader sequences of Streptococcus pneumoniae (from proteins NanA, NanB, LytA, PapA, pcpA, PsaA and PspA);

(ii) the leader sequence of Usp45, a secreted protein from Lactococcus lactis;

(iii) new hypothetical leader sequences derived from the searches in (i) and (ii);

(iv) the anchor motif LPxTG (SEQ ID NO: 364), a feature common to many Gram-positive bacteria surface proteins which are anchored by a mechanism involving the Sortase complex proteins.

Provided below is an example of this approach, with reference to the sequences derived from the database (see table 1).

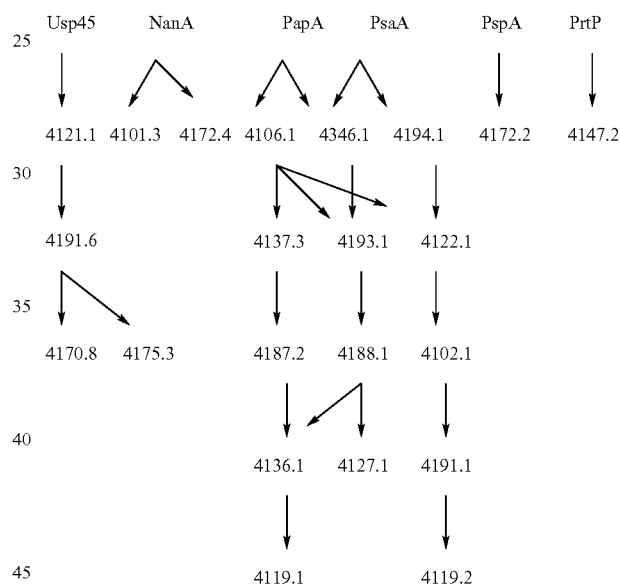

The protein leader sequences of different known exported proteins were used as a starting point for a search of the local pneumococcus database described above. The hypothetical proteins found with this search were then submitted to a Blast search in general databases such as EMBL, Swissprot etc. Proteins remaining unknown in the pneumococcus are kept and annotated. Then the search is performed again using the new potential protein leader sequence as a probe, using the TfastA procedure.

EXAMPLE 2

DNA Vaccine Trials pcDNA3.1+ as a DNA Vaccine Vector pcDNA3.1+

The vector chosen for use as a DNA vaccine vector was pcDNA3.1 (Invitrogen) (actually pcDNA3.1+, the forward orientation was used in all cases but may be referred to as pcDNA3.1 here on). This vector has been widely and successfully employed as a host vector to test vaccine candidate genes to give protection against pathogens in the literature (Zhang, et al., Kurar and Splitter, Anderson et al.). The vector was designed for high-level stable and non-replicative transient expression in mammalian cells. pcDNA3.1 contains the ColE1 origin of replication which allows convenient high-copy number replication and growth in *E. coli*. This in turn allows rapid and efficient cloning and testing of many genes. The pcDNA3.1 vector has a large number of cloning sites and also contains the gene encoding ampicillin resistance to aid in cloning selection and the human cytomegalovirus (CMV) immediate-early promoter/enhancer which permits efficient, high-level expression of the recombinant protein. The CMV promoter is a strong viral promoter in a wide range of cell types including both muscle and immune (antigen presenting) cells. This is important for optimal immune response as it remains unknown as to which cells types are most important in generating a protective response in vivo. A T7 promoter upstream of the multiple cloning site affords efficient expression of the modified insert of interest and which allows in vitro transcription of a cloned gene in the sense orientation.

Zhang, D., Yang, X., Berry, J. Shen, C., McClarty, G. and Brunham, R. C. (1997) "DNA vaccination with the major outer-membrane protein genes induces acquired immunity to *Chlamydia trachomatis* (mouse pneumonitis) infection". *Infection and Immunity*, 176, 1035-40.

Kurar, E. and Splitter, G. A. (1997) "Nucleic acid vaccination of *Brucella abortus* ribosomal L7/L12 gene elicits immune response". *Vaccine*, 15, 1851-57.

Anderson, R., Gao, X.-M., Papakonstantinopoulou, A., Roberts, M. and Dougan, G. (1996) "Immune response in mice following immunisation with DNA encoding fragment C of tetanus toxin". *Infection and Immunity*, 64, 3168-3173.

Preparation of DNA Vaccines

Oligonucleotide primers were designed for each individual gene of interest derived using the LEEP system. Each gene was examined thoroughly, and where possible, primers were designed such that they targeted that portion of the gene thought to encode only the mature portion of the gene protein. It was hoped that expressing those sequences that encode only the mature portion of a target gene protein, would facilitate its correct folding when expressed in mammalian cells. For example, in the majority of cases primers were designed such that putative N-terminal signal peptide sequences would not be included in the final amplification product to be cloned into the pcDNA3.1 expression vector. The signal peptide directs the polypeptide precursor to the cell membrane via the protein export pathway where it is normally cleaved off by signal peptidase I (or signal peptidase II if a lipoprotein). Hence the signal peptide does not make up any part of the mature protein whether it be displayed on the surface of the bacteria surface or secreted. Where a N-terminal leader peptide sequence was not immediately obvious, primers were designed to target the whole of the gene sequence for cloning and ultimately, expression in pcDNA3.1.

Having said that, however, other additional features of proteins may also affect the expression and presentation of a soluble protein. DNA sequences encoding such features in the genes encoding the proteins of interest were excluded during the design of oligonucleotides.

These features included:

1. LPXTG (SEQ ID NO: 364) cell wall anchoring motifs.

2. LXXC ipoprotein attachment sites.

3. Hydrophobic C-terminal domain.

4. Where no N-terminal signal peptide or LXXC was present the start codon was excluded.

5. Where no hydrophobic C-terminal domain or LPXTG (SEQ ID NO: 364) motif was present the stop codon was removed.

Appropriate PCR primers were designed for each gene of interest and any and all of the regions encoding the above features was removed from the gene when designing these primers. The primers were designed with the appropriate enzyme restriction site followed by a conserved Kozak nucleotide sequence (in all cases) GCCACC was used. The Kozak sequence facilitates the recognition of initiator sequences by eukaryotic ribosomes) and an ATG start codon upstream of the insert of the gene of interest. For example the forward primer using a BamHI site the primer would begin GCGG-GATCCGCCACCATG (SEQ ID NO: 365) followed by a small section of the 5' end of the gene of interest. The reverse primer was designed to be compatible with the forward primer and with a NotI restriction site at the 5' end in all cases (this site is TTGCGGCCGC) (SEQ ID NO:366).

PCR Primers

The following PCR primers were designed and used to amplify the truncated genes of interest.

ID210
Forward Primer
(SEQ ID NO: 367)
5' CGGATCCGCCACCATGTCTTCTAATGAATCTGCCGATG 3'

Reverse Primer
(SEQ ID NO: 368)
5' TTGCGGCCGCCTGTTTAGATTGGATATCTGTAAAGACTT 3'

4172.5
Forward Primer
(SEQ ID NO: 369)
5' CGCGGATCCGCCACCATGGATTTTCCTTCAAATTTGGAGG 3'

Reverse Primer
(SEQ ID NO: 370)
5' TTGCGGCCGCACCGTACTGGCTGCTGACT 3'

ID211
Forward Primer
(SEQ ID NO: 371)
5' CGGATCCGCCACCATGAGTGAGATCAAAATTATTAACGC 3'

Reverse Primer
(SEQ ID NO: 372)
5' TTGCGGCCGCCGTTCCATGGTTGACTCCT 3'

4197.4
Forward Primer
(SEQ ID NO: 373)
5' CGCGGATCCGCCACCATGTGGGACATATTGGTGAAAC 3'

Reverse Primer
(SEQ ID NO: 374)
5' TTGCGGCCGCTTCACTTGAGCAAACTGAATCC 3'

4122.1
Forward Primer
(SEQ ID NO: 375)
5' CGCGGATCCGCCACCATGTCACAAGAAAAAACAAAAAATGAA 3'

Reverse Primer
(SEQ ID NO: 376)
5' TTGCGGCCGCATCGACGTAGTCTCCGCC 3'

4126.7
Forward Primer
(SEQ ID NO: 377)
5' CGCGGATCCGCCACCATGCTGGTTGGAACTTTCTACTATCAAT 3'

Reverse Primer
(SEQ ID NO: 378)
5' TTGCGGCCGCAACTTTCGTCCCTTTTTGG 3'

-continued

```
4188.11
Forward Primer
                                      (SEQ ID NO: 379)
5' CGCGGATCCGCCACCATGGGCAATTCTGGCGGAA 3'

Reverse Primer
                                      (SEQ ID NO: 380)
5' TTGCGGCCGCTTGTTTCATAGCTTTTTTGATTGTT 3'

ID209
Forward Primer
                                      (SEQ ID NO: 381)
5' CGCGGATCCGCCACCATGCTATTGATACGAAATGCAGGG 3'

Reverse Primer
                                      (SEQ ID NO: 382)
5' TTGCGGCCGCAACATAATCTAGTAAATAAGCGTAGCC 3'

ID215
Forward Primer
                                      (SEQ ID NO: 383)
5' CGCGGATCCGCCACCATGACGGCGACGAATTTTC 3'

Reverse Primer
                                      (SEQ ID NO: 384)
5' TTGCGGCCGCTTAATTCGTTTTTGAACTAGTTGCT 3'

4170.4
Forward Primer
                                      (SEQ ID NO: 385)
5' CGCGGATCCGCCACCATGGCTGTTTTTCTTCGCTATCATG 3'

Reverse Primer
                                      (SEQ ID NO: 386)
5' TTGCGGCCGCTTTCTTCAACAAACCTTGTTCTTG 3'

4193.1
Forward Primer
                                      (SEQ ID NO: 387)
5' CGCGGATCCGCCACCATGGGTAACCGCTCTTCTCGTAAC 3'

Reverse Primer
                                      (SEQ ID NO: 388)
5' TTGCGGCCGCGCTTCCATCAAGGATTTTAGC 3'
```

Cloning

The insert along with the flanking features described above was amplified using PCR against a template of genomic DNA isolated from type 4 S. pneumoniae strain 11886 obtained from the National Collection of Type Cultures. The PCR product was cut with the appropriate restriction enzymes and cloned in to the multiple cloning site of pcDNA3.1 using conventional molecular biological techniques. Suitably mapped clones of the genes of interested were cultured and the plasmids isolated on a large scale (>1.5 mg) using Plasmid Mega Kits (Qiagen). Successful cloning and maintenance of genes was confirmed by restriction mapping and sequencing ~700 base pairs through the 5' cloning junction of each large scale preparation of each construct.

Strain Validation

A strain of type 4 was used in cloning and challenge methods which is the strain from which the S. pneumoniae genome was sequenced. A freeze dried ampoule of a homogeneous laboratory strain of type 4 S. pneumoniae strain NCTC 11886 was obtained from the National Collection of Type Strains. The ampoule was opened and the cultured re suspended with 0.5 ml of tryptic soy broth (0.5% glucose, 5% blood). The suspension was subcultured into 10 ml tryptic soy broth (0.5% glucose, 5% blood) and incubated statically overnight at 37° C. This culture was streaked on to 5% blood agar plates to check for contaminants and confirm viability and on to blood agar slopes and the rest of the culture was used to make 20% glycerol stocks. The slopes were sent to the Public Health Laboratory Service where the type 4 serotype was confirmed.

A glycerol stock of NCTC 11886 was streaked on a 5% blood agar plate and incubated overnight in a $CO_2$ gas jar at 37° C. Fresh streaks were made and optochin sensitivity was confirmed.

Pneumococcal Challenge

A standard inoculum of type 4 S. pneumoniae was prepared and frozen down by passaging a culture of pneumococcus 1× through mice, harvesting from the blood of infected animals, and grown up to a predetermined viable count of around $10^9$ cfu/ml in broth before freezing down. The preparation is set out below as per the flow chart.

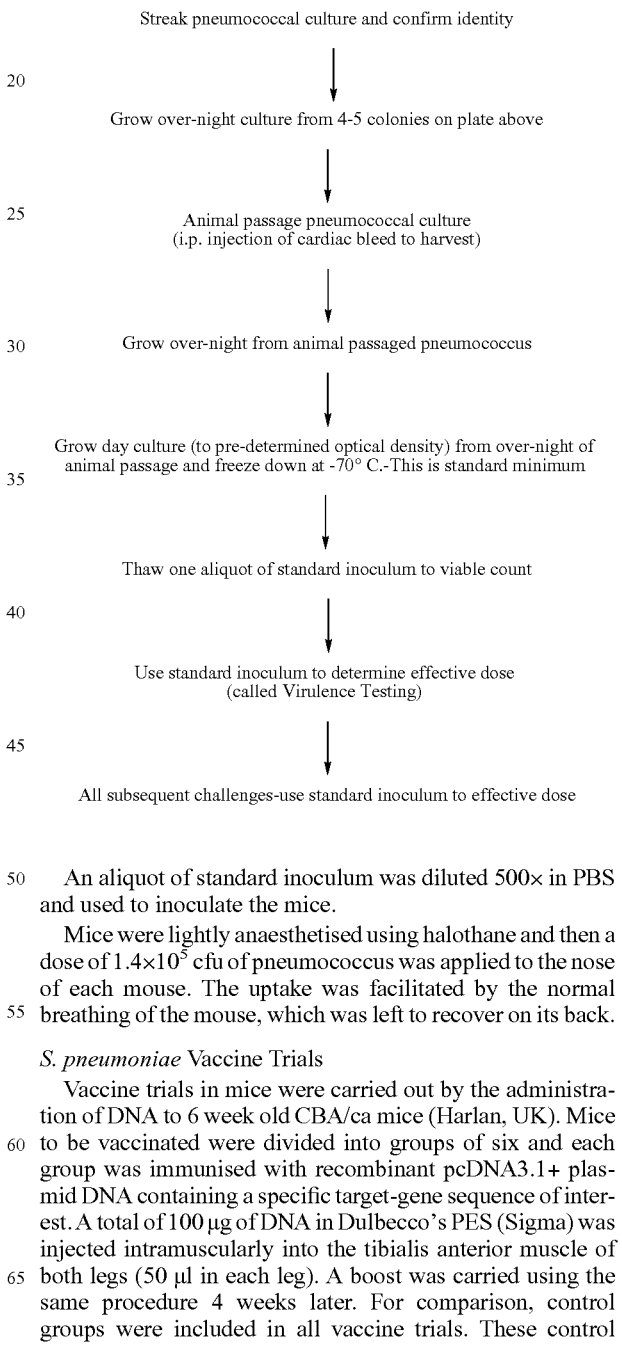

An aliquot of standard inoculum was diluted 500× in PBS and used to inoculate the mice.

Mice were lightly anaesthetised using halothane and then a dose of $1.4 \times 10^5$ cfu of pneumococcus was applied to the nose of each mouse. The uptake was facilitated by the normal breathing of the mouse, which was left to recover on its back.

S. pneumoniae Vaccine Trials

Vaccine trials in mice were carried out by the administration of DNA to 6 week old CBA/ca mice (Harlan, UK). Mice to be vaccinated were divided into groups of six and each group was immunised with recombinant pcDNA3.1+ plasmid DNA containing a specific target-gene sequence of interest. A total of 100 μg of DNA in Dulbecco's PES (Sigma) was injected intramuscularly into the tibialis anterior muscle of both legs (50 μl in each leg). A boost was carried using the same procedure 4 weeks later. For comparison, control groups were included in all vaccine trials. These control groups were either unvaccinated animals or those administered with non-recombinant pcDNA3.1+DNA (sham vaccinated) only, using the same time course described above. 3 weeks after the second immunisation, all mice groups were challenged intra-nasally with a lethal dose of S. pneumoniae serotype 4 (strain NCTC 11886). The number of bacteria administered was monitored by plating serial dilutions of the inoculum on 5% blood agar plates. A problem with intranasal immunisations is that in some mice the inoculum bubbles out of the nostrils, this has been noted in results table and taken account of in calculations. A less obvious problem is that a certain amount of the inoculum for each mouse may be swallowed. It is assumed that this amount will be the same for each mouse and will average out over the course of inoculations. However, the sample sizes that have been used are small and this problem may have significant effects in some experiments. All mice remaining after the challenge were killed 3 or 4 days after infection. During the infection process, challenged mice were monitored for the development of symptoms associated with the onset of S. pneumoniae induced-disease. Typical symptoms in an appropriate order included piloerection, an increasingly hunched posture, discharge from eyes, increased lethargy and reluctance to move. The latter symptoms usually coincided with the development of a moribund state at which stage the mice were culled to prevent further suffering. These mice were deemed to be very close to death, and the time of culling was used to determine a survival time for statistical analysis. Where mice were found dead, the survival time was taken as the last time point when the mouse was monitored alive.

Interpretation of Results

A positive result was taken as any DNA sequence that was cloned and used in challenge experiments as described above which gave protection against that challenge. Protection was taken as those DNA sequences that gave statistically significant protection (to a 95% confidence level ($p<0.05$)) and also those which were marginal or close to significant using Mann-Whitney or which show some protective features for example there were one or more outlying mice or because the time to the first death was prolonged. It is acceptable to allow marginal or non-significant results to be considered as potential positives when it is considered that the clarity of some of the results may be clouded by the problems associated with the administration of intranasal infections.

Results for vaccine trials 2, 7 and 8 (see FIG. 1)

| Mouse number | Unvacc control (2) | ID210 (2) | Unvacc control (7) | 4172.5 (7) | Unvacc control (8) | ID211 (8) | 4197.4 (8) | 4122.1 (8) | 4126.7 (8) |
|---|---|---|---|---|---|---|---|---|---|
| | | | | Mean survival times (hours) | | | | | |
| 1 | 49.0 | 55.0 | 59.6 | 72.6 | 45.1 | 102.3T | 60.1 | 50.6 | 60.0 |
| 2 | 51.0 | 46.5 | 47.2 | 67.9 | 50.8 | 55.5 | 54.9 | 77.2 | 60.0 |
| 3 | 49.0 | 49.0 | 59.6 | 54.4 | 60.4 | 60.6* | 68.4 | 60.3 | 54.8 |
| 4 | 55.0 | 59.0 | 59.2 | 70.9 | 75.3 | 55.2 | 45.3 | 60.1 | 50.6 | 52.6 |
| 5 | 49.0 | 55.0 | 68.6* | 70.9 | 45.1 | 55.5 | 54.9 | 50.6* | 54.8 |
| 6 | 49.0 | 49.0 | 76.0 | 75.3 | 45.1 | 102.3T | 52.7 | 44.9 | 60 |
| Mean | 50.3 | 52.3 | 63.6 | 69.4 | 50.2 | 70.2 | 58.5 | 55.7 | 57.0 |
| sd | 2.4 | 4.8 | 10.3 | 7.9 | 6.4 | 25.3 | 5.7 | 11.6 | 3.4 |
| p value 1 | — | 0.3333 | — | 0.2104 | — | 0.0215 | 0.0621 | 0.4038 | 0.0833 |

*bubbled when dosed so may not have received full inoculum.
T - terminated at end of experiment having no symptoms of infection.
Numbers in brackets - survival times disregarded assuming incomplete dosing
p value 1 refers to significance tests compared to unvaccinated controls
Statistical Analyses
Trial 2 - The group vaccinated with ID210 also had a longer mean survival time than the unvaccinated controls but the results are not statistically significant.
Trial 7 - The group vaccinated with 4172.5 showed much greater survival times than unvaccinated controls although the differences were not statistically significant.
Trial 8 - The group vaccinated with ID211 survived significantly longer than unvaccinated controls. 4197.4, 4122.1 and 4126.7 vaccinated groups showed longer mean survival times than the unvaccinated group but the results were not statistically significant. The 4197.4 and 4126.7 groups also showed a prolonged time to the first death and the 4122.1 group showed 1 outlying result.

Results of pneumococcal challenge DNA vaccination trials 9-11 (see FIG. 2).

| Mouse number | Unvacc control (9) | 4188.11 (9) | ID209 (9) | Unvacc control (10) | pcDNA3.1+ (10) | ID215 (10) | 4170.4 (10) | Unvacc control (11) | pcDNA3.1+ (11) | 4193.1 (11) |
|---|---|---|---|---|---|---|---|---|---|---|
| | | | | | Mean survival times (hours) | | | | | |
| 1 | (98.5)T | 69.4 | 60.2 | 68.4 | 58.6 | 79.2 | 68.1 | 60.0 | 53.2 | 54.8 |
| 2 | 53.4 | 53.7 | 60.2 | 59.0 | 58.6 | 54.2 | 58.6 | 50.0 | 50.4 | 54.8 |
| 3 | 53.4 | 51.2 | 60.2 | 59.0 | 50.8 | (103.2)*T | 50.9 | 60.0 | 55.4 | 68.7* |
| 4 | 53.4 | 75.0 | (98.0)*T | 45.1* | 58.8 | 58.8 | 72.1 | 55.0 | 60.6 | 54.8 |
| 5 | 70.8 | 51.2 | 60.2 | 68.4 | 46.5 | 68.3 | 68.1 | 60.0 | 50.4 | 68.7 |
| 6 | 53.4 | 61.2 | 52.9 | 59.0 | 48.9 | 58.8 | 54.0 | 50.0 | 60.6 | 68.7* |
| Mean | 56.9 | 60.3 | 58.8 | 59.8 | 53.6 | 63.9 | 62.0 | 55.8 | 55.1 | 61.7 |
| Sd | 7.8 | 10.0 | 3.3 | 8.5 | 5.6 | 10.0 | 8.7 | 5.0 | 4.6 | 7.6 |

-continued

Results of pneumococcal challenge DNA vaccination trials 9-11 (see FIG. 2).

| | Mean survival times (hours) | | | | | | | | | |
|---|---|---|---|---|---|---|---|---|---|---|
| Mouse number | Unvacc control (9) | 4188.11 (9) | ID209 (9) | Unvacc control (10) | pcDNA3.1+ (10) | ID215 (10) | 4170.4 (10) | Unvacc control (11) | pcDNA3.1+ (11) | 4193.1 (11) |
| p value 1 | — | 0.3894 | 0.2519 | — | 0.0307 | <30.0 | <39.0 | — | — | 0.1837 |
| p value 2 | — | — | — | — | — | 0.0168 | 0.0316 | — | — | 0.0829 |

*bubbled when dosed so may not have received full inoculum.
T - terminated at end of experiment having no symptoms of infection.
Numbers in brackets - survival times disregarded assuming incomplete dosing
p value 1 refers to significance tests compared to unvaccinated controls
p value 2 refers to significance tests compared to pcDNA3.1+ vaccinated controls
Statistical Analyses.
Trial 9 - Although not statistically significant the groups vaccinated with 4188.11 and ID209 did have noticeably higher mean survival times than unvaccinated controls.
Trial 10 - The unvaccinated control group survived for a significantly longer period than the pcDNA3.1+ vaccinated group. The groups vaccinated with ID215 and 4170.4 showed statistically significant longer survival times compared to the sham vaccinated group (p = 0.0168 and 0.0316) but not compared to the unvaccinated group.
Trial 11 - The group vaccinated with 4193.1 was the most promising and survived an average of 6.5 hours longer than the pcDNA3.1+ vaccinated group and 6 hours longer than the unvaccinated group although the results were not statistically significant.

TABLE 1

4101.1
(SEQ. ID. NO. 208)
ATGGAAGAGTTAGTGACCTTAGATTGTTTGTTTATTGACAGAACTAAGAT

TGAAGCCAATGCCAACAAGTATAGTTTTGTGTGGAAGAAAACGACAGAGA

AATTCTCCGCCAAACTTCAAGAACAGATACAGGTCTATTTTCAAGAAGAA

ATCACTCCCCTTCTGATTAAATATGCCATGTTTGATAAGAAACAAAAGAG

AGGGTATAAAGAGTCAGCTAAAAACTTAGCGAATTGGCACTATAATGACA

AGGAGGATAGCTACACACATCCTGATGGCTGGTATTATCGTTTTCACCAT

ACCAAATATCAGAAAACACAGACAGACTTTCAACAAGAAATCAAGGTTTA

CTACGCCGACGAACCTGAATCAGCCCCTCAAAAGGGACTGTATATGAACG

AACGCTATCAAAACTTGAAAGCTAAAGAATGTCAGGCGCTTTTATCTCCC

CAAGGTAGACAGATTTTCGCTCAACGCAAGATTGATGTGGAACCTGTCTT

TGGGCAGATAAAGGCTTCTTTGGGTTACAAGAGATGTAATCTGAGAGGGA

AGCGTCAAGTGAGAATTGACATGGGATTGGTACTTATGGCCAATAACCTC

CTAAAATATAGTAAAATGAAATAA 4101.3
(SEQ. ID. NO. 209)
ATGGGGAAAGGCCATTGGAATCGGAAAAGAGTTTATAGCATTCGTAAGTT

TGCTGTGGGAGCTTGCTCAGTAATGATTGGGACTTGTGCAGTTTTATTAG

GAGGAAATATAGCTGGAGAATCTGTAGTTTATGCGGATGAAACACTTATT

ACTCATACTGCTGAGAAACCTAAAGAGGAAAAATGATAGTAGAAGAAAA

GGCTGATAAAGCTTTGGAAACTAAAAATATAGTTGAAAGGACAGAACAAA

GTGAACCTAGTTCAACTGAGGCTATTGCATCTGAGAAGAAAGAAGATGAA

GCCGTAACTCCAAAAGAGGAAAAAGTGTCTGCTAAACCGAAGAAAAAGC

TCCAAGGATAGAATCACAAGCTTCAAATCAAGAAAAACCGCTCAAGGAAG

ATGCTAAAGCTGTAACAAATGAAGAAGTGAATCAAATGATTGAAGACAGG

AAAGTGGATTTTAATCAAAATTGGTACTTTAAACTCAATGCAAATTCTAA

TABLE 1-continued

GGAAGCCATTAAACCTGATGCAGACGTATCTACGTGGAAAAAATTAGATT

TACCGTATGACTGGAGTATCTTTAACGATTTCGATCATGAATCTCCTGCA

CAAAATGAAGGTGGACAGCTCAACGGTGGGGAAGCTTGGTATCGCAAGAC

TTTCAAACTAGATGAAAAAGACCTCAAGAAAAATGTTCGCCTTACTTTTG

ATGGCGTCTACATGGATTCTCAAGTTTATGTCAATGGTCAGTTAGTGGGG

CATTATCCAAATGGTTATAACCAGTTCTCATATGATATCACCAAATACCT

TCAAAAAGATGGTCGTGAGAATGTGATTGCTGTCCATGCAGTCAACAAAC

AGCCAAGTAGCCGTTGGTATTCAGGAAGTGGTATCTATCGTGATGTGACT

TTACAAGTGACAGATAAGGTGCATGTTGAGAAAAATGGGACAACTATTTT

AACACCAAAACTTGAAGAACAACAACATGGCAAGGTTGAAACTCATGTGA

CCAGCAAAATCGTCAATACGGACGACAAAGACCATGAACTTGTAGCCGAA

TATCAAATCGTTGAACGAGGTGGTCATGCTGTAACAGGCTTAGTTCGTAC

AGCGAGTCGTACCTTAAAAGCACATGAATCAACAAGCCTAGATGCGATTT

TAGAAGTTGAAAGACCAAAACTCTGGACTGTTTTAAATGACAAACCTGCC

TTGTACGAATTGATTACGCGTGTTTACCGTGACGGTCAATTGGTTCATGC

TAAGAAGGATTTGTTTGGTTACCGTTACTATCACTGGACTCCAAATGAAG

GTTTCTCTTTGAATGGTAACGTATTAAATTCCATGGAGTATCCTTGCAC

CACGACCATGGGGCGCTTGGAGCAGAAGAAAACTATAAAGCAGAATATCG

CCGTCTCAAACAAATGAAGGAGATGGGAGTTAACTCCATCCGTACAACCC

ACAACCCTGCTAGTGAGCAAACCTTGCAAATCGCAGCAGAACTAGGTTTA

CTCGTTCAGGAAGAGGCCTTTGATACGTGGTATGGTGGCAAGAAACCTTA

TGACTATGGACGTTTCTTTGAAAAAGATGCCACTCACCCAGAAGCTCGAA

AAGGTGAAAATGGTCTGATTTTGACCTACGTACCATGGTCGAAAGAGGC

AAAAACAACCCTGCTATCTTCATGTGGTCAATTGGTAATGAAATAGGTGA

AGCTAATGGTGATGCCCACTCTTTAGCAACTGTTAAACGTTTGGTTAAGG

TABLE 1-continued

```
TTATCAAGGATGTTGATAAGACTCGCTATGTTACCATGGGAGCAGATAAA
TTCCGTTTCGGTAATGGTAGCGGAGGGCATGAGAAAATTGCTGATGAACT
CGATGCTGTTGGATTTAACTATTCTGAAGATAATTACAAAGCCCTTAGAG
CTAAGCATCCAAAATGGTTGATTTATGGATCAGAAACATCTTCAGCTACC
CGTACACGTGGAAGTTACTATCGCCCTGAACGTGAATTGAAACATAGCAA
TGGACCTGAGCGTAATTATGAACAGTCAGATTATGGAAATGATCGTGTGG
GTTGGGGGAAAACAGCAACCGCTTCATGGACTTTTGACCGTGACAACGCT
GGCTATGCTGGACAGTTTATCTGGACAGGTACGGACTATATTGGTGAACC
TACACCATGGCACAACCAAAATCAAACTCCTGTTAAGAGCTCTTACTTTG
GTATCGTAGATACAGCCGGCATTCCAAAACATGACTTCTATCTCTACCAA
AGCCAATGGGTTTCTGTTAAGAAGAAACCGATGGTACACCTTCTTCCTCA
CTGGAACTGGGAAAACAAAGAATTAGCATCCAAAGTAGCTGACTCAGAAG
GTAAGATTCCAGTTCGTGCTTATTCGAATGCTTCTAGTGTAGAATTGTTC
TTGAATGGAAAATCTCTTGGTCTTAAGACTTTTCAATAAAAAACAAACCAG
CGATGGGCGGACTTACCAAGAAGGTGCAAATGCTAATGAACTTTATCTTG
AATGGAAAGTTGCCTATCAACCAGGTACCTTGGAAGCAATTGCTCGTGAT
GAATCTGGCAAGGAAATTGCTCGAGATAAGATTACGACTGCTGGTAAGCC
AGCGGCAGTTCGTCTTATTAAGGAAGACCATGCGATTGCAGCAGATGGAA
AAGACTTGACTTACATCTACTATGAAATTGTTGACAGCCAGGGGAATGTG
GTTCCAACTGCTAATAATCTGGTTCGCTTCCAATTGCATGGCCAAGGTCA
ACTGGTCGGTGTAGATAACGGAGAACAAGCCAGCCGTGAACGCTATAAGG
CGCAAGCAGATGGTTCTTGGATTCGTAAAGCATTTAATGGTAAAGGTGTT
GCCATTGTCAAATCAACTGAACAAGCAGGGAAATTCACCCTGACTGCCCA
CTCTGATCTCTTGAAATCGAACCAAGTCACTGTCTTTACTGGTAAGAAAG
AAGGACAAGAGAAGACTGTTTTGGGGACAGAAGTGCCAAAAGTACAGACC
ATTATTGGAGAGGCACCTGAAATGCCTACCACTGTTCCGTTTGTATACAG
TGATGGTAGCCGTGCAGAACGTCCTGTAACCTGGTCTTCAGTAGATGTGA
GCAAGCCTGGTATTGTAACGGTGAAAGGTATGGCTGACGGACGAGAAGTA
GAAGCTCGTGTAGAAGTGATTGCTCTTAAATCAGAGCTACCAGTTGTGAA
ACGTATTGCTCCAAATACTGACTTGAATTCTGTAGACAAATCTGTTTCCT
ATGTTTTGATTGATGGAAGTGTTGAAGAGTATGAAGTGGACAAGTGGGAG
ATTGCCGAAGAAGATAAAGCTAAGTTAGCAATTCCAGGTTCTCGTATTCA
AGCGACCGGTTATTTAGAAGGTCAACCAATTCATGCAACCCTTGTGGTAG
AAGAAGGCAATCCTGCGGCACCTGCAGTACCAACTGTAACGGTTGGTGGT
GAGGCAGTAACAGGTCTTACTAGTCAAAAACCAATGCAATACCGCACTCT
TGCTTATGGAGCTAAGTTGCCAGAAGTCACAGCAAGTGCTAAAAATGCAG
CTGTTACAGTTCTTCAAGCAAGCGCAGCAAACGGCATGCGTGCGAGCATC
TTTATTCAGCCTAAAGATGGTGGCCCTCTTCAAACCTATGCAATTCAATT
CCTTGAAGAAGCGCCAAAAATTGCTCACTTGAGCTTGCAAGTGGAAAAAG
CTGACAGTCTCAAAGAAGACCAAACTGTCAAATTGTCGGTTCGAGCTCAC
```

```
TATCAAGATGGAACGCAAGCTGTATTACCAGCTGATAAAGTAACCTTCTC
TACAAGTGGTGAAGGGGAAGTCGCAATTCGTAAAGGAATGCTTGAGTTGC
ATAAGCCAGGAGCAGTCACTCTGAACGCTGAATATGAGGGAGCTAAAGAC
CAAGTTGAACTCACTATCCAAGCCAATACTGAGAAGAAGATTGCGCAATC
CATCCGTCCTGTAAATGTAGTGACAGATTTGCATCAGGAACCAAGTCTTC
CAGCAACAGTAACAGTTGAGTATGACAAAGGTTTCCCTAAAACTCATAAA
GTCACTTGGCAAGCTATTCCGAAAGAAAAACTAGACTCCTATCAAACATT
TGAAGTACTAGGTAAAGTTGAAGGAATTGACCTTGAAGCGCGTGCAAAAG
TCTCTGTAGAAGGTATCGTTTCAGTTGAAGAAGTCAGTGTGACAACTCCA
ATCGCAGAAGCACCACAATTACCAGAAAGTGTTCGGACATATGATTCAAA
TGGTCACGTTTCATCAGCTAAGGTTGCATGGGATGCGATTCGTCCAGAGC
AATACGCTAAGGAAGGTGTCTTTACAGTTAATGGTCGCTTAGAAGGTACG
CAATTAACAACTAAACTTCATGTTCGCGTATCTGCTCAAACTGAGCAAGG
TGCAAACATTTCTGACCAATGGACCGGTTCAGAATTGCCACTTGCCTTTG
CTTCAGACTCAAATCCAAGCGACCCAGTTTCAAATGTTAATGACAAGCTC
ATTTCCTACAATAACCAACCAGCCAATCGTTGGACAAACTGGAATCGTAC
TAATCCAGAAGCTTCAGTCGGTGTTCTGTTTGGAGATTCAGGTATCTTGA
GCAAACGCTCCGTTGATAATCTAAGTGTCGGATTCCATGAAGACCATGGA
GTTGGTGTACCGAAGTCTTATGTGATTGAGTATTATGTTGGTAAGACTGT
CCCAACAGCTCCTAAAAACCCTAGTTTTGTTGGTAATGAGGACCATGTCT
TTAATGATTCTGCCAACTGGAAACCAGTTACTAATCTAAAAGCCCCTGCT
CAACTCAAGGCTGGAGAAATGAACCACTTTAGCTTTGATAAAGTTGAAAC
CTATGCTGTTCGTATTCGCATGGTTAAAGCAGATAACAAGCGTGGAACGT
CTATCACAGAGGTACAAATCTTTGCGAAACAAGTTGCGGCAGCCAAGCAA
GGACAAACAAGAATCCAAGTTGACGGCAAAGACTTAGCAAACTTCAACCC
TGATTTGACAGACTACTACCTTGAGTCTGTAGATGGAAAAGTTCCGGCAG
TCACAGCAAGTGTTAGCAACAATGGTCTCGCTACCGTCGTTCCAAGCGTT
CGTGAAGGTGAGCCAGTTCGTGTCATCGCGAAAGCTGAAAATGGCGACAT
CTTAGGAGAATACCGTCTGCACTTCACTAAGGATAAGAGCTTACTTTCTC
ATAAACCAGTTGCTGCGGTTAAACAAGCTCGCTTGCTACAAGTAGGTCAA
GCACTTGAATTGCCGACTAAGGTTCCAGTTTACTTCACAGGTAAAGACGG
CTACGAAACAAAAGACCTGACAGTTGAATGGGAAGAAGTTCCAGCGGAAA
ATCTGACAAAAGCAGGTCAATTTACTGTTCGAGGCCGTGTCCTTGGTAGT
AACCTTGTTGCTGAGATCACTGTACGAGTGACAGACAAACTTGGTGAGAC
TCTTTCAGATAACCCTAACTATGATGAAAACAGTAACCAGGCCTTTGCTT
CAGCAACCAATGATATTGACAAAAACTCTCATGACCGCGTTGACTATCTC
AATGACGGAGATCATTCAGAAAATCGTCGTTGGACAAACTGGTCACCAAC
ACCATCTTCTAATCCAGAAGTATCAGCGGGTGTGATTTTCCGTGAAAATG
GTAAGATTGTAGAACGGACTGTTACACAAGGAAAAGTTCAGTTCTTTGCA
GATAGTGGTACGGATGCACCATCTAAACTCGTTTTAGAACGCTATGTCGG
```

TABLE 1-continued

TCCAGAGTTTGAAGTGCCAACCTACTATTCAAACTACCAAGCCTACGACG
CAGACCATCCATTCAACAATCCAGAAAATTGGGAAGCTGTTCCTTATCGT
GCGGATAAAGACATTGCAGCTGGTGATGAAATCAACGTAACATTTAAAGC
TATCAAAGCCAAAGCTATGAGATGGCGTATGGAGCGTAAAGCAGATAAGA
GCGGTGTTGCGATGATTGAGATGACCTTCCTTGCACCAAGTGAATTGCCT
CAAGAAAGCACTCAATCAAAGATTCTTGTAGATGGAAAAGAACTTGCTGA
TTTCGCTGAAAATCGTCAAGACTATCAAATTACCTATAAAGGTCAACGGC
CAAAAGTCTCAGTTGAAGAAAACAATCAAGTAGCTTCAACTGTGGTAGAT
AGTGGAGAAGATAGCTTTCCAGTACTTGTTCGCCTCGTTTCAGAAAGTGG
AAAACAAGTCAAGGAATACCGTATCCACTTGACTAAGGAAAAACCAGTTT
CTGAGAAGACAGTTGCTGCTGTACAAGAAGATCTTCCAAAAATCGAATTT
GTTGAAAAGATTTGGCATACAAGACAGTTGAGAAAAAAGATTCAACACT
GTATCTAGGTGAAACTCGTGTAGAACAAGAAGGAAAAGTTGGAAAAGAAC
GTATCTTTACAGCGATTAATCCTGATGGAAGTAAGGAAGAAAAACTCCGT
GAAGTGGTAGAAGTTCCGACAGACCGCATCGTCTTGGTTGGAACCAAACC
AGTAGCTCAAGAAGCTAAAAAACCACAAGTGTCAGAAAAAGCAGATACAA
AACCAATTGATTCAAGTGAAGCTAGTCAAACTAATAAAGCCCAGTTACCA
AGTACAGGTAGTGCGGCAAGCCAAGCAGCAGTAGCAGCAGGTTTAACTCT
TCTAGGTTTGAGTGCAGGATTAGTAGTTACTAAAGGTAAAAAAGAAGACT
AG 4101.5
(SEQ. ID. NO. 210)
ATGGATGCAATCTTTGACCTAATCGGAAAGGTTTTCAATCCCATCTTAGA
AATGGGTGGACCTGTCATCATGTAATCATTTTGACAGTATTGGCTTTACT
TTTTGGAGTGAAATTCTCCAAAGCGCTTGAAGGTGGTATCAAACTTGCCA
TCGCTCTTACAGGTATCGGTGCTATCATCGGTATGCTAAACACTGCTTTC
TCAGCATCACTAGCAAAATTCGTTGAAAACACTGGTATCCAATTGAGTAT
TACCGACGTTGGTTGGGCACCACTTGCTACAATCACTTGGGGTTCTGCTT
GGACACTATACTTCTTGCTCATCATGTTGATTGTCAACATAGTGATGCTA
GCTATGAAGAAAACAGATACACTTGATGTCGATATCTTTGATATCTGGCA
CTTGTCTATCACAGGTCTCTTGATTAAATGGTATGCTGATAACAATGGTG
TGAGTCAAGGGGTTTCACTCTTTATTGCTACAGCAGCTATCGTCCTTGTC
GGTGTGTTGAAAATTATCAACTCTGACTTGATGAAACCTACATTTGATGA
CCTTCTTAACGCCCCAAGTTTCATCACCAATGACATCAACTCACATGAAC
TACATGATGAACCCAGTTATCATGGTTTTGGATAAGATTTTTGAAAAATT
CTTCCCAGGCCTTGATAAATATGACTTTGATGCTGCTAAATTGAACAAGA
AAATCGGTTTCTGGGGATCTAAATTCTTCATCGGTTTCATCCTTGGTATC
GTTATCGGTATTATGGGAACTCCACATCCAATTGCAGGTGTTGCAGATGC
AGATAAATGGCGTCTTGTTATCAAAGGATGGTTGTCTCTTGGTTTGACTG
CCGGTGTATCTTTGGAACTCTTCTCACTTATCGGTTCATGGTTCATCGCA
GCCGTAGAACCACTATCACAAGGTATTACAAACGTTGCTACTAAACGTCT

TCAAGGACGTAAATTCAATATCGGTCTTGACTGGCCATTCATCGCTGGTC
GTGCTGAAATCTGGGCTTGTGCCAACGTACTTGCACCAATCATGTTGATT
GAAGCAGTGCTTCTTTCAAAAGTTGGAAATGGTATCTTGCCACTTGCAGG
TATCATCGCTATGGGTGTTACTCCAGCTCTCTTGGTTGTAACTCGTGGTA
AATTGCTCCGTATGATTATCTTCGGAACACTCTTGTTGCCACTCTTCCTT
CTTTCAGGTACACTTATTGCACCATTTGCAACAGAACTTGCTAAAGGTGT
AGGTGCCTTCCCAGAAGGTGTGAGCCAAACTCAATTGATTACTCACTCTA
CTCTTGAAGGACCAATCGAAAAACTTCTTGGTTGGACAATTGGTAACACT
ACAACTGGTGATATCAAAGCAATCCTTGGTGCAGTAGTCTTCCTTGTATT
CTATATCGGTATCTTTGCTTGGTACAGAAAACAAATGATCAAACGTAACG
AAGAGTACGCAGCAAAAGCAAATAA 4102.1
(SEQ. ID. NO. 211)
ATGAAGATTATGAAAAAAAAATATTGGACTTTAGCGATATTATTCTTTTG
TTTGTTCAATAATTCTGTTACTGCTCAAGAAATACCTAAAAATCTTGATG
GCAATATAACTCACACTCAGACTAGCGAAAGTTTTTCTGAATCTGATGAA
AAACAGGTTGACTATTCTAATAAAAATCAAGAAGAAGTAGACCAAAATAA
ATTTCGTATTCAAATCGATAAGACAGAATTATTTGTAACAACAGATAAAC
ATTTAGAAAAAACTGTTGTAAATTGGAACTTGAACCACAAATAAATAAC
GATATTGTTAACTCTGAAAGTAATAATTTACTAGGCAAGATAATTTAGA
TAATAAAATTAAGGAAAATGTTTCTCATCTAGATAATAGAGGAGGAAATA
TAGAGCATGACAAAGATAACTTAGAATCGTCGATTGTAAGAAAATATGAA
TGGGATATAGATAAAGTTACTGGTGGAGGCGAAAGTTATAAATTATATTC
TAAAAGTAATTCTAAAGTTTCAATTGCTATTTTAGATTCAGGAGTCGATT
TACAAAATACTGGATTACTGAAAAATCTTTCAAATCACTCAAAAAACTAT
GTCCCCAATAAAGGATATTTAGGAAAAGAGGAGGGAGAGGAAGGAATAAT
ATCAGATATTCAAGATAGATTAGGTCATGGTACGGCTGTTGTAGCTCAAA
TTGTAGGGGATGACAATATTAATGGAGTAAATCCTCACGTTAATATTAAC
GTCTATAGAATATTTGGTAAGTCGTCAGCTAGTCCAGATTGGATTGTAAA
AGCAATTTTTGATGCTGTAGATGATGGCAATGATATTATCAATCTTAGTA
CTGGACAATATTTAATGATTGATGGAGAATATGAGGACGGAACAAATGAT
TTTGAAACATTTTTGAAGTATAAAAAGGCTATTGATTACGCGAATCAAAA
AGGAGTAATTATAGTAGCTGCATTAGGGAATGACTCCCTAAATGTATCAA
ATCAGTCAGATTTATTGAAACTTATTAGTTCACGCAAAAAAGTAAGAAAA
CCAGGATTAGTAGTTGATGTTCCAAGTTATTTCTCATCTACAATTTCGGT
CGGAGGCATAGATCGCTTAGGTAATTTATCAGATTTTAGCAATAAAGGGG
ATTCTGATGCAATATATGCGCCTGCAGGCTCAACATTATCTCTTTCAGAA
TTAGGACTTAATAACTTTATTAATGCAGAAAAATATAAAGAAGATTGGAT
TTTTTCGGCAACACTAGGAGGATATACGTATCTTTATGGAAACTCATTTG
CTGCTCCTAAAGTTTCTGGTGCGATTGCAATGATTATTGATAAATACAAA

TABLE 1-continued

```
TTAAAAGATCAGCCCTATAATTATATGTTTGTAAAAAAATTCTGGAAGAA
ACATTACCAGTAA
```

4106.1

(SEQ. ID. NO. 212)
```
ATGAAGAAAACATGGAAAGTGTTTTTAACGCTTGTAACAGCTCTTGTAGC
TGTTGTGCTTGTGGCCTGTGGTCAAGGAACTGCTTCTAAAGACAACAAAG
AGGCAGAACTTAAGAAGGTTGACTTTATCCTAGACTGGACACCAAATACC
AACCACACAGGGCTTTATGTTGCCAAGGAAAAAGGTTATTTCAAAGAAGC
TGGAGTGGATGTTGATTTGAAATTGCCACCAGAAGAAAGTTCTTCTGACT
TGGTTATCAACGGAAAGGCACCATTTGCAGTGTATTTCCAAGACTACATG
GCTAAGAAATTGGAAAAAGGAGCAGGAATCACTGCCGTTGCAGCTATTGT
TGAACACAATACATCAGGAATCATCTCTCGTAAATCTGATAATGTAAGCA
GTCCAAAAGACTTGGTTGGTAAGAAATATGGGACATGGAATGACCCAACT
GAACTTGCTATGTTGAAAACCTTGGTAGAATCTCAAGGTGGAGACTTTGA
GAAGGTTGAAAAAGTACCAAATAACGACTCAAACTCAATCACACCGATTG
CCAATGGCGTCTTTGATACTGCTTGGATTTACTACGGTTGGGATGGTATC
CTTGCTAAATCTCAAGGTGAGATGCTAACTTCATGTACTTGAAAGACTAT
GTCAAGGAGTTTGACTACTATTCACCAGTTATCATCGCAAACAACGACTA
TCTGAAAGATAACAAAGAAGAAGCTCGCAAAGTCATCCAAGCCATCAAAA
AAGGCTACCAATATGCCATGGAACATCCAGAAGAAGCTGCAGATATTCTC
ATCAAGAATGCACCTGAACTCAAGGAAAAACGTGACTTTGTCATCGAATC
TCAAAAATACTTGTCAAAAGAATACGCAAGCGACAAGGAAAAATGGGGTC
AATTTGACGCAGCTCGCTGGAATGCTTTCTACAAATGGGATAAAGAAAT
GGTATCCTTAAAGAAGACTTGACAGACAAAGGCTTCACCAACGAATTTGT
GAAATAA
```

4106.4

(SEQ. ID. NO. 213)
```
ATGATAAAAAATCCTAAATTATTAACCAAGTCTTTTTTAAGAAGTTTTGC
AATTCTAGGTGGTGTTGGTCTAGTCATTCATATAGCTATTTATTTGACCT
TTCCTTTTTATTATATTCAACTGGAGGGGAAAAGTTTAATGAGAGCGCA
AGAGTGTTTACGGAGTATTTAAAGACTAAGACATCTGATGAAATTCCAAG
CTTACTCCAGTCTTATTCAAAGTCCTTGACCATATCTGCTCACCTTAAAA
GAGATATTGTAGATAAGCGGCTCCCTCTTGTGCATGACTTGGATATTAAA
GATGGAAAGCTATCAAATTATATCGTGATGTTAGATATGTCTGTTAGTAC
AGCAGATGGTAAACAGGTAACCGTGCAATTGTTCACGGGGTGGATGTCT
ACAAAGAAGCAAAGAATATTTTGCTTTTGTATCTCCCATATACATTTTTG
GTTACAATTGCTTTTCCTTTGTTTTTCTTATTTTTATACTAAACGCTT
GCTCAATCCTCTTTTTTACATTTCAGAAGTGACTAGTAAATGCAAGATT
TGGATGACAATATTCGTTTTCATCAAACTAGGAAAGATGAAGTTGGTGAA
GTTGGAAAACAGATTAATGGTATGTATGAGCACTTGTTGAAGGTTATTTA
TGAGTTGGAAAGTCTGTAATGAGCAAATTGTAAAATTGCAAAATCAAAAG
GTTTCCTTTGTCCGCGGAGCATCACATGAGTTGAAAACCCCTTTAGCCAG
```

```
TCTTAGAATTATCCTAGAGAATATGCAGCATAATATTGGAGATTACAAAG
ATCATCCAAAATATATTGCAAAGAGTATAAATAAGATTGACCAGATGAGC
CACTTATTAGAAGAAGTACTGGAGTCTTCTAAATTCCAAGAGTGGACAGA
GTGTCGTGAGACCTTGACTGTTAAGCCAGTTTTAGTAGATATTTTATCAC
GTTATCAAGAATTAGCTCATTCAATAGGTGTTACAATTGAAAATCAATTG
ACAGATGCTACCAGGGTCGTCATGAGTCTTAGGGCATTGGATAAGGTTTT
GACAAACCTGATTAGTAATGCAATTAAATATTCAGATAAAAATGGGCGTG
TAATCATATCCGAGCAAGATGGCTATCTCTCTATCAAAAATACATGTGCG
CCTCTAAGTGACCAAGAACTAGAACATTTATTTGATATATTCTATCATTC
TCAAATCGTGACAGATAAGGATGAAAGTTCCGGTTTGGGTCTTTACATTG
TGAATAATATTTTAGAAAGCTATCAAATGGATTATAGTTTTCTCCCTTAT
GAACACGGTATGGAATTTAAGATTAGCTTGTAG
```

4106.6

(SEQ. ID. NO. 214)
```
ATGTATTTAGGAGATTTGATGGAGAAAGCCGAGTGTGGTCAATTTTCAAT
ACTTTCCTTTCTATTACAAGAGTCTCAGACGACCGTCAAGGCTGTAATGG
AAGAAACAGGATTTTCAAAAGCAACCCTAACCAAATATGTCACCCTGCTC
AATGACAAGGCTTTGGATAGTGGCTTAGAGCTGGCTATTCACTCAGAAGA
TGAAAATCTGCGTCTGTCTATCGGTGCAGCTACCAAGGGGAGAGATATTC
GGAGCTTGTTTTTGGAGAGTGCTGTTAAATACCAGATTTTGGTTTATCTT
CTCTACCACCAACAGTTTTTAGCCCATCAGCTGGCTCAAGAATTGGTGAT
TAGCGAGGCTACGCTTGGTCGTCACTTGGCTGGTTTAAATCAGATTTTGT
CAGAATTTGATTTATCCATCCAAAATGGCCGTTGGCGAGGTCCAGAGCAT
CAGATTCACTATTTCTATTTCTGTCTTTTCCGAAAGGTCTGGTCGAGTCA
GGAATGGGAAGGTCACATGCAGAAACCAGAGAGAAAACAGGAGATTGCCA
ATTTAGAGGAAATCTGCGGTGCAAGTTTGTCTGCGGGGCAGAAATTGGAC
TTGGTTCTCTGGGCTCACATCAGTCAACAACGTCTTCGGGTCAATGCTTG
TCAGTTTCAAGTCATAGAAGAGAAAATGCGAGGGTATTTTGACAATATCT
TTTATCTTCGTTTGCTGAGAAAGGTTCCGTCCTTTTTTGCTGGGCAACAT
ATTCCACTAGGAGTTGAGGATGGTGAGATGATGATATTCTTCTCTTTTCT
CCTATCTCATCGCATTCTTCCTCTTCATACTATGGAGTATATTCTTGGTT
TTGGAGGGCAGTTGGCAGATTTACTGACGCAATTGATTCAAGAAATGAAG
AAGGAGGAACTATTGGGGGATTATACAGAGGACCATGTCACCTATGAACT
CAGTCAGCTTTGTGCTCAAGTCTATCTCTATAAGGGCTATATTTTACAGG
ATCGCTACAAGTACCAGTTAGAGAATCGTCATCCATATTTACTGATGGAA
CATGATTTTAAAGAGACAGCAGAGGAGATTTTTCATGCTCTACCTGCTTT
TCAACAGGGGACAGATTTAGATAAGAAGATTCTCTGGGAATGGCTCCAGT
TAATCGAATATATGGCTGAAAACGGTGGCCAGCATATGCGGATTGGTCTG
GATTTGACATCTGGTTTTCTTGTCTTTTCAAGGATGGCAGCCATTTTGAA
ACGGTATTTGGAATACAATCGTTTTATTACCATTGAAGCTTATGACCCTA
GTCGGCATTATGATTTGCTGGTTACCAATAACCCGATTCATAAGAAGGAA
```

TABLE 1-continued

CAGACACCAGTCTATTATTTAAAAAATGACTTGGATATGGAGGATTTGGT
AGCGATTCGCCAGTTATTATTCACTTAA 4106.7
(SEQ. ID. NO. 215)
ATGGAATTTTCAAAAGAAAACACGTGAATTGTCAATTAAAAAAATGCAGG
AACGTACCCTGGACCTCTTGATTATCGGTGGAGGAATCACAGGAGCTGGT
GTAGCCTTGCAGGCGGCAGCTAGCGGTCTTGAGACTGGTTTGATTGAAAT
GCAAGACTTTGCAGAAGGAACATCTAGTCGTTCAACAAAATTGGTTCACG
GAGGACTTCGTTACCTCAAACAATTTGACGTAGAAGTGGTCTCAGATACG
GTTTCTGAACGTGCAGTGGTTCAACAAATCGCTCCACACATTCCAAAATC
AGATCCAATGCTCTTACCAGTTTACGATGAAGATGGAGCAACCTTTAGCC
TCTTCCGTCTTAAAGTAGCCATGGACTTGTACGACCTCTTGGCAGGTGTT
AGCAACACACCAGCTGCGAACAAGGTTTTGAGCAAGGATCAAGTCTTGGA
ACGCCAGCCAAACTTGAAGAAGGAAGGCTTGGTAGGAGGTGGAGTGTATC
TTGACTTCCGTAACAACGATGCGCGTCTCGTGATTGAAAACATCAAACGT
GCCAACCAAGACGGTGCCCTCATTGCCAACCACGTGAAGGCAGAAGGCTT
CCTCTTTGACGAAAGTGGCAAGATTACAGGTGTTGTAGCTCGTGATCTCT
TGACAGACCAAGTGTTTGAAATCAAGGCCCGTCTGGTTATTAATACAACA
GGTCCTTGGAGTGATAAAGTACGTAATTTGTCTAATAAGGGAACGCAATT
CTCACAAATGCGCCCAACTAAGGGAGTTCACTTGGTAGTAGATTCAAGCA
AAATCAAGGTTTCACAGCCAGTTTACTTCGACACAGGTTTGGGTGACGGT
CGTATGGTCTTTGTTCTCCCACGTGAAAACAAGACTTACTTTGGTACAAC
TGATACAGACTACACAGGTGATTTGGAGCATCCAAAAGTAACTCAAGAAG
ATGTAGATTATCTACTTGGCATTGTCAACAACCGCTTCCCAGAATCCAAC
ATCACCATTGATGATATCGAAAGCAGCTGGGCAGGTCTTCGTCCATTGAT
TGCAGGGAACAGTGCCTCTGACTATAATGGTGGAAATAACGGTACCATCA
GTGATGAAAGCTTTGACAACTTGATTGCGACTGTTGAATCTTATCTCTCC
AAAGAAAAAACACGTGAAGATGTTGAGTCTGCTGTCAGCAAGCTTGAAAG
TAGCACATCTGAGAAACATTTGGATCCATCTGCAGTTTCTCGTGGGTCTA
GCTTGGACCGTGATGACAATGGTCTCTTGACTCTTGCTGGTGGTAAAATC
ACAGACTACCGTAAGATGGCTGAAGGAGCTATGGAGCGCGTGGTTGACAT
CCTCAAAGCAGAATTTGACCGTAGCTTTAAATTGATCAATTCTAAAACTT
ACCCTGTTTCAGGTGGAGAATTGAACCCAGCAAATGTGGATTCAGAAATC
GAAGCCTTTGCGCAACTTGGAGTATCACGTGGTTTGGATAGCAAGGAAGC
TCACTATCTGGCAAATCTTTACGGTTCAAATGCACCGAAAGTCTTTGCAC
TTGCTCACAGCTTGGAACAAGCGCCAGGACTCAGCTTGGCAGATACTTTG
TCCCTTTCACTATGCAATGCGCAATGAGTTGACTCTTAGCCCAGTTGACT
TCCTTCTTCGTCGTACCAATCACATGCTCTTTATGCGTGATAGCTTGGAT
AGTATCGTTGAGCCAATTTTGGATGAAATGGACGATTCTATGACTGGAC
AGAAGAAGAAAAAGCAACTTACCGTGCTGATGTCGAAGCAGCTCTCGCTA
ACAACGATTTAGCAGAATTAAAAAATTAA 4106.8
(SEQ. ID. NO. 216)
ATGATGAATGAATTATTTGGAGAATTTCTAGGGACTTTAATCCTGATTCT
TCTAGGAAATGGTGTTGTTGCAGGTGTGGTTCTTCCTAAAACCAAGAGCA
ATAGCTCAGGTTGGATTGTGATTACTATGGGTTGGGGGATTGCAGTTGCG
GTTGCAGTCTTTGTATCTGGCAAGCTCAGTCCAGCTTATTTAAACCCAGC
TGTGACCATCGGTGTGGCCTTAAAAGGTGGTTTGCCTTGGGCTTCCGTTT
TGCCTTATATCTTAGCCCAGTTCGCAGGGGCCATGCTGGGTCAGATTTTG
GTTTGGTTGCAATTCAAACCTCACTATGAGGCAGAAGAAAATGCAGGCAA
TATCCTGGCAACCTTCAGTACTGGACCAGCCATCAAGGATACTGTATCAA
ACTTGATTAGCGAAATCCTTGGAACTTTTGTTTTGGTGTTGACAATCTTT
GCTTTGGGTCTTTACGACTTTCAGGCAGGTATCGGAACCTTTGCAGTGGG
AACTTTGATTGTCGGTATCGGTCTATCACTAGGTGGGACAACAGGTTATG
CCTTGAACCCAGCTCGTGACCTTGGACCTCGTATCATGCACAGCATCTTG
CCAATTCCAAACAAGGGAGACGGAGACTGGTCTTACGCTTGGATTCCTGT
TGTAGGCCCTGTTATCGGAGCAGCCTTGGCAGTGCTTGTATTCTCACTTT
TCTAG 4106.10
(SEQ. ID. NO. 217)
ATGAAAAGGACCTGGAGGAACTCATTCGTGACAAATCTTAATACACCTTT
TATGATTGGCAATATTGAGATTCCCAATCGTACCGTTTTAGCGCCTATGG
CTGGCGTGACCAACTCAGCCTTTCGTACTATCGCAAAGGAGCTCGGAGCT
GGACTCGTTGTAATGGAAATGGTCTCTGACAAGGGAATCCAATACAACAA
CGAAAAACCCTGCACATGCTTCATATCGATGAGGGCGAAAACCCTGTCT
CTATCCAACTTTTTGGTAGCGATGAAGACAGCCTAGCACGCGCAGCAGAA
TTCATCCAAGAAAACACCAAGACCGATATCGTCGATATCAACATGGGCTG
CCCTGTCAACAAAATCGTGAAGAACGAAGCTGGTGCTATGTGGCTCAAGG
ATCCAGACAAGATTTACTCCATCATCAACAAGGTCCAGTCTGTCCTTGAT
ATCCCACTTACTGTCAAAATGCGTACCGGCTGGGCGGACCCATCTCTTGC
AGTAGAAAATGCTCTCGCTGCTGAAGCTGCAGGTGTTTCTGCCCTCGCCA
TGCATGGCCGTACCCGTGAACAAATGTATACTGGCCACGCAGACCTTGAG
ACCCTTTACAAGGTTGCCCAAGCTCTAACCAAGATTCCATTCATCGCCAA
CGGTGATATCCGTACTGTCCAAGAAGCCAAGCAACGCATCGAAGAAGTTG
GTGCTGACGCAGTCATGATTGGCCGAGCTGCCATGGGAAATCCTTACCTC
TTCAACCAAATCAACCATTACTTTGAAACAGGAGAAATCCTACCTGATTT
GACCTTTGAAGACAAGATGAAGATCGCCTAGGAACACTTGAAACGATTGA
TTAACCTCAAAGGAGAAAACGTCGCAGTTCGTGAATTCCGCGGTCTCGCT
CCTCACTATCTCCGTGGAACATCTGGCGCTGCCAAACTCCGTGGAGCCAT
TTCGCAAGCCAGCACCCTGGCAGAGATTGAAACCCTCTTGCAATTGGAGA
AGGCTTAA

TABLE 1-continued 4107.1
(SEQ. ID. NO. 218)
ATGACAAAGAAGAAAATTGAGCGTATTTCTGTAATACACCGAGAAAAGAT
TTTATGGCTCAAGTGGTATTTCATGCGAGATAAAGAACAACCTAAGTATA
GTGTCCTTGAGCGTAAAATGTTTGATGCTGCTAAAAATCAAGATATGCTA
GCTTATCAAAAATACGCAACTATCAAGCAGATAACAGATATTAGGGTACA
AACAAGTGAGGCTGACATTTTAGAGGCTGTAAAAGAGGTTTATGTGTACA
ATCACATGAATGTTATCGGAGCTTGTCAGCGGATATTATTTATCAGTCAA
TCACCAGCTTATGATAAGTTAAATAAGTGGTTTAATATCTATTCTGATTT
GTATTTTAGCGTTGTACCCTTGCCCAAAATGGGGGTATATCATGAGATGG
TAGGTATCTAG 4107.2
(SEQ. ID. NO. 219)
ATGAAAAATTCCAACGAGGCTGAGATGAAATTACTTTATACTGATATTCG
GACTTCTTTGACAGAAATTCTAACAAGAGAGGCAGAAGAGCTAGTTGCAG
CTGGCAAGCGGGTCTTCTACATTGCCCCCAACTCTCTTTCTTTTGAAAAG
GAACGCGCCGTGCTGGAATACTTGTCCCAGCAGGCTTCTTTTTCGATTAC
CGTCACGCGCTTTGCTCAAATGGCTCGCTATCTGGTCTTGAATGATTTAC
CAGCTAAAACTACTCTTGATGATATCGGTCTTGGTTGGCCTTTTACAAA
TGCCTTGCCGAACTCGATCCCAAGGACTTGCGTGTTTATGGCGCTATTAA
GCAGGATCCTCAATTGATCCAGCAGTTAATTGAGCTTTACCATGAGATGA
CCAAATCTCAGATGAGTTTTTTGGACTTGGAGAATTTAACAGATGAGGAT
AAGAGGGCGGATTTACTCTTGATTTTTGAGAAAGTAACAGCCTATCTTAA
TCAAGGTCAGTTAGCCCAGGAAAGTCAGTTGTCCCATTTGATTGAGGCTA
TTGAGAATGACAAGGTAAGTAGTGATTTTAATCAAATCGCCTTGGTCATT
GACGGCTTTACTCGTTTTTCTGCTGAGGAAGAGCGGGTTGTGGACTTACT
TCACGGCAAAGGTGTTGAGATTGTTATCGGGGCTTATGCTAGTAAGAAAG
CCTATACCAGTCCTTTTAGCGAGGGCAATCTCTACCAAGCCAGCGTAAAA
TTTCTCCATCATCTGGCTTCTAAATACCAAACGCCTGCTCAGGACTGTTC
TCAAACTCATGAGAAGATGGATAGTTTTGACAAGGCCTCTCGTTTGTTGG
AGTCTTCTTATGACTTTTCAGAACTCGCTTTGGATGTCGATGAGAAAGAC
CGTGAAAATTTACAAATCTGGTCTTGTTTGACGCAAAAGGAGGAGTTGGA
GCTAGTAGCCCGTAGTATTCGTCAGAAATTACATGAGAACTCAGACCTGA
GCTACAAGCATTTTCGTATTCTCTTGGGGGATGTAGCTTCTTACCAGTTA
TCTCTCAAAACCATTTTTGACCAGTATCAGATTCCTTTTTATCTTGGTAG
AAGCGAAGCCATGGCTCATCATCCCTTGACTCAGTTTGTCGAGTCTATTT
TAGCTTTAAAACGTTACCGTTTTCGTCAGGAGGATTTGATTAATCTTCTT
AGAACTGATTTGTATACTGACCTCAGTCAGTCTGATATTGATGCTTTTGA
GCAATATATCCGCTATCTTGGTATCAATGGCTTGCCAGCCTTTCAGCAAA
CCTTCACCAAATCCCACCATGGAAAATTTAATCTTGAGCGTTTGAATGTC
CTCCGCCTGAGAATTTTAGCACCTCTTGAAACCCTCTTTGCCAGCCGAAA
ACAAAAGGCTGAAAAACTCCTACAAAAATGGAGTGTCTTTCTAAAAGAAG GAGCTGTGACCAAGCAGTTACAAGATTTGACAACCACTTTGGAAGCTGTA
GAACAGGAAAGACAAGCCGAAGTTTGGAAGGCTTTCTGCCATGTTTTAGA
ACAATTTGCGACTGTTTTTGCTGGTTCACAGGTTAGTCTGGAAGACTTCC
TAGCCTGCTCCATTCTGGAATGAGTTTGTCCCAATACCGTACCATTCCAG
CAACAGTGGACACTGTTCTGGTGCAGCGTTACGATTTGATTGCACCATTG
ACTGCTGACTTTGTCTATGCTATTGGACTAACTCAGGACCATTTACCAAA
AATTTCTCAAAACACCAGTCTTCTGACAGATGAAGAAAGGCAAAACCTAA
ACCAAGCGACCGAAGAAGGCGTTCAATTACTGATTGCCAGCAGTGAAAAT
CTCAAGAAAAATCGCTACACTATGCTTTCCTTGGTCAATTCTGCTCGTAA
GCAGTTGTTCTTGTCGGCTCCAAGCCTTTTTAACGAAAGTGAAAGTAAGG
AATCTGCCTATCTTCAAGAGTTGATCCATTTTGGATTTAGGCGGAGAGAG
AAGAGGATGAATCACAAAGGACTGTCTAAGGAGGATATGGGGTCCTATCA
CAGTCTTTTGTCTAGTCTGGTTGCCTATCACCAGCAGGGTGAGATGAGCG
ATACTGAGCAAGATTTGACTTTTGTCAAGGTTCTGTCGCGTGTCATAGGT
AAAAAACTAGATCAGCAAGGTCTGGAAAATCCAGCTATCCCAACCAGTCC
AAGCAGCAAGACCTTAGCCAAGGACACCTTGCAAGCTCTCTATCCTGCCA
AACAGGAGTTTTACCTGTCTACGTCGGGTTTGACAGAGTTTTATCGCAAT
GAATACAGTTATTTCCTACGCTACGTTTTAGGCTTGCAGGAGGAATTACG
TTTGCATCCTGATGCCCGTAGTCACGGGAATTTCTTGCATCGTATCTTTG
AACGCGCCTTACAGTTGCCTAATGAAGATTCCTTTGACCAACGTCTAGAA
CAAGCTATTCAAGAAACCAGTCAAGAACGCGAATTTGAAGCTATTTATCA
AGAAACTTTGGAAGCCCAGTTTACCAAGGAAGTTTTGCTTGATGTTGCAC
GGACAACTGGACATATTCTCCGACACAATCCAGCCATCGAAACCATCAAA
GAAGAAGCAAATTTTGGTGGAAAAGACCAAGCCTTTATTCAATTAGACAA
TGGACGCAGTGTCTTTGTACGAGGCAAGGTGGACCGGATTGACCGTTTGA
AAGCTAATGGAGCGATAGGAGTAGTAGACTACAAATCCAGTCTGACTCAG
TTCCAGTTTCCTCATTTCTTTAATGGGCTCAATTCTCAGTTACCAACCTA
TCTTGCTGCCCTAAAAAGAGAAGGGGAGCAGAACTTTTTCGGCGCCATGT
ACTTGGAAATGGCTGAACCTGTCCAATCTCTGATGGCGGTAAAAAGTCTG
GCAGGAGCAGTGGTAGAAGCCAGCAAATCTATGAAATACCAAGGGCTCTT
CTTGGAAAAGAAAGCAGTTATTTAGGCGAATTTATAACAAAAACAAGG
CTAATCAACTGACAGATGAGGAATTTCAGCTCCTACTGGACTACAATGCC
TATCTTTACAAGAAAGCTGCTGAGAAGATTTTAGCAGGCGGTTCGCCAT
CAATCCTTATACTGAAAATGGCAGAAGCATTGCCCCATACGTCCAGCAAC
ATCAGGCTATTACAGGCTTTGAAGCCAATTACCATCTGGGCCAAGCCCGT
TTCCTAGAAAAGTTGGACCTAGCTGATGGCAAGCGTCTGGTCGGAGAAAA
ACTCAAGCAAGCTTGGCTTGAAAAAATAAGAGAGGAGTTGAATCGATGA 4107.3
(SEQ. ID. NO. 220)
ATGAAGCTTATTCCCTTTTTAAGTGAGGAGGAGATTCAAAAACTGCAAGA
AGCAGAAGCAAATTCGAGCAAGGAACAGAAGAAAACTGCCGAGCAAATCG TABLE 1-continued

```
AAGCTATCTACACTTCTGCCCAGAATATCCTGGTCTCAGCATCGGCTGGT
TCTGGAAAGACCTTTGTCATGGCAGAGCGCATTCTGGACCAATTGGCGCG
TGGTGTCGAAATTTCTCAACTCTTTATCTCAACCTTTACCGTCAAGGCTG
CAACTGAACTTAAAGAACGTTTAGAGAAAAAAATCAGCAAGAAAATCCAA
GAAACAGATGATGTCGACCTCAAACAACACTTGGGTCGCCAGTTGGCAGA
CCTACCCAACGCTGCCATTGGAACCATGGATTCTTTCACACAAAAATTCC
TTGGCAAACATGGTTATCTGCTTGATATTGCACCTAATTTCCGTATTTTA
CAAAACCAAAGCGAGCAACTTATTCTCGAAAACGAAGTCTTTCATGAGGT
CTTTGAAGCGCATTACCAAGGTAAACAGAAAGAGACCTTTAGTCATTTGC
TGAAAAACTTTGCTGGGCGTGGCAAGGACGAACGGGGTCTGCGCCAGCAG
GTCTATAAAATCTATGACTTCCTCCAATCCACCAGTAATCCTCAAAAGTG
GCTGAGTGAATCTTTCCTCAAAGGATTTGAGAAAGCTGATTTTACCAGTG
AAAAAGAAAAACTGACCGAGCAAATCAAACAAGCCCTTTGGGATTTGGAA
AGCTTTTTCCGTTACCATCTGGATAACGATGCCAAGGAGTTTGCAAAGGC
TGCCTATTTAGAAAATGTTCAGTTAATTCTGGATGAAATTGGCTCCCTAA
ATCAGGAGTCCGATAGTCAGGCTTATCAGGCAGTGCTTGCGCGTGTTGTC
GCCATCTCTAAGGAGAAAAACGGTCGAGCTCTGACTAATGCCAGCCGTAA
GGCTGATTTGAAGCCCCTGGCTGATGCCTACAACGAAGAGAGAAAGACCC
AGTTTGCTAAACTAGGACAATTATCAGACCAGATAGCGATTCTCGACTAT
CAAGAACGTTATCATGGAGACACTTGGAAACTAGCTAAAACCTTCCAATC
TTTCATGAGCGATTTTGTAGAGGCTTATCGTCAGAGAAAACGACAGGAAA
ATGCCTTCGAATTCGCTGATATCAGCCATTACACCATTGAGATTTTAGAG
AATTTCCCACAAGTTCGTGAGTCTTATCAGGAGCGCTTCCATGAAGTCAT
GGTCGATGAGTATCAGGATACCAACCATATTCAAGAACGGATGCTGGAAT
TGTTGTCTAATGGCCACAATCGCTTTATGGTGGGAGATATCAAGCAATCC
ATCTATCGTTTCCGTCAGGCAGACCCGCAGATTTTCAATGAGAAATTCCA
ACGCTATGCGCAAAATCCCCAAGAAGGCAGGCTCATTATCCTCAAGGAAA
ATTTCCGTAGTAGTTCAGAAGTGCTGTCAGCAACCAATGATGTCTTTGAA
CGTCTCATGGACCAAGAGGTCGGCGAAATCAACTATGATAACAAGCACCA
GCTTGTTTTTGCCAATACCAAACTGACTCCCAATCCAGACAACAAGGCAG
CATTTCTCCTCTACGACAAGGACGATACAGGTGAGGAAGAAGAGAGTCAA
ACAGAAACGAAACTAACAGGCGAAATGCGCTTAGTTATCAAGGAGATTCT
GAAACTTCATCAAGAAAAGGTGTTGCCTTTAAGGAAATTGCCCTTCTGA
CCTCCAGCCGCAGTCGTAATGACCAGATTCTCCTCGCCCTGTCTGAGTAC
GGAATTCCTGTCAAAACTGACGGAGAGCAAAACAATTATCTCCAATCCCT
AGAAGTGCAAGTCATGCTAGACACTCTTCGTGTCATTCACAATCCCCTGC
AAGACTACGCCTTGGTTGCCCTTATGAAGTCTCCAATGTTTGGTTTTGAT
GAGGATGAGCTAGCACGTTTGTCCCTTCAGAAAGCAGAGGATAAAGTCCA
CGAAAATCTCTATGAGAAACTGGTCAATGCACAAAAAATGGCAAGTAGTC
AAAAAGGCTTGATTCACACAGCTCTAGCTGAAAAACTAAAGCAATTCATG
GATATCCTAGCTTCTTGGCGCTTGTATGCCAAAACCCACTCTCTCTATGA
CTTGATTTGGAAGATTTACAACGACCGTTTTTATTATGACTATGTTGGGG
CTTTGCCGAATGGTCCTGCTAGGCAGGCCAATCTCTATGCCCTAGCACTG
CGTGCTGATCAATTTGAAAAGAGCAATTTCAAAGGTTTGTCGCGTTTTAT
TCGTATGATTGACCAAGTCTTAGAAGCCCAGCACGATTTGGCAAGCGTGG
CCGTCGCACCGCCAAAAGATGCAGTAGAGCTCATGACCATCCACAAGAGT
AAAGGGCTGGAGTTTCCTTACGTCTTTATCCTCAATATGGATCAAGATTT
CAACAAGCAAGACTCTATGTCAGAAGTCATTCTCAGTCGTCAGAATGGTC
TTGGTGTCAAATATATTGCCAAGATGGAGACAGGGGCAGTAGAAGACCAC
TATCCTAAAACCATCAAACTCTCCATTCCTAGTCTGACCTATAGGCAGAA
CGAAGAGGAATTACAGCTAGCAAGCTATTCTGAGCAGATGCGTTTGCTGT
ATGTTGCTATGACGCGGGCTGAGAAAAAGCTCTATCTTGTCGGCAAGGGT
TCTCGTGAAAAGCTGGAATCCAAGGAATACCCAGCAGCCAAAAATGGGAA
ACTAAATAGCAATACTAGACTGCAAGCACGGAATTTCCAAGATTGGCTTT
GGGCTATCAGTAAAGTGTTTACTAAGGACAAGCTCAACTTTAGTTATCGT
TTTATTGGCGAAGATCAGTTGACCAGAGAAGCTATCGGAGAGTTGGAAAC
CAAGAGTCCTCTCCAAGATAGCTCCCAAGCAGACAATCGTCAGTCAGATA
CCATCAAAGAAGCTCTGGAAATGCTGAAGGAGGTGGAAGTTTATAATACT
CTTCACCGCGCAGCTATTGAACTTCCTAGTGTTCAAACCCCAAGTCAAAT
CAAGAAATTCTACGAACCAGTTATGGATATGGAAGGTGTCGAGATTGCTG
GTCAAGGTCAGTCAGTAGGCAAGAAAATCAGCTTCGATTTGCCAGATTTT
TCAACCAAAGAAAAGGTAACTGGAGCTGAGATTGGTAGTGCTACTCACGA
ACTCATGCAGAGAATTGACCTCAGCCAGCAACTAACCCTTGCTAGCCTAA
CAGAAACACTCAAACAAGTTCAAACTAGCCAAGCTGTCAGAGACAAGATC
AATCTTGATAAAATTCTTGCTTTCTTTGACACAGTACTCGGTCAGGAAAT
TCTTGCTAATACCGACCATCTTTATCGCGAGCAACCTTTCTCCATGCTCA
AACGAGACCAAAAGAGTCAGGAAGACTTTGTTGTCCGTGGTATCCTTGAT
GGCTATCTGCTTTACGAAAACAAAATTGTTCTGTTCGACTACAAGACAGA
CCGCTATGATGAACCAGTCAACTCGTAGACCGCTATCGTGGTCAGTTAG
CTCTATACGAAGAGGCTTTATCACGAGCCTATTCGATTGAAAATATTGAA
AAATACTTGATTTTACTCGGTAAAGACGAGGTTCAAGTTGTAAAAGTATA
A
```

4109.1

(SEQ. ID. NO. 221)

```
ATGGAACTTGCTCGCCATGCTGAAACGTTGGGAGTAGATGCTATTGCAAC
GATTCCACCAATTTATTTCCGCTTGCCAGAATACTCAGTTGCCAAATACT
GGAACGATATCAGTTCTGCAGCTCCAAACACAGACTACGTGATTTACAAC
ATTCCTCAATTGGCAGGGGTTGCTTTGACTCCAAGCCTTTACACAGAAAT
GTTGAAAAATCCTCGTGTTATCGGTGTGAAGAACTCTTCTATGCCAGTTC
AAGATATCCAAACCTTTGTCAGCCTTGGTGGAGAAGACCATATCGTCTTT
AATGGTCCTGATGAGCAGTTCCTAGGAGGACGCCTCATGGGGGCTAGGGC
```

TABLE 1-continued

```
TGGTATCGGTGGTACTTATGGTGCTATGCCAGAACTCTTCTTGAAACTCA
ATCAGTTGATTGCGGATAAGGACCTAGAAACAGCGCGTGAATTGCAGTAT
GCTATCAACGCAATCATTGGTAAACTCACTTCTGCTCATGGAAATATGTA
CGGTGTCATCAAAGAAGTCTTGAAAATCAATGAAGGCTTGAATATTGGAT
CTGTTCGTTCACCATTGACACCAGTGACTGAAGAAGATCGTCCAGTTGTA
GAAGCGGCTGCTGCCTTGATTCGTGAAACCAAGGAGCGCTTCCTCTAA
```

4110.2

(SEQ. ID. NO. 222)
```
ATGTATAAGACAAAGTGTTTACGAGAGAAGTTAGTATTATTTTTAAAAAT
TTTCTTCCCAATCCTGATCTACCAATTTGCCAATTATTCTGCCTCTTTTG
TTGATACTGCAATGACAGGTCAATACAACACTATGGACTTGGCTGGTGTA
TCTATGGCAACCAGTATCTGGAATCCTTTCTTTACATTTCTAACAGGGAT
TGTGTCAGCCTTGGTGCCTATCATTGGTCACCATCTTGGTCGAGGCAAAA
AGGAAGAAGTTGCGTCTGATTTTTACCAATTTATTTATTTGGCCTTGGGC
CTATCTGTGGTCTTGCTGGGGATGGTACTTTTCTTGGCACCAATAATCTT
GAATCATATTGGGTTAGAAGCAGCAGTAGCGGCAGTAGCGGTTCGCTATC
TTTGGTTTTTATCTATCGGATTATCCCCTTGTTGCTCTTTAGCGTCATT
CGTTCCTTGCTGGATTCGCTGGGCTTGACCAAACTGTCCATGTACCTCAT
GCTTTTCTTACTCCCTCTCAATAGCGGATTTAACTATCTCTTGATTTACG
GTGCCTTTGGTGTTCCACAACTGGGAGGGGCTGGTGCTGGTTTAGGAACA
TCCTTGGCCTACTGGGTCTTGCTTGGGATTTCTGTTCTGGTTTTATTTAA
AACAGGAGAAGCTCAAAGCCTTACACCTTGAGAAACGAATTCCACTTAAT
ATGGATAAAATTAAGGAAGGAGTTCGTTTAGGTCTGCCTATTGGGGAAC
TGTCTTCGCGGAAGTGGCTATCTTTTCAGTGGTTGGCTTGATTATGGCTA
AGTTTTCGCCCTTGATTATAGCTAGTCACCAGTCAGCTATGAACTTTTCA
AGTCTTATGTACGCCTTTCCTATGAGTATCTCATCGGCTATGGCTATTGT
CGTTTCCTATGAAGTGGGAGCCAAGCGATTTGATGATGCGAAAACCTATA
TTGGTCTAGGAAGATGGACTGCCCTCATTTTTGCGGCCTTCACCTTAACC
TTCCTTTACATTTTTAGGGGAAATGTGGCCAGTCTTTATGGTAACGACCC
AAAATTTATCGATTTGACAGTGCGTTTTTTAACTTATAGTCTTTTCTTCC
AGTTAGCAGATACCTTTGCGGCGCCGCTTCAGGGAATTTTGCGGGGTAT
AAGGATACAGTTATTCCTTTTTACCTTGGTTTGCTTGGTTATTGGGCGT
AGCAATCCCTGTGTACGCTATTTGA
```

4112.2

(SEQ. ID. NO. 223)
```
ATGAGTACTTTAGCAAAAATAGAAGCGCTCTTGTTTGTAGCGGGTGAAGA
TGGGATTCGGGTCCGCCAGTTAGCTGAACTCCTCTCTCTGCCACCGACAG
GCATCCAGCAAAGTTTAGGAAAATTAGCCCAGAAGTATGAAAAGGACCCA
GATTCCAGTTTGGCTTTGATTGAGACAAGTGGTGCTTATAGATTGGTGAC
CAAGCCTCAATTTGCAGAGATTTTGAAGGAATACTCTAAGGCGCCTATCA
ACCAGAGCTTGTCTCGGGCTGCCCTTGAGACCTTGTCCATTATTGCCTAC
AAACAGCCGATTACGCGGATAGAAATTGATGCCATCCGTGGAGTTAACTC
```

```
GAGTGGAGCCTTGGCAAAGTTGCAGGCTTTTGACCTGATAAAGGAAGACG
GGAAAAAGGAAGTATTGGGGCGCCCCAACCTCTATGTGACTACGGATTAT
TTCCTAGATTACATGGGGATAAACCATTTAGAAGAATTACCAGTGATTGA
TGAGCTTGAGATTCAAGCCCAAGAAAGCCAATTATTTGGTGAAAGGATAG
AAGAAGATGAGAATCAATAA
```

4113.1

(SEQ. ID. NO. 224)
```
ATGGATACGATGATTAGTAGATTTTTTCGCCATTTATTTGAAGCCTTAAA
AAGTTTGAAACGAAATGGTTGGATGACAGTAGCTGCTGTCAGTTCAGTCA
TGATTACTTTGACCTTGGTGGCAATATTTGCATCTGTTATTTTCAATACA
GCGAAACTAGCTACAGATATTGAAAATAATGTCCGTGTAGTAGTTTATAT
CCGAAAGGATGTGGAAGATAATAGTCAGACAATTGAAAAAGAAGGTCAAA
CTGTTACAAATAATGACTACCACAAGGTATATGATTCTTTGAAGAACATG
TCTACGGTTAAAAGTGTTACCTTTTCAAGTAAAGAAGAACAATATGAAAA
ATTAACCGAGATAATGGGAGATAACTGGAAAATCTTTGAAGGAGATGCCA
ATCCTCTCTATGATGCCTATATTGTAGAGGCAAACACTCCAAATGATGTA
AAAACTATAGCCGAAGATGCTAAAAAAATTGAAGGTGTCTCTGAGGTTCA
AGATGGCGGTGCCAATACAGAAAGACTCTTCAAGTTAGCTTCATTTATCC
GTGTTTGGGGACTAGGGATTGCTGCTTTGTTAATTTTTATCGCAGTTTTC
TTGATTTCAAATACCATTCGTATTACCATTATTTCCCGCAGTCGCGAAAT
TCAAATCATGCGCTTGGTCGGAGCTAAAAACAGTTATATCCGTGGACCGT
TCTTGTTAGAAGGAGCCTTTATCGGTTTATTGGGAGCTATCGCACCATCT
GTTTTGGTCTTTATTGTTTATCAAATTGTTTACCAATCTGTCAACAAATC
GTTGGTAGGGCAAAATCTATCCATGATTAGTCCAGATTTATTTAGTCCGT
TGATGATTGCCCTACTATTTGTGATTGGGGTTTTCATTGGTTCATTGGGA
TCAGGAATATCCATGCGCCGATTCTTGAAGATTTAG
```

4117.1

(SEQ. ID. NO. 225)
```
ATGAAGAAAGTAAGATTTATTTTTTTAGCTCTGCTATTTTTCTTAGCTAG
TCCAGAGGGTGCAATGGCTAGTGATGGTACTTGGCAAGGAAAACAGTATC
TGAAAGAAGATGGCAGTCAAGCAGCAAATGAGTGGGTTTTTGATACTCAT
TATCAATCTTGGTTCTATATAAAAGCAGATGCTAACTATGCTGAAAATGA
ATGGCTAAAGCAAGGTGACGACTATTTTTACCTCAAATCTGGTGGCTATA
TGGCCAAATCAGAATGGGTAGAAGACAAGGGAGCCTTTTATTATCTTGAC
CAAGATGGAAAGATGAAAAGAAATGCTTGGGTAGGAACTTCCTATGTTGG
TGCAACAGGTGCCAAAGTAATAGAAGACTGGGTCTATGATTCTCAATACG
ATGCTTGGTTTATATCAAAGCAGATGGACAGCACGCAGAGAAAGAATGG
CTCCAAATTAAAGGGAAGGACTATTATTTCAAATCCGGTGGTTATCTACT
GACAAGTCAGTGGATTAATCAAGCTTATGTGAATGCTAGTGGTGCCAAAG
TACAGCAAGGTTGGCTTTTTGACAAACAATACCAATCTTGGTTTTACATC
AAAGAAAATGGAAACTATGCTGATAAAGAATGGATTTTCGAGAATGGTCA
CTATTATTATCTAAAATCCGGTGGCTACATGGCAGCCAATGAATGGATTT
```

TABLE 1-continued

```
GGGATAAGGAATCTTGGTTTTATCTCAAATTTGATGGGAAAATGGCTGAA
AAAGAATGGGTCTACGATTCTCATAGTCAAGCTTGGTACTACTTCAAATC
CGGTGGTTACATGACAGCCAATGAATGGATTTGGGATAAGGAATCTTGGT
TTTATCTCAAATCTGATGGGAAAATAGCTGAAAAAGAATGGGTCTACGAT
TCTCATAGTCAAGCTTGGTACTACTTCAAATCCGGTGGTTACATGACAGC
CAATGAATGGATTTGGGATAAGGAATCTTGGTTTTACCTCAAATCTGATG
GGAAAATAGCTGAAAAAGAATGGGTCTACGATTCTCATAGTCAAGCTTGG
TACTACTTCAAATCGGTGGCTACATGGCGAAAAATGAGACAGTAGATGG
TTATCAGCTTGGAAGCGATGGTAAATGGCTTGGAGGAAAAACTACAAATG
AAAATGCTGCTTACTATCAAGTAGTGCCTGTTACAGCCAATGTTTATGAT
TCAGATGGTGAAAAGCTTTCCTATATATCGCAAGGTAGTGTCGTATGGCT
AGATAAGGATAGAAAAAGTGATGACAAGCGCTTGGCTATTACTATTTCTG
GTTTGTCAGGCTATATGAAAACAGAAGATTTACAAGCGCTAGATGCTAGT
AAGGACTTTATCCCTTATTATGAGAGTGATGGCCACCGTTTTTATCACTA
TGTGGCTCAGAATGCTAGTATCCCAGTAGCTTCTCATCTTTCTGATATGG
AAGTAGGCAAGAAATATTATTCGGCAGATGGCCTGCATTTTGATGGTTTT
AAGCTTGAGAATCCCTTCCTTTTCAAAGATTTAACAGAGGCTACAAACTA
CAGTGCTGAAGAATTGGATAAGGTATTTAGTTTGCTAAACATTAACAATA
GCCTTTTGGAGAACAAGGGCGCTACTTTTAAGGAAGCCGAAGAACATTAC
CATATCAATGCTCTTTATCTCCTTGCCCATAGTGCCCTAGAAAGTAACTG
GGAAGAAGTAAAATTGCCAAAGATAAGAATAATTTCTTTGGCATTACAG
CCTATGATACGACCCCTTACCTTTCTGCTAAGACATTTGATGATGTGGAT
AAGGGAATTTTAGGTGCAACCAAGTGGATTAAGGAAAATTATATCGATAG
GGGAAGAACTTTCCTTGGAAACAAGGCTTCTGGTATGAATGTGGAATATG
CTTCAGACCCTTATTGGGGCGAAAAAATTGCTAGTGTGATGATGAAAATC
AATGAGAAGCTAGGTGGCAAAGATTAG
```

4119.2

(SEQ. ID. NO. 226)
```
ATGAAAAAAGTATTACAAAAATATTGGGCATGGGCTTTTGTGGTCATCCC
CCTCTTGTTACAAGCAATTTTCTTCTATGTGCCGATGTTTCAAGGAGCCT
TTTACAGTTTTACCAACTGGACAGGATTGACTTATAACTACAAATTTGTT
GGCTTAAACAACTTTAAGCTCCTCTTCATGGATCCAAAATTCATGAATGC
GATTGGCTTTACCGCAATCATTGCGATTGCCATGGTGGTTGGTGAGATTG
CACTCGGGATCTTCATTGCGCGTGTCTTGAATTCTAAAATCAAAGGCCAA
ACCTTCTTCCGTGCTTGGTTCTTCTTCCCAGCTGTTTTATCTGGTTTGAC
AGTGGCTTTGATCTTCAAGCAAGTCTTCAACTACGGTCTTCCAGCGATTG
GAAATGCCCTTCATATTGAATTTTTCCAAACCAGTCTTTTAGGGACTAAG
TGGGGAGCAATCTTGCGGCTGTCTTTGTCCTCTTTGGCAAGGGGTGGC
TATGCCCATCATCATCTTCCTAGCTGGTTTGCAATCTATTCCAACTGAGA
TTACAGAGGCAGCAAGGATTGATGGTGCGACTAGCAAGCAAGTTTTCTGG
AACATTGAATTGCCTTACTTGCTACCAAGTGTCTCTATGGTCTTTATCCT
```

AGCCTAAAAGGTGGGCTGACTGCCTTTGACCAAGTCTTTGCCATGACCGG
TGGTGGTCCAAACAATGCCACAACCTCACTTGGGCTCTTGGTTTATAACT
ATGCCTTTAAAAACAACCAATTCGGTTATGCCAATGCCATTGCCGTAATC
TTGTTCTTCTTAATTGTAGTGATTTCGATCATCCAATTGAGAGTATCTAA
GAAATTTGAAATTTAA 4119.3

(SEQ. ID. NO. 227)
```
ATGATGAAACAAGATGAAAGAAAAGCCCTGATTGGCAAATACATTCTATT
GATTCTAGGATCGGTTCTGATTTTAGTGCCGCTCCTTGCTACCCTCTTTA
GTTCCTTCAAACCCACTAAGGATATTGTAGATAATTTCTTTGGCTTTCCA
ACCAACTTCACATGGGACAACTTTAGCCGTCTCTTAGCTGATGGGATTGG
AGGCTATTATTGGAACTCTGTCGTCATCACTGTCTTGTCTTTACTTGCAG
TAATGATCTTTATCCCTATGGCAGCGTACTCCATCGCTCGCAATATGAGT
AAAAGAAAAGCCTTTACCATCATGTATACCCTCTTAATCCTCGGAATCTT
CGTACCTTTCCAAGTCATCATGATTCCGATTACGGTTATGATGAGTAAAC
TCGGTTTGGCTAATACCTTTGGTTTGATCTTGCTCTACTTGACCTATGCG
ATTCCACAGACCCTCTTTCTCTATGTTGGCTATATCAAAATCTCGATTCC
AGAAAGTCTGGATGAAGCAGCAGAGATCGATGGGGCTAATCAATTTACAA
CCTATTCCGCATCATCTTCCCAATGATGAAACCGATGCATGCGACAACC
ATGATCATCAATGCCCTTTGGTTCTGGAATGACTTCATGTTGCCACTCCT
TGTCTTGAACCGGGATTCCAAAATGTGGACTCTGCCTTTGTTCCAATACA
ACTACGCAGGCCAATATTTCAACGACTACGGACCAAGCTTTGCCTCTTAC
GTGGTCGGCATTATCAGTATCACCATTGTCTATCTCTTCTTCCAACGCCA
TATCATTTCAGGAATGAGCAACGGGGCAGTGAAGTAA
```

4119.4

(SEQ. ID. NO. 228)
```
ATGAAAAGTATTCTTCAGAAAATGGGGAGCATCCGATGCTGCTTCTTTT
TCTTAGCTATAGTACTGTTTATATCCATTCTTGCACAAAATTGGATGGGT
CTTGTGGCTTCAGTAGGAATGTTTCTATTTACTATTTTCTTTTTGCACTA
TCAGTCGATTTTATCCCATAAATTCTTTCGATTGATTTTGCAGTTTGTCT
TGTTTGGTAGTGTCTTGTCAGCTGCTTTTGCCAGTTTAGAACATTTCCAA
ATTGTGAAGAAATTTAACTATGCTTTTCTTTCACCCAATATGCAGGTGTG
GCATCAGAACCGGGCAGAAGTGACCTTCTTTAATCCTAATTATTATGGAA
TTATTTGTTGTTTCTGTATTATGATTGCTTTCTATCTGTTTACAACGACC
AAGTTGAATTGGTTGAAAGTATTCTGTGTGATTGCAGGCTTTGTTAATCT
CTTTGGTTTGAACTTTACTCAAAATCGAACTGCCTTTCCTGCTATTATCG
CTGGAGCAATTATCTATCTCTTTACGACTATTAAAAACTGGAAGGCCTTT
TGGCTTAGTATTGGGGTCTTCGCGATTGGTTTGAGTTTCCTCTTTTCTAG
TGATTTGGGAGTTCGAATGGGTACTTTAGACTCTTCTATGGAAGAACGCA
TTTCTATCTGGGATGCTGGGATGGCCTTGTTTAAGCAAAATCCTTTTTGG
GGTGAAGGGCCATTGACCTATATGAACTCTTATCCTCGGATACATGCTCC
TTATCATGAACATGCCCACAGTCTTTATATTGATACGATTCTGAGTTACG
```

TABLE 1-continued

GAATTGTGGGGACTATTTTATTAGTTTTGTCTTCTGTTGCTCCTGTTCGC
TTGATGATGGATATGAGTCAGGAGTCGGGGAAACGTCCGATTATCGGCCT
TTATCTATCTTTCCTTACAGTGGTTGCTGTGCACGGAATTTTTGACTTGG
CTCTCTTCTGGATTCAGTCAGGCTTTATTTTCTTGCTAGTTATGTGCAGT
ATTCCATTGGAGCATCGAATGTTGGTATCGGACATGACGGATTAA 4120.1

(SEQ. ID. NO. 229)
ATGTCAAAGATGGATGTTCAGAAAATCATTGCACCGATGATGAAGTTTGT
GAATATGCGTGGCATTATAGCTCTAAAAGATGGGATGTTAGCAATTTTGC
CATTGACAGTAGTTGGTAGTTTGTTCTTGATTATGGGACAATTGCCGTTC
GAAGGATTAAATAAGAGCATTGCTAGTGTTTTGGAGCTAATTGGACAGA
GCCGTTTATGCAAGTATATTCAGGAACTTTTGCTATTATGGGTCTAATTT
CTTGTTTTTCAATTGCCTATTCTTATGCTAAGAATAGCGGCGTAGAGGCT
TTACCAGCTGGACTTCTATCTGTATCTGCATTCTTTATTTTGCTAAGATC
ATCTTATATCCCTAAACAAGGTGAGGCGATTGGGACGCTATTAGTAAAG
TTTGGTTTGGAGGCCAAGGAATTATCGGTGCTATCATTATAGGTTTGGTA
GTAGGAAGTATTTATACCTTCTTTATAAAGAGAAAAATTGTTATTAAGAT
GCCAGAACAAGTTCCACAAGCTATTGCCAAACAGTTTGAAGCAATGATTC
CAGCATTTGTAATTTTCTTATCTTCTATGATTGTATATATTTTAGCGAAG
TCATTGACTAATGGCGGAACATTCATAGAAATGATTTATTCTGCTATTCA
AGTTCCGTTGCAAGGTTTAACTGGATCTTTGTATGGTGCTATTGGAATTG
CATTCTTTATATCATTTTTGTGGTGGTTTGGTGTTCATGGGCAATCGGTA
GTAAATGGAGTAGTGACAGCTCTGCTTTTATCTAATCTTGATGCTAATAA
AGCTATGTTAGCCTCTGCTAATCTATCATTAGAAAATGGTGCACATATTG
TTACTCAACAATTTTTAGATTCATTTTTAATTCTATCAGGTTCAGGGATT
ACGTTTGGTCTTGTAGTTGCCATGCTTTTTGCAGCAAAATCAAAACAATA
CCAAGCCTTAGGAAAAGTTGCAGCTTTTCCAGCAATATTTAACGTAAATG
AGCCAGTTGTATTTGGATTTCCGATTGTCATGAATCCAGTTATGTTTGTA
CCTTTCATTCTTGTTCCTGTACTTGCAGCTGTGATAGTATATGGAGCTAT
TGCAACAGGTTTCATGCAGCCATTCTCAGGGGTAACATTGCCTTGGAGTA
CACCAGCTATTTTATCAGGATTTTGGTGGGTGGATGGCAAGGAGTTATT
ACTCAGCTGGTGATATTAGCGATGTCTACATTGGTTTATTTTCCATTCTT
TAAAGTACAGGATCGTTTAGCTTACCAAAATGAAATCAAACAATCTTAG 4121.2

(SEQ. ID. NO. 230)
ATGAAGAAAAAGGACTTAGTAGACCAACTAGTCTCAGAGATCGAGACGGG
GAAAGTCAGGACACTGGGAATATACGGTCATGGAGCTTCAGGTAAATCAA
CCTTTGCACAGGAATTGTACCAAGCTTTAGATTCTACTACAGTAAATTTG
CTAGAGACAGATCCTTATATCCCTCAGGACGCCATCTGGTACTACCCAA
GGACGCGCCGAATCAAAAGGTGACAGCCAGTCTGCCAGTGGCGCATGAAC
TGGAGAGTTTGCAGAGAGATATCCTTgCTTGCAGGCGGGTATGGATGTCT
TGA 4122.1

(SEQ. ID. NO. 231)
ATGAAGAAAAGATACCTAGTCTTGACAGCTTTGCTAGCCTTGAGTCTAGC
AGCTTGTTCACAAGAAAAAACAAAAAATGAAGATGGAGAAACTAAGACAG
AACAGACAGCCAAAGCTGATGGAACAGTCGGTAGTAAGTCTCAAGGAGCT
GCCCAGAAGAAAGCAGAAGTGGTCAATAAAGGTGATTACTACAGCATTCA
AGGGAAATACGATGAAATCATCGTAGCCAACAAACACTATCCATTGTCTA
AAGACTATAATCCAGGGGAAAATCCAACAGCCAAGGCAGAGTTGGTCAAA
CTCATCAAAGCGATGCAAGAGGCAGGTTTCCCTATTAGTGATCATTTACA
GTGGTTTTAGAAGTTATGAAAACTCAGACCAAGCTCTATCAAGATTATGT
CAACCAAGATGGAAAGGCAGCAGCTGACCGTTACTGCCCGTCCTGGCT
ATAGCGAACACCAGACAGGCTGGCCTTTGATGTGATTGGGACTGATGGTG
ATTTGGTGACAGAAGAAAAGCAGCCCAATGGCTCTTGGATCATGCAGCT
GATTATGGCTTTGTTGTCCGTTATCTCAAAGGCAAGGAAAAGGAAACAGG
CTATATGGCTGAAGAATGGCACCTGCGTTATGTAGGAAAAGAAGCTAAAG
AAATTGCTGCAAGTGGTCTCAGTTTGGAAGAATACTATGGCTTTGAAGGC
GGAGACTACGTCGATTAA 4125.6

(SEQ. ID. NO. 232)
ATGCGTAAATTCTTAATTATTTTGTTGCTACCAAGTTTTTTGACCATTTC
AAAAGTCGTTAGCACAGAAAAAGAAGTCGTCTATACTTCGAAAGAAATTT
ATTACCTTTCACAATCTGACTTTGGTATTTATTTTAGAGAAAAATTAAGT
TCTCCCATGGTTTATGGAGAGGTTCCTGTTTATGCGAATGAAGATTTAGT
AGTGGAATCTGGGAAATTGACTCCCAAAACAAGTTTTCAAATAACCGAGT
GGCGCTTAAATAAACAAGGAATTCCAGTATTTAAGCTATCAAATCATCAA
TTTATAGCTGCGGACAAACGATTTTTATATGATCAATCAGAGGTAACTCC
AACAATAAAAAAGTATGGTTAGAATCTGACTTTAAACTGTACAATAGTC
CTTATGATTTAAAAGAAGTGAAATCATCCTTATCAGCTTATTCGCAAGTA
TCAATCGACAAGACCATGTTTGTAGAAGGAAGAGAATTTCTACATATTGA
TCAGGCTGGATGGGTAGCTAAAGAATCAACTTCTGAAGAAGATAATCGGA
TGAGTAAAGTTCAAGAAATGTTATCTGAAAAATATCAGAAAGATTCTTTC
TCTATTTATGTTAAGCAACTGACTACTGGAAAAGAAGCTGGTATCAATCA
AGATGAAAAGATGTATGCAGCCAGCGTTTTGAAACTCTCTTATCTCTATT
ATACGCAAGAAAAATAAATGAGGGTCTTTATCAGTTAGATACGACTGTA
AAATACGTATCTGCAGTCAATGATTTTCCAGGTTCTTATAAACCAGAGGG
AAGTGGTAGTCTTCCTAAAAAAGAAGATAATAAAGAATATTCTTTAAAGG
ATTTAATTACGAAAGTATCAAAAGAATCTGATAATGTAGCTCATAATCTA
TTGGGATATTACATTTCAAACCAATCTGATGCCACATTCAAATCCAAGAT
GTCTGCCATTATGGGAGATGATTGGGATCCAAAAGAAAATTGATTTCTT
CTAAGATGGCCGGGAAGTTTATGGAAGCTATTTATAATCAAATGGATTT
GTGCTAGAGTCTTTGACTAAAACAGATTTTGATAGTCAGCGAATTGCCAA
AGGTGTTTCTGTTAAAGTAGCTCATAAAATTGGAGATGCGGATGAATTTA

TABLE 1-continued

AGCATGATACGGGTGTTGTCTATGCAGATTCTCCATTTATTCTTTCTATT
TTCACTAAGAATTCTGATTATGATACGATTTCTAAGATAGCCAAGGATGT
TTATGAGGTTCTAAAATGA 4125.7
(SEQ. ID. NO. 233)
ATGAAAAAACAAAATAATGGTTTAATTAAAAATCCTTTTCTATGGTTATT
ATTTATCTTTTTCCTTGTGACAGGATTCCAGTATTTCTATTCTGGGAATA
ACTCAGGAGGAAGTCAGCAAATCAACTATACTGAGTTGGTACAAGAAATT
ACCGATGGTAATGTAAAAGAATTAACTTACCAACCAAATGGTAGTGTTAT
CGAAGTTTCTGGTGTCTATAAAAATCCTAAAACAAGTAAAGAAGAAACAG
GTATTCAGTTTTTCACGCCATCTGTTACTAAGGTAGAGAAATTTACCAGC
ACTATTCTTCCTGCAGATACTACCGTATCAGAATTGCAAAAACTTGCTAC
TGACCATAAAGCAGAAGTAACTGTTAAGCATGAAAGTTCAAGTGGTATAT
GGATTAATCTACTCGTATCCATGTGCCATTTGGAATTCTATTCTTCTTCC
TATTCTCTATGATGGGAAATATGGGAGGAGGCAATGGCCGTAATCCAATG
AGTTTTGGACGTAGTAAGGCTAAAGCAGCAAATAAAGAAGATATTAAAGT
AAGATTTTCAGATGTTGCTGGAGCTGAGGAAGAAAAACAAGAACTAGTTG
AAGTTGTTGAGTTCTTAAAAGATCCAAAACGATTCACAAAACTTGGAGCC
CGTATTCCAGCAGGTGTTCTTTTGGAGGGACCTCCGGGGACAGGTAAAAC
TTTGCTTGCTAAGGCAGTCGCTGGAGAAGCAGGTGTTCCATTCTTTAGTA
TCTCAGGTTCTGACTTTGTAGAAATGTTTGTCGGAGTTGGAGCTAGTCGT
GTTCGCTCTCTTTTTGAGGATGCCAAAAAAGCAGCACCAGCTATCATCTT
TATCGATGAAATTGATGCTGTTGGACGTCAACGTGGAGTCGGTCTCGGCG
GAGGTAATGACGAACGTGAACAAACCTTGAACCACTTTTGATTGAGATGG
ATGGTTTTGAGGGAAATGAAGGGATTATCGTCATCGCTGCGACAAACCGT
TCAGATGTACTTGACCCTGCCCTTTTGCGTCCAGGACGTTTTGATAGAAA
AGTATTGGTTGGTCGTCCTGATGTTAAAGGTCGTGAAGCAATCTTGAAAG
TTCACGCTAAGAATAAGCCTTTAGCAGAAGATGTTGATTTGAAATTAGTG
GCTCAACAAACTCCAGGCTTTGTTGGTGCTGATTTAGAGAATGTCTTGAA
TGAAGCAGCTTTAGTTGCTGCTCGTCGCAATAAATCGATAATTGATGCTT
CAGATATTGATGAAGCAGAAGATAGAGTTATTGCTGGACCTTCTAAGAAA
GATAAGACAGTTTCACAAAAAGAACGAGAATTGGTTGCTTACCATGAGGC
AGGACATACCATTGTTGGTCTAGTCTTGTCGAATGCTCGCGTTGTCCATA
AGGTTACAATTGTACCACGCGGCCGTGCAGGCGGATACATGATTGCACTT
CCTAAAGAGGATCAAATGCTTCTATCTAAAGAAGATATGAAAGAGCAATT
GGCTGGCTTAATGGGTGGACGTGTAGCTGAAGAAATTATCTTTAATGTCC
AAACCACAGGAGCTTCAAACGACTTTGAACAAGCGACACAAATGGCACGT
GCAATGGTTACAGAGTACGGTATGAGTGAAAAACTTGGCCCAGTACAATA
TGAAGGAAACCATGCTATGCTTGGTGCACAGAGTCCTCAAAAATCAATTT
CAGAACAAACAGCTTATGAAATTGATGAAGAGGTTCGTTCATTATTAAAT
GAGGCACGAAATAAAGCTGCTGAAATTATTCAGTCAAATCGTGAAACTCA

CAAGTTAATTGCAGAAGCATTATTGAAATACGAAACATTGGATAGTACAC
AAATTAAAGCTCTTTACGAAACAGGAAAGATGCCTGAAGCAGTAGAAGAG
GAATCTCATGCACTATCCTATGATGAAGTAAAGTCAAAAATGAATGACGA
AAAATAA 4125.10
(SEQ. ID. NO. 234)
ATGAGGGAACCAGATTTTTTAAATCATTTTCTCAAGAAGGGATATTTCAA
AAAGCATGCTAAGGCGGTTCTAGCTCTTTCTGGTGGATTAGATTCCATGT
TTCTATTTAAGGTATTGTCTACTTATCAAAAAGAGTTAGAGATTGAATTG
ATTCTAGCTCATGTGAATCATAAGCAGAGAATTGAATCAGATTGGGAAGA
AAAGGAATTAAGGAAGTTGGCTGCTGAAGCAGAGCTTCCTATTTATATCA
GCAATTTTTCAGGAGAATTTTCAGAAGCGCGTGCACGAAATTTTCGTTAT
GATTTTTTTCAAGAGGTCATGAAAAAGACAGGTGCGACAGCTTTAGTCAC
TGCCCACCATGCTGATGATCAGGTGGAAACGATTTTTATGCGCTTGATTC
GAGGAACTCGCTTGCGCTATCTATCAGGAATTAAGGAGAAGCAAGTAGTC
GGAGAGATAGAAATCATTCGTCCCTTCTTGCATTTTCAGAAAAAAGACTT
TCCATCAATTTTTCACTTTGAAGATACATCAAATCAGGAGAATCATTATT
TTCGAAATCGTATTCGAAATTCTTACTTACCAGAATTGGAAAAGAAAAT
CCTCGATTAGGGATGCAATCTTAGGCATTGGCAATGAAATTTTAGATTA
TGATTTGGCAATAGCTGAATTATCTAACAATATTAATGTGGAAGATTTAC
AGCAGTTATTTTCTTACTCTGAGTCTACACAAAGAGTTTTACTTCAAACT
TATCTGAATCGTTTTCCAGATTTGAATCTTACAAAAGCTCAGTTTGCTGA
AGTTCAGCAGATTTTAAAATCTAAAAGCCAGTATCGTCATCCGATTAAAA
ATGGCTATGAATTGATAAAAGAGTACCAACAGTTTCAGATTTGTAAAATC
AGTCCGCAGGCTGATGAAAAGGAAGATGAACTTGTGTTACACTATCAAAA
TCAGGTAGCTTATCAAGGATATTTATTTTCTTTTGGACTTCCATTAGAAG
GTGAATTAATTCAACAAATACCTGTTTCACGTGAAACATCCATACACATT
CGTCATCGAAAACAGGAGATGTTTTGATTAAAAATGGGCATAGAAAAAA
ACTCAGACGTTTATTTATTGATTTGAAAATCCCTATGGAAAAGAGAAACT
CTGCTCTTATTATTGAGCAATTTGGTGAAATTGTCTCAATTTTGGGAATT
GCGACCAATAATTTGAGTAAAAAAACGAAAAATGATATAATGAACACTGT
ACTTTATATAGAAAAAATAGATAGGTAA 4126.1
(SEQ. ID. NO. 235)
ATGAAGCGTTCTTCTCTTTTAGTTAGAATGGTTATTTCCATCTTTCTGGT
CTTTCTCATTCTCCTAGCTCTGGTTGGAACTTTCTACTATCAATCAAGTT
CTTCAGCCATTGAGGCCACCATTGAGGGCAACAGCCAAACGACCATCAGC
CAGACTAGCCACTTTATTCAGTCTTATATCAAAAAACTAGAAACCACCTC
GACTGGTTTGACCCAGCAGACGGATGTTCTGGCCTATGCTGAGAATCCCA
GTCAAGACAAGGTCGAGGGAATCCGAGATTTGTTTTTGACCATCTTGAAG
TCAGATAAGGACTTGAAAACTGTTGTGCTGGTGACCAAATCTGGTCAGGT
CATTTCTACAGATGACAGTGTGCAGATGAAAACTTCCTCTGATATGATGG

TABLE 1-continued

```
CTGAGGATTGGTACCAAAAGGCCATTCATCAGGGAGCTATGCCTGTTTTG
ACTCCAGCTCGTAAATCAGATAGTCAGTGGGTCATTTCTGTCACTCAAGA
ACTTGTTGATGCAAAGGGAGCCAATCTTGGTGTGCTTCGTTTGGATATTT
CTTATGAAACTCTGGAAGCCTATCTCAATAACTCCAGTTGGGGCAGCAG
GGCTTTGCCTTCATTATCAATGAAAACCATGAATTTGTCTACCATCCTCA
ACACACAGTTTATAGTTCGTCTAGCAAAATGGAGGCTATGAAACCCTACA
TCGATACAGGTCAGGGTTATACTCCTGGTCACAAATCCTACGTCAGTCAA
GAGAAGATTGCAGGAACTGATTGGACGGTGCTTGGCGTGTCATCATTGGA
AAAGTTAGACCAGGTTCGGAGTCAGCTCTTGTGGACCTTGCTTGGGGCCA
GTGTCACATCTCTTCTTGTCTGTCTCTGCTTAGTGTGGTTCAGTCTTAAA
CGCTGGATTGCTCCTTTGAAGGATTTGAGAGAAACCATGTTGGAAATTGC
TTCTGGTGCTCAAAATCTTCGTGCCAAGGAAGTTGGTGCCTATGAACTGA
GAGAAGTAACTCGCCAATTTAATGCTATGTTGGATCAGATTGATCAGTTG
ATGGTAGCTATTCGTAGCCAGGAAGAAACGACCCGTCAGTACCAACTTCA
AGCCCTTTCGAGCCAGATTAATCCACATTTCCTCTATAACACTTTGGACA
CCATCATCTGGATGGCTGAATTTCATGATAGTCAGCGAGTGGTGCAGGTG
ACCAAGTCCTTGGCAACCTATTTCCGCTTGGCGCTCAATCAAGGCAAGGA
CTTGATTTGTCTCTCTGACGAAATCAATCATGTCCGCCAGTATCTCTTTA
TCCAGAAACAACGCTATGGAGATAAGCTTGGAATACGAAATTAATGAAAA
TGTTGCCTTTGATAATTTAGTCTTACCCAAGCTGGTCCTACAACCCCTTG
TAGAAAATGCTCTTTACCATGGCATTAAGGAAAAGGAAGGTCAGGGCCAT
ATTAAACTTTCTGTCCAGAAACAGGATTCGGGATTGGTCATCCGTATTGA
GGATGATGGCGTTGGCTTCCAAGATGCTGGTGATAGTAGTCAAAGTCAAC
TCAAACGTGGGGGAGTTGGTCTTCAAAATGCGATCAACGGCTCAAACTTC
ATTTTGGAGCCAATTACCATATGAAGATTGATTCTAGACCCCAAAAGGG
ACGAAAGTTGAAATATATATAAATAGAATAGAAACTAGCTAA
```

4126.7
(SEQ. ID. NO. 236)
```
ATGAAGCGTTCTTCTCTTTTAGTTAGAATGGTTATTTCCATCTTTCTGGT
CTTTCTCATTCTCCTAGCTCTGGTTGGAACTTTCTACTATCAATCAAGTT
CTTCAGCCATTGAGGCCACCATTGAGGGCAACAGCCAAACGACCATCAGC
CAGACTAGCCACTTTATTCAGTCTTATATCAAAAAACTAGAAACCACCTC
GACTGGTTTGACCCAGCAGACGGATGTTCTGGCCTATGCTGAGAATCCCA
GTCAAGACAAGGTCGAGGGAATCCGAGATTGTTTTTGACCATCTTGAAG
TCAGATAAGGACTTGAAAACTGTTGTGCTGGTGACCAAATCTGGTCAGGT
CATTTCTACAGATGACAGTGTGCAGATGAAAACTTCCTCTGATATGATGG
CTGAGGATTGGTACCAAAAGGCCATTCATCAGGGAGCTATGCCTGTTTTG
ACTCCAGCTCGTAAATCAGATAGTCAGTGGGTCATTTCTGTCACTCAAGA
ACTTGTTGATGCAAAGGGAGCCAATCTTGGTGTGCTTCGTTTGGATATTT
CTTATGAAACTCTGGAAGCCTATCTCAATAACTCCAGTTGGGGCAGCAG
GGCTTTGCCTTCATTTATCAATGAAAACCATGAATTTGTCTACCATCCTC
AACACACAGTTTATAGTTCGTCTAGCAAAATGGAGGCTATGAAACCCTAC
ATCGATACAGGTCAGGGTTATACTCCTGGTCACAAATCCTACGTCAGTCA
AGAGAAGATTGCAGGAACTGATTGGACGGTGCTTGGCGTGTCATCATTGG
AAAAGTTAGACCAGGTTCGGAGTCAGCTCTTGTGGACCTTTGCTTGGGGC
CAGTGTCACATCTCTTCTTGTCTGTCTCTGCTTAGTGTGGTTCAGTCTTA
AACGCTGGATTGCTCCTTTGAAGGATTTGAGAGAAACCATGTTGGAAATT
GCTTCTGGTGCTCAAAATCTTCGTGCCAAGGAAGTTGGTGCCTATGAACT
GAGAGAAGTAACTCGCCAATTTAATGCTATGTTGGATCAGAGATTCAGTT
GATGGTAGCTATTCGTAGCCAGGAAGAAACGACCCGTCAGTACCAACTTC
AAGCCCTTTCGAGCCAGATTAATCCACATTTCCTCTATAACACTTTGGAC
ACCATCATCTGGATGGCTGAATTTCATGATAGTCAGCGAGTGGTGCAGGT
GACCAAGTCCTTGGCAACCTATTTCCGCTTGGCGCTCAATCAAGGCAAGG
ACTTGATTTGTCTCTCTGACGAAATCAATCATGTCCGCCAGTATCTCTTT
ATCCAGAAAACAACGCTATGGAGATAAGCTGGAATACGAAATTAATGAAA
ATGTTGCCTTTGATAATTTAGTCTTACCCAAGCTGGTCCTACAACCCCTT
GTAGAAAATGCTCTTTACCATGGCATTAAGGAAAAGGAAGGTCAGGGCCA
TATTAAACTTTCTGTCCAGAAACAGGATTCGGGATTGGTCATCCGTATTG
AGGATGATGGCGTTGGCTTCCAAGATGCTGGTGATAGTAGTCAAAGTCAA
CTCAAACGTGGGGGAGTTGGTCTTCAAAATGTCGATCAACGGCTCAAACT
TCATTTTGGAGCCAATTACCATATGAAGATTGATTCTAGACCCCAAAAAG
GGACGAAAGTTGAAATATATATAAATAGAATAGAAACTAGCTAA
```
4127.4
(SEQ. ID. NO. 237)
```
ATGTTTTTAAATTATTAAGAGAAGCTCTTAAAGTCAAGCAGGTTCGATC
AAAAATTTTATTTACAATTTTTATCGTTTTGGTCTTTCGTATCGGAACTA
GCATTACAGTTCCTGGTGTGAATGCCAATAGCTTGAATGCTTTAAGTGGA
TTATCCTTCTTAAACATGTTGAGCTTGGTGTCGGGGAATGCCCTAAAAAA
CTTTTCGATTTTTGCCCTAGGAGTTAGTCCCTATATCACCGCTTCTATTG
TTGTCCAACTCTTGCAAATGGATATTTTACCCAAGTTTGTAGAGTGGGGT
AAACAAGGGGAAGTAGGTCGAAGAAAATTGAATCAAGCTACTCGTTATAT
TGCTCTAGTTCTCGCTTTTGTGCAATCTATCGGGATTACAGCTGGTTTTA
ATACCTTGGCTGGAGCTCAATTGATTAAAACTGCTTTAACTCCACAAGTT
TTTCTGACGATTGGTATCATCTTAACAGCTGGTAGTATGATTGTCACTTG
GTTGGGTGAGCAAATTACAGATAAGGGATACGGAAACGGTGTTTCCATGA
TTATCTTTGCCGGGATTGTTTCCTCAATTCCAGAGATGATTCAGGGCATC
TATGTGGACTACTTTGTGAACGTCCCAAGTAGCCGTATCACTTCATCTAT
CATTTTCGTAATCATTTTGATTATTACTGTATTGTTGATTATTTACTTTA
CAACTTATGTTCAACAAGCAGAATACAAAATTCCAATCCAATATACTAAG
GTTGCACAAGGTGCTCCATCTAGCTCTTACCTTCCGTTAAAAGTAAACCC
TGCTGGAGTTATCCCTGTTATCTTTGCCAGTTCGATTACTGCAGCGCCTG
CGGCTATTCTTCAGTTTTTGAGTGCCACAGGTCATGATTGGGCTTGGGTA
```

TABLE 1-continued

AGGGTAGCACAAGAGATGTTGGCAACTACTTCTCCAACTGGTATTGCCAT
GTATGCTTTGTTGATTATTCTCTTTACATTCTTCTATACGTTTGTACAGA
TTAATCCTGAAAAAGCAGCAGAGACCTACAAAAGAGTGGTGCCTATATCC
ATGGAGTTCGTCCTGGTAAAGGTACAGAAGAATATATGTCTAAACTTCTT
CGTCGTCTTGCAACTGTTGGTTCCCTCTTCCTTGGTGTGA 4127.5

(SEQ. ID. NO. 238)
ATGGATATTAGACAAGTTACTGAAACCATCGCCATGATTGAGGAGCAAAA
CTTCGATATTAGAACCATTACCATGGGATTTCTCTTTTGGACTGTATCG
ATCCAGATATCAATCGTGCTGCGGAGAAAATCTATCAAAAAATTACGACA
AAGGCGGCTAATTTAGTAGCTGTTGGTGATGAAATTGCGGCTGAGTTGGG
AATTCCTATCGTTAATAAGCGTGTATCGGTGACACCTATTTCTCTGATTG
GGGCAGCGACAGATGCGACGGACTACGTGGTTCTGGCAAAAGCGCTTGAT
AAGGCTGCGAAAGAGATTGGTGTGGACTTTATTGGTGGTTTTTCTGCCTT
AGTACAAAAAGGTTATCAAAAGGGAGATGAGATTCTCATCAATTCCATTC
CTCGCGCTTTGGCTGAGACGGATAAGGTCTGCTCGTCAGTCAATATCGGC
TCAACCAAGTCTGGTATTAATATGACGGCTGTGGCAGATATGGGACGAAT
TATCAAGGAAACAGCAAATCTTTCAGATATGGGAGTGGCCAAGTTGGTTG
TATTCGCTAATGCTGTTGAGGACAATCCATTTATGGCGGGTGCCTTTCAT
GGTGTTGGGGAAGCAGATGTTATCATCAATGTCGGAGTTTCTGGTCCTGG
TGTTGTGAAACGTGCTTTGGAAAAAGTTCGTGGACAGAGCTTTGATCTAG
TAGCCGAAACAGTTAAGAAAACTGCCTTTAAAATCACTCGTATCGGTCAA
TTGGTTGGTCAAATGGCCAGTGAGAGACTGGGTGTGGAGTTTGGTATTGT
GGACTTGAGTTTGGCACCAACCCCTGCGGTTGGAGACTCTGTGGCACGTG
TCCTTGAGGAAATGGGGCTAGAAACAGTTGGCACGCATGGAACGACGGCT
GCCTTGGCCCTCTTGAACGACCAAGTTAAAAAGGGTGGAGTGATGGCCTG
CAACCAAGTCGGTGGTTTATCTGGTGCCTTTATCCCTGTTTCTGAGGATG
AAGGAATGATTGCTGCAGTGCAAAATGGCTCTCTTAATTTAGAAAAACTA
GAAGCTATGACGGCTATCTGTTCTGTTGGATTGGATATGATTGCCATCCC
AGAAGATACGCCTGCTGAAACTATTGCGGCTATGATTGCGGATGAAGCAG
CAATCGGTGTTATCAACATGAAAACAACAGCTGTTCGTATCATTCCCAAA
GGAAAAGAAGGCGATATGATTGAGTTTGGTGGTCTATTAGGAACTGCACC
CGTTATGAAGGTTAATGGGGCTTCGTCTGTCGACTTCATCTCTCGCGGTG
GACAAATCCCAGCACCAATTCATAGTTTTAAAAATTAA 4128.1

(SEQ. ID. NO. 239)
ATGACACAGATTATTGATGGGAAAGCTTTAGCGGCCAAATTGCAGGGGCA
GTTGGCTGAAAAGACTGCAAAATTAAAGGAAGAAACAGGTCTAGTGCCTG
GTTTGGTAGTGATTTTGGTTGGGGACAATCCAGCCAGCCAAGTCTACGTT
CGCAACAAGGAGAGGTCAGCCCTTGCGGCTGGTTTCCGTAGCGAAGTAGT
ACGGGTTCCAGAGACCATTACTCAAGAGGAATTCTTAGACCTGATTGCTA
AATACAATCAGGATCCAGCTTGGCATGGGATTTTGGTTCAGTTGCCATTA

CCAAAACACATTGATGAAGAGGCGGTTCTATTGGCTATTGACCCAGCAAA
AGGATGTGGATGGTTTCCATCCTCTAAACATGGGGCGTCTTTGGTCTGGT
CATCCAGTCATGATTCCTTCGACACCGGCAGGAATTATGGAAATGTTCCA
TGAATATGGGATTGACT6TGGAAGGTAAAAATGCAGTCGTCATCGGTCGA
TCCAATATTGTCGGAAAACCTATGGCCCAGCTTCTTTTGGCAAAGAATGC
AACAGTAACCTTGACTCACTCACGTACTCATAATCTTTCCAAGGTGGCTG
CAAAAGCAGATATTCTGGTTGTTGCAATCGGTCGTGCCAAGTTTGTGACT
GCTGACTTTGTCAAACCAGGTGCGGTAGTCATTGACGTTGGGATGAACCG
CGATGAAAATGGTAAGCTCTGTGGGGATGTTGATTATGAGGCGGTTGCCC
CACTTGCTAGCCACATTACGCCAGTCCCTGGAGGTGTCGGTCCTATGACC
ATTACTATGCTGATGGAGCAAACCTATCAGGCAGCACTTAGGACATTGGA
TAGAAAATAA 4128.2

(SEQ. ID. NO. 240)
ATGTCTAAATTTAATCGTATTCATTTGGTGGTACTGGATTCTGTAGGAAT
CGGTGCAGCACCAGATGCTAATAACTTTGTCAATGCAGGGGTTCCAGATG
GAGCTTCTGACACACTGGGACACATTTCAAAAACAGTTGGTTTGAATGTC
CCAAACATGGCTAAAATAGGTCTTGGAAATATTCCTCGTGAAACTCCTCT
TAAGACTGTAGCAGCTGAAAGCAATCCAACTGGATATGCAACAAAATTAG
AGGAAGTATCTCTTGGTAAGGATACTATGACTGGACACTGGGAAATCATG
GGACTCAACATTACTGAGCCTTTCGATACTTTCTGGAACGGATTCCCAGA
AGAAATCCTGACAAAAATCGAAGAATTCTCAGGACGCAAGGTTATTCGTG
AAGCCAACAAACCTTATTCAGGAACGGCTGTTATCTATGATTTTGGACCA
CGTCAGATGGAAACTGGAGAGTTGATTATCTATACTTCAGCTGACCCTGT
TTTGCAGATTGCTGCCCACGAAGACATTATTCCTTTGGATGAATTGTACC
GTATCTGTGAATACGCTCGTTCGATTACCCTTGAGCGTCCTGCCCTTCTT
GGTCGCATCATTGCTCGCCCTTATGTAGGTAACCAGGTAACTTCACTCG
TACGGCAAACCGTCGTGACTTGGCTGTATCTCCATTTTTCCCAACTGTTT
TGGATAAATTGAATGAGGCTGGTATCGATACTTATGCTGTGGGTAAAATC
AACGATATCTTTAACGGTGCTGGTATCAACCATGACATGGGTCACAACAA
GTCAAATAGTCATGGAATTGATACACTATTGAAGACTATGGGACTTGCTG
AGTTTGAAAAAGGATTCTCATTCACAAACCTAGTTGACTTTGATGCCCTT
TACGGCCATCGTCGTAATGCTCACGGTTACCGTGATTGCTTGCATGAGTT
TGATGAACGCTTACCTGAAATTATCGCAGCTATGAGAGAGAATGACCTTC
TCTTGATTACTGCGGACCATGGAAATGACCCAACGTATGCAGGAACGGAT
CACACTCGGGAATATATTCCATTGTTGGCCTATAGCCCTGCCTTTAAAGG
AAATGGTCTCATTCCAGTAGGACATTTTGCAGATATTTCAGCGACTGTTG
CCGATAACTTTGGTGTGGAAACTGCTATGATTGGGGAAAGTTTCTTAGAT
AAATTGGTATAA

TABLE 1-continued 4129.2
(SEQ. ID. NO. 241)
ATGTTTATTTCCATCAGTGCTGGAATTGTGACATTTTTACTAACTTTAGT
AGAAATTCCGGCCTTTATCCAATTTTATAGAAAGGCGCAAATTACAGGCC
AGCAGATGCATGAGGATGTCAAACAGCATCAGGCAAAAGCTGGGACTCCT
ACAATGGGAGGTTTGGTTTTCTTGATTACTTCTGTTTTGGTTGCTTTCTT
TTTCGCCCTATTTAGTAGCCAATTCAGCAATAATGTGGGAATGATTTTGT
TCATCTTGGTCTTGTATGGCTTGGTCGGATTTTTAGATGACTTTCTCAAG
GTCTTTCGTAAAATCAATGAGGGGCTTAATCCTAAGCAAAAATTAGCTCT
TCAGCTTCTAGGTGGAGTTATCTTCTATCTTTTCTATGAGCGCGGTGGCG
ATATCCTGTCTGTCTTTGGTTATCCAGTTCATTTGGGATTTTTCTATATT
TTCTTCGCTCTTTTCTGGCTAGTCGGTTTTTCAAACGCAGTAAACTTGAC
AGACGGTGTTGACGGTTAGCTAGTATTTCCGTTGTGATTAGTTTGTCTG
CCTATGGAGTTATTGCCTATGTGCCAGGTCAGATGGATATTCTTCTAGTA
ATTCTTGCCATGATTGGTGGTTTGCTCGGTTTCTTCATCTTTAACCATAA
GCCTGCCAAGGTCTTTATGGGTGATGTGGGAAGTTTGGCCCTAGGTGGGA
TGCTGGCAGCTATCTCTATGGCTCTCCACCAAGAATGGACTCTCTTGATT
ATCGGAATTGTGTATGTTTTTGAAACAACTTCTGTTATGATGCAAGTCAG
TTATTTCAAACTGACAGGTGGTAAACGTATTTTCCGTATGACGCCTGTAC
ATCACCATTTTGAGCTTGGGGGATTGTCTGGTAAAGGAAATCCTTGGAG
CGAGTGGAAGGTTGACTTCTTCTTTTGGGGAGTGGGACTTCTAGCAAGTC
TCCTGACCCTAGCAATTTTATATTTGATGTAA 4133.1
(SEQ. ID. NO. 242)
TTGTTTAAGAAAAATAAAGACATTCTTAATATTGCATTGCCAGCTATGGG
TGAAAACTTTTTGCAGATGCTAATGGGAATGGTGGACAGTTATTGGTTG
CTCATTTAGGATTGATAGCTATTTCAGGGGTTTCAGTAGCTGGTAATATT
ATCACCATTTATCAGGCGATTTTCATCGCTCTGGGAGCTGCTATTTCCAG
TGTTATTTCAAAAAGCATAGGGCAGAAAGACCAGTCGAAGTTGGCCTATC
ATGTGACTGAGGCGTTGAAGATTACCTTACTATTAAGTTTCCTTTTAGGA
TTTTTGTCCATCTTCGCTGGGAAGAGATGATAGGACTTTTGGGGACGGA
GAGGGATGTAGCTGAGAGTGGTGGACTGTATCTATCTTTGGTAGGCGGAT
CGATTGTTCTCTTAGGTTTAATGACTAGTCTAGGAGCCTTGATTCGTGCA
ACGCATAATCCACGTCTGCCTCTCTATGTTAGTTTTTTATCCAATGCCTT
GAATATTCTTTTTTCAAGTCTAGCTATTTTTGTTCTGGATATGGGGATAG
CTGGTGTTGCTTGGGGACAATTGTGTCTCGTTTGGTTGGTCTTGTGATT
TTGTGGTCACAATTAAAACTGCCTTATGGGAAGCCAACTTTTGGTTTAGA
TAAGGAACTGTTGACCTTGGCTTTACCAGCAGCTGGAGAGCGACTTATGA
TGAGGGCTGAGATGTAGTGATCATTGCCTTGGTCGTTTCTTTTGGGACG
GAGGCAGTTGCTGGGAATGCAATCGGAGAAGTCTTGACCCAGTTTAACTA
TATGCCTGCCTTTGGCGTCGCTACGGCAACGGTCATGCTGTTGGCCCGAG
CAGTTGGAGAGGATGATTGGAAAAGAGTTGCTAGTTTGAGTAAACAAACC TTTTGGCTTTCTCTGTTCCTCATGTTGCCCCTGTCCTTTAGTATATATGT
CTTGGGTGTACCATTAACTCATCTCTATACGACTGATTCTCTAGCGGTGG
AGGCTAGTGTTCTAGTGACACTGTTTTCACTACTTGGGACCCCTATGACG
ACAGGAACAGTCATCTATACGGCAGTCTGGCAGGGATTAGGAAATGCACG
CCTCCCTTTTATGCGACAAGTATAGGAATGTGGTGTATCCGCATTGGGA
CAGGATATCTGATGGGATTGTGCTTGGTTGGGGCTTGCCTGGTATTTGG
GCAGGGTCTCTCTTGGATAATGGTTTTCGCTGGTTATTTCTACGCTATCG
TTACCAGCGCTATATGAGCTTGAAAGGATAG 4135.2
(SEQ. ID. NO. 243)
ATGCAAACCAAGAAAAACACTCGCAAGCAGCCGTTCTTGGCTTGCAGCAC
TTACTAGCCATGTACTCAGGATCTATCCTGGTTCCCATCATGATTGCGAC
AGCCCTTGGCTATTCAGCTGAGCAGTTGACCTACCTGATTTCTACAGATA
TCTTCATGTGTGGGGTGGCAACCTTCCTCCAACTCCAACTCAACAAATAC
TTTGGGATGGACTCCCAGTCGTTCTTGGAGTTGCATTCCAGTCGGTCGCT
CCCTTGATTATGATTGGGCAAAGCCATGGTAGTGGCGCTATGTTTGGTGC
CCTTATCGCATCTGGGATTACGTGGTTCTTGTTTCAGGCATCTTCTCAA
AAGTAGCCAATCTCTTCCCATCTATCGTAACAGGATCTGTTATTACCACG
ATTGGTTTAACCTTGATCCCTGTCGCTATTGAAATATGGGAAATAACGT
TCCAGAGCCAACTGGTCAAAGTCTCTTGCTTGCAGCTATTACTGTTCTGA
TTATCCTCTTGATCAACATCTTTACCAAAGGATTATCAAGTCTATCTCT
ATTTTGATTGGTCTGGTTGTTGGAACTGCCATTGCTGCTACTATGGGCTT
GGTGGACTTCTCTCCTGTTGCGGTAGCTCCACTTGTCCATGTCCCAACTC
CACTCTACTTTGGGATGCCAACCTTTGAAATCTCATCTATTGTCATGATG
TGTATCATCGCAACGGTGTCTATGGTTGAGTCAACTGGTGTTTATCTGGC
CTTGTCTGATATCACAAAGGAATCCAATCGACAGCACGCGCCTTCGCAAC
GGATACCGCGCAGAAGGTTTGGCCGTACTTCTCGGAGGAATCTTTAACAC
CTTCCCTTACACCGGATTTTCACAAAACGTTGGTTTGGTTAAATTGTCAG
GCATCAAAAAACGCCTGCCAATCTACTACGCAGCTGGTTTCCTGGTTCTC
CTTGGACTGCTTCCTAAGTTTGGCGCCCTTGCCCAAATCATTCCAAGCTC
CGTCCTCGGTGGTGCCATGCTGGTAATGTTTGGTTTTGTATCAATTCAAG
GGATGCAAATCCTCGCCCGTGTTGACTTTGCTAACAATGAACACAACTTC
CTTATCGCAGCTGTTTCAATCGCTGCAGGTGTCGGTCTCAACAACAGTAA
TCTCTTTGTCAGCATGCCGACAGCCTTCCAAATGTTCTTCTCAAACGGAA
TCGTCGTAGCCAGCCTACTCGCTATTGTCCTCAATGCCGTATTAAATCAT
AAAAAGAAATAA 4136.2
(SEQ. ID. NO. 244)
ATGAAAGATAGAATAAAAGAATATTTACAAGACAAGGGAAAGGTGACTGT
TAATGATTTGGCTCAGGCTTGGGAAAAGACAGTTCCAAGGATTTTCGTGA
GTTGATTAAAACCTTGTCCTTAATGGAAAGAAAGCACCAAATTCGTTTGA
AGAAGATGGTAGTCTGACATTAGAAATTAAGAAAAAACATGAGATTACCC TABLE 1-continued

```
TCAAGGGGATTTTTCATGCCCATAAAAATGGCTTTGGCTTTGTTAGTCTG
GAAGGCGAGGAGGACGACCTTTTTGTAGGGAAAAATGATGTCAACTATGC
TATTGATGGTGATACCGTCGAGGTAGTGATTAAGAAAGTCGCTGACCGCA
ATAAGGGAACAGCAGCAGAAGCCAAAATTATTGATATCCTAGAACACAGT
TTGACAACAGTTGTCGGGCAAATCGTTCTGGATCAGGAAAAACCTAAGTA
TGCTGGCTATATTCGTTCAAAAAATCAGAAAATCAGTCAACCGATTTATG
TTAAGAAACCAGCCCTAAAATTAGAAGGAACAGAAGTTCTCAAAGTCTTT
ATCGATAAATACCCAAGCAAGAAACATGATTTCTTTGTCGCGAGTGTTCT
CGATGTAGTGGGACACTCAACGGATGTCGGAATTGATGTTCTTGAGGTCT
TGGAATCAATGGACATTGTATCCGAGTTTCCAGAAGCTGTTGTTAAGGAA
GCAGAAAGTGTGCCTGATGCTCCGTCTCAAAAGGATATGGAAGGTCGTCT
GGATCTAAGAGATGAAATTACCTTTACCATTGACGGTGCGGATGCCAAGG
ACTTGGACGATGCAGTGCATATCAAGGCTCTGAAAAATGGCAATCTGGAG
TTTGGGGTTCACATCGCAGATGTTTCTTATTATGTGACCGAGGGGTCTGC
CCTTGACAAGGAAGCCCTTAACCGTGCGACTTCTGTTTACGTGACAGACC
GAGTGGTGCCAATGCTTCCAGAACGACTATCAAATGGCATCTGCTCTCTC
AATCCCCAAGTTGACCGCCTGACCCAGTCTGCTATTATGGAGATTGATAA
ACATGGTCGTGTGGTCAACTATACCATTACACAAACAGTTATCAAGACCA
GTTTTCGTATGACCTATAGCGATGTCAATGATATCCTAGCTGGCGATGAA
GAAAAGAGAAAAGAATATCATAAAATTGTATCAAGTATCGAACTCATGGC
CAAGCTTCATGAAACTTTAGAAAACATGCGTGTGAAACGTGGAGCTCTCA
ATTTTGATACCAATGAAGCGAAGATTTTAGTGGATAAACAAGGTAAGCCT
GTTGATATCGTTCTTCGGCAGCGTGGTATTGCCGAGCGGATGATTGAGTC
TTTTTATGTTGATGGCTAATGAAACAGTTGCCGAACATTTCAGCAAGTTGG
ATTTGCCTTTTATCTATCGAATTCACGAGGAGCCTAAGGCTGAAAAGGTT
CAGAAGTTTATTGATTATGCTTCGAGTTTTGGCTTGCGCATTTATGGAAC
TGCCAGTGAGATTAGTCAGGAGGCACTTCAAGACATCATGCGTGCTGTTG
AGGGAGAACCTTATGCAGATGTATTGTCCATGATGCTTCTTCGCTCTATG
CAGCAGGCTCGTTATTCGGAGCACAATCACGGCCACTATGGACTAGCTGC
TGACTATTATACTCACTTTACCAGTCCAATTCGTCGTTATCCAGACCTTC
TTGTTCACCGTATGATTCGGGATTACGGCCGTTCTAAGGAAATAGCAGAG
CATTTTGAACAAGTGATTCCAGAGATTGCGACCCAGTCTTCCAACCGTGA
ACGTCGTGCCATAGAAGCTGAGCGTGAAGTCGAAGCCATGAAAAAGGCTG
AGTATATGGAAGAATACGTGGGTGAAGAGTATGATGCAGTTGTATCAAGT
ATTGTCAAATTCGGTCTCTTTGTCGAATTGCCAAACACAGTTGAAGGCTT
GATTCACATCACTAATCTGCCTGAATTTTATCATTTCAATGAGCGTGATT
TGACTCTTCGTGGAGAAAAATCAGGTATCACTTTCCGAGTGGGTCAGCAG
ATCCGTATCCGTGTTGAAAGAGCGGATAAAATGACTGGAGAGATTGATTT
TTCATTCGTACCTAGTGAGTTTGATGTGATTGAAAAAGGCTTGAAACAGT
CTAGTCGTAGTGGCAGAGGGCGTGATTCAAATCGTCGTTCGGATAAGAAG
GAAGACAAGAGAAAATCAGGACGCTCAAATGATAAGCGTAAGCATTCACA
AAAAGACAAGAAGAAAAAAGGAAAGAAACCTTTTTCACCGGAAGTAGCTA
AGAAAGGAGCCAAGCATGGCAAAGGGCGAGGGAAAGGTCGTCGCACAAAA
TAA
```

4137.2

(SEQ. ID. NO. 245)
```
ATGGGCACAACAGGATTTACAATAATTGACTTAATTATCTTGATTGTTTA
TTTACTTGCGGTGTTGGTTGCAGGTATCTATTTCTCTAAAAAAGAGATGA
AAGGAAAGAGTTCTTTAAAGGAGATGGTTCGGTTCCTTGGTATGTTACT
TCGGTATCCATTTTTGCCACAATGCTCAGTCCGATTTCCTTCTTGGGACT
CGCTGGTAGCTCTTATGCAGGTAGCTGGATTTTATGGTTTGCTCAATTAG
GGATGGTAGTAGCTATTCCACTGACAATTCGTTTTATCTTACCTATCTTT
GCACGGATAGACATCGATACGGCATATGATTACTTGGATAAACGTTTTAA
TTCTAAAAGCACTTCGTATTATTTCAGCACTCTTGTTTATTATTTATCAA
TTGGGACTATGTCTATCATTATGTACCTCCCATCAGCTGGTTTATCAGT
ATTGACAGGAATTGACATCAATATTTTGATTATTTTGATGGGTGTAGTTG
CAATTGTTTATTCTTATACTGGTGGTCTAAAATCCGTATTATGGACAGAC
TTTATTCAAGGTGTGATTCTGATTAGTGGTGTCGTTTTAGCTTTATTTGT
ACTGATTGCTAATATTAAAGGTGGCTTTGGTGCAGTAGCAGAAACATTAG
CAAACGGGAAATTCCTTGCTGCAAATGAAAAACTTTTCGATCCTAACTTG
CTTTCAAACTCCATCTTTTTAATTGTGATGGGTTCAGGCTTTACAATCTT
GTCTTCCTATGCTTCATCTCAAGATTTGGTTCAACGTTTTACTACAACAC
AAAATATTAAGAAACTTAATAAGATGTTGTTCACAAACGGTGTTTTGTCA
CTTGCAACTGCAACAGTCTTTTACTTGATTGGTACAGGCTTGTACGTATT
CTATCAAGTACAAAATGCAGATAGTGCAGCTAGCAATATCCCTCAAGACC
AAATCTTTATGTACTTTATTGCATACCAGTTACCAGTAGGTATCACAGGT
TTGATCTTGGCAGCGATTTATGCAGCATCTCAATCAACTATTTCAACAGG
TTTGAACTCTGTTGCAACTTCATGGACATTGGATATTCAAGATGTCATTT
CTAAAAATATGTCAGACAATCGTCGTACGAAAATTGCACAATTCGTATCT
CTAGCAGTAGGTTTATTCTCAATTGGTGTTTCCATTGTCATGGCTCACTC
AGATATTAAATCTGCATACGAATGGTTCAATAGTTTCATGGGACTTGTAC
TTGGTCTACTTGGTGGTGTATTTATTCTTGGATTTGTTTCTAAAAAAGCA
AATAAACAAGGTGCTTATGCAGCGCTGATTGTATCAACCATCGTCATGGT
ATTTATTAAATACTTCCTTCCTCCAACAGCTGTTAGCTACTGGGCATATT
CATTGATTTCAATCTCTGTATCAGTAGTTTCAGGTTATATTGTATCTGTT
CTTACTGGAAATAAAGTATCTGCACCTAAATATACAACGATTCATGATAT
TACAGAAATTAAAGCGGATTCAAGTTGGGAAGTTCGTCACTAA
```

4138.1

(SEQ. ID. NO. 246)
```
ATGAAATTTAGTAAAAAATATATAGCAGCTGGATCAGCTGTTATCGTATC
CTTGAGTCTATGTGCCTATGCACTAAACCAGCATCGTTCGCAGGAAAATA
AGGACAATAATCGTGTCTCTTATGTGGATGGCAGCCAGTCAAGTCAGAAA
```

TABLE 1-continued

AGTGAAAACTTGACACCAGACCAGGTTAGCCAGAAAGAAGGAATTCAGGC
TGAGCAAATTGTAATCAAAATTACAGATCAGGGCTATGTAACGTCACACG
GTGACCACTATCATTACTATAATGGGAAAGTTCCTTATGATGCCCTCTTT
AGTGAAGAACTCTTGATGAAGGATCCAAACTATCAACTTAAAGACGCTGA
TATTGTCAATGAAGTCAAGGGTGGTTATATCATCAAGGTCGATGGAAAAT
ATTATGTCTACCTGAAAGATGCAGCTCATGCTGATAATGTTCGAACTAAA
GATGAAATCAATCGTCAAAAACAAGAACATGTCAAAGATAATGAGAAGGT
TAACTCTAATGTTGCTGTAGCAAGGTCTCAGGGACGATATACGACAAATG
ATGGTTATGTCTTTAATCCAGCTGATATTATCGAAGATACGGGTAATGCT
TATATCGTTCCTCATGGAGGTCACTATCACTACATTCCCAAAAGCGATTT
ATCTGCTAGTGAATTAGCAGCAGCTAAAGCACATCTGGCTGGAAAAAATA
TGCAACCGAGTCAGTTAAGCTATTCTTCAACAGCTAGTGACAATAACACG
CAATCTGTAGCAAAAGGATCAACTAGCAAGCCAGCAAATAAATCTGAAAA
TCTCCAGAGTCTTTTGAAGGAACTCTATGATTCACCTAGCGCCCAACGTT
ACAGTGAATCAGATGGCCTGGTCTTTGACCCTGCTAAGATTATCAGTCGT
ACACCAAATGGAGTTGCGATTCCGCATGGCGACCATTACCACTTTATTCC
TTACAGCAAGCTTTCTGCCTTAGAAGAAAGATTGCCAGAATGGTGCCTA
TCAGTGGAACTGGTTCTACAGTTTCTACAAATGCAAAACCTAATGAAGTA
GTGTCTAGTCTAGGCAGTCTTTCAAGCAATCCTTCTTCTTTAACGACAAG
TAAGGAGCTCTCTTCAGCATCTGATGGTTATATTTTTAATCCAAAAGATA
TCGTTGAAGAAACGGCTACAGCTTATATTGTAAGACATGGTGATCATTTC
CATTACATTCCAAAATCAAATCAAATTGGGCAACCGACTCTTCCAAACAA
TAGTCTAGCAACACCTTCTCCATCTCTTCCAATCAATCCAGGAACTTCAC
ATGAGAAACATGAAGAAGATGGATACGGATTTGATGCTAATCGTATTATC
GCTGAAGATGAATCAGGTTTTGTCATGAGTCACGGAGACCACAATCATTA
TTTCTTCAAGAAGGACTTGACAGAAGAGCAAATTAAGGTGCGCAAAAACA
TTTAG 4139.1
(SEQ. ID. NO. 247)
ATGAAAAAAAGAGCAATAGTGGCAGTCATTGTACTGCTTTTGATTGGGCT
GGATCAGTTGGTCAAATCCTATATCGTCCAGCAGATTCCACTGGGTGAAG
TGCGCTCCTGGATCCCCAATTTCGTTAGCTTGACCTACCTGCAAAATCGA
GGTGCAGCCTTTTCTATCTTACAAGATCAGCAGCTGTTATTCGCTGTCAT
TACTCTGGTTGTCGTGATAGGTGCCATTTGGTATTTACATAAAACACATG
GAGGACTCATTCTGGATGGTCTTGGGTTTGACTCTAATAATCGCGGGTGG
TCTTGGAAACTTTATTGACAGGGTCAGTCAGGGCTTTGTTGTGGATATGT
TCCACCTTGACTTTATCAACTTTGCAATTTTCAATGTGGCAGATAGCTAT
CTGACGGTTGGAGTGATTATTTTATTGATTGCAATGCTAAAAGAGGAAAT
AAATGGAAATTAA 4139.5
(SEQ. ID. NO. 248)
ATGAATACAAATCTTGCAAGTTTTATCGTTGGACTGATCATCGATGAAAA
CGACCGTTTTTACTTTGTGCAAAAGGATGGTCAAACCTATGCTCTTGCTA
AGGAAGAAGGCCAACATACAGTAGGGGATACGGTCAAAGGTTTTGCATAC
ACGGATATGAAGCAAAAACTCCGCCTGACAACCTTAGAAGTGACTGCCAC
TCAGGACCAATTTGGTTGGGACGTGTCACAGAGGTTCGTAAGGACTTGG
GTGTCTTTGTGGATACAGGCCTTCCTGACAAGGAAATCGTTGTGTCACTC
GATATTCTCCCTGAGCTCAAGGAACTCTGGCCTAAGAAGGGCGACCAACT
CTACATCCGTCTTGAAGTGGATAAGAAAGACCGTATCTGGGCCTCTTGG
CTTATCAAGAAGACTTCCAACGTCTTGCTCGTCCTGCCTACAACAACATG
CAGAACCAAAACTGGCCAGCCATTGTTTACCGTCTCAAGCTGTCAGGAAC
TTTTGTTTACCTACCAGAAAATAATATGCTTGGTTTTATTCATCCTAGCG
AGCGTTACGCAGAGCCACGTTGGGGCAAGTATTAGATGCGCGCGTTATTG
GTTTCCGTAAGTGGACCGCACTCTGAACCTCTCCCTCAAACCACGCTCCT
TTGAAATGTTGGAAAACGATGCTCAGATGATTTTGACTTATTTGGAAAGC
AATGGCGGTTTCATGACCTTAAATGACAAGTCATCTCCAGACGACATCAA
GGCAACCTTTGGCATTTCTAAAGGTCAGTTCAAGAAAGCTTTAGGTGGTC
TTATGAAGGCTGGTAAAATCAAGCAGGACCAGTTTGGGACAGAGTTGATT
TAG 4139.8
(SEQ. ID. NO. 249)
ATGAAAGATGTTAGTCTATTTTTATTGAAAAAAGTTTTCAAAAGCCGCTT
AAACTGGATTGTCTTAGCTTTATTTGTATCTGTACTCGGTGTTACCTTTT
ATTTAAATAGTCAGACTGCAAACTCACACAGCTTGGAGAGCAGGTTGGAA
AGTCGCATTGCAGCCAACGAGAGGGCTATCAATGAAAATGAAGAGAAACT
CTCCCAAATGTCTGATACCAGCTCGGAGGAATACCAGTTTGCTAAAAATA
ATTTAGACGTGCAAAAAAATCTTTTGACGCGAAAGACAGAAATTCTGACT
TTATTAAAGAAGGGCGCTGGAAAGAAGCCTACTATTTGCAGTGGCAAGA
TGAAGAGAAGAATTATGAATTTGTATCAAATGACCCGACTGCTAGCCCTG
GCTTAAAAATGGGGGTTGACCGCGAACGGAAGATTTACCAAGCCCTGTAT
CCCTTGAACATAAAAGCACATACTTTGGAGTTTCCGACCCACGGGATTGA
TCAGATTGTCTGGATTTTAGAGGTTATCATCCCAAGTTTGTTTGTGGTTG
CTATTATTTTTATGCTAACACAACTATTTGCAGAAAGATATCAAAATCAT
CTGGACACAGCTCACTTATATCCTGTTTCAAAAGTGACATTTGCAATATC
CTCTCTTGGAGTTGGAGTGGGATATGTAACTGTGCTGTTTATCGGAATCT
GTGGCTTTTCTTTTCTAGTGGGAAGTCTGATAAGTGGTTTTGGACAGTTA
GATTATCCCTACCCAATTTATAGCTTAGTGAATCAAGAAGTAACTATTGG
GAAAATACAAGATGTATTATTTCCTGGCTTGCTCTTAGCTTTCTTAGCCT
TTATCGTCATTGTGGAAGTTGTGTACTTGATTGCTTACTTTTTCAAGCAA
AAAATGCCTGTCCTCTTTCTTCACTCATTGGGATTGTTGGCTTATTGTT
TGGTATCCAAACCATTCAGCCTCTTCAAAGGATTGCACATCTGATTCCCT

TABLE 1-continued

TTACTTACTTGCGTTCAGTGGAGATTTTATCTGGAAGATTACCTAAGCAG

ATTGATAATGTCGATCTAAATTGGAGCATGGGAATGGTCTTACTTCCTTG

CCTGATTATCTTTTTGCTATTGGGAATTCTATTTATTGAAAGATGGGGAA

GTTCACAGAAAAAGAATTTTTTAATAGATTCTAG 4141.1
(SEQ. ID. NO. 250)
ATGATGAAGTTCATATTGGATATTGTTAGTACACCAGCTATTTTAGTAGC

TTTAATTGCAATCTTAGGATTAGTTCTTCAGAAGAAGAAATTACCTGATA

TTATTAAAGGTGGAATTAAGACCTTTGTTGGTTTCTTAGTTGTATCTGGT

GGTGCAGGAATTGTACAAAATTCTTTAAATCCATTTGGTACCATGTTTGA

GCATGCTTTTCATTTATCTGGCGTTGTGCCGAATAATGAAGCAATTGTAG

CTGTAGCTTTAACAACATATGGCTCAGCTACTGCAATGATTATGTTTGCA

GGCATGGTGTTCAATATCTTAATCGCTCGTTTTACTCGATTTAAATATAT

TTTTTTAACAGGGCACCACACTCTATATATGGCATGTATGATTGCGGTCA

TTTTATCAGTTGCTGGCTTTACTAGCTTGCCTCTCATCTTACTAGGAGGA

TTAGCACTCGGTATTATTATGAGTATTTCCCCAGCATTTGTGCAAAAATA

TATGGTTCAATTAACTGGAAATGACAAGGTAGCTTTAGGTCATTTCAGTT

CTTTGGGATATTGGTTGAGTGGTTTTACTGGTAGCCTTATCGGTGACAAA

TCAAAATCAACAGAGGACATTAAATTTCCAAAGAGTTTAGCTTTTTTACG

TGATAGTACTGTTAGTATTACTTTATCCATGGCAGTTATTTACATTATTG

TAGCTATCTTTGCAGGGTCAGAATATATAGAAAAAGAAATCAGTAGTGGT

ACAAGTGGTCTAGTTTATGCTTTACAATTAGCAGGTCAATTTGCAGCAGG

GGTATTTGTTATTTTAGCAGGTGTTCGCCTTATTTTGGGCGAAATTGTTC

CAGCCTTTAAAGGTATTTCAGAGCGTCTTGTACCTAATTCAAAACCTGCT

TTGGATTGTCCGATTGTTTATACTTATGCACCCAATGCAGTTCTAATTGG

ATTTATCTCTAGTTTTGTTGGTGGTTTAGTAAGTATGGTAATTATGATTG

CTTCAGGAACGGTTGTTATCTTACCAGGTGTTGTGCCTCATTTCTTCTGT

GGAGCGACTGCAGGTGTCATTGGGAATGCATCTGGTGGTGTTCGTGGAGC

CACTATTGGAGCATTTTTACAAGGTATTTTAATCAGTTTTCTTCCAGTCT

TTTTAATGCCAGTTTTGGGAGGACTTGGTTTCCAAGGATCAACTTTCTCA

GATGCAGATTTTGGTCTATCAGGAATTATTTTAGGAATGTTAAATCAATT

TGGCTCACAAGCAGGCATTGTGATTGGTCTTGTTCTTATTCTAGCAGTTA

TGTTTGGAGTATCCTTTATTAAAAAGCCATCTGCAACGGAGGAATAA 4142.3
(SEQ. ID. NO. 251)
ATGATTAAAACATTTCTCTCTGCCCTTTCGGTCATTCTCTTTTCTATCCC

TATCATAACTTATTCTTTTTTCCCATCTTCTAATCTTAACATTTGGCTAT

CTACCCAACCTATCTTGGCACAGATTTATGCCTTCCCCTTAGCTACTGCA

ACTATGGCTGCTATTTTAAGTTTCTTATTTTTTTCCTATCTTTTTACAA

GAAAAATAAACAAATACGGTTTTACTCTGGCATTTTGCTCTTACTATCGC

TCATATTACTATTATTCGGAACAGATAAAACCCTTTCTTCTGCATCAAAT

AAGACTAAAAACTTAAAATTAGTAACTTGGAACGTCGCTAATCAAATAGA

AGCACAACATATTGAGCGAATTTTTAGCCATTTTGACGCCGATATGGCTA

TATTCCCTGAACTAGCTACCAATATCAGAGGTGAGCAAGAAAACCAGAGA

ATCAAACTATTGTTTCATCAAGTTGGACTTTCTATGGCCAACTATGATAT

TTTCACTTCTCCACCTACCAATAGTGGAATAGCTCCTGTGACTGTGATTG

TCAAGAAAAGTTATGGTTTCTATACAGAAGCTAAAACTTTTCATACAACA

CGGTTCGGGACAATTGTATTACATTCGAGAAAACAAAATATACCAGATAT

CATTGCCTTGCATACTGCGCCTCCTCTGCCAGGTTTAATGGAAATCTGGA

AGCAAGACTTAAACATCATTCATAATCAATTGGCTTCAAAATATCCAAAG

GCTATTATTGCAGGTGATTTTAATGCAACTATGCGTCATGGAGCACTTGC

AAAAATAAGCTCTCATAGGGACGCATTAAATGCACTGCCACCTTTTGAAA

GAGGAACTTGGAATAGCCAAAGTCCAAAACTTTTTAATGCAACAATAGAT

CATATTTTATTGCCTAAAAACCACTACTATGTTAAAGATTTAGACATTGT

AAGTTTTCAAAACTCTGATCATAGATGTATTTTTACAGAAATCACATTTT

AA 4142.4
(SEQ. ID. NO. 252)
ATGAATCCAATCCAAAGATCTTGGGCTTATGTCAGCAGAAAGCGACTGAG

AAGTTTTATTTTATTTCTGATTTTATTGGTCTTATTGGCCGGAATTTCAG

CCTGTTTGACTCTGATGAAGTCCAACAAAACAGTAGAAAGCAATCTTTAT

AAATCACTCAATACATCTTTTTCTATTAAGAAGATAGAGAATGGTCAGAC

ATTCAAGTTGTCAGACCTAGCATCTGTAAGCAAGATTAAGGGGCTGGAAA

ATGTCTCTCCTGAACTTGAGACGGTCGCAAAACTAAAAGACAAGGAAGCA

GTGACTGGCGAGCAGAGCGTGGAGCGTGATGATTTATCAGCTGCAGACAA

TAACTTGGTTAGCTTAACGGCTCTTGAGGATTCATCCAAGGATGTAACCT

TTACCAGTTCGGCTTTCAATCTAAAAGAAGGGCGACACCTTCAAAAAGGG

GATTCCAAGAAAATCCTTATCCACGAAGAATTGGCTAAGAAGAACGGTCT

TTCGCTTCATGACAAGATTGGCTTGGATGCTGGTCAGTCTGAATCTGGAA

AAGGACAAACAGTAGAGTTTGAGATTATCGGCATCTTTTCTGGTAAAAAA

CAAGAGAAATTCACAGGCTTGTCTTCTGACTTCAGTGAAAATCAAGTCTT

TACAGACTATGAAAGTAGCCAAACCCTTTTGGGCAATAGTGAAGCTCAAG

TCAGTGCAGCACGCTTCTATGTAGAAAATCCTAAGGAAATGGACGGACTC

ATGAAGCAGGTAGAAAACTTGGCCTTGGAAAATCAAGGCTACCAAGTCGA

AAAGGAAAACAAGGCTTTTGAACAAATCAAAGACTCAGTTGCAACTTTCC

AAACCTTCCTGACCATCTTCCTTTATGGGATGTTGATAGCAGGAGCTGGA

GCCTTAATTCTGGTTTTGTCTCTCTGGTTGAGAGAACGGGTCTATGAAGT

GGGGATTTACTTGCACTTGGAAAAGGCAAGAGCTCGATCTTCCTACAAT

TCTGTTTAGAGGTAGTTTTGGTATCTCTTGGAGCTTTGCTTCCAGCATTT

GTTGCAGGAAACGCAATCACAACTTACCTACTCCAAACTCTACTAGCAAG

TGGAGATCAGGCAAGCTTACAAGATACACTAGCCAAAGCAAGCAGTTTAT

CAACTAGCATCTTATCTTTTGCAGAATCCTATGTTTTTCTAGTTCTGCTT

AGTTGCTTATCTGTAGCCCTTTGTTTCCTATTCTTATTTAGAAAATCACC
GAAAGAAATTTTATCATCTATTAGTTAA 4142.5

(SEQ. ID. NO. 253)
ATGTTACACAACGCATTTGCCTATGTTACAAGGAAGTTTTTCAAATCGAT
TGTCATCTTCCTGATTATTCTCCTCATGGCGAGCTTGAGTTTGGTCGGCT
TGTCAATCAAGGGAGCTACTGCCAAGGCTTCTCAGGAGACCTTTAAAAAT
ATCACCAATAGCTTCTCCATGCAAATCAATCGTCGCGTCAACCAAGGAAC
GCCTCGTGGTGCTGGGAATATCAAGGGTGAAGACATCAAAAAAATCACCG
AAAACAAGGCCATTGAGTCTTATGTCAAACGTATCAACGCTATCGGAGAT
TTGACTGGATATGACCTGATTGAAACGCCAGAAACCAAGAAGAATCTCAC
TGCTGATCGTGCCAAGCGTTTTGGAAGTAGCTTGATGATTACAGGTGTCA
ATGACTCCTCTAAAGAAGACAAGTTTGTCTCTGGTTCTTATAAACTAGTC
GAAGGAGAGCACTTAACCAACGACGACAAGGATAAAATCCTCTTGCACAA
GGACTTGGCAGCCAAACACGGCTGGAAAGTAGGGGACAAGGTTAAACTGG
ACTCTAATATCTACGATGCAGATAATGAAAAGGAGCCAAGGAAACAGTT
GAAGTGACAATCAAGGGACTCTTTGATGGTCATAATAAGTCAGCAGTAAC
CTACTCACAAGAACTTTACGAAAACACAGCTATTACAGACATTCACACTG
CTGCAAAACTTTATGGATACACAGAAGACACAGCCATTTATGGGGACGCA
ACCTTCTTTGTAACAGCAGACAAGAACTTGGATGATGTTATGAAAGAGTT
GAATGGCATCAGTGGTATCAACTGGAAGAGCTACACACTCGTCAAGAGCT
CCTCTAACTACCCAGCTCTTGAGCAATCTATCTCTGGTATGTACAAGATG
GCCAACCTCCTCTTCTGGGGTAGCTTGAGCTTCTCAGTTCTCCTCCTTGC
CCTCTTGCTCAGCCTTTGGATCAACGCCCGTCGCAAGGAAGTGGGAATTC
TCCTCTCTATCGGCCTCAAGCAGGCAAGTATCTTGGGTCAATTCATCACC
GAATCTATCTTGATTGCTATCCCTGCTCTAGTTTCTGCTTACTTCCTAGC
TAATTACACTGCCCGTGCAATTGGAAACACTGTCCTTGCCAATGTGACTT
CAGGTGTTGCCAAACAGGCTAGTAAGGCGGCTCAAGCCTCTAACCTTGGT
GGTGGTGCAGAAGTAGATGGCTTTAGCAAGACCTTGTCGAGCCTAGACAT
TTCCATTCAGACATCAGACTTTATCATCATTTTTGTCCTTGCCTTGGTTC
TAGTGGTTCTCGTTATGGCGCTTGCTTCAAGCAATCTCCTTAGAAAACAA
CCAAAAGAGCTCTTGCTGGATGGTGAATAA 4144.1

(SEQ. ID. NO. 254)
ATGTCACAGGATAAACAAATGAAAGCTGTTTCTCCCCTTCTGCAGCGAGT
TATCAATATCTCATCGATTGTCGGTGGGGTTGGGAGTTTGATTTTCTGTA
TTTGGGCTTATCAGGCTGGGATTTTACAATCCAAGGAAACCCTCTCTGCC
TTTATCCAGCAGGCAGGCATCTGGGGTCCACCTCTCTTTATCTTTTTACA
GATTTTACAGACTGTCGTCCCTATCATTCAGGGGCCTTGACCTCGGTGG
CTGGGGTCTTTATCTACGGGCACATCATCGGGACTATCTACAACTATATC
GGCATCGTGATTGGCTGTGCCATTATCTTTTATCTAGTGCGCCTATACGG
AGCTGCCTTTGTCCAGTCTGTCGTCAGCAAGCGCACCTACGACAAGTACA

TCGACTGGCTAGATAAGGGCAATCGTTTTGACCGCTTCTTTATTTTTATG
ATGATTTGGCCCATTAGCCCAGCTGACTTTCTCTGTATGCTGGCTGCCCT
GACCAAGATGAGCTTCAAGCGCTACATGACCATCATCATTCTGACCAAAC
CCTTTACCCTCGTGGTTTATACCTACGGTCTGACCTATATTATTGACTTT
TTCTGGCAAATGCTTTGA 4144.2

(SEQ. ID. NO. 255)
ATGAGAAATATGTGGGTTGTAATCAAGGAAACCTATCTTCGACATGTCGA
GTCATGGAGTTTCTTCTTTATGGTGATTTCGCCGTTCCTCTTTTTAGGAA
TCTCTGTAGGAATTGGGCATCTCCAAGGTTCTTCTATGGCTAAAAATAAT
AAAGTGGCAGTAGTGACAACAGTGCCATCTGTAGCAGAAGGACTGAAGAA
TGTAAATGGTGTTAACTTCGACTATAAAGACGAAGCAAGTGCCAAAGAAG
CAATTAAAGAAGAAAAATTAAAAGGTTATTTGACCATTGATCAAGAAGAT
AGTGTTCTAAAGGCAGTTTATCATGGCGAAACATCGCTTGAAAATGGAAT
TAAATTTGAGGTTACAGGTACACTCAATGAACTGCAAATCAGCTTAATC
GTTCAACTGCTTCCTTGTCTCAAGAGCAGGAAAAACGCTTAGCGCAGACA
ATTCAATTCACAGAAAAGATTGATGAAGCCAAGGAAAATAAAAAGTTTAT
TCAAACAATTGCAGCAGGTGCCTTAGGATTCTTTCTTTATATGATTCTGA
TTACCTATGCGGGTGTAACAGCTCAGGAAGTTGCCAGTGAAAAAGGCACC
AAAATTATGGAAGTCGTTTTTTCTAGCATAAGGGCAAGTCACTATTTCTA
TGCGCGGATGATGGCTCTGTTTCTAGTGATTTTAACGCATATTGGGATCT
ATGTTGTAGGTGGTCTGGCTGCCGTTTTGCTCTTTAAAGATTTGCCATTC
TTGGCTCAGTCTGGTATTTTGGATCACTTGGGAGATGCTATCTCACTGAA
TACCTTGCTCTTTATTTTGATCAGTCTTTTCATGTACGTAGTCTTGGCAG
CCTTCCTAGGATCTATGGTTTCTCGTCCTGAGGACTCAGGGAAAGCCTTG
TCGCCTTTGATGATTTTGATTATGGGTGGTTTTTTGGAGTGACAGCTCT
AGGTGCAGCTGGTGACAATCTCCTCTTGAAGATTGGTTCTTATATTCCCT
TTATTTCGACCTTCTTTATGCCGTTTCGAACGATTAATGACTATGCGGGG
GGAGCAGAAGCATGGATTTCACTTGCTATTACAGTGATTTTGCGGTGGT
AGCAACAGGATTTATCGGACGCATGTATGCTAGTCTCGTTCTTCAAACGG
ATGATTAGGGATTTGGAAAACCTTTAAACGTGCCTTATCTTATAAATAG 4144.3

(SEQ. ID. NO. 256)
ATGACAGAAACCATTAAATTGATGAAGGCTCATACTTCAGTGCGCAGGTT
TAAAGAGCAAGAAATTCCCCAAGTAGACTTAAATGAGATTTTGACAGCAG
CCCAGATGGCATCATCTTGGAAGAATTTCCAATCCTACTCTGTGATTGTG
GTACGAAGTCAAGAGAAGAAAGATGCCTTGTATGAATTGGTACCTCAAGA
AGCCATTCGCCAGTCTGCTGTTTTCCTTCTCTTTGTCGGAGATTTGAACC
GAGCAGAAAAGGGAGCCCGACTTCATACCGACACCTTCCAACCCCAAGGT
GTGGAAGGTCTCTTGATTAGTTCGGTCGATGCAGCTCTTGCTGGACAAAA
CGCCTTGTTGGCAGCTGAAAGCTTGGGCTATGGTGGTGTGATTATCGGTT
TGGTTCGATACAAGTCTGAAGAAGTGGCAGAGCTCTTTAACCTACCTGAC

TABLE 1-continued

TACACCTATTCTGTCTTTGGGATGGCACTGGGTGTGCCAAATCAACATCA

TGATATGAAACCGAGACTGCCACTAGAGAATGTTGTCTTTGAGGAAGAAT

ACCAAGAACAGTCAACTGAGGCAATCCAAGCTTATGACCGTGTTCAGGCT

GACTATGCTGGGGCGCGTGCGACCACAAGCTGGAGTCAGCGCCTAGCAGA

ACAGTTTGGTCAAGCTGAACCAAGCTCAACTAGAAAAAATCTTGAACAGA

AGAAATTATTGTAG 4146.1

(SEQ. ID. NO. 257)
ATGTTAAAACTTATTGCTATTGTTGGAACAAATTCAAAACGTTCTACAAA

CCGTCAATTGCTTCAATACATGCAAAAACACTTTACTGACAAAGCTGAAA

TTGAACTTGTTGAAATCAAGGCCATTCCTGTCTTCAACAAACCAGCTGAC

AAGCAAGTACCTGCTGAAATATTGGAAATTGCTGCTAAAATCGAAGAGGC

AGATGGCGTTATTATCGGTACTCCTGAGTATGATCACTCTATTCCAGCTG

TTTTGATGAGCGCTCTTGCTTGGTTGTCTTATGGTATTTACCCACTTTTG

AACAAACCAATCATGATTACAGGTGCTTCTTACGGTACGCTTGGTTCATC

TCGTGCCCAATTGCAACTTCGTCAAATCTTGAATGCTCCTGAAATCAAGG

CAAATGTTCTTCCAGATGAATTCTTGCTCTCACACTCTCTTCAAGCATTT

AACCCAAGTGGCGACTTGGTTGACCTTGATGTTATCAAGAAATTGGATGC

CATCTTTGATGACTTCCGTATCTTTGTAAAAATCACAGAAAAATTACGTA

ATGCACAAGAATTACTTCGCAAAGATGCTGAAGACTTTGACTGGGAAAAT

TTGTAA 4146.2

(SEQ. ID. NO. 258)
ATGAATACCTATCAATTAAATAATGGAGTAGAAATTCCAGTATTGGGATT

TGGAACTTTTAAGGCTAAGGATGGAGAAGAAGCCTATCGTGCAGTGTTAG

AAGCCTTGAAGGCTGGTTATCGTCATATTGATACGGCGGCGATTTATCAG

AATGAAGAAAGTGTTGGTCAAGCAATCAAAGATAGCGGAGTTCCACGTGA

AGAAATGTTCGTAACTACCAAGCTTTGGAATAGTCAGCAAACCTATGAGC

AAACTCGTCAAGCTTTGGAAAAATCTATAGAAAAACTGGGCTTGGATTAT

TTGGATTTGTATTTGATTCATTGGCCGAACCCAAAACCGCTCAGAGAAAA

TGACGCATGGAAAACTCGCAATGCGGAAGTTTGGAGAGCGATGGAAGACC

TCTATCAAGAAGGGAAAATCCGTGCTATCGGCGTTAGCAATTTTCTTCCC

CATCATTTGGATGCCTTGCTTGAAACTGCAACTATCGTTCCTGCGGTCAA

TCAAGTTCGCTTGGCGCCAGGTGTGTATCAAGATCAAGTCGTAGCTTACT

GTCGTGAAAAGGGAATTTTATTGGAAGCTTGGGGCCTTTTGGACAAGGA

GAACTGTTTGATAGCAAGCAAGTCCAAGAAATAGCAGCAAATCACGGAAA

ATCGGTTGCTCAGATAGCCTTGGCCTGGAGCTTGGCAGAAGGATTTTTAC

CACTTCCAAAATCTGTCACAACCTCTCGTATTCAAGCTAATCTTGATTGC

TTTGGAATTGAACTGAGTCATGAGGAGAGAGAAACCTTAAAAACGATTGC

TGTTCAATCGGGTGCTCCACGAGTTGATGATGTGGATTTCTAG 4147.1

(SEQ. ID. NO. 259)
ATGAGGTGCAAAATGCTTGATCCAATTGCTATTCAACTAGGACCCCTAGC

CATTCGTTGGTATGCCTTATGTATTGTGACAGGCTTGATTCTTGCGGTTT

ATTTGACCATGAAAGAAGCACCTAGAAAGAAGATCATACCAGACGATATT

TTAGATTTTATCTTAGTAGCCTTTCCCTTGGCTATTTTAGGAGCTCGTCT

CTACTATGTTATTTTCCGATTTGATTACTATAGTCAGAATTTAGGAGAGA

TTTTTGCCATTTGGAATGGTGGTTTGGCCATTTACGGTGGTTTGATAACT

GGGGCTCTTGTGCTCTATATCTTTGCTGACCGTAAACTCATCAATACTTG

GGATTTTCTAGATATTGCGGCGCCTAGCGTTATGATTGCTCAAAGTTTGG

GGCGTTGGGGTAATTTCTTTAACCAAGAAGCTTATGGTGCAACAGTGGAT

AATCTGGATTATCTACCTGGCTTTATCCGTGACCAGATGTATATTGAGGG

GAGCTACCGTCAACCGACTTTCCTTTATGAGTCTCTATGGAATCTGCTTG

GCTTTGCCTTGATTCTGATTTTTAGACGGAAATGGAAGAGTCTCAGACGA

GGTCATATCACGGCCTTTTACTTGATTTGCTATGGTTTCGGTCGTATGGT

TATCGAAGGTATGCGAACAGATAGTCTCATGTTCTTCGGCTTTCGAGTGT

CCCAATGGCTGTCAGTTGTCCTTATCGGTCTCGGTATAATGATCGTTATT

TATCAAAATCGAAAGAAGGCCCCTTACTATATTACAGAGGAGGAAAACTA

A 4147.2

(SEQ. ID. NO. 260)
ATGGGTAAATTATCCTCAATCCTTTTAGGAACCGTTTCAGGTGCAGCTCT

TGCCTTGTTTTTAACAAGTGATAAGGGCAAACAAGTTTGCAGTCAGGCTC

AAGATTTTCTAGATGATTTGAGAGAAGATCCGGAGTATGCCAAGGAGCAA

GTCTGTGAAAAACTGACAGAAGTTAAGGAGCAGGCTACAGATTTTGTTCT

GAAAACAAAAGAACAGGTTGAGTCAGGTGAAATCACTGTGGACAGTATAC

TTGCTCAAACTAAATCCTATGCTTTTCAAGCGACAGAAGCATCAAAAAAT

CAATTAAATAATCTCAAGGAGCAATGGCAAGAAAAAGCCGAAGCTCTTGA

TGACTCAGAAGAGATTGTGATTGATATAACAGAAGAATAA 4147.3

(SEQ. ID. NO. 261)
ATGAAAACTAAATTGATCTTTTGGGGCTCTATGCTCTTTCTCCTCTCCCT

CTCCATCCTTCTGACCATTTATCTGGCTTGATTTTCTATCCTATGGAGAT

TCAGTGGCTAAACTTAACGAATCGAGTCTATCTAAAACCAGAAACCATTC

AATACAATTTTCATATCTTGATGAATTATCTGACCAATCCTTTTAGTCAG

GTCTTACAGATGCCTGATTTTCGTTCGTCAGCAGCTGGTCTGCACCATTT

CGCAGTGGTCAAGAATCTCTTTCATTTGGTTCAGCTAGTAGCTCTAGTGA

CACTGCCAAGTTTCTATGTCTTTGTCAATAGGATTGTGAAAAGGACTTT

TTGTCTCTTTATCGAAAAAGTCTCCTGGCTCTAGTAGTCTTACCTGTGAT

GATTGGACTTGGGGAGTTTTCATTGGTTTTGACCAATTCTTTACTCTTT

TCCATCAAATTCTCTTTGTGGGAGATGATACCTGGCTTTTTGATCCAGCC

AAGGATCCTGTTATTATGATTTTGCCAGAGACCTTCTTTCTTCATGCCTT

TABLE 1-continued

CCTCCTCTTTTTTGCCCTCTATGAAAACTTCTTTGGCTATCTGTATCTGA
AAAGTCGTAGGAAGTGA 4149.1

(SEQ. ID. NO. 262)
ATGACTTATCATTTTACTGAAGAATACGATATTATTGTAATTGGTGCGGG
ACACGCTGGGGTTGAGGCTTCCTTGGCCGCTAGCCGTATGGGCTGTAAGG
TCCTGCTTGCGACCATCAATATTGAAATGCTGGCTTTCATGCCTTGTAAT
CCCTCTATCGGTGGTTCTGCCAAGGGGATTGTCGTGCGTGAAGTCGATGC
CCTCGGTGGCGAGATGGCCAAAACCATTGACAAGACTTACATCCAGATGA
AGATGCTAAACACAGGGAAGGGGCCAGCTGTCCGTGCCCTTCGTGCGCAG
GCTGACAAGGAACTTTACTCTAAGGAGATGCGCAAGACGGTTGAAAACCA
AGAAAATCTGACCCTTCGTCAAACCATGATTGATGAGATTTTGGTGGAAG
ATGGCAAGGTTGTCGGTGTGCGTACAGCCACCCATCAAGAATATGCTGCT
AAGGCTGTTATTGTGACGACAGGGACTGCTCTCCGTGGGGAAATTATCAT
CGGAGACCTCAAGTACTCATCAGGTCCTAACCACAGCTTGGCTTCTATTA
ACCTAGCTGACAATCTCAAGGAACTGGGTCTCGAAATCGGTCGTTTCAAG
ACAGGACCCCTCCACGTGTCAAGGCTTCTTCTATCAATTACGATGTGACA
GAAATTCAGCCAGGAGACGAAGTGCCTAATCATTTCTCATACACTTCACG
TGATGAGGATTATGTCAAGGACCAAGTACCATGCTGGTTGACCTATACCA
ATGGTACCAGTCATGAGATTATCCAAAACAACCTCCACCGTGCGCCTATG
TTTACAGGTGTGGTCAAGGGAGTGGGGCCTCGTTACTGTCCGTCGATTGA
AGACAAGATTGTGCGCTTTGCGGACAAGGAACGTCACCAACTCTTCCTTG
AGCCAGAAGGGCGCATTACTGAGGAAGTCTATGTGCAAGGACTTTCAACC
AGTCTGCCTGAGGATGTCCAGCGTGACTTGGTGCATTCCATCAAAGGTTT
GGAAAATGCAGAGATGATGCGGACAGGTTATGCTATTGAGTATGATATGG
TCTTGCCTCATCAGTTGCGTGCGACTTTGGAAACCAAGAAAATCTCAGGT
CTCTTCACTGCTGGTCAGACAAATGGAACATCAGGTTACGAAGAGGCAGC
AGGCCAAGGGATTATCGCGGGTATCAATGCGGCTCTGAAAATCCAAGGCA
AGCCTGAATTGATTTTGAAGCGCAGTGATGGTTATATCGGGGTGATGATC
GACGACTTGGTGACCAAGGGAACCATTGAACCCTACCGTCTCTTGACCAG
TCGTGCTGAATACCGTCTCATTCTTCGTCATGACAATGCTGATATGCGCT
TGACTGAGATGGGACGCGAGATTGGCCTTGTGGACGATGAACGCTGGGCT
CGTTTTGAAATCAAGAAAAATCAATTTGATAATGAGATGAAGCGCCTAGA
CAGTATCAAACTCAAGCCAGTCAAGGAAACCAATGCCAAGGTTGAGGAGA
TGGGCTTCAAACCCTTGACCGATGCAGTGACAGCCAAGGAATTCCTTCGC
CGTCCAGAAGTTTCTTACCAAGATGTGGTGGCCTTCATCGGACCAGCTGC
AGAAGACTTGGATGACAAGATTATCGAATTGATTGAAACAGAAATCAAGT
ATGAAGGCTATATTTCCAAAGCCATGGACCAGGTTGCCAAGATGAAACGC
ATGGAAGAAAACGCATTCCGGCCAATATCGACTGGGATGACATTGATTC
TATCGCAACCGAAGCCCGTCAGAAGTTCAAACTCATCAATCCAGAAACCA
TCGGCCAAGCCAGCCGTATTTCGGGAGTAAACCCAGCAGATATTTCTATT

TTGATGGTGTATCTGGAAGGTAAAAATCGTAGTATTTCTAAAACTCTTCA
AAAATCAAAATGA 4149.2

(SEQ. ID. NO. 263)
ATGAAAGTATTAGCTTTTGATACGTCCAGCAAGGCTCTTTCTCTGGCTAT
TTTAGAGGATAAGCAGGTTCTTGCCGAGACGACGATTAATATTAAGAAAA
ATCACAGTATTACTCTTATGCCTGCCATCGATTTTTTGATGGCAAGTTTG
GATTGGACACCCAAGGATTTGGACCGAATCGTGGTAGCTGAAGGGCCGGG
TAGCTATACAGGCTTGCGAATTGCGGTAGCAACTGCTAAGACCTTAGCTC
ACACCCTGAACATCGAGTTGGTTGGTATGTCGAGTCTCTTGGCTCTGGTG
CCCCATCAACAAGAAGGTTTGTTTGTCCCCTTGATGGATGCGCGTCGCAA
TAATGTTTATGCAGGATTTTATGAAAATGCCAAACCTGTCATGGCAGAAG
CGCACCTATCTTTTGAAGAGGTGCTAGAAAAAGTCAAGGGTACTAGTCAG
GTAACCTTTGTCGGAGAAGTTGGCCCCTTTTGTTGAGCAGATTCAAAAAC
ACTTGCCAAGGACTGATTACAAAGAAACATTGCCCAATGCAGCTAATCTA
GCTCTTTTGGCCTGGGACAAGGAAGCAGACTCCTTGCATGATTTTGTGCC
GAATTACCTCAAACGAGTCGAGGCTGAGGAAAACTGGCTCAAGAACCATA
CCGAGTCTGGCGAGTCTTACATTAAACGCCTATGA 4149.3

(SEQ. ID. NO. 264)
ATGATAGAAATCAAGCGAATTCAACAACAGCCTGACCTAGCTCAAGCCAT
CTACGCTGTTATGGCAGCTGTTTACCTAGTCAGTCCTTGGACTCTGGAGC
AAATCCAAGCAGATCTGTCCCAAGACCAGACTTGGTATGCATTGGCTTAT
GATGGGGCAGAAGTGATTGGATTTCTAGCTGTGCAGGAGAATCTTTTTGA
AGCAGAAGTCCTGCAAATCGCTGTCAAAGGAGCTTATCAGGGTCAGGGGA
TTGCGTCagCCTTGTTTGCTCAATTGCCGACAGACAAGGAAATTTTCCTC
GAAGTCAGACAGTCAAATCAACGAGCGCAAGCATTTTACAAGAAAGAAAA
GATGACAGTTATCGCTGAGCGAAAGGCCTACTACCATGACCCAGTCGAGG
ACGCCATTATCATGAAGAGAGAAATAGATGAAGGATAG 4152.2

(SEQ. ID. NO. 265)
ATGACAAAACAAGTCTTATTAGTGGATGATGAAGAACACATTCTGAATT
GCTTGACTACCATTTAAGTAAGGAAGGCTTTTCTACTCAATTGGTGACAA
ATGGACGGAAGGCCTTAGCTTTGGCAGAAACAGAACCCTTTGATTTTATC
TTGCTTGATATCATGTTACCACAATTAGATGGCATGGAAGTTTGTAAGCG
GCTGAGAGCCAAAGGCGTCAAAACTCCAATTATGATGGTTTCTGCGAAAA
GTGATGAATTTGATAAGGTTTTGGCCTTGGAATTAGGGGCTGATGACTAC
CTGACCAAGCCTTTTAGCCCTAGAGAATTGCTGGCGGCGTGCAAGGCTGT
CCTCAGGCGAACTAAAGGAGAACAAGAAGGAGATGATTCAGATAATATCG
CTGACGATTCTTGGCTATTTGGGACCTTGAAAGTATACCCTGAGCGTCAT
GAAGTCTACAAGGCGAATAAGTTACTGAGTTTGACCCCAAAAGAATTTGA
AAGCGATAAAAATCCGTTTTTTGAAGTTTTCAAAGTTTCGAAAGTAACCG
CCCAATAA

TABLE 1-continued 4154.1
(SEQ. ID. NO. 266)
ATGACTACTTTTAAAGATGGATTTTTATGGGGTGGTGCTGTTGCTGCTCA
TCAACTTGAAGGTGGATGGCAAGAAGGTGGCAAGGGAATTAGTGTTGCTG
ATGTTATGACTGCTGGTCGTCATGGAGTAGCTCGTGAAATACTTTGGGAG
TTTTAGAGGGTAAATATTATCCAAATCATGAGGCGATAGATTTTTATCAC
CGTTATAAAGAAGATATAGCACTTTTTGCTGAAATGGGATTCAAGTGCTT
CCGTACCTCTATTGCATGGACACGTATCTTTCCAAAAGGTGATGAGTTAG
AGCCGAATGAAGAAGGATTACAGTTTTATGATAATCTTTTTGATGAATGC
TTAAAGAATGGTATTGAACCTGTCATCACTCTATCTCATTTTGAAATGCC
TTATCACTTAGTGACCGAATATGGTGGTTGGAAAAATAGGAAATTGATTG
ATTTCTTTGCTCGTTTTGCAGAAGTCGTATTTAAACGTTACAAAGATAAG
GTTAAATATTGGATGACTTTCAATGAAATCAATAATCAAGCGAATTATCA
GGAAGATTTTGCACCATTTACTAACTCAGGTATTGTATATGAGGAAGGTG
ATAATAGAGAAGCAATTATGTATCAAGCAGCACATTACGAATTAGTTGCT
TCTGCACGAGCTGTAAAAATTGGTCATGAGATTAATCCAGATTTTCAAAT
AGGTTGTATGATTGCGATGTGTCCAATTTATCCAGTTACTTGCAATCCTA
AGGATATCTTAATGGCAATGAAAGCTATGCAGAAGCGTTATTATTTTGCT
GATGTGCATGTTTTAGGTAAATATCCTGAGCATATTTTCAAGTATTGGGA
ACGAAAAGGTATTTCAGTTGATTTTACTGCCCAGGATAAAGAAGATTTAC
TTGGTGGGACTGTAGATTACATTGGTTTCAGTTACTATATGTCCTTTGCT
ATCGACTCTCATCGTGAAAATAATCCTTATTTTGATTATCTTGAAACAGA
AGATTTAGTGAAAAATAATTATGTTAAGGCTTCTGAATGGGAGTGGCAAA
TTGATCCAGAAGGTTTGCGTTATGCGTTAAATTGGTTTACAGACCACTAT
CACTTACCACTCTTTATTGTTGAAAATGGTTTTGGAGCTATAGATCAAGT
TGCAGCAGATGGTATGGTACATGATGATTATAGAATTGAATATCTAGGTG
CCCATATTCGTGAAATGAAAAAGGCTGTAGTTGAAGATGGTGTTGATTTA
ATGGGTTATACTCCATGGGGATGTATTGATTTGGTTTCAGCTGGTACCGG
TGAAATGCGGAAACGTTATGGCTTTATTTATGTAGATAAAGATGATAATG
GGAAGGGAAGTTATAATCGTTCCCCGAAAAAATCTTTTGGCTGGTATAAG
GAAGTTATTTCATCTAACGGTGAATCAGTAGAATAG 4154.2
(SEQ. ID. NO. 267)
ATGGATCAACAAAACGGGTTGTTTGGTTTTCTTGAAAACCATGTTATGGG
ACCAATGGGCAAACTTGCTCAGTTTAAAGTAGTACGTGCTATCACGGCTG
CAGGTATGGCTGCTGTACCATTTACTATTGTAGGATCAATGTTTTTGGTA
TTCAGTATTTTGCCACAAGCTTTCTCATTTTGGCCAATTGTGGCAGATAT
TTTCTCTGCTTCATTTGATAAATTCACATCACTTTACATGGTTGCAAACT
ATGCGACTATGGTTCTCTATCTCTTTATTTCGTTCTATCACTTGCATAT
GAATTGACAAAAATTTATGCAGAGGAAGAAGAACTCAATATGAATCCTCT
TAATGGTGCCTTGCTTGCCTTGATGGCTTTTGTCATGACAGTACCGCAAA
TCATTTTTGATGGTGGAATGATGAAGACTGTGACAAGTCTAAAAGAAGGT TABLE 1-continued GCAGTAATTGCAGATGGATGGGCAATGGGAAATGTCGTCGCACGTTTTGG
GACAACAGGGATTTTTACCGCAATCATTATGGCAATTGTGACTGTTCTTA
TTTATCGTATGTGTGTTAAACATAATTGGGTTATTAAAATGCCTGAAGCT
GTTCCAGAAGGAGTTTCTCGTGGATTTACCGCTTTGGTTCCGGGATTTGT
TGTTGCATTTGTTGTTATCTTTATCAACGGTCTTCTTGTAGCAATGGGAA
CAGATATTTTTAAAGTCATTGCAATTCCATTTGGTTTTGTATCCAATCTG
ACTAATTCGTGGATTGGTTTAATGATTATTTATCTATTGACTCAACTACT
TTGGATTGTAGGTATCCACGGTGCGAACATTGTTTTTGCATTTGTTAGTC
CAATTGCTCTTGCTAACATGGCTGAAAATGCTGCTGGCGGGCACTTCGCT
GTTGCAGGTGAATTTTCTAATATGTTTGTAATTGCAGGTGGTTCTGGTGC
AACTTTAGGACTATGTTTATATATTGCTTTTGCCTCTAAATCTGAACAGC
TTAAAGCAATAGGACGAGCATCTGTAGTTCCAGCCTTATTTAATATTAAT
GAACCATTAATTTTTGGATTACCTATTATCTATAATCCAGCCTTGGCTAT
ACCATTTATTTTAGCACCAATGGTTACTGCTACTATTTATTACGTAGCGA
ATTCTCTAAACTTTATTAAGCCAATTATCGCACAGGTTCCATGGCCAACT
CCAGTAGGGATTGGAGCTTTCTTAGGGACAGCAGATCTTCGAGCTGTATT
AGTTGCTCTAGTATGTGCATTTGCAGCATTCCTAGTCTATCTTCCATTCA
TCCGTGTATATGATCAAAAATTGGTGAAAGAAGAGCAAGGTATCTAA 4155.1
(SEQ. ID. NO. 268)
ATGAAAAAATTTTATGTAAGTCCAATTTTTCCTATTCTAGTAGGATTGAT
TGCGTTTGGAGTCTTATCCACTTTCATTATTTTTGTTAATAATAATCTGT
TGACGGTTTTAATTTTGTTTCTTTTTGTAGGAGGCTATGTTTTTTTATTT
AAGAAACTGAGAGTGCATTATACAAGGAGTGATGTAGAACAGATACAGTA
TGTAAACCACCAAGCGGAAGAAAGTTTGACAGCTCTATTGGAACAGATGC
CTGTAGGTGTTATGAAATTGAATTTATCTTCTGGAGAGGTTGAGTGGTTT
AATCCCTATGCTGAATTGATTTTGACCAAGGAAGATGGTGATTTTGATTT
AGAAGCTGTTCAAACGATTATCAAGGCTTCAGTAGGAAATCCGTCTACTT
ATGCCAAGCTTGGTGAGAAGCGTTATGCTGTTCATATGGATGCTTCTTCC
GGTGTTTTGTATTTTGTAGATGTATCCAGGGAACAAGCCATAACAGATGA
ATTGGTAACAAGTAGACCAGTGATTGGGATTGTCTCTGTGGATAATTATG
ATGATTTGGAGGATGAAACTTCTGAGTCAGATATTAGTCAAATCAATAGT
TTTGTAGCTAATTTTATATCAGAGTTTTCAGAAAAACACATGATGTTTTC
TCGTCGGGTAAGTATGGATCGATTTTATCTATTTACTGACTACACGGTGC
TTGAGGGCTTGATGAATGATAAATTTTCTGTTATTGATGCTTTCAGAGAA
GAGTCGAAACAGAGACAGTTGCCCTTGACCTTAAGTATGGGATTTTCTTA
TGGCGATGGAAATCATGATGAGATAGGGAAAGTTGCTTTGCTCAATTTGA
ACTTGGCTGAAGTACGTGGTGGCGACCAGGTGGTTGTTAAGGAAAACGAC
GAAACGAAAAATCCAGTTTATTTTGGTGGTGGGTCTGCTGCTTCAATCAA
GCGTACACGGACTCGTACGCGCGCTATGATGACAGCTATTTCAGATAAGA
TTCGGAGTGTAGATCAGGTTTTTGTAGTCGGTCACAAAAAATTTAGACATG GATGCTTTGGGCTCTGCTGTAGGTATGCAGTTGTTCGCCAGCAATGTGAT
TGAAAATAGCTATGCTCTTTATGATGAAGAACAAATGTCTCCAGATATTG
AACGAGCTGTTTCATTCATAGAAAAGAAGGAGTTACGAAGTTGTTGTCT
GTTAAGGATGCAATGGGATGGTGACCAATCGTTCTTTGTTGATTCTTGT
AGACCATTCAAAGACAGCCTTAACATTATCAAAAGAATTTTATGATTTAT
TTACCCAAACCATTGTTATTGACCACCATAGAAGGGATCAGGATTTTCCA
GATAATGCGGTTATTACTTATATCGAAAGTGGTCAAGTAGTGCCAGTGA
GTTGGTAACGGAATTGATTCAGTTCCAGAATTCTAAGAAAAATCGTTTGA
GTCGTATGCAAGCAAGTGTCTTGATGGCTGGTATGATGTTGGATACTAAA
AATTTCACCTCGCGAGTAACTAGTCGGACATTTGATGTTGCTAGCTATCT
CAGAACGCGCGGAAGTGATAGTATTGCTATCCAGGAAATCGCTGCGACAG
ATTTTGAAGAATATCGTGAGGTCAATGAACTTATTTTACAGGGGCGTAAA
TTAGGTTCAGATGTACTAATAGCAGAGGCTAAGGACATGAAATGCTATGA
TACAGTTGTTATTAGTAAGGCAGCAGATGCCATGTTAGCCATGTCAGGTA
TTGAAGCGAGTTTTGTTCTTGCGAAGAATACACAAGGATTTATCTCTATC
TCAGCTCGAAGTCGTAGTAAACTGAATGTACAACGGATTATGGAAGAGTT
AGGCGGTGGAGGCCACTTTAATTTGGCAGCAGCTCAAATTAAAGATGTAA
CCTTGTCAGAAGCAGGTGAAAAACTGACAGAAATTGTATTAAATGAAATG
AAGGAAAAGGAGAAAGAAGAATGA 4156.1

(SEQ. ID. NO. 269)

ATGAAAGAGAAAAATATGTGGAAAGAATTGTTGAATCGTGCAGGCTGGAT
TTTGGTCTTTTTACTTGCCGTCCTTTTATATCAGGTTCCCCTAGTGGTTA
CCTCTATTTTGACTTTAAAAGAAGTAGCCCTGCTACAGTCAGGGCTGATA
GTTGCTGGCCTTTCAATTGTGGTTCTGGCTCTATTTATTATGGGAGCTCG
TAAAACCAAGTTAGCTAGTTTTAATTTTCTTTTTTTAGAGCTAAAGATT
TGGCACGTTTGGGCTTGAGTTATCTAGTTATTGTCGGGTCAAATATACTT
GGTTCCATTTTATTGCAACTGTCAAATGAGACGACAACAGCTAACCAGTC
TCAGATTAATGATATGGTTCAAAATAGTTCGTTGATTTCCAGTTTCTTCT
TGCTAGCCTTGCTTGCTCCGATTTGTGAGGAAATCTTGTGTCGTGGGATT
GTTCCTAAAAAGATTTTCCGAGGCAAGGAGAACTTGGGATTTGTAGTCGG
TACGATTGTGTTTGCTTATTGCATCAACCAAGTAATTTACCTTCTTTAT
TGATTTATGGAGGTATGTCGACAGTTCTATCTTGGACAGCCTACAAGACC
CAACGTTTGGAAATGTCGATCTTGCTTCACATGATTGTTAATGGGATTGC
TTTCTGTTTGTTGGCTCTTGTGGTGATTATGAGTCGGACATTAGGAATTT
CTGTTTAAATGAAAGAGAAAATATGTGGAAAGAATTGTTGAATCGTGCA
GGCTGGATTTTGGTCTTTTTACTTGCCGTCCTTTTATATCAGGTTCCCCT
AGTGGTTACCTCTATTTTGACTTTAAAAGAAGTAGCCCTGCTACAGTCAG
GGCTGATAGTTGCTGGCCTTTCAATTGTGGTTCTGGCTCTATTTATTATG
GGAGCTCGTAAAACCAAGTTAGCTAGTTTTAATTTTCTTTTTTTAGAGC
TAAAGATTTGGCACGTTTGGGCTTGAGTTATCTAGTTATTGTCGGGTCAA

ATATACTTGGTTCCATTTTATTGCAACTGTCAAATGAGACGACAACAGCT
AACCAGTCTCAGATTAATGATATGGTTCAAAATAGTTCGTTGATTTCCAG
TTTCTTCTTGCTAGCCTTGCTTGCTCCGATTTGTGAGGAAATCTTGTGTC
GTGGGATTGTTCCTAAAAAGATTTTCCGAGGCAAGGAGAACTTTGGGATT
GTAGTCGGTACGATTGTGTTTGCTTTATTGCATCAACCAAGTAATTTACC
TTCTTTATTGATTTATGGAGGTATGTCGACAGTTCTATCTTGGACAGCCT
ACAAGACCCAACGTTTGGAAATGTCGATCTTGCTTCACATGATTGTTAAT
GGGATTGCTTTCTGTTTGTTGGCTCTTGTGGTGATTATGAGTCGGACATT
AGGAATTTCTGTTTAA 4156.4

(SEQ. ID. NO. 270)

ATGGATACACAAAAGATTGAAGCGGCTGTAAAAATGATTATCGAGGCTGT
AGGAGAGGACGCTAATCGCGAGGGCTTGCAGGAAACACCTGCTCGTGTAG
CCCGTATGTATCAAGAGATTTTTTCAGGTCTTGGTCAAACAGCAGAGGAA
CATTTGTCAAAATCCTTTGAAATTATTGACGATAATATGGTGGTAGAAAA
GGATATCTTTTTCCATACCATGTGTGAACACCACTTCTTGCCATTTTATG
GTAGAGCGCACATTGCCTACATTCCAGATGGTCGTGTGGCAGGCTTGTCT
AAGCTAGCCCGTACGGTTGAAGTTTATTCGAAAAAACCACAAATTCAAGA
ACGTTTGAATATCGAAGTGGCCGATGCCTTGATGGACTATCTAGGTGCTA
AAGGAGCCTTTGTTGTCATTGAGGCGGAACATATGTGTATGAGTATGCGT
GGTGTTAGAAAACCAGGCACTGCAACCTTGACGACAGTAGCTCGTGGTCT
ATTTGAAACAGATAAGGATCTCCGTGACCAAGCTTATCGTTTAATGGGGC
TATAA 4157.2

(SEQ. ID. NO. 271)

ATGAAAGACTTGTTTTTAAAGAGAAAGCAGGCCTTTCGTAAGGAGTGTCT
TGGTTATCTGCGCTATGTGCTCAATGACCACTTTGTCTTGTTCCTGCTTG
TCCTGTTGGGCTTTCTAGCCTACCAGTACAGTCAACTCTTACAACATTTT
CCTGAAAATCATTGGCCTATCCTTTTGTTTGTAGGAATTACGTCTGTTTT
ACTTTTACTTTGGGGAGGAACTGCCACCTATATGGAGGCTCCAGACAAGC
TCTTTCTCTTAGTTGGAGAAGAGGAAATTAAGCTCCATCTCAAGCGTCAA
ACTGGCATTTCCCTAGTCTTTTGGCTCTTTGTACAGACCCTTTTCTTGCT
GTTATTTGCGCCTTTATTTTTAGCAATGGGTTATGGCTTGCCAGTTTTTC
TGCTCTATGTGCTTTTATTGGGGGTAGGAAAATATTTCCACTTTTGTCAA
AAGGCCAGCAAATTTTTCACTGAAACTGGACTGGACTGGGACTATGTTAT
TTCTCAAGAAAGCAAGCGTAAGCAAGTCTTGCTTCGTTTCTTTGCCCTCT
TTACGCAGGTCAAGGGAATTTCAAACAGCGTTAAGCGTCGTGCCTATCTG
GACTTTATTTTAAAGGCTGTTCAGAAGGTGCCTGGGAAGATTTGGCAAAA
TCTCTATCTGCGTTCTTATCTGCGAAATGGCGACCTCTTTGCTCTCAGTC
TTCGTCTTCTCTTGCTTTGCCTTGCTGGCGCAGGTTTTTATCGAGCAAGC
TTGGATTGCGACAGCAGTGGTAGTTCTCTTTAACTACCTCTTGCTCTTCC
AGTTGCTGGCCCTCTATCATGCCTTTGACTACCAGTATTTGACCCAACTC

TTTCCGCTGGACAAGGGGCAAAAGGAAAAAGGCTTACAGGAGGTAGTTCG
AGGATTGACCAGTTTTGTTTTACTTGTGGAATTAGTTGTTGGGTTGATTA
CCTTCCAAGAAAAACTAGCCCTTCTAGCCTTACTAGGAGCTGGTTTGGTT
TTACTAGTCTTGTATTTGCCTTATCAGGTAAAACGTCAGATGCAGGACTA
A 4258.2
(SEQ. ID. NO. 272)
ATGAGAAAATCAATAGTATTAGCGGCAGATAATGCCTATCTTATTCCTTT
AGAGACGACTATAAAGTCTGTATTGTATCACAATAGAGATGTTGATTTTT
ATATTCTCAACAGTGATATAGCTCCTGAATGGTTTAAATTATTGGGGAGA
AAAATGGAAGTTGTGAATTCTACAATTCGCAGTGTACACATTGATAAAGA
ACTTTTTGAAAGCTATAAAACAGGACCTCATATAAATTATGCTTCTTACT
TTAGATTTTTTGCGACAGAAGTGGTTGAATCTGATAGGGTATTGTATCTG
GATTCCGATATCATTGTAACTGGGGAACTAGCTACTTTGTTTGAGATAGA
TCTCAAAGGATATTCAATTGGTGCTGTTGATGATGTCTATGCCTATGAAG
GACGAAAATCTGGATTTAATACTGGTATGTTACTAATGGATGTTGCAAAG
TGGAAAGAACATTCTATTGTCAATAGTTTATTGGAATTAGCGGCCGAGCA
GAATCAAGTTGTTCATCTTGGGGATCAGAGTATTTTAAATATTTATTTTG
AGGATAATTGGCTAGCCTTAGATAAAACATATAATTATATGGTGGGTATT
GATATTTATCACCTTGCTCAAGAATGTGAACGTCTAGATGACAATCCACC
TACAATTGTTCACTATGCTAGTCATGATAAACCTTGGAATACATATAGTA
TATCTAGACTACGTGAATTATGGTGGGTTTATAGAGATTTGGATTGGTCA
GAGATTGCTTTTCAACGTTCCGATTTAAATTATTTTGAAAGAAGCAATCA
GTCTAAAAAACAAGTGATGCTTGTGACATGGAGTGCAGATATAAAACATT
TAGAGTATTTAGTACAACGGTTACCTGATTGGCATTTTCATTTGGCTGCA
CCGTGTGATTGTTCTGAGGAGCTGACCTCTCTATCACAGTATACGAATGT
AACAGTATATCAAAATGTATTACATAGTAGAATTGATTGGCTATTGGACG
ATTCTATAGTTTATTTAGATATTAATACAGGTGGAGAGGTTTTTAATGTA
GTTACAAGGGCACAAGAAAGTGGCAAGAAAATCTTCGCTTTTGATATCAC
ACGTAAAAGTATGGATGATGGACTCTATGACGGTATTTTTTCTGTGGAGA
GACCAGATGATTTAGTGGATAGAATGAAGAATATAGAGATAGAGTAA 4158.2
(SEQ. ID. NO. 273)
ATGACTAAGATTTATTCGTCAATAGCAGTAAAAAAAGGACTATTTACCTC
ATTTCTACTGTTTATCTATGTATTGGGAAGTCGTATTATTCTCCCTTTTG
TTGACCTAAATACTAAAGATTTTTTAGGAGGTTCAACAGCCTATCTAGCC
TTCTCAGCCGCCCTAACAGGTGGGAATCTAAGAAGTTTATCAATTTTTTC
TGTTGGATTATCCCCTTGGATGTCCGCCATGATTTTATGGCAGATGTTTT
CTTTTTCTAAACGGTTGGGTTTAACATCTACGTCTATAGAAATACAAGAT
CGCCGTAAAATGTACCTGACCTTGCTAATTGCTGTGATTCAATCCTTGGC
AGTTAGCTTGAGACTGCCAGTACAATCCTCCTATTCTGCAATATTGGTTG
TTCTAATGAATACAATATTGCTGATAGCAGGAACATTTTTTCTTGTTTGG

TTGTCAGATTTAAATGCGAGTATGGGGATTGGAGGTTCTATTGTAATCCT
CCTATCCAGTATGGTTTTAAATATTCCTCAGGATGTTTTGGAAACATTTC
AGACAGTACACATTCCAACAGGGATTATTGTGTTACTTGCTTTATTAACC
CTTGTCTTTTCTTATTTACTTGCCCTTATGTATCGAGCTCGCTATTTGGT
TCCTGTTAATAAAATTGGCTTACACAATCGATTTAAACGCTATTCTTATC
TCGAAATCATGTTGAATCCTGCAGGTGGGATGCCTTATATGTATGTGATG
AGTTTTCTTAGTGTACCAGCTTATTTGTTCATCTTGTTGGGATTTATTTT
CCCTAATCATTCAGGGTTAGCGGCTTTATCAAAGGAATTTATGGTTGGAA
AGCCTTTGTGGGTCTATGTTTATATTTCGGTCTTATTTTTATTTAGTATC
ATTTTTGCTTTTGTTACGATGAATGGAGAAGAGATTGCAGACCGTATGAA
AAAATCTGGAGAATACATTTATGGTATTTATCCAGGTGCGGATACTAGTC
GATTTATTAATCGATTGGTCCTTCGTTTCTCAGTCATAGGTGGTCTCTTT
AATGTGATTATGGCAGGTGGTCCCATGCTTTTTGTTTTGTTTGATGAAAA
GTTATTACGATTGGCAATGATTCCAGGCTTATTTATGATGTTCGGGGGCA
TGATTTTTACGATTAGAGACGAGGTCAAGGCTTTAAGGCTAAATGAGACC
TATAGACCTTTGATTTAG 4158.3
(SEQ. ID. NO. 274)
ATGTCCTCTCTTTCGGATCAAGAATTAGTAGCTAAAACAGTAGAGTTTCG
TCAGCGTCTTTCCGAGGGAGAAAGTCTAGACGATATTTTGGTTGAAGCTT
TTGCTGTGGTGCGTGAAGCAGATAAGCGGATTTTAGGGATGTTTCCTTAT
GATGTTCAAGTCATGGGAGCTATTGTCATGCACTATGGAAATGTTGCTGA
GATGAATACGGGGAAGGTAAGACCTTGACAGCTACCATGCCTGTCTATT
TGAACGCTTTTTCAGGAGAAGGAGTGATGGTTGTGACTCCTAATGAGTAT
TTATCAAAGCGTGATGCCGAGGAAATGGGTCAAGTTTATCGTTTTCTAGG
ATTGACCATTGGTGTACCATTTACGGAAGATCCAAAGAAGGAGATGAAAG
CTGAAGAAAAGAAGCTTATCTATGCTTCGGATATCATCTACACAACCAAT
AGTAATTTAGGTTTTGATTATCTAAATGATAACCTAGCCTCGAATGAAGA
AGGTAAGTTTTACGACCGTTTAACTATGTGATTATTGATGAAATTGATG
ATATCTTGCTTGATAGTGCACAAACTCCTCTGATTATTGCGGGTTCTCCT
CGTGTTCAGTCTAATTACTATGCGATCATTGATACACTTGTAACAACCTT
GGTCGAAGGAGAGGATTATATCTTTAAAGAGGAGAAAGAGGAGGTTTGGC
TCACTACTAAGGGGCCAAGTCTGCTGAGAATTTCCTAGGGATTGATAAT
TTATACAAGGAAGAGCATGCGTCTTTTGCTCGTCATTTGGTTTATGCGAT
TCGAGCTCATAAGCTCTTTACTAAAGATAAGGACTATATCATTCGTGGAA
ATGAGATGGTACTGGTTGATAAGGGAACAGGGCGTCTAATGGAAATGACT
AAACTTCAAGGAGGTCTCCATCAGGCTATTGAAGCCAAGGAACATGTCAA
ATTATCTCCTGAGACGCGGGCTATGGCCTCGATCACCTATCAGAGTCTTT
TTAAGATGTTTAATAAGATATCTGGTATGACAGGGACAGGTAAGGTCGCG
GAAAAAGAGTTTATTGAAACTTACAATATGTCTGTAGTACGCATTCCAAC
CAATCGTCCGAGACAACGGATTGACTATCCAGATAATCTATATATCACTT

TABLE 1-continued

```
TACCTGAAAAAGTGTATGCATCCTTGGAGTACATCAAGCAATACCATGCT

AAGGGAAATCCTTTACTCGTTTTTGTAGGCTCAGTTGAAATGTCTCAACT

CTATTCGTCTCTCTTGTTTCGTGAAGGGATTGCCCATAATGTCCTAAATG

CTAATAATGCGGCGCGTGAGGCTCAGATTATCTCCGAGTCAGGTCAGATG

GGGGCTGTGACAGTGGCTACCTCTATGGCAGGACGTGGTACGGATATCAA

GCTTGGTAAAGGAGTCGCAGAGCTTGGGGGCTTGATTGTTATTGGGACTG

AGCGGATGGAAAGTCAGCGGATCGACCTACAAATTCGTGGCCGTTCTGGT

CGTCAGGGAGATCCTGGTATGAGTAAATTTTTGTATCCTTAGAGGATGA

TGTTATCAAGAAATTTGGTCCATCTTGGGTGCATAAAAAGTACAAAGACT

ATCAGGTTCAAGATATGACTCAACCGGAAGTATTGAAAGGTCGTAAATAC

CGGAAACTAGTCGAAAAGGCTCAGCATGCCAGTGATAGTGCTGGACGTTC

AGCACGTCGTCAGACTCTGGAGTATGCTGAAAGTATGAATATACAACGGG

ATATAGTCTATAAAGAGAGAAATCGTCTAATAGATGGTTCTCGTGACTTA

GAGGATGTTGTTGTGGATATCATTGAGAGATATACAGAAGAGGTAGCGGC

TGATCACTATGCTAGTCGTGAATTATTGTTTCACTTTATTGTGACCAATA

TTAGTTTTCATGTTAAAGAGGTTCCAGATTATATAGATGTAACTGACAAA

ACTGCAGTTCGTAGCTTTATGAAGCAGGTGATTGATAAAGAACTTTCTGA

AAAGAAAGAATTACGTTAATCAACATGACTTATATGAACAGTTTTTACGA

CTTTCACTGCTTAAAGCCATTGATGACAACTGGGTAGAGCAGGTAGACTA

TCTACAACAGCTATCCATGGCTATCGGTGGTCAATCTGCTAGTCAGAAAA

ATCCAATCGTAGAGTACTATCAAGAAGCCTACGCGGGCTTTGAAGCTATG

AAAGAACAGATTCATGCGGATATGGTGCGTAATCTCCTGATGGGGCTGGT

TGAGGTCACTCCAAAAGGTGAAATCGTGACTCATTTTCCATAA
```

4158.4
(SEQ. ID. NO. 275)
```
ATGATAGGGACTTTCGCCGCTGCTCTTGTAGCTGTACTAGCAAATTTCAT

CGTCCCTATTGAAATTACCCCAAATAGTGCCAATACTGAAATTGCACCAC

CAGATGGGATTGGGCAGGTTCTCAGCAACCTCTTGCTCAAACTGGTTGAC

AACCCAGTCAACGCCCTGTTACTGCTAACTATATTAGAATCTTATCTTGG

GCAGTCATTTTTGGAATCGCTATGAGAGAAGCCAGTAAAAATAGTCAAGA

ATTGCTAAAAACTATCGCTGACGTGACTTCTAAAATTGTCGAATGGATCA

TCAATCTGGCTCCATTTGGAATCCTTGGTCTTGTTTTAAAACCATTTCT

GACAAGGGAGTCGGAAGCCTTGCCAACTACGGTATTTTATTGGTTCTATT

AGTAACGACTATGCTTTTTGTTGCCCCTGTGGTCAACCCTTTGATTGCCT

TCTTCTTTATGAGACGCAATCCTTACCCTCTAGTTTGGAACTGCCTCCGT

GTCAGCGGTGTGACAGCCTTTTTCACTCGTAGTTCTGCGACTAACATTCC

TGTCAACATGAAACTCTGCCATGACCTTGGACTCAACCCAGATACCTATT

CTGTTTCTATCCCACTCGGTTCTACTATCAATATGGCTGGAGTAGCGATT

ACCATTAACCTTTTGACCCTTGCTGCAGTTAACACTCTTGGAATTCCTGT

TGACTTTGCCACAGCCTTTGTCCTCAGTGTGGTAGCAGCTATCTCATCCT

GTGATGCTTCAGGTATTGCCGGAGGTTCCCTCCTTCTTATCCCAGTTGCT
```

```
TGTAGCCTTTTCGGTATTTCTAACGATATTGCCATACAAATTGTTGGGGT

TGGTTTTGTGATTGGTGTCATCCAAGACTCATGTGAAACAGCCCTTAACT

CTTCTACAGATGTCCTCTTTACCGCCGTTGCCGAATACGCAGCAACCCGT

AAAAAATAA
```

4158.5
(SEQ. ID. NO. 276)
```
ATGTCTATTAGCCAACGTACGACCAAGCTCATCTTAGCTACCTGTCTTGC

CTGCCTGCTTGCTTATTTTCTCAATCTTTCGTCAGCAGTTTCGGCTGGAA

TTATCGCTCTCTTGAGCCTATCTGATACGCGTAGAAGTACTTTAAAACTG

GCTCGCAATCGTCTTTTTTCTATGCTTCTAGCTCTGGCTATCGGTGTTCT

AGCTTTTCACTTGAGCGGATTTCATATCTGGAGTCTCGGCCTCTATCTGG

CCTTCTACGTTCCTTTAGCCTACAAGATGGGCTGGGAAATTGGCATCACA

CCAAGCACTGTTTTGGTTAGCCATCTCTTGGTTCAAGAGTCAACCTCTCC

AGACCTTCTAGTCAATGAATTCCTTCTCTTTGCTATTGGTACAGGATTTG

CCTTGCTTGTTAATCTCTATATGCCTTCACGAGAAGAGGAAATCCAGCAC

TACCACACGCTGGTGGAAGAAAAGTTAAAAGATATCCTCCAGCGCTTCAA

ATACTATTTATCCAGAGGAGACGGACGCAACCGAGCACAGCTGGTAGCAG

AATTAGACACGCTTTTGAAAGAAGCCCTCAGACTGGTCTATTTGGATCAC

TCTGACCACCTCTTTCACCAGACAGACTACCATATCCACTACTTTGAGAT

GAGACAGCGACAAAGTCGTATCCTGAGAAACATGGCCCAACAGATTAACA

CTTGTCACCTTGCCGCCAGTGAAAGCCTGATCTTAGCGCAACTCTTTTCA

AAAAATTGCAGGTCAACTGAGCCAGACCAATCCTGCTTCTGATTTGCTAGA

TGAAATTGAACGTTATCTGGAAGTCTTCCGGAACCGCAGTCTGCCCAAGA

CAAGAGAAGAATTTGAAACCCGCGCCACCCTTCTTCAACTCCTACGTGAA

GCCAAAACCTTCATCCAAGTAAAAGTTGATTTTTACCAAAAATATAGACA

GTAA
```

4158.6
(SEQ. ID. NO. 277)
```
ATGGAAATCATGTCGCTTGCGATTGCTGTTTTTGCCGTCATCATTGGTTT

AGTCATTGGATATGTCAGCATCTCAGCTAAGATGAAATCATCTCAGGAAG

CTGCAGAGTTGATGCTTTTAAATGCTGAACAAGAAGCAACTAATTTACGT

GGACAAGCTGAGCGTGAAGCGGATTTACTTGTTAATGAAGCCAAACGTGA

AAGCAAGTCTCTTAAAAAAGAAGCACTATTGGAGGCAAAGAAGAAGCCA

GAAAATACCGTGAAGAAGTGGACGCTGAATTCAAATCAGAACGTCAAGAA

CTCAAACAAATCGAAAGTCGTTTGACAGAGAGAGCTACTAGCCTTGACCG

TAAGGACGACAATTTGACGAGTAAAGAACAAACACTTGAACAAAAAGAAC

AAAGTATTTCTGATAGAGCGAAAAACCTTGATGCGCGTGAAGAGCAATTA

GAGGAAGTCGAAAGACAAAAAGAAGCAGAACTAGAGCGTATTGGTGCGCT

GTCTCAGGCAGAAGCACGAGATATTATCTTGGCTCAGACAGAGGAAAACT

TGACCAGGAGATTGCCAGTCGCATTCGCGAAGCTGAGCAAGAGGTCAAG

GAACGTTCTGACAAAATGGCCAAGGACATCTTGGTTCAAGCTATGCAACG

TATCGCTGGTGAATATGTAGCGGAGTCAACAAACTCAACAGTTCATCTGC
```

TABLE 1-continued

CAGACGATACTATGAAGGGACGCATTATTGGTCGTGAAGGTCGTAACATT
CGTACCTTTGAAAGTTTGACAGGGGTCGATGTGATTATCGACGATACACC
AGAAGTGGTGACCTTGTCAGGATTTGATCCGATTCGTCGTGAGATTGCCC
GTATGACTATGGAAATGTTGCTCAAAGATGGTCGTATACATCCAGCTCGT
ATCGAAGAGTTGGTTGAGAAAAACCGTCAAGAGATTGACAATAAGATTCG
TGAATACGGTGAGGCTGCTGCCTATGAAATTGGTGCGCCAAACCTTCATC
CAGACTTGATGAAGATTATGGGACGTTTGCAGTTCCGTACTTCATATGGA
CAAAATGTTTTGCGCCATTCGATTGAGGTTGCTAAGTTGGCTGGTATCAT
GGCGAGCGAACTTGGTGAAAATGCGGCTCTTGCCCGTCGTGCTGGATTCC
TTCACGATATCGGGAAAGCCATTGACCATGAGGTTGAAGGTAGCCACGTT
GAAATCGGTATGGAATTGGCCCGTAAGTACAAGGAACCCCCAGTTGTGGT
GAATACGATTGCTAGTCACCACGGAGATGTTGAAGCTGAGAGCGTGATAG
CAGTTATCGTCGCTGCAGCAGATGCCTTGAGCGCAGCCCGTCCAGGTGCT
CGTAGTGAGTCTCTTGAAAGCTACATCAAGCGTCTCCATGATTTGGAAGA
AATTGCTAACGGCTTGAAGGAGTGCAAACTAGCTTTGCCCTTCAAGCAGG
ACGTGAAATTCGTATCATGGTCAATCCAGGAAAAATCAAGGACGACAAAG
TCACAATCTTGGCTCACAAAGTTCGTAAGAAAATTGAAAACAATCTCGAT
TATCCAGGAAATATCAAGGTAACCGTGATTCGCGAGCTTCGTGCAGTAGA
TTATGCTAAATAA 4158.7
(SEQ. ID. NO. 278)
ATGATGTTAAAACCCTCTATTGATACCTTGCTCGACAAGGTTCCTTCAAA
ATATTCACTCGTAATCTTGGAAGCAAAACGTGCCCACGAATTGGAAGCAG
GTGCCCCAGCAACTCAAGGTTTCAAGTCTGAAAAATCAACTCTTCGCGCT
TTAGAAGAAATCGAATCAGGAAACGTTACAATTCACCCAGATCCAGAAGG
AAAACGTGAAGCAGTGCGTCGCCGTATCGAAGAAGAAAACGCCGCAAGA
AGAAGAAGAAAAGAAAATCAAAGAGCAAATTGCTAAAGAAAAAGAAGATG
GTGAAAAAATTTAA 4161.1
(SEQ. ID. NO. 279)
ATGTCAGCATATCAATTACCGACCGTATGGCAGGATGAAGCTAGTAATCA
AGGAGCTTTTACGGGGCTAAACAGACCAACAGCAGGTGCCCGTTTCGAAC
AAAACTTGCCAAAAGGAGAACAAGCTTTTCAGCTTTATTCACTGGGAACA
CCAAATGGTGTGAAGGTTACTATCTTATTGGAAGAATTACTAGAAGCTGG
TTTTTAAGGAAGCGGCTTACGACTTGTATAAGATTGCTATCATGGATGGG
ATCAATTCGGATCAGACTTTGTGAAGCTCAATCCAAATTCCAAGATTCCA
GCCTTATTGGACCAGTCAGGTACTGAAAACGTAAGAGTCTTTGAGTCTGC
TCATATTCTTCTTTACCTTGCTGAGAAATTTGGAGCCTTTTTACCAAGTA
ATCCTGTGGAAAAGGTAGAAGTTTTGAATTGGCTATTCTGGCAAGCAGGT
GCAGCACCTTTTCTAGGTGGGGATTTGGACATTTCTTCAATTATGCTCC
TGAAAAATTGGAATATCCTATTAACCGTTTTACGATGGAAGTGAAACGCC
AGTTGGATTTATTGGATAAGGAATTGGCTCAGAAACCTTATATTGCAGGC

TABLE 1-continued

AATGACTATACGATTGCAGATATTGCTATCTGGTCTTGGTATGGACAGTT
AGTTCAAGGAAATCTTTACCAAGGTTCTGCAAAATTCTTGGATGCCTCAA
GTTATCAAAATCTAGTAAAATGGGCAGAAAAAATTGCCAATCGTCCAGCT
GTTAAGCGTGGCTTGGAAGTAACTTATACAGAAATTAAATAG 4161.2
(SEQ. ID. NO. 280)
TTGGCAAGCTTGATCACTTCTATCATCATGTTCTATGTCGGTTTCGATGT
TCTAAGAGATACCATTCAAAAGATTCTCAGTCGGGAAGAAACGGTCATTG
ATCCTCTTGGTGCAACTCTAGGAATCATTTCTGCAGCGATTATGTTTGTG
GTCTATCTCTACAATACTCGCCTCAGTAAGAAATCCAACTCCAATGCGCT
GAAGGCAGCTGCTAAGGACAATCTTTCTGACGCTGTTACCTCACTTGGAA
CCGCCATTGCCATCCTAGCTAGTAGTTTCAATTATCCGATTGTGGATAAA
CTGGTTGCTATCATCATCACTTTCTTTATCTTGAAGACTGCCTATGATAT
CTTCATCGAGTCTTCCTTTAGTCTTTCAGATGGCTTTGACGACCGCCTGC
TCGAGGACTACCAAAAGGCTATCATGGAAATTCCCAAAATCAGCAAGGTC
AAATCGCAAAGAGGTCGCACCTACGGTAGCAACATCTACCTGGATATTAC
ACTAGAGATGAATCCTGACTTGTCTGTTTTTGAAAGCCATGAAATCGCGG
ATCAGGTCGAGTCTATGCTGGAGGAGCGTTTTGGCGTCTTTGATACCGAT
GTCCATATCGAACCAGCACCTATCCCTGAGGATGAAATTTTAGACAATGT
CTATAAAAAATTGCTTATGCGTGAACAATTGATTGACCAAGGAAACCAAC
TAGAAGAACTCTTGACTGATGATTTTGTCTATATTCGCCAAGATGGAGAG
CAGATGGATAAAGAGGCTTATAAGACCAAAAAAGAGTTAAATTCTGCTAT
CAAGGACATTCAAATTACTTCCATCAGTCAAAAAACCAAACTCATCTGCT
ATGAGTTAGATGGTATCATCCATACCAGTATCTGGCGTCGCCACGAAACC
TGGCAAAATATCTTTCATCAAGAAACCAAAAAAGAATAG 4162.1
(SEQ. ID. NO. 281)
ATGACAATTAAACTAGTAGCAACGGATATGGACGGAACCTTCCTAGATGG
GAATGGACGCTTTGATATGGATCGTCTCAAGTCTCTCTTGGTTTCCTACA
AGGAAAAAGGGATTTACTTTGCGGTAGCTTCGGGTCGGGGATTTCTGTCT
CTAGAAAAATTATTTGCTGGTGTTCGTGATGACATTATTTTCATCGCGGA
AAATGGCAGTTTGGTAGAGTATCAAGGTCAGGACTTGTATGAAGCGACTA
TGTCTCGTGACTTTTATCTGGCAACTTTTGAAAAGCTGAAAACTTCACCT
TATGTAGATATCAATAAACTGCTCTTGACGGGTAAGAAGGGTTCATATGT
TCTAGATACGGTTGATGAGACCTATTTGAAAGTGAGTCAGCACTATAATG
AAAATATCCAAAAAGTAGCGAGTTTGGAAGATATCACAGATGACATTTTC
AAATTTACAACCAACTTCACAGAAGAAACGCTGGAAGATGGGGAGGCTTG
GGTAAACGAAAACGTTCCTGGTGTTAAGGCCATGACAACTGGCTTTGAAT
CCATTGATATTGTTCTGGACTATGTCGATAAGGGAGTGGCCATTGTTGAA
TTAGTTAAAAAACTTGGTATCACAATGGATCAGGTCATGGCTTTTGGAGA
CAATCTTAATGACTTACATATGATGCAGGTTGTGGGACATCCTGTAGCTC

TABLE 1-continued

CTGAAAATGCACGACCTGAAATTTAGAATTAGCAAAGACTGTGATTGGTC
ACCATAAGGAACGGTCGGTTATAGCTTATATGGAGGGCTTATAA 4162.2
(SEQ. ID. NO. 282)
ATGGCAGATATAAAATTGATTGCATTGGACTTGGACGGGACCTTGCTGAC
TACTGATAAAAGGCTGACGGATCGTACCAAGGAAACCTTGCAAGCTGCGC
GTGATCGTGGTATCAAGGTCGTATTGACAACTGGTCGTCCCTTAAAAGCC
ATGGATTTCTTTCTCCATGAGTTAGGGACTGACGGTCAGGAAGATGAGTA
TACCATTACTTTTAATGGTGGATTAGTTCAGAAAAATACAGGAGAAATCC
TTGATAAAACAGTCTTTTCATATGATGATGTGGCACGTTTGTATGAAGAA
ACAGAGAAATTATCACTGCCTCTTGATGCCATCTCAGAAGGAACAGTTTA
TCAAATCCAATCGGACCAAGAAAGTCTTTATGCCAAATTCAATCCAGCTT
TGACCTTTGTTCCAGTGGACTTTGAAGACTTATCTAGTCAAATGACCTAC
AACAAATGCGTGACTGCCTTTGCTCAAGAACCCTTGGATGCAGCCATTCA
GAAGATTCTCCAGAATTGTTGACCAATATGAAATCTTTAAATCACGTGA
AATGTTGCTAGAATGGTCACCAAAGAATGTTCATAAAGCAACAGGTTTGG
CAAAACTAATCAGCCATCTTGGAATCGACCAAAGTCAAGTGATGGCTTGT
GGTGACGAGGCCAATGACCTCTCTATGATTGAATGGGCAGGTCTTGGTGT
TGCTATGCAAAACGCTGTTCCTGAAGTAAAGGCAGCCGCAAATGTAGTGA
CGCCGATGACCAACGATGAGGAAGCTGTCGCCTGGGCTATCGAAGAATAT
GTGCTAAAGGAGAACTAA 4164.2
(SEQ. ID. NO. 283)
ATGGAAAGTTTACTTATTCTATTATTAATTGCCAATCTAGCTGGTCTCTT
TCTGATTTGGCAAAGGCAGGATAGGCAGGAGAAACACTTAAGTAAGAGCT
TGGAGGATCAGGCAGATCATTTGTCAGACCAGTTGGATTACCGCTTTGAC
CAAGCCAGACAAGCCAGCCAGTTAGACCAAAAAGATTTGGAAGTGGTTGT
CAGCGACCGTTTGCAAGAAGTGCGGATTGAATTGCACCAAGGTCTGACCC
AAGTCCGTCAAGAAATGACAGATAATCTCCTCCAAACTAGAGACAAGACA
GACCAACGTCTCCAAGCCTTGCAGGAATCAAATGAGCAACGTTTGGAACA
AATGCGCCAGACGGTCGAGGAAAAACTAGAAAAGACCTTGCAGACACGCT
TACAGGCTTCCTTTGAGACAGTTTCTAAACAACTGGAGTCTGTCAATCGT
GGCCTTGGAGAAATGCAGACAGTTGCCCGTGATGTCGGAGCTCTTAACAA
GGTTCTCTCTGGAACCAAGACGCGAGGGATTCTGGGAGAATTGCAACTGG
GGCAAATTATTGAAGACATCATGACACCTGCCCAGTACGAACGAGAATAC
GCAACGGTTGAAAACTCTAGTGAACGAGTGGAGTATGCCATCAAGTTACC
CGGACAAGGCGACCAAGAATACGTCTATCTGCCAATTGACTCTAAGTTTC
CACTGGCAGATTATTACCGCTTGGAAGAAGCCTATGAGACAGGTGACAAG
GATGAGATTGAACGCTGTCGTAAGTCACTCCTAGCAAGCGTCAAGCGCTT
TGCTAGGGATATTAGGAACAAGTACATAGCACCACCTCGGACGACCAATT
TTGGAGTTTTGTTTGTTCCGACAGAAGGTCTCTACTCAGAAATCGTCCGC
AATCCGGTCTTCTTTGATGATTTGAGACGGGAAGAACAGATTATTGTTGC

AGGACCAAGTACCCTATCAGCCCTTCTTAACTCCCTATCAGTTGGTTTCA
AGACCCTTAATATCCAAAAGAGTGCCGACCATATCAGCAAGACTCTTGCC
AGTGTCAAGACCGAGTTTGGCAAGTTGGTGGTATTCTGGTCAAGGCACA
AAAACATCTCCAACATGCCTCTGGCAATATTGATGAATTATTAAACCGTC
GTACCATAGCTATCGAGCGGACGATCCGTCACATTGAGTTGTCAGAAGGT
GAGCCTGCGCTTGATCTACTCCATTTTCAAGAAAATGAGGAAGAATATGA
AGATTAG 4164.3
(SEQ. ID. NO. 284)
ATGAAGATTAGTCACATGAAAAAAGATGAGTTATTTGAAGGCTTTTACCT
AATCAAATCAGCTGACCTGAGGCAAACTCGAGCTGGGAAAAACTACCTAG
CCTTTACCTTCCAAGATGATAGTGGCGAGATTGATGGGAAGCTCTGGGAT
GCCCAACCTCATAACATTGAGGCCTTTACCGCAGGTAAGGTTGTCCACAT
GAAAGGACGCCGAGAAGTTTATAACAATACCCCTCAAGTCAATCAAATTA
CTCTCCGCCTGCCTCAAGCTGGTGAACCCAATGACCCAGCTGATTTCAAG
GTCAAGTCACCAGTTGATGTCAAGGAAATTCGTGACTACATGTCGCAAAT
GATTTTCAAAATTGAAAATCCTGTCTGGCAACGGATTGTCCGAAATCTCT
ACACCAAGTATGATAAGGAATTCTACTCCTATCCAGCTGCCAAGACCAAC
CACCATGCCTTTGAAACGGGCTTGGCCTATCATACGGCGACCATGGTGCG
TTTGGCAGACGCTATTAGCGAAGTTTATCCTCAGCTCAATAAGAGCCTGC
TCTATGCGGGATTATGTTGCATGACTTAGCTAAGGTCATCGAGTTGACG
GGGCCAGACCAGACAGAGTACACAGTGCGAGGTAATCTTCTTGGACATAT
CGCTCTCATTGATAGCGAAATTACCAAGACAGTTATGGAACTCGGCATCG
ATGATACCAAGGAAGAAGTCGTTTTGCTTCGTCATGTCATCCTCAGTCAC
CACGGCTTGCTTGAGTATGGAAGCCCAGTCCGTCCACGCATTATGGAAGC
AGAGATTATCCATATGATTGACAATCTGGATGCAAGCATGATGATGATGT
CAACAGCTCTTGCTTTGGTGGATAAAGGAGAGATGACCAATAAAATCTTC
GCTATGGATAATCGTTCCTTCTATAAACCAGATTTAGATTAA 4166.2
(SEQ. ID. NO. 285)
ATGAGTGAAAAAGCTAAAAAAGGGTTTAAGATGCCTTCATCTTACACCGT
ATTATTGATAATCATTGCTATTATGGCAGTGCTAACTTGGTTTATCCCTG
CGGGGGGCCTTTATAGAAGGTATTTACGAGACTCAGCCTCAAAATCCACAA
GGGATTTGGGATGTCCTGATGGCACCGATTCGGGCTATGCTAGGTACTCA
TCCAGAGGAAGGTTCGCTCATTAAAGAAACGAGCGCAGCGATTGATGTAG
CCTTCTTCATCCTTATGGTTGGTGGTTTCCTTGGCATTGTCAACAAAACT
GGTGCTCTTGACGTAGGGATTGCCTCTATCGTGAAGAAGTATAAGGGCCG
CGAAAAAATGTTAATTTTGGTACTGATGCCTTTGTTTGCCCTCGGTGGTA
CAACTTATGGTATGGGTGAAGAAACAATGGCCTTCTATCCACTCCTTGTG
CCAGTTATGATGGCCGTTGGTTTTGATAGCCTGACTGGTGTTGCAATTAT
TTTGCTCGGTTCTCAAATCGGCTGTTTGGCATCTACTCTGAATCCATTTG
CGACAGGTATTGCTTCAGCGACTGCGGGAGTTGGTACAGGGGACGGTATC

TABLE 1-continued

GTACTTCGTCTGATCTTCTGGGTTACCTTGACTGCTCTTAGTACTTGGTT
TGTTTACCGTTATGCGGATAAGATTCAAAAAGATCCGACTAAGTCACTGG
TTTATAGTACTCGCAAAGAAGATTTGAAACACTTTAACGTAGAAGAATCT
TCATCTGTAGAATCTACACTTAGCAGCAAACAAAAATCAGTTCTCTTCTT
ATTTGTGTTGACATTCATCTTGATGGTATTGAGCTTCATTCCATGGACAG
ACCTTGGCGTTACCATTTTTGATGACTTTAATACTTGGTTGACTGGTCTT
CCAGTTATTGGTAATATTGTCGGTTCATCTACTTCTGCACTAGGTACTTG
GTACTTCCCAGAAGGCGCAATGCTCTTTGCCTTTATGGGTATCCTGATTG
GTGTTATTTATGGTCTTAAAGAAGATAAGATTATCTCTTCCTTCATGAAT
GGTGCTGCTGACTTGCTCAGTGTTGCCTTGATCGTAGCGATTGCTCGTGG
TATTCAAGTTATCATGAACGACGGTATGATTACCGATACAATCCTCAACT
GGGGTAAAGAAGGCTTGAGCGGTCTATCTTCACAAGTCTTTATCGTTGTA
ACTTATATCTTCTATCTACCTATGTCATTCTTGATCCCATCTTCATCTGG
TCTTGCCAGCGCAACTATGGGTATCATGGCTCCACTTGGAGAATTTGTAA
ATGTCCGTCCTAGCTTGATTATCACTGCTTACCAATCTGCTTCAGGTGTC
TTGAACTTGATTGCACCAACATCTGGTATTGTGATGGGAGCTCTTGCACT
TGGACGTATCAACATTGGTACTTGGTGGAAATTCATGGGCAAACTCGTAG
TCGCTATTATTGTAGTGACCATCGCCCTTCTTCTCCTTGGAACCTTCCTT
CCATTCCTATAA 4166.3

(SEQ. ID. NO. 286)

ATGAAAATAGATATAACAAATCAAGTTAAAGATGAATTTCTTATATCATT
AAAAACCTTGATTTCCTATCCTTCAGTACTCAATGAAGGAGAAAATGGAA
CACCTTTTGGACAAGCAATCCAAGATGTCCTAGAAAAAACTTTAGAGATT
TGTCGAGACATAGGTTTCACTACCTATCTTGACCCTAAAGGTTATTACGG
ATATGCAGAAATCGGTCAGGGAGCAGAGCTTCTGGCCATTCTCTGTCATT
TGGATGTTGTTCCATCAGGTGATGAAGCAGATTGGCAGACACCGCCATTT
GAAGCAACTATCAAAGACGGCTGGGTATTCGGACGTGGTGTCCAAGATGA
TAAAGGCCCTTCGCTCGCAGCTCTCTATGCAGTAAAAAGCTTGCTGGACC
AAGGTATTCAGTTCAAAAAGCGCGTACGCTTTATCTTTGGTACCGATGAG
GAAACCCTCTGGCGCTGCATGGCACGCTACAATACCATCGAAGAACAGGC
CAGTATGGGCTTTGCACCTGACTCATCTTTTCCTCTGACCTATGCTGAAA
AAGGGCTTCTACAGGTCAAACTTCATGGCCCTGGATCGGATCAACTAGAG
CTTGAAGTAGGAGGCGCCTTTAACGTTGTACCAGACAAGGCCAACTACCA
AGGTCTCCTCTATGAACAGGTTTGTAACGGTCTCAAAGAAGCTGGTTATG
ATTACCAAACCACTGAACAAACCGTAACGGTTCTCGGAGTGCCAAAGCAT
GCTAAGGATGCTAGTCAAGGTATCAATGCTGTCATCCGACTAGCTACCAT
TCTTGCTCCTCTCCAAGAACACCCTGCTCTCAGTTTTCTTGCAACACAAG
CAGGTCAAGACGGCACAGGAAGACAAATCTTTGGTGATATAGCAGATGAA
CCTTCTGGTCACCTATCCTTTAATGTCGCAGGTCTCATGATCAATCATGA
ACGTTCTGAAATCCGTATTGACATTCGGACTCCTGTCTTAGCTGACAAGG

AAGAACTAGTAGAGTTGCTTACAAGATGTGCACAAAACTACCAACTCCGC
TACGAAGAGTTTGACTATCTAGCGCCTCTATACGTCGCAGAAGACAGTAA
ACTCGTTAGCACACTGATGCAAATCTACCAAGAAAAGACTGGCGATAACA
GTCCTGCTATTTCATCCGGTGGTGCCACTTTTGCTCGCACCATGCCAAAT
TGTGTAGCCTTCGGCGCCTTATTCCCAGGAGCGAAGCAGACAGAACATCA
GGCAAATGAATGTGCCGTTCTAGAAGATTTGTACCGTGCTATGGATATTT
ATGCCGAAGCCGTCTATCGACTTGCAACTTAA 4169.1

(SEQ. ID. NO. 287)

ATGTCTAATTCATTTGTCAAGTTGTTAGTCTCTCAATTATTTGCAAATTT
AGCAGATATTTTCTTTAGAGTAACAATCATTGCTAACATATACATTATTT
CAAAATCAGTAATTGCCACATCACTAGTTCCTATCTTAATAGGAATATCC
TCTTTTGTTGCGAGTCTTTTAGTTCCGTTGGTTACTAAAAGGTTAGCGCT
AAATAGGGTTTTATCTTTATCTCAATTTGGAAAGACTATATTATTGGCGA
TACTGGTAGGAATGTTTACCGTAATGCAATCCGTAGCGCCTTTGGTGACC
TATCTATTTGTTGTTGCAATTTCCATACTAGATGGTTTTGCAGCACCCGT
TTCCTATGCTATTGTGCCACGCTATGCGACCGATTTGGGTAAGGCTAATT
CAGCCTTATCAATGACTGGTGAAGCTGTTCAATTGATAGGTTGGGGATTA
GGTGGACTCTTGTTTGCAACAATTGGTCTGTTACCTACCACGTGTATCAA
TTTAGTCTTGTATATCATTTCTAGCTTTCTGATGTTATTCTTCCTAACG
CTGAAGTGGAGGTGTTAGAGTCAGAAACTAATCTTGAAATTTTGCTCAAA
GGTTGGAAGTTAGTTGCTAGAAATCCTAGATTAAGACTTTTTGTATCAGC
AAATTTATTGGAAATTTTTTCAAATACGATTTGGGTTTCTTCCATTATAC
TTGTTTTTGTAACGGAGTTATTAAATAAAACGGAAAGTTACTGGGGATAT
TCTAATACAGCATACTCTATTGGTATTATAATTAGTGGCTTAATTGCTTT
TAGGCTATCTGAAAAGTTCCTTGCTGCTAAATGGGAAGGGGAATTATTCA
CCCCAAATCTAAAAACCATCCAGAATCCTGCCTTAGCTTAGATCCTGGAT
GGTTTCTTTTTTCACCCAATGGGTGTTTTTTACTAGACAAAAAAGAGTTT
CCCCTTTATGGTATAAGTGTAGAAAAAAAACACAAAAAGAAAGGAAACTCA
CATGAACAGTTTACCAAATCATCACTTCCAAAACAAGTCTTTTTACCAAC
TATCTTTCGATGGAGGTCATTTAACCCAGTATGGTGGTCTTATCTTTTTT
CAGGAACTTTTTTCCCAGTTGAAACTAAAAGAGCGGATTTCTAAGTATTT
AGTAACGAATGACCAACGCCGCTACTGTCGTTATTCGGATTCAGATATCC
TTGTCCAGTTCCTCTTTCAACTGTTAACAGGTTATGGAACGGACTATGCT
TGTAAAGAATTGTCAGCTGATGCCTACTTTCCAAAATTGTTGGAAGGAGG
GCAGCTTGCTTCACAGCCAACCTTATCCCGTTTTCTTTCCAGAACTGACG
AGGAAACAGTCCATAGTTTGCGATGCCTCAACCTTGAATTGGTCGAATTC
TTTTTACAGTTTCACCAGCTAAACCAACTCATTGTAGATATCGATTCTAC
CCATTTCACAACTTATGGCAAGCAAGAAGGTGTTGCTTATAACGCCCACT
ATCGTGCTCATGGCTATCATCCTCTTTATGCTTTCGAGGGGAAGACAGGT
TATTGTTTCAATGCCCAGCTTCGTCCTGGTAATCGTTATTGTTCTGAAGA

TABLE 1-continued

GGCAGACAGCTTTTATCACACCTGTTTTAGAACGGTTTAATCAACTTCTC
TTTCGAATGGATAGTGGCTTTGCGACCCCAAAATTATACGATTTAATTGA
AAAAACAGGGCAATACTACCTCATAAAACTCAAGAAAAATACTGTTCTGA
GCCGTCTTGGAGACCTTTCCCTCCCTTGCCCACAGGATGAGGACTTAACC
ATCTTGCCCCACTCCGCCTACTCAGAAACTCTCTATCAAGCAGGATCTTG
GTCGCACAAGCGTCGTGTCTGCCAGTTCTCTGAACGAAAAGAAGGAAACT
TGTTCTACGATGTTATTTCTCTCGTTACAAATATGACGAGTGGAACAAGC
CAAGACCAGTTTCAGCTTTATCGTGGACGTGGTCAAGCCGAGAATTTCAT
CAAGGAGATGAAGGAGGGATTTTTTGGCGATAAAACGGATAGTTCAACCT
TAATCAAAAACGAAGTTCGTATGATGATGAGCTGTATCGCCTACAATCTC
TATCTTTTTCTCAAACATCTAGCTGGAGGTGACTTCCAAACTTTAACAAT
CAAACGCTTCCGCCATCTTTTTCTTCACGTGGTGGGAAAATGTGTTCGAA
CAGGACGCAAGCAGCTCCTCAAATTGTCTAGTCTCTATGCCTATTCCGAA
TTGTTTTCAGCACTTTATTCTAGGATTAGAAAAGTCAACCTGAATCTTCC
TGTTCCTTATGAACCACCTAGAAGAAAAGCGTCGTTAATGATGCATTAA
4169.3
(SEQ. ID. NO. 288)
ATGATGGAGTTTTTTCAACAGCTTCCTCATTTAGAGCCATATGGCAATCC
TCAGTATTTTGTTTATGTGATTGCTGCAACCTTGCCCATCTTTATAGGTC
TCTTTTTCAAGAAACGCTTTGCCTGGTATGAAGTGTTGGTAAGTCTCTTC
TTTATTGTCACCATGTTGGTGGGTGGAAAGACCAATCAACTAGCTGCCTT
GGGTATTTACCTTTGCTGGGAAATATTGCTCCTGCTTTTCTACAAGCATT
ATCGAAAAGCAAGGATGGCAAGTGGGTCTTCTACTTAGTTAGTTTTCTG
TCCCTACTTCCGATTATCTTTGTCAAGGTGCAACCAGCTATCAATGGAAC
GCAGTCTTTGCTTGGGTTCTTGGGAATTTCTTACCTGACCTTTCGTTCGG
TTGGAATTGTCATCGAGCTGAGAGATGGAGTGATTAAGGATTTTACCCTC
TGGGAATTCCTCCGTTTCCTTCTCTTCATGCCAACTTTCTCGAGTGGTCC
AATCGATCGCTTTAAGCGATTTAATGAAAATTATCAGGCTATTCCTGAGC
GAGATGAGTTGATGGATATGCTGGATGAATCTGTCCGCTATATCATGTGG
GGCTTTTTGTATAAGTTTATCCTAGCTCATGTTTTAGGAGAGACCTTACT
ACCTCCTCTGAAGAATTTAGCCTTGCAGTCAGGTGGCTTCTTTAATCTCT
ATGCCTTGGCAGTTATGTATACTTTTGGTCTGGAACTCTTCTTTGACTTT
GCAGGTTATTCTATGTTTGCTTTGGCCATCTCAAACTTGATGGGAATCCG
TAGCCCTATCAACTTTAACAAGCCCTTTTTATCAAGGGATTTAAAGGAGT
TTTGGAATCGCTGGCATATGAGTCTGTCCTTCTGGTTCCGTGACTTTGTC
TTTATGCGAATGGTGATGGTGTTAACCAGAAAGAAGTCTTTAAAAATCG
TAATGTAACCTCAAGCATGGCCTACATTGTAAATATGCTGATTATGGGAT
TTTGGCATGGTGTGACCTGGTACTATATCGCCTATGGACTCTTTCATGGA
CTAGGCTTGGTCATCAATGATGCCTGGGTTCGCAAGAAAAAAACGCTCAA
TAAGGAACGGAAAAAAGCAGGGAAGGCTGCCCTACCTGAGAATCGCTGGA

TTCAGTTGCTTGGCATGGTTGTCACTTTCCATGTTGTCATGTTGTCATTC
TTAATCTTTTCTGGATTCTTGAATAATCTATGGTTTAAAAAATAA
4169.4
(SEQ. ID. NO. 289)
ATGCTTAAACGCTTATGGATGATCTTCGGACCGGTCTTGATCGCTGGTTT
GTTGGTTTTTCTGCTCATTTTCTTTTATCCTACTGAGATGCATCATAATC
TAGGAGCTGAAAAGCGTTCAGCAGTGGCTACTACTATCGATAGTTTTAAG
GAGCGAAGTCAAAAAGTCAGAGCACTATCTGATCCAAATGTGCCGTTTTGT
TCCCTTCTTTGGCTCTAGTGAATGGCTTCGTTTTGACGGTGCTCATCCTG
CGGTATTAGCTGAGAAATACAATCGTTCCTACCGTCCTTATCTTTTAGGA
CAGGGGGGAGCTGCATCGCTTAACCAATATTTTGGAATGCAACAGATGTT
ACCACAGCTGGAGAATAAACAAGTTGTGTATGTTATCTCACCTCAGTGGT
TCAGTAAAAATGGCTATGATCCAGCAGCCTTCCAGCAGTATTTTAATGGA
GACCAGTTGACTAGTTTTCTGAAACATCAATCTGGGGATCAGGCTAGTCA
ATATGCAGCGACTCGCTTACTGCAACAGTTCCCAAACGTAGCTATGAAGG
ACCTGGTTCAGAAGTTGGCAAGTAAAGAAGAATTGTCGACAGCAGACAAT
GAAATGATTGAATTATTGGCTCGTTTTAATGAACGCCAAGCTTCCTTTTT
TGGTCAGTTTTCGGTTAGAGGCTATGTTAACTACGATAAGCATGTAGCTA
AGTATTTAAAAATCTTGCCAGACCAGTTTTCTTATCAGGCAATAGAAGAT
GTTGTCAAAGCAGATGCTGAAAAAAATACTTCCAATAATGAGATGGGAAT
GGAAAATTATTTCTATAATGAGCAGATCAAGAAGGATTTGAAGAAATTAA
AGGATTCTCAGAAAAGCTTTACCTATCTCAAGTCGCCAGAGTATAATGAC
TTGCAGTTGGTTTTAACACAGTTTTCTAAATCTAAGGTAAACCCGATTTT
TATCATTCCACCTGTTAATAAAAAATGGATGAACTATGCTGGTCTACGAG
AGGATATGTACCAACAAACGGTGCAGAAGATTCGCTACCAGTTAGAAAGT
CAAGGTTTTACCAATATAGCAGATTTTTCTAAGGACGGCGGGGAGCCTTT
CTTTATGAAGGACACCATTCACCTTGGTTGGTTGGGTTGGTTGGCTTTTG
ACAAGGCAGTTGATCCTTTCCTATCCAATCCCACACCAGCTCCGACTTAC
CATCTGAATGAGCGCTTTTTCAGCAAAGATTGGGCGACTTATGATGGAGA
TGTCAAAGAATTTCAATAG
4169.6
(SEQ. ID. NO. 290)
ATGGAGAAAAACCTCAAGGCTTTGAAACAAACAACAGACCAAGAAGGCCC
AGCAATTGAACCTGAAAAGGCAGAGGATACCAAGACAGTCCAAAATGGTT
ACTTCGAGGATGCAGCTGTCAAGGACCGCACCTTGAGTGACTATGCAGGT
AACTGGCAATCAGTTTATCCTTTCCTTGAAGACGGCACGTTTGACCAAGT
CTTTGACTACAAGGCTAAGTTGACTGGTAAGATGACCCAGGCTGAGTACA
AGGCTTACTATACAAAAGGCTATCATACAGATGTGACTAAGATTAACATT
ACTGATAATACTATGGAATTTGTTCAAGGTGGACAAAGCAAGAAATACAC
TTACAAGTATGTCGGTAAGAAAATTTTGACTTACAAGAAAGGCAATCGTG
GCGTGCGTTTCCTCTTTGAAGCCACAGATGCTGACGCTGGACAATTCAAG
TATGTTCAGTTTAGTGACCACAATGTTGCCCCAGTTAAGGCAGAACATTT

TABLE 1-continued

CCATATCTTCTTTGGAGGCACAAGCCAAGAAGCCCTCTTTGAAGAAATGG
ACAACTGGCCAACCTACTACCCAGATAACCTATCTGGCCAAGAAATCGCC
CAAGAAATGTTGGCGCATTGA 4170.3
(SEQ. ID. NO. 291)
ATGAAAGATGGTCATTTGCTAGCCCATCATATTCGTTTGTTGAATGGGCG
GATTTTTCAAAAGTTACTGAGTCAAGATCCTGAGGCTCTTTATAGGGGTG
AACAGGGCAAGATTTTAGCGGTTTTATGGAATAGTGAAACTGGCTGCGCA
ACTGCGACAGATATCGCGCTTGCGACTGGACTTGCGAATAATACGCTGAC
GACTATGATAAAAAAGCTAGAGGAACAAAAGCTTGTAATTGTTAGTCCGT
GTGGAAAAGACAAGCGTAAGAAGTATTTAGTTTTAACGGAGTTAGGCAAG
TCCCAGAAAGAAGTGGGGCATCGTGTCAGTCAGAAATTGGATACTATCTT
TTACAAAGGATTTTCAGAGGAAGAAATTCACCAATTTGAAGGTTTTCAAG
AAAGAATTTTGGCGAATCTGAAAGAGAAGGGAAATGAGGTTTAG 4170.4
(SEQ. ID. NO. 292)
ATGACTAATTTAATTGCAACTTTTCAGGATCGTTTTAGTGATTGGTTGAC
AGCTCTATCTCAACATTTGCAGTTGTCGCTTTTGACCTTGTTACTAGCTA
TTTTGCTTGCGATTCCCTTGGCTGTTTTTCTTCGCTATCATGAGAAGCTG
GCCGACTGGGTCTTGCAGATTGCAGGTATTTTCCAGACCATCCCGTCTCT
GGCCTTGTTGGGGCTCTTTATCCCTTTGATGGGAATTGGGACCTTGCCGG
CTTTGACAGCTCTAGTGATTTATGCGATTTTCCCTATTTTGCAAAATACT
ATCACTGGGCTGAAGGGAATTGATCCGAACCTGCAAGAGGCTGGGATTGC
CTTTGGGATGACCAGATGGGAACGTCTCAAGAAATTTGAAATTCCACTCG
CCATGCCTGTTATCATGTCTGGGATTCGGACGGCAGCTGTTTTGATTATC
GGTACGGCAACCTTGGCGGCCTTGATTGGTGCAGGGGGACTAGGTTCCTT
TATTCTTTTGGGAATTGACCGTAATAATGCCAGTTTGATTTTGATTGGGG
CACTTTCTTCTGCAGTGCTAGCCATTGCCTTTAACTTCCTACTAAAAGTG
ATGGAAAAAGCAAAATTACGGACGATTTTCTCAGGTTTTGCCTTGGTGGC
TTTATTACTGGGTCTGTCTTATAGTCCAGCTCTTTTGGTTCAAAAAGAGA
AGGAAAACTTGGTTATTGCTGGGAAATAGGTCCAGAACCAGAAATTTTG
GCCAATATGTATAAGTTGCTGATTGAAGAAAATACCAGCATGACTGCGAC
TGTTAAACCGAATTTTGGGAAGACAAGCTTCCTTTATGAAGCTCTGAAAA
AAGGCGATATTGACATCTATCCTGAATTTACTGGTACGGTGACTGAAAGT
TTGCTTCAACCATCACCCAAGGTGAGTCATGAACCAGAACAGGTTTATCA
GGTGGCGCGTGATGGCATTGCTAAGCAGGATCATCTAGCCTATCTCAAAC
CCATGTCTTATCAAACACCTATGCTGTAGCTGTTCCGAAAAAGATTGCT
CAAGAATATGGCTTGAAGACCATTTCAGACTTGAAAAAGTGGAAGGGCA
GTTGAAGGCAGGTTTTACACTCGAGTTTAACGACCGTGAAGATGAAATA
AGGGCTTGCAATCAATGTATGGTCTCAATCTCAATGTAGCGACCATTGAG
CCAGCCCTTCGCTATCAGGCTATTCAGTCAGGGGATATTCAAATCACGGA
TGCCTATTCGACTGATGCGGAATTGGAGCGTTATGATTTACAGGTCTTGG

AAGATGACAAGCAACTCTTCCCACCTTATCAAGGGGCTCCACTCATGAAA
GAAGCTCTTCTCAAGAAACACCCAGAGTTGGAAAGAGTTCTTAATACATT
GGCTGGTAAGATTACAGAAAGCCAGATGAGCCAGCTCAACTACCAAGTCG
GTGTTGAAGGCAAGTCAGCAAAGCAAGTAGCCAAGGAGTTTCTCCAAGAA
CAAGGTTTGTTGAAGAAATGA 4170.5
(SEQ. ID. NO. 293)
ATGATGCATACTTATTTGCAAAAGAAAATTGAAAATATCAAAACAACCCT
AGGTGAAATGTCAGGTGGTTACCGTCGTATGGTTGCGGCTATGGCTGATT
TAGGATTTTCAGGAACTATGAAGGCTATCTGGGATGACCTCTTTGCCCAT
CGTAGTTTTGCCCAGTGGATTTATTTGCTGGTTTTAGGAAGTTTTCCTCT
CTGGCTGGAGTTGGTTTACGAACATCGTATTGTTGACTGGATTGGGATGA
TTTGTAGCTTGACAGGGATTATCTGTGTAATCTTTGTATCGGAAGGTCGA
GCAAGTAATTATCTTTTGGCTTGATTAACTCTGTTATTTACCTTATTTT
GGCCCTACAGAAAGGCTTTTATGGTGAGGTGCTGACGACACTTTACTTCA
CAGTCATGCAGCCAATTGGACTTCTAGTTTGGATTTATCAGGCACAGTTT
AAGAAGGAAAAGCAGGAGTTTGTCGCGCGTAAACTGGACGGCAAGGGCTG
GACAAAGTATCTTTCCATTAGTGTGCTTTGGTGGTTGGCCTTTGGCTTCA
TTTATCAGTCTATTGGTGCCAATCGTCCCTATCGTGATTCAATCACAGAT
GCAACCAATGGGGTAGGGCAAATCCTCATGACAGCTGTTTACCGTGAACA
GTGGATATTCTGGGCGGCTACCAATGTCTTTTCAATCTATCTCTGGTGGG
GAGAAAGCCTGCAAATTCAAGGGAAATATCTAATTTATCTCATTAACAGT
CTAGTTGGTTGGTATCAATGGAGCAAGGCAGCTAAGCAGAATACTGATTT
ACTTAACTAG 4170.6
(SEQ. ID. NO. 294)
ATGAGAAATATGAAGGCAAAATATGCTGTTTGGGTGGCTTTTTTCTTAAA
TTTGACTTATGCCATTGTTGAGTTTATGCAGGTGGAGTATTTGGTTCTAG
CGCTGTTCTTGCTGACTCTGTGCATGACTTGGGAGATGCGATTGCAATTG
GAATATCAGCTTTTCTAGAAACAATCTCCAATCGTGAAGAAGACAATCAG
TACACCTTGGGCTATAAGCGGTTTAGCCTGCTAGGAGCCTTGGTAACAGC
TGTGATTCTCGTAACGGGCTCTGTTCTAGTCATTTTGGAAAATGTCACGA
AGATTTGCATCCGCAACCAGTCAATGATGAGGGATTCTCTGGTTAGGAA
TTATTGCGATTACTATCAATCTGTTAGCGAGTCTGGTGGTTGGTAAGGGA
AAGACAAAGAATGAGTCTATTCTGAGTCTGCATTTTCTGGAAGATACGCT
AGGGTGGGTAGCTGTTATCCTGATGGCGATTGTTCTTCGATTTACGGACT
GGTATATCCTAGATCCTCTTTTGTCCCTTGTCATTTCTTCTTTATTCTT
TCAAAAGCCCTTCCACGTTTTTGGTCTACACTCAAGATTTTCTTGGATGC
TGTGCCAGAAGGTCTTGATATCAAGCAAGTAAAGAGTGGCCTGGAGCGAT
TGGACAATGTGGCCAGCCTTAATCAGCTTAATCTCTGGACTATGGATGCT
TTGGAAAAAATGCCATTGTCCATGTTTGTCTAAAAGAAATGGAACATAT
GGAAACTTGTAAAGAGTCTATTCGAATTTTCCTAAAAGATTGTGGTTTTC

TABLE 1-continued

AAAATATTACCATTGAAATTGATGCTGACCTAGAAACTCACCAAACCCAT
AAGCGAAAGGTGTGTGACTTGGAACGGAGTTATGAGCATCAACATTAG 4170.8
(SEQ. ID. NO. 295)
ATGATTGAATACAAAAATGTAGCACTGCGCTACACAGAAAAGGATGTCTT
GAGAGATGTCAACTTACAGATTGAGGATGGGGAATTTATGGTTTTAGTAG
GGCCTTCTGGGTCAGGTAAGACGACCATGCTCAAGATGATTAACCGTCTT
TTGGAACCAACTGATGGAAATATTTATATGGATGGGAAGCGCATCAAAGA
CTATGATGAGCGTGAACTTCGTCTTTCTACTGGTTATGTTTTACAGGCTA
TTGCTCTTTTTCCAAATCTAACAGTTGCGGAAAATATTTGCTCTCATTCC
TGAAATGAAGGGGTGGAGCAAGGAAGAAATTACGAAGAAAACAGAAGAGC
TTTTGGCTAAGGTTGGTTTACCAGTAGCCGAGTATGGGCATCGCTTACCT
AGTGAATTATCTGGTGGAGAACAGCAACGGGTCGGTATTGTCCGAGCTAT
GATTGGTCAGCCCAAGATTTTCCTCATGGATGAACCCTTTTCGGCCTTGG
ATGCTATTTCGAGAAAACAGTTGCAGGTTCTGACAAAAGAATTGCATAAA
GAGTTTGGGATGACAACGATTTTTGTAACCCATGATACGGATGAAGCCTT
GAAGTTGGCGGACCGTATTGCTGTCTTGCAGGATGGAGAAATTCGCCAGG
TAGCGAATCCCGAGACAATTTTAAAAGCGCCTGCAACAGACTTTGTAGCA
GACTTGTTTGGAGGTAGTGTTCATGACTAA 4171.1
(SEQ. ID. NO. 296)
ATGTCAGCAGTTGCTATTTCAGCTATGACCAAGGTTATGCAAGAAACCCA
CGGAAATCCTTCTAGTATTCATGGTCATGGTCGTCAAGCTGGCAAACTCT
TGCGAGAAGCCCGTCAGGAACTAGCCCAGTTACTAAGGACAAAACCTCAA
CATATCTTTTTCACTTCTGGTGGGACTGAAGGCAATAATACTACCATCAT
TGGCTACTGTCTTCGTCACCAAGAACAAGGAAAACATATCATCACAACTG
CCATCGAGCACCATGCTGTCCTTGAAACAATTGATTACTTGGTTCAACAC
TTTGGGTTTGAAGCAACCATTATCCAGCCAGAAAATCAAGAAATCACAGC
CCAGCAAATTCAAAAGGCTTTACGTGACGATACGATTTTGGTTTCTACCA
TGTTTGTCAATAATGAGACAGGAAACCTACTGCCCATCGCTGAAATTGGC
CAAATACTCAAGCAACACCCTGCTGCCTATCATGTTGATGCAGTTCAGGC
TATTGGTAAAATCCCAATTCATTCAGAAGAATTGGGCATTGATTTTCTCA
CTGCTTCTGCCCACAAATTCCATGGTCCTAAGGGAATCGGTTTTCTCTAC
GCATCTAGCATGGACTTTGATTCCTATCTACATGGCGGAGACCAGGAACA
GAAAAAACGTGCAGGAACTGAAAATCTGCCTGCCATTGTAGGCATGGTTG
CAGCCCTAAAAGAAGACCTAGAAAACAAGAAGAACATTTTCAACATGTA
CAAAATCTAGAAACTGCCTTTCTGGCAGAGCTGGAGGGCATTCAGTATTA
CCTGAATAGAGGAAAACATCATCTCCCTTATGTTCTCAATATTGGATTTC
CTGGTCAGAAAAATGACCTCTTACTCCTTCGGCTAGATTTAGCTGGAATT
TCAATCTCTACTGGCTCAGCCTGTACTGCAGGCGTTGTCCAATCCAGCCA
TGTTCTTGAAGCCATGTATGGCGCAAATTCAGAACGCTTGAAGGAATCCC

TABLE 1-continued

TTCGCATCAGTTTGTCGCCACAAAATACCGTTGAAGACCTACAAACCCTC
GCAAAAACCTTAAAAGAAATTATCGGAGGTTAG 4172.1
(SEQ. ID. NO. 297)
ATGTTATTCAAATTATCTAAGGAAAAAATAGAGCTAGGCTTATCTCGTTT
ATCGCCAGCCCGTCGTATTTTTTTGAGTTTTGCCTTGGTCATTTTACTAG
GCTCTCTTCTTTTGAGCTTGCCCTTTGTCCAAGTTGAAAGCTCACGAGCG
ACTTATTTTGATCATCTTTTCACTGCTGTCTCTGCAGTCTGTGTGACGGG
TCTCTCAACCCTTCCAGTAGCTCACACCTATAATATCTGGGGTCAAATAA
TCTGTTTGCTCTTGATTCAGATCGGTGGTCTAGGGCTCATGACCTTTATT
GGGGTTTTCTATATCCAGAGCAAGCAAAAGCTTAGTCTTCGTAGCCGTGC
AACTATTCAGGATAGTTTTAGTTATGGAGAAACTCGATCTTTGAGAAAGT
TTGTCTATTCTATTTTTCTCACGACCTTTTTGGTTGAGAGCTTGGGAGCT
ATTTTGCTTAGTTTTCGCCTTATTCCTCAACTTGGCTGGGGACGTGGTCT
TTTTAGTTCCATTTTTCTAGCGATCTCAGCCTTCTGTAATGCCGGTTTTG
ATAATTTAGGGAGCACCAGTTTATTTGCTTTTCAGACCGATTTACTGGTC
AATCTGGTGATTGCAGGCTTGATTATTACAGGCGGCCTTGGTTTTATGGT
CTGGTTTGATTTGGCTGGTCATGTAGGAAGAAAGAAAAAAGGACGTCTGC
ACTTTCATACGAAGCTTGTACTATTATTGACTATAGGTTTGTTGTTATTT
GGAACAGCAACTACTCTCTTTCTTGAGTGGAACAATGCTGGAACGATTGG
CAATCTCCCTGTTGCCGATAAGGTTTTAGTTAGCTTTTTTCAAACAGTGA
CGATGCGAACAGCTGGCTTTTCTACGATAGATTATACTCAGGCTCATCCT
GTGACTCTTTTGATTTATATCTTACAGATGTTTCTAGGTGGGGCACCTGG
AGGAACAGCTGGGGGACTCAAGATTACGACATTTTTTGTCCTCTTGGTCT
TTGCACGAAGTGAGCTTCTAGGCTTGCCTCATGCCAATGTTGCGAGACGA
ACGATCGCGCCGCGAACGGTTCAAAAATCCTTTAGTGTCTTTATTATCTT
TTTGATGAGCTTCTTGATAGGATTGATTCTGCTAGGGATAACAGCCAAAG
GCAATCCTCCCTTTATCCACCTCGTATTTGAAACCATTTCAGCTCTTAGT
ACAGTTGGTGTAACGGCAAATCTGACTCCTGACCTTGGGAAATTGGCTCT
CAGTGTTATCATGCCACTTATGTTTATGGGACGAATTGGTCCCTTGACCT
TGTTTGTTAGCTTGGCAGATTACCATCCAGAAAAGAAAGATATGATTCAC
TATATGAAAGCAGATATTAGTATTGGTTAA 4172.2
(SEQ. ID. NO. 298)
ATGTCAGATCGTACGATTGGAATTTTGGGCTTGGGAATTTTTGGGAGCAG
TGTCCTAGCTGCCCTAGCCAAGCAGGATATGAATATTATCGCTATTGATG
ACCACGCAGAGCGCATCAATCAGTTTGAGCCAGTTTTGGCGCGTGGAGTG
ATTGGTGACATCACAGATGAAGAATTATTGAGATCAGCAGGGATTGATAC
CTGCGATACCGTTGTAGTCGCGACAGGTGAAAATCTGGAGTCGAGTGTGC
TTGCGGTTATGCACTGTAAGAGTTTGGGGGTACCGACTGTTATTGCTAAG
GTCAAAAGTCAGACCGCTAAGAAAAGTGCTAGAAAAGATTGGAGCTGACT
CGGTTATCTCGCCAGAGTATGAAATGGGGCAGTCTCTAGCACAGACCATT

TABLE 1-continued

CTTTTCCATAATAGTGTTGATGTCTTTCAGTTGGATAAAAATGTGTCTAT
CGTGGAGATGAAAATTCCTCAGTCTTGGGCAGGTCAAAGTCTGAGTAAAT
TAGACCTCCGTGGCAAATACAATCTGAATATTTTGGGTTTCCGAGAGCAG
GAAAATTCCCCATTGGATGTTGAATTTGGACCAGATGACCTCTTGAAAGC
AGATACCTATATTTTGGCAGTCATCAACAACCAGTATTTGGATACCCTAG
TAGCATTGAATTCGTAA 4172.3
(SEQ. ID. NO. 299)
ATGAAGTTATTGTCTATCGCAATTTCTAGCTATAATGCAGCAGCCTATCT
TCATTACTGTGTGGAGTCGCTAGTGATTGGTGGTGAGCAAGTTGGGATTT
TGATTATCAATGACGGGTCTCAGGATCAGACTCAGGAAATCGCTGAGTGT
TTAGCTAGCAAGTATCCTAATATCGTTAGAGCCATCTATCAGGAAAATAA
ATGCCATGGCGGTGCGGTCAATCGTGGCTTGGTAGAGGCTTCTGGGCGCT
ATTTTAAAGTAGTTGACAGTGATGACTGGGTGGATCCTCGTGCCTACTTG
AAAATTCTTGAAACCTTGCAGGAACTTGAGAGCAAAGGTCAAGAGGTGGA
TGTCTTTGTGACCAATTTTGTCTATGAAAAGGAAGGGCAGTCTCGTAAGA
AGAGTATGAGTTACGATTCAGTCTTGCCTGTTCGGCAGATTTTTGGCTGG
GACCAGGTCGGAAATTTCTCCAAAGGCCAGTATACCATGATGCACTCGCT
GATTTATCGGACAGATTTGTTGCGTGCTAGCCAGTTCTAA 4172.4
(SEQ. ID. NO. 300)
ATGAAATTCAATCCAAATCAAAGATATACTCGTTGGTCTATTCGCCGTCT
CAGTGTCGGTGTTGCCTCAGTTGTTGTGGCTAGTGGCTTCTTTGTCCTAG
TTGGTCAGCCAAGTTCTGTACGTGCCGATGGGCTCAATCCAACCCCAGGT
CAAGTCTTACCTGAAGAGACATCGGGAACGAAAGAGGGTGACTTATCAGA
AAAACCAGGAGACACCGTTCTCACTCAAGCGAAACCTGAGGGCGTTACTG
GAAATACGAATTCACTTCCGACACCTACAGAAAGAACTGAAGTGAGCGAG
GAAACAAGCCCTTCTAGTCTGGATACACTTTTTGAAAAAGATGAAGAAGC
TCAAAAAAATCCAGAGCTAACAGATGTCTTAAAAGAAACTGTAGATACAG
CTGATGTGGATGGGACACAAGCAAGTCCAGCAGAAACTACTCCTGAACAA
GTAAAAGGTGGAGTGAAAGAAAATACAAAAGACAGCATCGATGTTCCTGC
TGCTTATCTTGAAAAAGCTGAAGGGAAAGGTCCTTTCACTGCCGGTGTAA
ACCAAGTAATTCCTTATGAACTATTCGCTGGTGATGGTATGTTAACTCGT
CTATTACTAAAAGCTTCGGATAATGCTCCTTGGTCTGACAATGGTACTGC
TAAAAATCCTGCTTTACCTCCTCTTGAAGGATAACAAAGGGAAATACTT
CTATGAAGTAGACTTAAATGGCAATACTGTTGGTAAACAAGGTCAAGCTT
TAATTGATCAACTTCGCGCTAATGGTACTCAAACTTATAAAGCTACTGTT
AAAGTTTACGGAAATAAAGACGGTAAAGCTGACTTGACTAATCTAGTTGC
TACTAAAAATGTAGACATCAACATCAATGGATTAGTTGCTAAAGAAACAG
TTCAAAAAGCCGTTGCAGACAACGTTAAGACAGTATCGATGTTCCAGCA
GCCTACCTAGAAAAAGCCAAGGGTGAAGGTCCATTCACAGCAGGTGTCAA
CCATGTGATTCCATACGAACTCTTCGCAGGTGATGGCATGTTGACTCGTC
TCTTGCTCAAGGCATCTGACAAGGCACCATGGTCAGATAACGGCGACGCT
AAAAACCCAGCCCTATCTCCACTAGGCGAAAACGTGAAGACCAAAGGTCA
ATACTTCTATCAAGTAGCCTTGGACGGAAATGTAGCTGGCAAAGAAAAC
AAGCGCTCATTGACCAGTTCCGAGCAAATGGTACTCAAACTTACAGCGCT
ACAGTCAATGTCTATGGTAACAAAGACGGTAAACCAGACTTGGACAACAT
CGTAGCAACTAAAAAAGTCACTATTAACATAAACGGTTTAATTTCTAAAG
AAACAGTTCAAAAAGCCGTTGCAGACAACGTTAAAGACAGTATCGATGTT
CCAGCAGCCTACCTAGAAAAAGCCAAGGGTGAAGGTCCATTCACAGCAGG
TGTCAACCATGTGATTCCATACGAACTCTTCGCAGGTGATGGTATGTTGA
CTCGTCTCTTGCTCAAGGCATCTGACAAGGCACCATGGTCAGATAACGGT
GACGCTAAAAACCCAGCCCTATCTCCACTAGGTGAAAACGTGAAGACCAA
AGGTCAATACTTCTATCAATTAGCCTTGGACGGAAATGTAGCTGGCAAAG
AAAACAAGCGCTCATTGACCAGTTCCGAGCAAACGGTACTCAAACTTAC
AGCGCTACAGTCAATGTCTATGGTAACAAAGACGGTAAACCAGACTTGGA
CAACATCGTAGCAACTAAAAAAGTCACTATTAACATAAACGGTTTAATTT
CTAAAGAAACAGTTCAAAAAGCCGTTGCAGACAACGTTAAGACAGTATCG
ATGTTCCAGCAGCCTACCTAG 4172.5
(SEQ. ID. NO. 301)
ATGAAACTAAAAAGTTATATTTTGGTTGGATATATTATTTCAACCCTCTT
AACCATTTGGTTGTTTTTTGGGCTGTTCAAAAAATGCTGATTGCGAAAG
GCGAGATTTACTTTTTGCTTGGGATGACCATCGTTGCCAGCCTTGTCGGT
GCTGGGATTAGTCTCTTTCTCCTATTGCCAGTCTTTACGTCGTTGGGCAA
ACTCAAGGAGCATGCCAAGCGGGTAGCGGCCAAGGATTTTCCTTCAAATT
TGGAGGTTCAAGGTCCTGTAGAATTTCAGCAATTAGGGCAAACTTTTAAT
GAGATGTCCCATGATTTGCAGGTAAGCTTTGATTCCTTGGAAGAAAGCGA
ACGAGAAAAGGGCTTGATGATTGCCCAGTTGTCGCATGATATTAAGACTC
CTATCACTTCGATCCAAGCGACGGTAGAAGGGATTTTGGATGGGATTATC
AAGGAGTCGGAGCAAGCTCATTATCTAGCAACCATTGGACGCCAGACGGA
GAGGCTCAATAAACTGGTTGAGGAGTTGAATTTTTTGACCCTAAACACAG
CTAGAAATCAGGTGGAAACTACCAGTAAAGACAGTATTTTTCTGGACAAG
CTCTTAATTGAGTGCATGAGTGAATTTCAGTTTTTGATTGAGCAGGAGAG
AAGAGATGTCCACTTGCAGGTAATCCCAGAGTCTGCCCGGATTGAGGGAG
ATTATGCTAAGCTTTCTCGTATCTTGGTAATCTGGTCGATAACGCTTTT
AATATTCTGCTCCAGGAACCAAGCTGGAAGTGGTGGCTAAGCTGGAGAA
GGACCAGCTTTCAATCAGTGTGACCGATGAAGGGCAGGGTATTGCCCCAG
AGGATTTGGAAATATTTTCAAACGCCTTTATCGTGTCGAAACTTCGCGT
AACATGAAGACAGGTGGTCATGGATTAGGACTTGCGATTGCGCGTGAATT
GGCCCATCAATTGGGTGGGAAATCACAGTCAGCAGCCAGTACGGTCTAG
GAAGTACCTTTACCCTCGTTCTCAACCTCTCTGGTAGTGAAAATAAAGCC
TAA

TABLE 1-continued 4172.6
(SEQ. ID. NO. 302)
ATGTTTGGTCAAACGGCTCAACATGGTCTTACGAATAGCCTGAAAGACTT
CTGGATTTTTCTGCTGAATATAGGTCCACAATTGGCGTTTTTTTGCCAGA
TGCTCCGCTGTTCCAGATCGGTTGAGCAGGGTACTGGAAATCACCGTCGT
GAGTTCAATATGATTCAGCAGATATTCTCGCATTTTGGGATGACTCACTT
GGGACAAATCAAGTTGGTCTATCAAGAGTCGATTGACCTTGAGTTGCTGG
TCAATGCACTTAATCATCACTTGCTCATTGACAGACTGGTCCTCACGCCC
AATCAAATAACGATAGAAATCGACAGGCAGATAGTACATGGTCTTGACCT
GCTGAAGGGCGTAAAGACAAAGAGATTATCGACATAAAAAGTATGTTCA
GGCAGTTAGAACTGGCTAGCACGCAACAAATCTGTCCGATAAATCAGCGA
GTGCATCATGGTATACTGGCCTTGGAGAAATTTCCGACCTGGTCCCAGCC
AAAAATCTGCCGAACAGGCAAGACTGA 4174.1
(SEQ. ID. NO. 303)
ATGGAACATTTAGCAACTTATTTTTCAACCTATGGAGGAGCTTTCTTCGC
TGCATTGGGAATTGTATTGGCGGTTGGATTAAGCGGTATGGGGTCTGCTT
ATGGAGTTGGTAAGGCTGGGCAATCTGCCGCAGCTTTACTGAAAGAACAG
CCTGAAAAGTTTGCCTCAGCTTTGATATTGCAATTATTGCCCGGAACACA
AGGATTATATGGTTTTGTTATTGGAATTTTAATTTGGTTGCAATTAACTC
CAGAACTTCCTTTAGAAAAGGCGTTGCTTATTTCTTTGTAGCTCTTCCA
ATTGCTATTGTAGGATACTTTTCAGCTAAGCATCAAGGAAATGTAGCAGT
AGCGGGAATGCAAATCTTGGCTAAAAGACCAAAAGAATTCATGAAGGGAG
CAATTTTAGCTGCCATGGTAGAAACCTATGCAATTCTTGCTTTTGTCGTA
TCATTCATTTTGACCCTTCGTGTATTA 4175.2
(SEQ. ID. NO. 304)
ATGTTAAAATCAGAAAAACAATCACGTTATCAAATGTTAAATGAAGAATT
GTCCTTCCTATTGGAAGGCGAAACCAATGTTTTGGCTAATCTTTCCAACG
CCAGTGCTCTCATAAAATCACGTTTTCCTAATACCGTATTTGCAGGCTTT
TATTTGTTCGATGGAAAGGAATTGGTTTTAGGCCCCTTCCAAGGAGGTGT
TCCTGCATCCGTATTGCACTAGGCAAGGGTGTTTGTGGTGAGGCAGCTC
ACTTTCAGGAAACTGTTATTGTTGGAGATGTGACGACCTATCTCAACTAT
ATTTCTTGTGATAGTCTAGCTAAAAGTGAAATTGTGGTGCCGATGATGAA
GAATGGTCAGTTACTTGGAGTTCTGGATCTGGATTCTTCAGAGATTGAGG
ATTACGATGCTATGGATCGAGATTATTTGGAACAATTTGTCGCTATTTTG
CTTGAAAAGACAGCATGGGACTTTACGATGTTTGAGGAAAAATCTTAA 4175.3
(SEQ. ID. NO. 305)
ATGTCAGTATTAGAGATCAAAGATCTTCACGTTGAGATTGAAGGAAAAGA
AATTTTAAAGGGGTTAACCTGACCCTGAAACAGGAGAAATTGCCGCTA
TCATGGGACCAAATGGTACAGGTAAATGACTCTTTCTGCCGCTATCATG
GGAAATCCAAACTATGAAGTAACTAAAGGTGAAGTTTTGTTTGATGGCGT
AAACATCCTTGAGTTGGAAGTGGATGAGCGTGCGCGTATGGGACTTTTCC TTGCTATGCAATACCCATCAGAAATCCCTGGAATTACCAATGCTGAGTTT
CTTCGTGCCGCTATGAATGCGGGTAAAGAAGATGATGAGAAGATTTCAGT
TCGTGAGTTTATTACTAAGCTAGATGAAAAAATGGAATTGCTCAACATGA
AGAAGAAATGGCAGAGCGTTACCTCAACGAAGGCTTCTCTGGTGGTGAG
AAAAAACGCAATGAAATTCTTCAACTTTTGATGTTGGAGCCAACATTTGC
TCTTTTGGACGAGATTGACTCAGGTCTTGATATTGACGCTCTTAAAGTTG
TGTCTAAAGGTGTCAATGCCATGCGTGGTGAAGGTTTTGGTGCTATGATC
ATCACTCACTACCAACGTCTTTTGAACTATATCACACCTGATGTGGTACA
CGTGATGATGGAAGGTCGTGTTGTCCTTTCTGGTGGTCCAGAATTGGCTG
CGCGTTTGGAACGTGAAGGATACGCAAAATTAGCTGAAGAACTTGGCTAC
GACTACAAGGAAGAATTGTAA 4174.4
(SEQ. ID. NO. 306)
ATGCCCTACAAAAGACAAAGGAGTTTTTCAATGGCACTTTCTAAACTAGA
TAGCCTTTATATGGCAGTGGTAGCAGACCATTCGAAAAATCCACATCACC
AAGGGAAGTTAGAAGATGCTGAGCAAATCAGTCTCAACAATCCGACTTGT
GGGGATGTCATCAACCTCTCTGTCAAGTTTGATGCAGAGGACCGTTTGGA
AGATATTGCTTTTCTAAATTCAGGATGCACGATTTCAACTGCTTCTGCTA
GTATGATGACAGATGCCGTTTTAGGAAAAACCAAACAAGAAATTTTAGAA
CTGGCGACTATTTTTTCTGAAATGGTTCAAGGGCAAAAAGATGAGCGTCA
AGACCAACTTGGAGACGCGGCATTCTTGTCAGGTGTTGCCAAATTCCCTC
AAAGAATCAAGTGTGCAACCCTAGCTTGGAATGCCCTTAAGAAAACAATT
GAAAATCAAGAAAAACAGTAA 4175.5
(SEQ. ID. NO. 307)
ATGAAAAATTCAAGACCTATTGAGAAAAGATGTCATGTTGCTAGATTTGCA
GGCAACTGAAAAAACAGCTGTCATCGACGAGATGATTAAAAATTTGACAG
ACCACGGTTATGTAACAGATTTTGAAACATTTAAAGAAGGAATTTTGGCG
CGTGAAGCTTTGACTTCTACTGGTTTGGGTGATGGAATCGCAATGCCTCA
CAGCAAAAACGCTGCTGTCAAAGAAGCGACAGTTCTATTTGCTAAGTCAA
ATAAGGGTGTTGACTACGAGAGCTTGGATGGACAAGCAACTGACCTCTTC
TTCATGATTGCAGCTCCAGAAGGTGCCAATGATACTCACTTGGCAGCCTT
GGCAGAATTGTCTCAATACTTGATGAAAGACGGTTTTGCAGACAAACTTC
GTCAAGCAACATCTGCAGACCAAGTTATCGAACTTTTTGACCAAGCTTCA
GAAAAAACTGAGGAACTTGTTCAAGCACCTGCTAATGACTCTGGTGACTT
TATCGTAGCTGTTACAGCTTGTACAACAGGTATTGCCCACACTTACATGG
CCCAAGAAGCCCTTCAAAAAGTAGCTGCTGAAATGGGGGTTGGTATCAAG
GTCGAAACCAACGGTGCTAGCGGTGTTGGAAATCAACTAACTGCAGAAGA
TATCCGTAAGGCTAAAGCTATTATCATTGCAGCAGACAAGGCCGTTGAAA
TGGATCGATTTGATGGAAAACCATTGATCCATCGTCCAGTTGCTGACGGT
ATCCGTAAGACAGAAGAGCTAATTAACTTGGCTCTTTCAGGAGATACTGA
AGTCTACCGTGCCGCTAATGGTGCCAAAGCTGCAACAGCCTCTAACGAAA TABLE 1-continued AACAAAGCCTTGGTGGTGCCTTGTACAAACACTTGATGAGTGGTGTATCT
CAAATGTTACCATTCGTTATCGGTGGTGGTATCATGATTGCCCTTGCCTT
CTTGATTGACGGTGCTTTGGGTGTTCCAAATGAAAACCTTGGCAATCTTG
GTTCTTACCATGAGTTAGCTTCTATGTTCATGAAAATTGGTGGAGCTGCC
TTTGGTTTGATGCTTCCAGTCTTTGCGGGTTATGTTGCCTACTCTATTGC
TGAAAAACCGGGTTTGGTAGCAGGTTTCGTGGCTGGTGCTATTGCCAAAG
AAGGTTTTGCCTTTGGTAAAATTCCTTATGCCGCAGGTGGTGAAGCAACT
TCAACTCTTGCAGGTGTCTCATCTGGTTTCCTAGGTGCCCTTGTTGGTGG
ATTTATCGCAGGTGCCTTGGTTCTTGCCATCAGAAATACGTTAAAGTTCC
TCGTTCACTCGAAGGTGCTAAATCAATCCTTCTATTGCCACTTCTTGGAA
CAATCTTGACAGGATTTGTTATGCTAGCTGTGAATATCCCAATGGCTGCA
ATCAACACTGCTATGAATGACTTCCTAGGCGGTCTTGGAGGAGGTTCAGC
TGTCCTTCTTGGTATCGTCCTTGGTGGAATGATGGCTGTTGACATGGGTG
GACCAGTTAATAAAGCAGCTTATGTCTTTGGTACAGGTACGCTTGCAGCA
ACTGTTTCTTCAGGTGGTTCTGTAGCCATGGCAGCAGTTATGGCTGGAGG
AATGGTGCCACCACTTGCAATCTTTGTCGCAACTCTTCTTTTCAAAGATA
AATTTACTAAGGAAGAACGTAACTCTGGTTTGACAAACATCATCATGGGC
TTGTCATTTATCACTGAGGGAGCGATTCCATTTGGTGCCGCTGACCCAGC
TCGTGCGATTCCAAGCTTCATCCTTGGTTCAGCAGTAGCAGGTGGACTCG
TTGGTCTTACTGGTATCAAACTCATGGCGCCACACGGAGGAATCTTCGTT
ATCGCCCTTACTTCAAATGCTCTCCTTTACCTCGTTTCTGTCTTGGTAGG
AGCAATCGTAAGTGGTGTGGTTTATGGTTACCTACGCAAACCACAAGCAT
AA 4175.6
(SEQ. ID. NO. 308)
ATGGCAAACAAGAATACAAGTACAACAAGACGGAGACCGTCTAAAGCAGA
ACTGGAAAGAAAAGAAGCGATTCAACGAATGTTGATTTCGTTAGGAATTG
CGATTTTATTGATTTTCGCAGCCTTCAAATTAGGGGCTGCAGGTATAACC
CTTTATAATTTAATTCGCTTGCTAGTGGGTAGCCTAGCTTATCTGGCGAT
ATTCGGCCTATTAATCTATCTCTTCTTTTTCAAGTGGATACGAAAACAGG
AAGGACTCTTATCTGGCTTTTTCACCATATTTGCTGGCTTACTCTTGATT
TTTGAGGCCTACTTGGTTTGGAAATATGGTTTGGACAAGTCCGTTCTAAA
AGGGACCATGGCTCAGGTTGTGACAGATCTGACTGGTTTTCGAACGACTA
GCTTTGCTGGAGGGGGCTTGATCGGGGTCGCTCTTTATATTCCACAGCCT
TTCTCTTTTCAAATATCGGAACTTACTTTATTGGTTCTATCTGATTTTAG
TGGGTTCTCTCCTAGTCAGCCCTTGGTCTGTTTACGATATTGCTGAATTT
TCAGTAGAGGCTTTGCCAAATGTGGGAAGGGCACGAGCGTCGAAAAGA
GGAACGCTTTGTCAAACAAGAAGAAAAAGCTCGCCAAAAGGCTGAGAAAG
AGGCTAGATTAGAACAAGAAGAGACTGAAAAAGCCTTACTCGATTTGCCT
CCTGTTGATATGGAAACGGGTGAAATTCTGACAGAGGAAGCTGTTCAAAA
TCTTCCACCTATTCCAGAAGAAAAGTGGGTGGAACCAGAAATCATCCTGC CTCAAGCTGAACTTAAATTCCCTGAACAGGAAGATGACTCAGATGACGAA
GATGTTCAGGTCGATTTTTCAGCCAAAGAAGCCCTTGAATACAAACTTCC
AAGCTTACAACTCTTTGCACCAGATAAACCAAAAGATCAGTCTAAAGAGA
AGAAAATTGTCAGAGAAAATATCAAAATCTTAGAAGCAACCTTTGCTAGC
TTTGGTATTAAGGTAACAGTTGAACGGGCCGAAATTGGGCCATCAGTGAC
CAAGTATGAAGTCAAGCCGGCTGTTGGTGTAAGGGTCAACCGCATTTCCA
ATCTATCAGATGACCTCGCTCTAGCCTTGGCTGCCAAAGATGTCCGGATT
GAAGCACCAATCCCTGGGAAATCCCTAATCGGAATTGAAGTGCCCAACTC
CGATATTGCCACTGTATCTTTCCGAGAACTATGGGAACAATCGCAAACGA
AAGCAGAAAATTCTTGGAAATTCCTTTAGGGAAGGCTGTTAATGGAACC
GCAAGAGCTTTTGACCTTTCTAAAATGCCCCACTTGCTAGTTGCAGGTTC
AACGGGTTCAGGGAAGTCAGTAGCAGTTAACGGCATTATTGCTAGCATTC
TCATGAAGGCGAGACCAGATCAAGTTAAATTTATGATGGTCGATCCCAAG
ATGGTTGAGTTATCTGTTTACAATGATATTCCCCACCTCTTGATTCCAGT
CGTGACCAATCCACGCAAAGCCAGCAAGGCTCTGCAAAAGGTTGTGGATG
AAATGGAAAACCGTTATGAACTCTTTGCCAAGGTGGGAGTTCGGAATATT
GCAGGTTTTAATGCCAAGGTAGAAGAGTTCAATTCCCAGTCTGAGTACAA
GCAAATTCCGCTACCATTCATTGTCGTGATTGTGGATGAGTTGGCTGACC
TCATGATGGTGGCCAGCAAGGAAGTGGAAGATGCTATCATCCGTCTTGGG
CAGAAGGCGCGTGCTGCAGGTATCCACATGATTCTTGCAACTCAGCGTCC
ATCTGTTGATGTCATCTCTGGTTTGATTAAGGCCAATGTTCCATCTCGTG
TAGCATTTGCGGTTTCATCAGGAACAGACTCCCGTACGATTTTGGATGAA
AATGGAGCAGAAAACTTCTTGGTCGAGGAGACATGCTCTTTAAACCGAT
TGATGAAAATCATCCAGTTCGTCTCCAAGGCTCCTTTATCTCGGATGACG
ATGTTGAGCGCATTGTGAACTTCATCAAGACTCAGGCAGATGCAGACTAC
GATGAGAGTTTTGATCCAGGTGAGGTTTCTGAAAATGAAGGAGAATTTTC
GGATGGAGATGCTGGTGGTGATCCGCTTTTTGAAGAAGCTAAGTCTTTGG
TTATCGAAACACAGAAAGCCAGTGCGTCTATGATTCAGCGTCGTTTATCA
GTTGGATTTAACCGTGCGACCCGTCTCATGGAAGAACTGGAGATAGCAGG
TGTCATCGGTCCAGCTGAAGGTACCAAACCTCGAAAAGTGTTACAACAAT
AA 4176.1
(SEQ. ID. NO. 309)
ATGAGTTATTTTAAAAAATATAAATTCGATAAATCCCAGTTCAAACTTGG
TATGCGAACCTTTAAAACAGGTATTGCTGTTTTTCTAGTTCTCTTGATTT
TTGGCTTTTTGGCTGGAAAGGTCTTCAAATTGGTGCTTTGACAGCCGTT
TTTAGCCTGAGGGAGAGTTTTGATGAGAGTGTTCATTTTGGGACTTCGCG
TATTCTAGGAAATAGTATCGGTGGACTCTATGCCTTGGTCTTCTTCTTAT
TAAATACCTTTTTCCACGAAGCCTTTTGGGTGACCTTGGTAGTTGTTCCA
ATCTGCACCATGTTAACCATTATGACAAATGTAGCCATGAATAACAAAGC
AGGGGTTATTGGTGGTGTAGCAGCTATGTTAATCATTACCCTATCAATTC TABLE 1-continued CAAGTGGTGAGACAATTTTGTACGTGTTTGTGCGTGTATTAGAAACGTTT
ATGGGAGTTTTTGTCGCAATTATCGTAAATTACGATATTGATCGTATTCG
TCTCTTTTTAGAGAAAAAGAAAAATAA 4178.2
(SEQ. ID. NO. 310)
ATGAATAAATCAGAACACCGCCACCAACTTATACGCGCTCTTATCACAAA
AAACAAGATTCATACACAGGCTGAGTTGCAAGCCCTTCTTGCTGAGAACG
ACATTCAAGTAACCCAGGCAACCCTCTCACGCGACATCAAAAATATGAAC
CTATCAAAAGTCCGCGAAGAAGATAGCGCTTATTATGTTCTTAACAATGG
TTCCATCTCAAAATGGGAAAAACGTCTCGAACTCTACATGGAAGACGCCC
TTGTCTGGATGCGCCCAGTCAACACCAAGTCCTACTAAAAACCCTTCCT
GGACTGGCTCAATCCTTTGGTTCTATCATTGATACTTTGAGCTTCCCTGA
CGCTATCGCTACCCTTTGTGGTAATGATGTCTGTCTTATCATCTGTGAAG
ATGCAGATACTGCTCAAAAGTGCTTTGAAGAACTGAAAAAATTCGCCCCA
CCATTTTTCTTTGAAGAATAA 4179.1
(SEQ. ID. NO. 311)
ATGAAAAGTATAAAATTAAATGCTCTATCTTACATGGGAATTCGTGTCTT
GAATATTATTTTTCCCATCCTAACTGGAACCTATGTCGCGCGTGTCTTGG
ACCGAACTGACTATGGTTACTTCAACTCAGTCGACACTATTTTGTCATTT
TTCTTGCCCTTTGCAACTTATGGTGTCTATAACTACGGTTTAAGGGCTAT
CAGTAATGTCAAGGATAACAAAAAAGATCTTAACAGAACCTTTTCTAGTC
TTTTTTATTTGTGCATCGCTTGTACGATTTTGACCACTGCTGTCTATATC
CTAGCCTATCCTCTCTTCTACTGATAATCCAATCGTCAAAAAGGTCTACC
TTGTTATGGGGATTCAACTCATTGCCCAGATTTTTTCAATCGAATGGGTC
AATGAAGCTCTGGAAAATTACAGTTTTCTCTTTTACAAAACTGCCTTCAT
CCGTATCCTGATGCTGGTCTCTATTTTCTTATTTGTTAAAAATGAACACG
ATATTGTTGTCTATACACTTGTGATGAGTTTATCGACGCTGATTAACTAC
CTGATTAGTTATTTTTGGATTAAAAGAGACATCAAACTTGTTAAAATTCA
CCTAAGTGATTTTAAACCACTCTTTCTCCCTCTGACAGCCATGTTAGTCT
TTGCCAATGCCAATATGCTCTTCACTTTTTTAGATCGCCTCTTCCTCGTT
AAAACAGGGATTGATGTCAACGTTAGTTACTATACCATAGCTCAGCGAAT
TGTGACCGTTATAGCTGGGGTTGTAACAGGTGCAATTGGAGTGAGTGTGC
CTCGTCTCAGTTACTATCTGGGGAAAGGAGACAAAGAAGCCTATGTTTCT
CTGGTTAATAGAGGTAGTCGAATCTTTAACTTCTTTATCATTCCACTGAG
TTTTGGACTCATGGTTTTAGGACCAAATGCCATCCTACTTTACGGTAGTG
AAAAATATCGGAGGCGGCATCTTGACCTCTCTCTTCGCTTTTCGTACG
ATTATCCTGGCCTTAGATACCATTCTTGGTTCCCAAATTCTCTTTACCAA
TGGCTATGAAAAACGTATCACAGTCTATACAGTCTTTGCTGGGCTACTCA
ATTTGGGCTTGAATAGTCTCCTTTTTTTCAACCATATCGTGGCTCCTGAA
TACTACTTACTGACAACTATGCTATCAGAGACTTCTCTACTTGTTTTCTA
TATCATTTTCATCCATAGAAAACAACTCATCCACTTGGGACATATCTTTA TABLE 1-continued GCTATACTGTTCGATACTCTCTCTTTTCACTTTCCTTTGTAGCAATTTAT
TTCCTGATTAATTTCGTGTATCCTGTAGATATGGTCATTAATTTGCCATT
TTTGATTAATACTGGTTTGATTGTCTTGCTATCAGCTATCTCTTATATTA
GTCTACTTGTCTTCACAAAAGATAGCATTTTCTATGAATTTTTAAACCAT
GTCCTAGCCTTAAAAAATAAATTTAAAAAATCATAG 4179.2
(SEQ. ID. NO. 312)
ATGAAACAACTAACCGTTGAAGATGCCAAACAAATTGAATTAGAAATTTT
GGATTATATTGATACTCTCTGTAAAAAGCACAATATCAACTATATTATTA
ACTACGGTACTCTGATTGGGGCGGTTCGACATGAGGGCTTTATCCCTTGG
GACGACGATATTGATCTGTCCATGCCTAGAGAAGACTACCAACGATTTAT
TAACATTTTTCAAAAGGAAAAAAGCAAGTATAAGCTCCTATCCTTAGAAA
CTGATAAGAACTACTTTAACAACTTTATCAAGATAACCGACAGTACGACT
AAAATTATTGATACTCGAAATACAAAAACCTATGAGTCTGGTATCTTTAT
CGATATTTTCCCTATAGATCGCTTTGATGATCCTAAGGTCATTGATACTT
GTTATAAACTGGAAAGCTTCAAACTGCTGTCTTTCAGTAAACATAAAAAT
ATTGTCTATAAGGATAGCCTTTTAAAAGATTGGATACGAACAGCCTTCTG
GTTACTCCTTCGACCGGTTTCTCCTCGTTATTTTGCAAATAAAATCGAGA
AAGAAATTCAAAAATATAGTCGTGAAAATGGGCAATATATGGCTTTTATC
CCTTCAAAATTTAAGGAAAAGGAAGTCTTCCCAAGTGGTACCTTTGATAA
AACAATCGATTTACCCTTTGAGAATTTAAGCCTTCCTGCACCTGAAAAAT
TTGATACTATTTTGACACAATTTTATGGAGATTATATGACCCTACCACCA
GAAGAAAAACGCTTCTACAGTCATGAATTTCACGCTTATAAATTGGAGGA
TTAG 4179.3
(SEQ. ID. NO. 313)
ATGATAAAAATCAATCATCTAACCATCACACAAAACAAAGATTTACGAGA
TCTTGTATCTGACCTAACCATGACCATCCAAGACGGGGAAAAGGTTGCTA
TTATTGGTGAAGAAGGAAATGGCAAATCAACCTTACTTAAAATTTTAATG
GGGGAAGCTTTGTCTGATTTCACTATCAAGGGAAACATCCAATCTGACTA
TCAGTCACTGGCCTACATTCCTCAAAAAGTCCCTGAGGACCTAAAAAAGA
AAACTTTACACGACTACTTCTTTTTAGATTCTATTGATTTAGACTACAGT
ATCCTCTATCGTTTGGCGGAGGAATTGCATTTTGATAGCAATCGTTTCGC
AAGTGACCAAGAGATTGGCAATCTATCAGGGGGCGAAGCTTTGAAAATTC
AGCTTATCCATGAGTTAGCCAAACCCTTTGAGATTCTATTTTTAGATGAA
CCTTCAAATGACCTAGACCTTGAGACAGTTGATTGGCTAAAAGGCCAGAT
TCAAAGACCAGGCAAACCGTTATTTTCATTTCCCATGATGAAGACTTTC
TTTCTGAAACGGCAGACACTATTGTTCACTTGCGACTGGTCAAACACCGT
AAAGAAGCGGAAACGCTAGTAGAGCATTTAGACTATGATAGCTATAGTGA
GCAGAGAAAGGCTAATTTTGGCAAACAAAGTCAGCAAGCTGCTAACAACC
AAAGAGCCTACGATAAAACCATGGAAAAACATCGGAGAGTTAAGCAAAAT
GTAGAAACTGCGCTTCGAGCTACCAAAGATAGTACTGCCGGTCGCCTATT TABLE 1-continued

GGCTAAAAAGATGAAAACTGTCCTCTCACAAGAAAAACGCTACGAAAAGG

CAGCTCAGTCCATGACTCAAAAGCCACTTGAAGAGGAACAAATCCAACTT

TTCTTTTCAGACATCCAACCATTACCAGCTTCTAAAGTCTTAGTCCAACT

GGAAAAAGAAAATTTGTCCATTGACGACCGAGTTTTGGTTCAAAAACTAC

AACTAACTGTCCGTGGCCAAGAAAAAATCGGTATTATCGGGCCAAATGGT

GTTGGGAAATCAACTCTGTTAGCCAAGTTACAGAGACTTCTGAATGATAA

AAGAGAGATTTCACTTGGTTTTATGCCACAAGATTACCACAAAAAACTGC

AATTGGATTTATCCCCAATAGCCTATCTCAGTAAAACTGGGGAAAAAGAG

GAACTACAGAAAATCCAATCTCACCTAGCTAGTCTCAATTTCAGTTATCC

AGAAATGCAGCATCAAATTCGCTCCTTATCTGGCGGACAACAGGGAAAAC

TCCTGCTTTTGGATTTAGTCCTGCGCAAACCAAACTTTCTCCTGCTGGAT

GAACCCACACGAAACTTTTCTCCCACTTCTCAACCCCAAATCAGAAAACT

CTTTGCTACCTATCCAGGCGGTCTCATCACTGTTTCGCATGACCGTCGTT

TCTTAAAAGAAGTCTGCTCGATCATCTATCGCATGACAGAACACGGTTTG

AAGCTAGTTAATTTAGAAGATTTATAA 4179.4

(SEQ. ID. NO. 314)
ATGAAACCAAAAACATTTTACAACTTGCTTGCCGAGCAGAATCTTCCACT

TTCGGACCAGCAAAAAGAACAATTTGAACGTTATTTTGAGCTCTTGGTCG

AGTGGAATGAGAAGATTAATTTGACGGCGATTACGGACAAGGAAGAAGTT

TATCTCAAACATTTTTACGATTCGATTGCACCCATTCTTCAAGGTTTGAT

TCCCAATGAAACTATCAAACTTCTTGATATCGGGGCTGGGGCAGGATTTC

CTAGTCTACCAATGAAAATTCTCTATCCGGAGTTAGATGTGACCATTATT

GATTCACTCAATAAGCGCATCAACTTCCTACAACTCTTGGCTCAAGAACT

GGATTTGAACGGAGTTCATTTCTACCACGGACGTGCCGAAGATTTTGCCC

AAGACAAGAACTTCCGTGCTCAATATGATTTTGTAACAGCTCGTGCGGTT

GCCCGTATGCAGGTCCTATCTGAATTGACTATTCCCTACCTTAAGGTTGG

TGGCAAACTATTAGCACTCAAGGCTAGCAATGCGCCTGAGGAATTATTAG

AAGCTAAGAATGCCCTCAATCTCCTTTTTAGTAAGGTCGAAGACAATCTC

AGctACGCCCTACCGAATAGAGATCCGCGCTATATCACAGTGGTAGAAAA

GAAAAAAGAAACACCAAATAAATATCCACGTAAGGCTGGTATGCCAAATA

AACGCCCACTTTAA 4179.6

(SEQ. ID. NO. 315)
ATGAGTATTAAACTAATTGCCGTTGATATCGACGGAACCCTTGTCAACAG

CCAAAAGGAAATCACTCCTGAAGTTTTTTCTGCCATCCAAGATGCCAAAG

AAGCTGGTGTCAAAGTCGTGATTGCAACTGGCCGCCCTATCGCAGGCGTT

GCCAAACTTCTAGACGACTTGCAGTTGAGAGACGAGGGGGACTATGTGGT

AACCTTCAACGGTGCCCTTGTCCAAGAAACTGCTACAGGACATGAGATTA

TCAGCGAATCCTTGACTTATGAGGATTATCTAGATATGGAATTCCTCAGT

CGCAAGCTCGGTGTCCACATGCATGCCATTACCAAGGACGGTATCTATAC

TGCAAATCGCAATATCGGAAAATACACTGTACACGAATCAACCCTCGTCA

GCATGCCTATCTTCTACCGTACCCCTGAAGAAATGGCTGGCAAAGAAATT

GTTAAATGTATGTTTATCGATGAACCAGAAATTCTCGATGCTGCGATTGA

AAAAATTCCAGCAGAATTTTACGAGCGCTACTCCATCAACAAATCTGCTC

CTTTCTACCTCGAACTCCTTAAAAAGAATGTAGACAAGGGTTCAGCCATT

ACTCACTTGGCTGAAAAACTCGGATTGACCAAAGATGAAACCATGGCAAT

CGGTGATGAAGAAAATGACCGTGCCATGCTGGAAGTCGTTGGAAACCCCG

TTGTCATGGAAAATGGAAATCCAGAAATCAAAAAAATCGCCAAATACATC

ACCAAAACAAATGACGAATCCGGCGTTGCCCATGCCATCCGAACATGGGT

ACTGTAA 4179.7

(SEQ. ID. NO. 316)
ATGACTTGGATTATTCTTGGAGTTATCGCTCTTATTGTTATTTTTGTGAT

TGTTAGCTATAACGGTTTGGTTAAAAATCGTATGCAAACCAAGGAGGCTT

GGAGTCAGATTGATGTTCAGTTGAAACGTCGCAATGACCTCTTGCCAAAC

TTGATTGAGACTGTAAAAGGTTATGCCAAATATGAAGGTTCTACCCTTGA

AAAGGTGGCAGAACTACGTAACCAAGTGGCGGCAGCGACTTCACCAGCAG

AAGCTATGAAAGCCAGTGATGCCCTCACTCGTCAGGTTTCAGGTATTTTT

GCAGTTGCAGAAAGCTATCCAGATTTGAAAGCTAGTGCTAACTTTGTTAA

ATTGCAAGAGGAGTTGACAAACACAGAAAATAAAATTTCTTACTCTCGTC

AACTCTATAACAGTGTTTGTCAGCAACTACAATGTAAAATTAGAAACTTT

CCCGAGCAATATTATCGCTGGAATGTTTGGATTTAAAGCGGCAGATTTCC

TTCAAACACCTGAAGAGGAAAAGTCGGTTCCTAAAGTTGATTTTAGCGGT

TTAGGTGACTAA 4179.8

(SEQ. ID. NO. 317)
ATGTTGTTTGATCAAATTGCAAGCAATAAACGAAAAACCTGGATTTTGTT

GCTGGTATTTTTCCTACTCTTAGCTCTTGTTGGTTATGCGGTTGGTTATC

TCTTTATAAGATCTGGACTTGGTGGTTTGGTTATTGCACTGATTATCGGC

TTTATCTACGCTTTGTCTATGATTTTTCAATCGACAGAGATTGTCATGTC

CATGAATGGAGCGCGTGAGGTGGATGAGCAAACGGCACCAGACCTCTACC

ATGTAGTGGAAGATATGGCTCTGGTCGCTCAGATTCCTATGCCCCGTGTT

TTCATCATTGATGATCCAGCCTTAAATGCCTTTGCGACAGGTTCTAATCC

TCAAAATGCGGCTGTTGCTGCGACTTCAGGTCTACTAGCTATCATGAATC

GTGAAGAACTAGAAGCTGTTATGGGACATGAAGTCAGTCATATTCGTAAT

TATGATATCCGTATTTCGACTATTGCAGTTGCCCTTGCTAGTGCTATCAC

CATGCTTTCTAGTATGGCAGGTCGTATGATGTGGTGGGGTGGAGCAGGTC

GCAGACGAAGTGATGATGACCGAGATGGAAATGGTCTTGAAATCATTATG

CTAGTGGTTTCCCTACTAGCTATTGTACTGGCACCCTCTCGCTGCAACCTT

GGTTCAGCTCGCTATTTCTCGTCAGAGGGAATTTCTGGCAGATGCATCTA

GTGTCGAGCTGACTCGCAATCCCCAGGGAATGATTAATGCCCTAGATAAG

TTGGACAATAGCAAACCTATGAGTCGCCACGTCGATGATGCTAGCAGTGC

TABLE 1-continued

CCTTTATATCAATGATCCTAAGAAAGGTGGGGGGTTCCAAAAACTCTTTT
ATACCCACCCACCTATCTCAGAACGGATTGAACGTTTAAAACAGATGTAA 4179.9
(SEQ. ID. NO. 318)
ATGAAATTAAATATTCAAGAAATTCGTAAGCAGTCTGAAGGTTTGAACTT
TGAACAAACGTTAGATTTAGTTGATGACCTGCGTGCACGTAATCAAGAAA
TTTTAGATGTAAAAGATATCCTTGCAGTTGGGAAAGTACAATATGAAGAC
CGTATGTATTTCTTAGATTATCAACTATCTTATACCATTGTTCTTGCTTC
GAGTCGCAGTATGGAGCCAGTTGAGTTAGTTGAATCTTATCCAGTCACGG
AAGTTTTCATGGAAGGCGCAACTAACCAGCTAGATCAAGAAGTTTTAGAT
GATGACTTGGTCTTGCCCATCGAAAATGGGGAGCTTGACCTTGCTGAGAG
TGTATCAGACAATATCCTGCTAAACATTCCTATCAAGGTCTTGACGGCTG
AAGAAGAAGCTGGTCAAGGATTTATCTCAGGAAATGACTGGCAAATCATG
ACAGAGGAAGAATACCAAGCTCAAAAAGCAGTAAAGAAAGAAGAAAACAG
TCCTTTTGCTGGCTTACAAGGACTATTTGACGGAGATGAATAA 4179.12
(SEQ. ID. NO. 319)
ATGGAGTTATTTATGAAAATCACAAACTATGAAATCTATAAGTTAAAAAA
ATCAGGTTTGACCAATCAACAGATTTTGAAAGTGCTAGAATACGGTGAAA
ATGTTGATCAGGAGCTTTTGTGGGTGATATTGCAGATATCTCAGGTTGCC
GTAATCCAGCCGTTTTTATGGAACGTTATTTTCAGATAGACGATGCGCAT
TTGTCGAAAGAGTTTCAAAAATTTCCATCTTTCTCTATTTTAGATGACTG
TTATCCTTGGGATTTGAGTGAAATATATGATGCGCCTGTACTTTTATTTT
ACAAGGGAAATCTTGACCTCCTGAAATTCCCGAAGGTAGCGGTCGTGGGC
AGTCGTGCTTGTAGCAAACAGGGAGCTAAGTCAGTTGAAAAAGTCATTCA
AGGCTTGGAAAATGAACTGGTTATTGTCAGTGGTCTGGCCAAGGGCATTG
ACACAGCAGCTCATATGGCAGCTCTTCAGAATGGCGGAAAAACCATTGCA
GTGATTGGAACAGGACTGGATGTGTTTTATCCTAAAGCCAATAAACGCTT
GCAAGACTACATCGGCAATGACCATCTGGTTCTAAGTGAATATGGACCTG
GTGAACAACCTCTGAAATTTCATTTTCCTGCCCGTAATCGCATCATTGCT
GGACTTTGTCGTGGTGTGATTGTAGCAGAGGCTAAGATGCGTTCAGGTAG
TCTCATTACGTGTGAGCGAGCAATGGAAGAAGGACGCGATGTCTTTGCTA
TTCCTGGTAGCATTTTAGATGGACTATCAGACGGTTGCCATCATTTGATT
CAAGAAGGAGCAAAATTGGTCACCAGTGGGCAAGATGTTCTTGCGGAATT
TGAATTTTAA 4181.1
(SEQ. ID. NO. 320)
ATGAAACGTCAATTAGCCTTGGTCGTCTTTAGTGGTGGTCAAGATTCAAC
AACCTGCCTTTTCTGGGTCATGCAACACTATGAAACAGTCGAAGCTGTCA
CCTTTGCCTACGGCCAACGTCATCACCTCGAAATTCAAATTACTAGAGAA
ATCGCTAAGGAACAGGGCATTCGTCACCATATCCTCGATATGTCTCTGCT
GGGACAAATCACTGCTCAGCCAGACTTTGCGACGATTCATATTTCCTACA
TTCCTGACAAGCTCTGTGTCGAGTCAAAATCCCTCAAACTATATCTATTT

AGCTACCGAAACCACGGAGATTTCCACGAAAACTGTATCAACACCATCGG
GAAAGACTTGGTCAACTTGCTAGACCCTCGCTATTTAGAAGTCTGGGGAA
AATTCACTCCGCGCGGTGGCATTTCAATCGACCCCTACTACAACTACGGT
AAGCAAGGAACTAAGTATGAGGGCTTGGCAGAACAACGCCTCTTCCAACA
CGACCTTTATCCAGAGAAAATTGACAACCGCTAA 4181.2
(SEQ. ID. NO. 321)
ATGACCGAAACGGTAGAAGATAAAGTAAGTCATTCAATTACTGGGCTTGA
TATCCTCAAGGGGATAGTTGCTGCGGGAGCTGTCATAAGTGGAACCGTTG
CAACTCAAACGAAGGTATTTACAAATGAGTCAGCAGTACTTGAAAAAACT
GTAGAGAAAACGGATGCTTTGGCAACAAATGATACAGTAGTTCTAGGTAC
GATATCTACAAGTAATTCAGCGAGTTCAACTAGTTTGTCAGCTTCAGAGT
CGGCAAGTACATCTGCATCTGAGTCAGCCTCAACCAGCGCTTCGACCTCA
GCAAGTACAAGTGCATCAGAATCAGCAAGTACATCGGCTTCGACAAGTAT
TTCTGCATCATCTACTGTGGTAGGTTCACAAACAGCTGCCGCTACAGAAG
CAACTGCTAAGAAGGTCGAAGAAGATCGTAAGAAACCAGCTAGTGATTAT
GTAGCATCAGTTACAAATGTCAATCTCCAATCTTATGCTAAGCGACGCAA
GCGTTCAGTGGATTCCATCGAGCAATTGCTGGCTTCTATAAAAAATGCTG
CTGTTTTTTCTGGCAATACGATTGTAAATGGCGCCCCTGCAATTAATGCA
AGTCTAAACATTGCTAAAAGTGAGACAAAAGTTTATACAGGTGAAGGTGT
AGATTCGGTATATCGTGTTCCAATTTACTATAAAATTGAAAGTGACAAATG
ATGGTTCAAAATTGACCTTTACCTATACGGTTACGTATGTGAATCCTAAA
ACAAATGATCTTGGTAATATATCAAGTATGCGTCCTGGATATTCTATCTA
TAATTCAGGTACTTCAACACAAACAATGTTAACCCTTGGCAGTGATCTTG
GTAAACCTTCAGGTGTAAAGAACTACATTACTGACAAAAATGGTAGACAG
GTTCTATCCTATAATACATCTACAATGACGACGCAGGGTAGTGGGTATAC
TTGGGGAAATGGTGCCCAAATGAATGGTTTCTTTGCTAAGAAAGGATATG
GATTAACATCATCTTGGACTGTACCAATTACTGGAACGGATACATCCTTT
ACATTTACCCCTTACGCTGCTAGAACAGATAGAATTGGAATTAACTACTT
CAATGGTGGAGGAAGGTAGTTGAATCTAGCACGACCAGTCAGTCACTTT
CACAGTCTAAGTCACTCTCAGTAAGTGCTAGTCAAAGCGCCTCAGCTTCA
GCATCAACAAGTGCGTCGGCTTCAGCATCAACCAGTGCCTCGGCTTCAGC
GTCAACCAGTGCGTCAGCTTCAGCAAGTACCAGTGCTTCAGTCTCAGCAT
CAACAAGTGCTTCAGCCTCAGCATCGACAAGTGCCTCGGCTTCAGCAAGC
ACATCAGCATCTGAATCAGCGTCAACCAGTGCTTCGGCTTCAGCAAGTAC
CAGTGCTTCAGCTTCAGCATCAACCAGCGCCTCGGCCTCAGCAAGCACCT
CAGCTTCTGAATCGGCCTCAACCAGCGCCTCGGCCTCAGCAAGCACCTCA
GCTTCTGAATCGGCCTCAACCAGCGCCTCAGCCTCAGCATCAACGAGTGC
TTCGGCTTCAGCAAGCACAAGCGCCTCGGGTTCAGCATCAACGAGTACGT
CAGCTTCAGCGTCAACCAGTGCTTCAGCCTCAGCATCAACAAGTGCGTCA
GCCTCAGCAAGTATCTCAGCGTCTGAATCGGCATCAACGAGTGCGTCTGA

TABLE 1-continued

```
GTCAGCATCAACGAGTACGTCAGCCTCAGCAAGCACCTCAGCTTCTGAAT
CGGCCTCAACCAGTGCGTCAGCCTCAGCATCGACAAGCGCCTCAGCTTCA
GCAAGTACCAGTGCTTCAGCCTCAGCGTCGACAAGTGCGTCGGCCTCAAC
CAGTGCATCTGAATCGGCATCAACCAGTGCGTCAGCCTCAGCAAGTACTA
GTGCATCGGCTTCAGCATCAACCAGTGCCTCGGCTTCAGCGTCAACCAGT
GCGTCAGCTTCAGCAAGTACCAGTGCTTCAGTCTCAGCATCAACAAGTGC
TTCAGCCTCAGCATCGACAAGTGCCTCGGCTTCAGCAAGCACATCAGCAT
CTGAATCAGCGTCGACAAGCGCCTCAGCTTCAGCAAGTCCCAGTGCGTCA
GCTTCAGCATCAACCAGCGCCTCGGCCTCAGCAAGCACCTCAGCTTCTGA
ATCGGCCTCAACCAGCGCCTCGGCCTCAGCAAGCACCTCAGCTTCTGAAT
CGGCCTCAACCAGCGCCTCAGCCTCAGCATCAACGAGTGCTTCGGCTTCA
GCAAGCACAAGCGCCTCGGTTCAGCATCAACGAGTACGTCAGCTTCAGC
GTCAACCAGTGCTTCAGCCTCAGCATCAACAAGTGCGTCAGCCTCAGCAA
GTATCTCAGCGTCTGAATCGGCATCAACGAGTGCGTCTGAGTCAGCATCA
ACGAGTACGTCAGCCTCAGCAAGCACCTCAGCTTCTGAATCGGCCTCAAC
CAGTGCGTCAGCCTCAGCATCGACAAGCGCCTCAGCTTCAGCAAGTACCA
GTGCTTCAGCCTCAGCTCGACAAGTGCGTCGGCCTCAACCAGTGCATCTG
AATCGGCATCAACCAGTGCGTCAGCCTCAGCAAGTACTAGTGCATCAGCT
TCAGCATCAACGAGTGCATCGGCTTCAGCATCAACCAGTGCCTCGGCTTC
AGCGTCAACCAGTGCGTCAGCTTCAGCAAGTACCAGTGCTTCAGTCTCAG
CATCAACAAGTGCTTCAGCCTCAGCATCGACAAGTGCcTCGGCTTCAGCA
AGCACATCAGCATCTGAATCAGCGTCGACAAGCGCcTCAGCTTCAGCAAG
TACCAGTGCGTCAGCCTCAGCGTCGACAAGTGCGTCAGCCTCAGCAAGTA
CTAGTGCATCAGCTTCAGCATCAACGAGTGCATCGGCTTCGGCGTCAACC
AGTGCATCAGAGTCAGCAAGTACCAGTGCGTCAGCTTCCGCATCAACAAG
TGCCTCGGCTTCAGCAAGCACCAGTGCGTCGGCTTCAGCAAGTACTAGCG
CCTCAGCCTCAGCCTCAACCAGTGCGTCAGCCTCAGCAAGTATCTCAGCG
TCTGAATCGGCATCAACGAGTGCGTCCGCTTCAGCAAGTACTAGCGCCTC
AGCCTCAGCGTCAACAAGTGCATCGGCTTCAGCGTCAACGAGTGCGTCTG
AATCGGCATCAACGAGTGCGTCCGCTTCAGCAAGTACTAGCGCCTCAGCC
TCAGCGTCAACAAGTGCATCGGCTTCAGCATCAACGAGTGCGTCCGCTTC
AGCAAGTACTAGCGCCTCAGCCTCAGCGTCAACAAGTGCATCGGCTTCAG
CGTCAACGAGTGCGTCTGAGTCAGCATCAACGAGTGCGTCAGCCTCAGCA
AGCACATCAGCTTCTGAATCTGCATCAACCAGTGCGTCAGCCTCAGCATC
GACAAGCGCCTCAGCTTCAGCAAGTACCAGTGCGTCAGCCTCAGCGTCGA
CAAGTGCGTCGGCTTCAGCAAGTACCAGTGCGTCAGCCTCAGCAAGTACC
AGTGCGTCAGCCTCAGCGTCGACAAGTGCGTCGGCCTCAACCAGTGCATC
TGAATCGGCATCAACCAGTGCGTCAGCCTCAGCAAGTACTAGTGCATCAG
CTTCAGCATCAACGAGTGCATCGGCTTCAGCATCAACCAGTGCATCAGAG
```

```
TCAGCAAGTACCAGTGCGTCAGTTCCGCATCAACAAGTGCCTCGGCTTCA
GCAAGTACTAG
```

4183.1
(SEQ. ID. NO. 322)
```
ATGGGGGTCGAAACTTGGTTTTATTCTAGCATCTGCTGGCTGGCCATCGG
GCTTGGTTCCGTTTGGAAGTTTCCCTACATGACTGCTGCTAATGGCGGTG
GAGGCTTTTTACTAATCTTTCTCATTTCCACTATTTTAATCGGTTTCCCT
CTCCTGCTGGCTGAGTTTGCCCTTGGCCGTAGTGCTGGCGTTTCCGCTAT
CAAAACCTTTGGAAAACTGGGCAAGAATAACAAGTACAACTTTATCGGTT
GGATTGGCGCCTTTGCCCTCTTTATCCTCTTATCTTTTTACAGTGTTATC
GGAGGATGGATTCTAGTCTATCTAGGTATTGAGTTTGGGAAATTGTTCCA
ACTTGGTGGAACGGGTGATTATGCTCAGTTATTTACTTCAATCATTTCAA
ATCCAGCCATTGCCCTAGGAGCTCAAGCGGCCTTTATCCTATTGAATATC
TTCATTGTATCACGTGGGGTTCAAAAAGGGATTGAAAGAGCTTCGAAAGT
CATGATGCCCCTGCTCTTTATCGTCTTTGTTTTTATCATCGGTCGCTCTC
TCAGTTTGCCAAATGCCATGGAAGGGGTTCTTTACTTCCTCAAACCAGAC
TTTTTCAAAACTGACTAGCACTGGTCTCCTCTATGCTCTGGGACAATCTTT
CTTTGCCCTCTCACTAGGGGTTACAGTCATGTTGACCTATGCTTCTTACT
TAGACAAGAAACCAATCTAGTCCAGTCAGGAATCTCCATCGTAGCCATG
AATATCTCGATATCCATCATGGCAGGTCTAGCCATTTTCCAAGCTCGATC
CCCCTTCAATATCCAGTCTGAAGGGGGACCCAGCCTGCTCTTTATCGTCT
TGCCTCAACTCTTTGACAAGATGCCTTTTGGAACCATTTTCTACGTCCTC
TTCCTCTTGCTCTTCCTTTTTGCGACAGTCACTTTTTCTGTCGTGATGCT
GGAAATCAATGTAGACAATATCACCAACCAGGATAACAGCAAACGTGCCA
AATGGAGTGTTATTTTAGGAATTTTTGACCTTTGTCTTTGGCATTCCTTCA
GCCCTATCTTACGGTGTCATGGCGGATGTTCACATTTTTGGTAAGACCTT
CTTTGACGCTATGGACTTCTTGGTTTCCAATCTCCTCATGCCATTTGGAG
CTCTCTACCTTCACTTTTTACAGGCTATATCTTTAAAAAGGCTCTTGCAA
TGGAGGAACTCCATCTCGATGAAAGAGCATGGAAACAAGGACTGTTCCAA
GTCTGGCTCTTCCTTCTTCGTTTCTTCGTTTCGTCATTCCAATCATCATC
ATTGTGGTCTTCATTGCCCAATTTATGTAATCAAAAAGGACTTGAGTAG
```

4183.5
(SEQ. ID. NO. 323)
```
ATGTTGAAAAAATGGCAGTTAAAAGATGTTATCTTGCTTGCTTTCTTGTC
TATCTTTTTTGGTGGGGTTTTCGTTGGTTCAGGATATGTGTATAATATTC
TCAGTCTACTCTTAACACCCTCTTGGTTTGCAGGCCTTTGCCAATGAAATC
CTCTTCGGTCTCTGGTGTATGGCTGCGCCCATTGCTGCCATCTTTGTTCC
GAGAGTCGGAAGTGCAACGATTGGAGAAGTGCTAGCTGCGCTTGCTGAAG
TCCTTTATGGTAGCCAATTTGGTCTAGGAGCTCTTTTGTCTGGCTTTGTT
CAAGGTTTGGGAAGTGAATTTGGTTTTATCGTAACTAAGAATCGCTATGA
AAGTTGGCTCTCTCTAACTGCTAATAGTATTGGGATTACGCTTGTTAGCT
TTGTCTATGAATACATTAAGTTAGGTTACTACGCCTTTTCCCTTCCGTTT
```

TABLE 1-continued

GTCCTTTCCTTGCTTGTGGTACGTTTTATTTCTGTTTATTTCTTCTGTAC

CATCTTGGTTCGTGCCATTGTCAAACTCTATCATCAGTTTGCAACTGGAG

GAAAAGCATAG 4183.6

(SEQ. ID. NO. 324)
ATGGTCAAAGTAGCAACCCAGACACCGATTATCAGTCTCTTCTTGCTGAT

TTTATCCTTGGAAACATCTTTCATTCCTTCGATTGCTCTGACTCTTTCGG

TAGTCGCATTTTGTATTCTCTTTATGCTCTATTACCGTCGATTTAAAATG

TTAGCTTGGATGATCATACTTGCCATTTTACCATCTTTTGCCAACTACTG

GGCAGTTCAGTTACACGGAGATGCTTCACAGGCAGTCATGCTTGGAACGA

GGGCCTTTGTGACAGTTTGTATCGGCCTTGTCTTTGTTTCCTCTGTTTCA

CTAAAAGAGCTTCTCTTGTACTTGGCTCAAAAGGGGCTATCACGCTCTTG

GTCCTATGCCTTGATTGTGGTATTCAATTCTTTTCCTCTCATTCAGCAAG

AAATCAAGTCCCTCAAAGAAGCTTGCCTATTACGTGGTCAAGAACTACAT

TTTTGGTCGCCCTTGATTTACAGTAAGGTTCTGATGACAGTCTTTAGGTG

GCGCCATCTTTACCTGAGAGCTCTATCTGCTCACGGATATGACGAACATG

CACAGTTGAAGAATAGCTATCGGACTTTTTATATTCCTAAAAAAACAAAA

TTAATCTACCTGCTTTTCTTTTTATTGCTTCAAACCAGTCTATTTTTATA

A 4183.7

(SEQ. ID. NO. 325)
ATGAGAAAGCACCAATTACAAGTTCACAAATTAACCATTTTATCTATGAT

GATTGCCCTTGATGTAGTCCTTACACCTATCTTTCGAATTGAGGGAATGG

CACCGATGTCCAGTGTAGTCAATATTCTAGCAGGAATCATGATGGGACCT

GTTTATGCCTTGGCTATGGCTACAGTCACAGCCTTTATCCGTATGACGAC

TCAAGGGATTCCGCCTTTAGCTCTCACAGGAGCGACTTTTGGAGCCCTTC

TAGCAGGTCTCTTTTATAAGTACGGTCGAAAATTTCACTATTCTGCTCTA

GGAGAGATTTTGGGAACAGGTATTATTGGTTCCATTGTTTCCTATCCTGT

TATGGTACTCTTTACAGGATCAGCTGCTAAGCTTAGCTGGTTTATCTACA

CGCCTCGATTTTTCGGAGCAACCTTGATTGGTACAGCGATTTCCTTTATT

GCCTTTCGATTTTTAATCAAGCAGGAATTCTTTAAAAAAGTGCAGGGATA

TTTCTTTAGTGAAAGGATAGACTGA 4183.8

(SEQ. ID. NO. 326)
ATGCAGGAATTTACAAATCCCTTTCCTATAGGCTCTAGTTCCCTCATTCA

CTGCATTACCAATGAGATTTCTTGTGAGATGCTGGCAAATGGGATTTTGG

CTCTGGGATGCAAACCTGTCATGGCAGATGATTCCCGTGAAGTTCTTGAT

TTTACTAAGCAAAGTCAGGCTCTCTTCATCAATTTGGGGCATTTGTCAGC

TGAGAAGGAAAAGCAATCCGCATGGCAGCTTCGTATGCAAACCAATCTT

CTCTCCCGATGGTAGTAGATGCGGTTGGCGTAACGACTTCATCCATTCGT

AAGAGCTTAGTTAAAGACCTTTTAGACTATAGACCTACGGTCCTTAAAGG

AAACATGTCAGAAATTCGAAGTCTTGTTGGATTAAAGCACCACGGCGTTG

GGGTCGATGCGAGTGCTAAAGATCAAGAAACGGAGGATTTGCTTCAAGTC

TTGAAAGACTGGTGTCAGACCTATCCTGGTATGTCTTTCTTAGTCACAGG

TCCCAAGGACCTCGTCGTTTCGAAAAATCAGGTCGCTGTACTGGGAAATG

GCTGTACTGAATTAGACTGGATAACAGGGACAGGAGACTTGGTTGGAGCC

TTAACAGCTGTTTTTCTCAGCCAAGGAAAGACTGGTTTTGAAGCTTCTTG

CTTAGCAGTCTCTTATCTCAATATCGCTGCTGAGAAAATAGTTGTTCAAG

GAATGGGATTGGAAGAATTTCGTTACCAAGTACTCAATCAGCTTTCGCTC

CTAAGAAGAGATGAAAATTGGCTAGATACCATCAAAGGAGAGGTTTATGA

ATAG 4185.3

(SEQ. ID. NO. 327)
ATGAACCATAAAATCGCAATTTTATCAGATGTTCATGGCAATGCGACGGC

GCTAGAAGCAGTGATTGCAGATGCTAAAAATCAAGGGGCCAGTGAATATT

GGCTTCTGGGAGATATTTTCTTCCTGGTCCAGGCGCAAATGACTTAGTC

GCCCTGCTAAAGGACCTTCCTATCACAGCAAGTGTTCGAGGCAATTGGGA

TGATCGTGTCCTTGAGGCTTTAGATGGGCAATATGGCTTAGAAGACCCAC

AGGAAGTTCAGCTCTTGCGTATGACACAGTATTTGATGGAGCGAATGGAT

CCTGCAACGATTGTCTGGCTACGAAGCTTGCCTTTGCTGGAAAAGAAAGA

AATTGACGGATTGCGCTTTTCTATCTCTCATAATTTACCTGACAAAAACT

ATGGTGGTGACTTGCTAGTTGAGAATGATACAGAGAAATTTGACCAACTG

CTAGATGCGGAAACGGACGTGGCAGTTTATGGTCATGTTCACAAGCAGTT

GCTTCGTTATGGAAGTCAAGGGCAACAAATCATCAATCCAGGGTCGATTG

GCATGCCCTATTTTAATTGGGAGGCGTTAAAAAATCACCGTTCCCAGTAT

GCCGTGATAGAAGTTGAAGATGGGGAATTACTCAATATCCAATTTCGTAA

AGTTGCTTATGATTACGAAGCTGAGTTAGAATTGGCCAAGTCCAAGGGGC

TTCCCTTTATCGAAATGTATGAAGAACTGCGTCGTGACGATAACTATCAG

GGGCACAATCTGGAATTATTAGCCAGCTTAATAGAAAAGCATGGGTATGT

AGAGGATGTGAAGAATTTTTTTGATTTTTTGTAA 4186.1

(SEQ. ID. NO. 328)
ATGAATGTAAATCAGATTGTACGGATTATTCCTACTTTAAAAGCTAATAA

TAGAAAATTAAATGAAACATTTTATATTGAAACCCTTGGAATGAAGGCCT

TGTTAGAAGAATCGGCCTTTCTGTCACTAGGTGACCAAACGGGTCTTGAA

AAGCTGGTTTTAGAAGAAGCTCCCAGTATGCGTACTCGTAAGGTAGAGGG

AAGAAAAAAACTAGCTAGATTGATTGTCAAGGTGGAAAATCCCTTAGAAA

TTGAAGGAATCTTATCTAAAACAGATTCGATTCATCGATTATATAAAGGT

CAAAATGGCTACGCTTTTGAAATTTTCTCACCAGAAGATGATTTGATTTT

GATTCATGCGGAAGATGACATAGCAAGTCTAGTAGAAGTAGGAGAAAAGC

CTGAATTTCAAACAGATTTGGCATCAATTTCTTTAAGTAAATTTGAGATT

TCTATGGAATTACATCTCCCAACTGATATCGAAAGTTTCTTGGAATCATC

TGAAATTGGGGCATCCCTTGATTTTATTCCAGCTCAGGGGCAGGATTTGA

CTGTGGACAATACGGTTACCTGGGACTTATCTATGCTCAAGTTCTTGGTC

AATGAATTAGACATAGCAAGTCTTCGCCAGAAGTTTGAGTCTACTGAATA

TABLE 1-continued

TTTTATTCCTAAGTCTGAAAAATTCTTCCTTGGTAAAGATAGAAATAATG
TTGAATTGTGGTTTGAAGAAGTATGA 4186.2
(SEQ. ID. NO. 329)
ATGAAGTGGACCAAGATTATTAAAAAAATAGAAGAACAAATCGAGGCAGG
GATTTATCCCGGAGCCTCTTTTGCGTATTTTAAGGACAATCAATGGACAG
AGTTCTATTTAGGCCAGAGTGACCCAGAGCATGGCTTGCAGACTGAGGCA
GGACTAGTTTATGACCTAGCTAGTGTCAGCAAGGTTGTTGGGGTTGGCAC
AGTTTGTACCTTCTTGTGGGAAATAGGTCAATTAGATATTGATAGACTGG
TAATAGATTTTTTACCTGAGAGTGATTATCCAGACATCACTATTCGCCAG
CTCTTGACTCATGCAACAGACCTTGATCCTTTTATTCCTAATCGTGATCT
TTTAACAGCCCCTGAATTAAAGGAAGCGATGTTTCATCTCAACAGACGAA
GTCAGCCAGCCTTTCTTTATTCGGATGTCCATTTTTTGCTGTTGGGCTTT
ATTTTGGAAAGAATTTTTAATCAAGATTTGGATGTGATTTTAAAGGATCA
AGTCTGGAAACCTTGGGGAATGACGGAAACTAAGTTTGGGCCAGTTGAGC
TTGCTGTTCCAACAGTTAGAGGTGTAGAGGCAGGCATAGTGCATGATCCC
AAGGCTCGTCTCCTGGGTAGACATGCTGGGAGTGCTGGTTTATTTTCGAC
TATAAAGGATTTACAAATCTTTTTAGAACACTATTTAGCAGATGATTTTG
CAAGAGACTTAAATCAAAATTTTTCTCCTTTGGATGACAAGGAACGTTCT
TTAGCATGGAATTTGGAAGGAGATTGGCTAGACCATACGGGCTATACAGG
TACCTTTATCATGTGGAATCGTCAGAAGCAAGAAGCCACTATTTTCCTAT
CGAATCGTACCTATGAAAAGGACGAGAGAGCTCAATGGATATTAGACCGC
AATCAAGTGATGAACTTGATTCGCAAAGAAGAGTAA 4187.2
(SEQ. ID. NO. 330)
ATGATGAAGAAGACTTATAATCATATTTTGGTCTGGGGAGTCATTTTCTA
TAGCATTTGCATTGTCTGTTTTTGCTTTACTCCTCAAGAACAATCTACCG
TGGGAGTGGGAACTCCAGGTATTCAGCATCTTGGACGCCTGGTTTTTCTT
TTGACTCCTTTCAATTCTCTCTGGAAACTGGGCGAAGTGAGTGACATTGG
ACAATTATGTTGGATTTTTTACAAAATATCCTCAATGTCTTCTTGTTTT
TTCCTCTGATTTTCCAACTCCTTTATCTATTTCCAAATTTGCGGAAAACA
AAAAAGGTCCTTCTTTTTAGTTTTCTTGTGAGTCTTGGAATCGAGTGTAC
GCAATTAATCTTGGACTTTTTCTTTGATTTCAATCGCGTCTTTGAGATTG
ATGATTTGTGGACCAACACTTTGGGTGGCTATCTGGCTTGGCTCCTTTAT
AAACGATTACATAAAAACAAGGTAAGGAATTAA 4188.1
(SEQ. ID. NO. 331)
ATGAAGATTCCTCTCTTAACTTTTGCAAGGCATAAATTTGTTTATGTCTT
GCTTACTTTGCTTTTTCTTGCTTTGGTTTATCGTGATGTTTTGATGACTT
ATTTCTTTTTTGATATTCATGCGCCCGATCTAGCTAAATTCGATGGACAA
GCAATTAAAAATGACTTATTAAAATCAGCATTAGATTTTCGTATTCTCCA
GTTCAATCTAGGTTTTTATCAATCATTTATTATTCCAATCATCATTGTTT
TGCTAGGTTTTCAATATATTGAGCTGAAAAATAAAGTTTTACGATTGAGT

ATTGGAAGAGAAGTGAGTTATCAAGGGTTAAAAAGAAAGTTGACTTTGCA
AGTTGCAAGTATCCCTTGTTTGATATATTTAGTGACTGTGCTGATAATTG
CAATTATAACCTATTTCTTTGGGACTTTTTCTCCTCTTGGATGGAATTCT
CTATTTTCTGATGGAAGTGGTTTACAAAGACTCCTAGATGGAGAGATAAA
AAGCTATTTGTTCTTTACTTGTGTCCTACTAATCGGTATTTTCATCAATG
CAATCTATTTTTACAAATAGTTGATTATGTGGGGAATGTGACTCGTTCG
GCAATCACCTATTTGATGTTTCTTTTGGCTTGGTTCTATGCTGCTTTATA
GTGCCTTGCCTTACTATATGGTTCCTATGACGAGTTTGATGCAAGCTAGC
TATGGGGATGTAAGTTTGATGAAACTCTTTACTCCTTATATCCTTTATAT
TGTCCCTTACATGGTGCTTGAAAAATATGAAGATAATGTTTAA 4188.2
(SEQ. ID. NO. 332)
ATGAAGATAATGTTTAAGAATTTTAACATATTTTGCTAAATAGAAAGAT
TGTTTTACTACTTCGTATAGTTCTGATGATGATTTTGATAAACCATCTAT
TGTCAACAGCGGTTCAAAGCAGGATGCTGTTATCTTTTTCAAGAGAGAAT
TGATTTCAATTTTTTCCTATAATGACTATTCTGAAGCGAATTTAGAAATC
CCCAAACTATTGTTAAACCTTTCGCTTTTCATGGTAGGATGGCTCTCTGT
CATTTTACTTGAAAGTGATTTGGCAGACCATTACCATCACTTGATTCGCT
ATCAATCAAGCTCCTTTTTCGATTATACAAGGAAACGATTGGTTGTCATT
TCTAAATTTTTACTCAAGATTTGTTTGTCTGGTTTCTTGGTTTACTTCC
TCTAGGAATTCATTTCAAAACAGTCGCACTTTTCTTTTTACTTGCTCAGT
TAATGATGTTGTACTTACTACTGTCTTATCTGATAGCACTGATTAGTGCG
GGCGCTGGTTTTTCCTTTTTTCTCTATTTTTTAGCATTTGTGGGACAAGA
ATGGATGATGGATCATATTGTAACAGTGTATTTAGTACTCTTAAGTTTAT
TAGTTATGTTGATTGTTAGTCGCTTGGAAGAGAAATTTAAGAAAGGATAA 4188.5
(SEQ. ID. NO. 333)
ATGGGCAAAGGAGAGATGGGCAAAGGAGTTATTGGCTTGGAGTTCGACTC
AGAAGTATTGGTCAACAAGGCTCCAACCCTTCAATTGGCAAATGGTAAAA
CAGCGACTTTCCTAACCCAGTATGATAGCAAGACCTTGTTGTTTGCAGTA
GATAAGGAAGATATCGGACAGGAAATTATTGGTATAGCTAAAGGAAGCAT
CGAAAGTATGCATAATCTTCCTGTAAATCTAGCAGGTGCCAGAGTTCCTG
GCGGAGTAAATGGTAGCAAAGCAGCGGTGCATGAAGTTCCAGAATTTACA
GGGGGAGTTAATGGTACAGAGCCAGCTGTTCATGAAATCGCAGAGTATAA
GGGATCTGATCGCTTGTAACTCTTACTACAAAAAAAGATTATACTTACAA
AGCTCCTCTTGCTCAGCAGGCACTTCCTGAAACAGGAAACAAGGAGAGTG
ACCTCCTAGCTTCACTAGGACTAACAGCTTTCTTCCTTGGTCTGTTTACG
CTAGGGAAAAGAGAGAACAATAA 4188.10
(SEQ. ID. NO. 334)
ATGTTTAAAGTTTTACAAAAAGTTGGAAAAGCTTTTATGTTACCTATAGC
TATACTTCCTGCAGCAGGTCTACTTTTGGGGATTGGTGGTGCACTTTCAA
ACCCAACCACGATAGCAACTTATCCAATACTAGACAATAGTATTTTTCAA

TABLE 1-continued

```
TCAATATTCCAAGTAATGAGCTCTGCAGGAGAGGTTGTATTCAGTAATTT
GTCACTACTTCTCTGTGTGGGATTATGTATTGGCTTAGCGAAACGAGATA
AAGGAACCGCTGCGTTAGCAGGAGTAACTGGTTACTTAGTTATGACTGCA
ACGATCAAAGCTTTGGTAAAACTTTTTATGGCAGAAGGATCTGCAATTGA
TACTGGAGTTATTGGAGCATTAGTTGTCGGAATAGTTGCCGTATATTTGC
ACAACCGATATAACAATATTCAATTACCTTCCGCTTTAGGATTCTTTGGA
GGTTCACGCTTCGTTCCTATTGTTACATCGTTCTCTTCTATCTTGATTGG
CTTTGTCTTCTTTGTTATTTGGCCACCTTTCCAACAACTTCTTGTTTCTA
CAGGTGGATATATTTCTCAGGCGGGTCCAATTGGAACTTTTCTATATGGA
TTTTTAATGAGACTTTCTGGAGCAGTAGGCTTACATCATATAATTTACCC
TATGTTTTGGTATACTGAACTTGGTGGTGTTGAAACTGTTGCAGGACAAA
CAGTGGTTGGAGCTCAAAAAATATTTTTTGCTCAATTAGCCGATTTGGCC
CATTCTGGATTATTTACAGAAGGAACAAGGTTTTTTGCAGGTCGTTTCTC
AACAATGATGTTCGGTTTACCGGCTGCCTGTTTAGCGATGTACCATAGTG
TTCCTAAAAATCGTCGTAAAAAATACGCGGGTTTGTTTTTTGGAGTTGCT
TTAACATCTTTTATTACCGGTATTACAGAACCAATTGAATTTATGTTTCT
ATTCGTCAGTCCGGTTCTATATGTTGTTCACGCATTCCTTGATGGTGTTA
GCTTCTTTATTGCAGACGTCTTAAATATTTCAATAGGAAACACATTTTCA
GGAGGTGTAATCGATTTCACTTTATTTGGAATTTTGCAGGGGAACGCTAA
GACGAATTGGGTCTTCAGATTCCATTTGGACTTATTTGGAGTGTTTTGT
ATTATATTATTTTTAGATGGTTCATTACTCAATTCAACGTTCTAACGCCA
GGGCGAGGAGAAGAAGTAGATTCTAAAGAAATTTCTGAATCCGCAGATTC
AACTTCAAATACTGCAGATTATTTAAAACAGGATAGCCTACAAATTATCA
GAGCCTTGGGTGGATCAAATAATATAGAAGATGTAGATGCTTGTGTGACA
CGTTTACGTGTAGCTGTAAAAGAAGTTAATCAAGTTGATAAAGCACTTTT
AAAACAAATTGGTGCAGTTGATGTCTTAGAAGTGAAGGGTGGCATTCAAG
CAATCTATGGAGCAAAAGCAATCTTATATAAAAATAGTATTAATGAAATT
TTAGGTGTAGATGATTAA
```

4188.11

(SEQ. ID. NO. 335)
```
ATGAAATTTAGAAAATTAGCTTGTACAGTACTTGCGGGTGCTGCGGTTCT
TGGTCTTGCTGCTTGTGGCAATTCTGGCGGAAGTAAAGATGCTGCCAAAT
CAGGTGGTGACGGTGCCAAAACAGAAATCACTTGGTGGGCATTCCCAGTA
TTTACCCAAGAAAAAACTGGTGACGGTGTTGGAACTTATGAAAAATCAAT
CATCGAAGCGTTTGAAAAAGCAAACCCAGATATAAAAGTGAAATTGGAAA
CCATCGACTTCAAGTCAGGTCCTGAAAAAATCACAACAGCCATCGAAGCA
GGAACAGCTCCAGACGTACTCTTTGATGCACCAGGACGTATCATCCAATA
CGGTAAAAACGGTAAATTGGCTGAGTTGAATGACCTCTTCACAGATGAAT
TTGTTAAAGATGTCAACAATGAAAACATCGTACAAGCAAGTAAAGCTGGA
GACAAGGCTTATATGTATCCGATTAGTTCTGCCCCATTCTACATGGCAAT
GAACAAGAAAATGTTAGAAGATGCTGGAGTAGCAAACCTTGTAAAAGAAG
GTTGGACAACTGATGATTTTGAAAAAGTATTGAAAGCACTTAAAGACAAG
GGTTACACACCAGGTTCATTGTTCAGTTCTGGTCAAGGGGGAGACCAAGG
AACACGTGCCTTTATCTCTAACCTTTATAGCGGTTCTGTAACAGATGAAA
AAGTTAGCAAATATACAACTGATGATCCTAAATTCGTCAAAGGTCTTGAA
AAAGCAACTAGCTGGATTAAAGACAATTTGATCAATAATGGTTCACAATT
TGACGGTGGGGCAGATATCCAAAACTTTGCCAACGGTCAAACATCTTACA
CAATCCTTTGGGCACCAGCTCAAAATGGTATCCAAGCTAAACTTTTAGAA
GCAAGTAAGGTAGAAGTGGTAGAAGTACCATTCCCATCAGACGAAGGTAA
GCCAGCTCTTGAGTACCTTGTAAACGGGTTTGCAGTATTCAACAATAAAG
ACGACAAGAAAGTCGCTGCATCTAAGAAATTCATCCAGTTTATCGCAGAT
GACAAGGAGTGGGGACCTAAAGACGTAGTTCGTACAGGTGCTTTCCCAGT
CCGTACTTCATTTGGAAAACTTTATGAAGACAAACGCATGGAAACAATCA
GCGGCTGGACTCAATACTACTCACCATACTACAACACTATTGATGGATTT
GCTGAAATGAGAACACTTTGGTTCCCAATGTTGCAATCTGTATCAAATGG
TGACGAAAAACCAGCAGATGCTTTGAAAGCCTTCACTGAAAAAGCGAACG
AAACAATCAAAAAAGCTATGAAACAATAG
```

4188.12

(SEQ. ID. NO. 336)
```
ATGCAATCTACAGAAAAAAAACCATTAACAGCCTTTACTGTTATTTCAAC
AATCATTTTGCTCTTGTTGACTGTGCTGTTCATCTTTCCATTCTACTGGA
TTTTGACAGGGGCATTCAAATCACAACCTGATCAATTGTTATTCCTCCT
CAGTGGTTCCCTAAAATGCCAACCATGGAAAACTTCCAACAACTCATGGT
GCAGAACCCTGCCTTGCAATGGATGTGGAACTCAGTATTTATCTCATTGG
TAACCATGTTCTTAGTTTGTGCAACCTCATCTCTAGCAGGTTATGTATTG
GCTAAAAAACGTTTCTATGGTCAACGCATTCTATTTGCTATCTTTATCGC
TGCTATGGCGCTTCCAAAACAAGTTGTCCTTGTACCATTGGTACGTATCG
TCAACTTCATGGGAATCCATGATACTCTCTGGGCAGTTATCTTGCCTTTG
ATTGGATGGCCATTCGGTGTCTTCCTCATGAAACAGTTCAGTGAAAATAT
CCCTACAGAGTTGCTTGAATCAGCTAAAATCGACGGTTGTGGTGAGATTC
GTACCTTCTGGAGTGTAGCCTTCCCGATTGTGAAACCAGGGTTTGCAGCC
CTTGCAATCTTTACCTTCATCAATACTTGGAATGACTACTTCATGCAATT
GGTAATGTTGACTTCACGTAACAATTTGACCATCTCACTTGGGGTTGCGA
CCATGCAGGCTGAAATGGCAACCAACTATGGTTTGATTATGGCAGGAGCT
GCCCTTGCTGCTGTTCCAATCGTCACAGTCTTCCTAGTCTTCCAAAAATC
CTTCACACAGGGTATTACTATGGGAGCGGTCAAAGGATAA
```

4191.1

(SEQ. ID. NO. 337)
```
ATGAAAAAACTTTTTTCTTACTGGTGTTAGGCTTGTTTTGCCTTCTTCC
ACTCTCTGTTTTTGCCATTGATTTCAAGATAAACTCTTATCAAGGGGATT
TGTATATTCATGCAGACAATACGGCAGAGTTTAGACAGAAGATAGTTTAC
CAGTTTGAGGAGGACTTTAAGGGCCAAATCGTGGGACTTGGACGTGCTGG
TAAGATGCCTAGCGGGTTTGACATTGACCCTCATCCAAAGATTCAGGCCG
```

TABLE 1-continued

```
CGAAAAACGGTGCAGAACTAGCAGATGTGACTAGCGAAGTAACAGAAGAA
GCGGATGGTTATACTGTGAGAGTCTATAATCCAGGTCAGGAGGGCGACAT
AGTTGAAGTTGACCTCGTCTGGAACTTAAAAAATTTACTTTTCCTTTATG
ATGATATCGCTGAATTAAATTGGCAACCTCTGACAGATAGTTCAGAGTCT
ATTGAAAAGTTTGAATTTCATGTAAGGGGAGACAAGGGGGCTGAAAAACT
CTTTTTCCATACAGGGAAACTTTTTAGAGAGGGAACGATTGAAAAGAGTA
ACCTTGATTATACTATCCGTTTAGACAATCTTCCGGCTAAGCGTGGAGTT
GAGTTGCATGCCTATTGGCCTCGGACCGATTTTGCTAGCGCTAGGGATCA
GGGATTGAAAGGGAATCGTTTAGAAGAGTTTAATAAGATAGAAGACTCGA
TTGTTAGAGAAAAGATCAGAGTAAACAACTCGTTACTTGGGTCCTCCCT
TCGATCCTTTCCATCTCCTTGTATTGAGTGTCTGCTTCTATTTTATTTAT
AGAAGAAAGACCACTCCTTCAGTCAAATATGCCAAAAATCATCGTCTCTA
TGAACCACCAATGGAATTAGAGCCTATGGTTTTATCAGAAGCAGTCTACT
CGACCTCCTTGGAGGAAGTGAGTCCCTTGGTCAAGGGAGCTGGAAAATTC
ACCTTTGATCAACTTATTCAAGCTACCTTGCTAGATGTGATAGACCGTGG
GAATGTCTCTATCATTTCAGAAGGAGATGCAGTTGGTTTGAGGCTAGTAA
AAGAAGATGGTTTGTCAAGCTTTGAGAAAGACTGCCTAAATCTAGCTTTT
TCAGGTAAAAAGAAGAAACTCTTTCCAATTGTTTGCGGATTACAAGGTA
TCTGATAGTCTTTATCGTAGAGCCAAAGTTTCTGATGAAAAACGGATTCA
AGCAAGAGGGCTTTCAACTCAAATCTTCTTTTGAAGAGGTATTGAACCAG
ATGCAAGAAGGAGTGAGAAAACGAGTTTCCTTCTGGGGGCTCCCAGATTA
TTATCGTCCTTTAACTGGTGGGGAAAAGGCCTTGCAAGTGGGTATGGGTG
CCTTGACTATCCTGCCCCTATTTATCGGATTTGGTTTGTTCTTGTACAGT
TTAGACGTTCATGGCTATCTTTACCTCCCTTTGCCAATACTTGGTTTTCT
AGGGTTAGTTTTGTCTGTTTTCTATTATTGGAAGCTTCGACTAGATAATC
GTGATGGTGTTCTAAATGAAGCGGGAGCTGAGGTCTACTATCTCTGGACC
AGTTTTGAAAATATGTTGCGTGAGATTGCACGATTGGATCAGGCTGAACT
GGAAAGTATTGTGGTCTGGAATCGCCTCTTGGTCTATGCGACCTTATTTG
GCTATGCGGACAAGGTTAGTCATTTGATGAAGGTTCATCAGATTCAAGTG
GAAAATCCAGATATCAATCTCTATGTAGCTTATGGCTGGACAGTACGTT
TTATCATTCAACAGCACAAATGAGCCATTATGCTAGTGTCGCAAATACAG
CAAGCACCTACTCTGTATCTTCTGGAAGTGGAAGTTCTGGTGGTGGCTTC
TCTGGAGGCGGAGGTGGCGGCAGTATCGGTGCCTTTTAA
4191.2
                                       (SEQ. ID. NO. 338)
ATGAAAAAAGTAAGAAAGATATTTCAGAAGGCAGTTGCAGGACTGTGCTG
TATATCTCAGTTGACAGCTTTTTCTTCGATAGTTGCTTTAGCAGAAACGC
CTGAAACCAGTCCAGCGATAGGAAAAGTAGTGATTAAGGAGACAGGCGAA
GGAGGAGCGCTTCTAGGAGATGCCGTCTTTGAGTTGAAAAACAATACGGA
TGGCACAACTGTTTCGCAAAGGACAGAGGCGCAAACAGGAGAAGCGTATT
TTTCAAACATAAAACCTGGGACATACACCTTGACAGAAGCCCAACCTCCA
```

```
GTTGGTTATAAACCCTCTACTAAACAATGGACTGTTGAAGTTGAGAAGAA
TGGTCGGACGACTGTCCAAGGTGAACAGGTAGAAAATCGAGAAGAGGCTC
TATCTGACCAGTATCCACAAACAGGGACTTATCCAGATGTTCAAACACCT
TATCAGATTATTAAGGTAGATGGTTCGGAAAAAAACGGACAGCACAAGGC
GTTGAATCCGAATCCATATGAACGTGTGATTCCAGAAGGTACACTTTCAA
AGAGAATTTATCAAGTGAATAATTTGGATGATAACCAATATGGAATCGAA
TTGACGGTTAGTGGGAAAACAGTGTATGAACAAAAAGATAAGTCTGTGCC
GCTGGATGTCGTTATCTTGCTCGATAACTCAAATAGTATGAGTAACATTC
GAAACAAGAATGCTCGACGTGCGGAAAGAGCTGGTGAGGCGACACGTTCT
CTTATTGATAAAATTACATCTGATTCAGAAAATAGGGTAGCGCTTGTGAC
TTATGCTTCCACTATCTTTGATGGGACCGAGTTTACAGTAGAAAAGGGG
TAGCAGATAAAACGGAAAGCGATTGAATGATTCTCTTTTTTGGAATTAT
GATCAGACGAGTTTTACAACCAATACCAAAGATTATAGTTATTTAAAGCT
GACTAATGATAAGAATGACATTGTAGAATTAAAAAATAAGGTACCTACCG
AGGCAGAAGACCATGATGGAAATAGATTGATGTACCAATTCGGTGCCACT
TTTACTCAGAAAGCTTTGATGAAGGCAGATGAGATTTTGACACAACAAGC
GAGACAAAATAGTCAAAAAGTCATTTTCCATATTACGGATGGTGTCCCAA
CTATGTCGTATCCGATTAATTTTAATCATGCTACGTTTGCTCCATCATAT
CAAAATCAACTAAATGCATTTTTTAGTAAATCTCCTAATAAAGATGGAAT
ACTATTAAGTGATTTTATTACGCAAGCAACTAGTGGAGAACATACAATTG
TACGCGGAGATGGGCAAAGTTACCAGATGTTTACAGATAAGACAGTTTAT
GAAAAAGGTGCTCCTGCAGCTTTCCCAGTTAAACCTGAAAAATATTCTGA
AATGAAGGCGGCTGGTTATGCAGTTATAGGCGATCCAATTAATGGTGGAT
ATATTTGGCTTAATTGGAGAGAGTATTCTGGCTTATCCGTTTAATTCT
AATACTGCTAAAATTACCAATCATGGTGACCCTACAAGATGGTACTATAA
CGGGAATATTGCTCCTGATGGGTATGATGTCTTTACGGTAGGTATTGGTA
TTAACGGAGATCCTGGTACGGATGAAGCAACGGCTACTAGTTTTATGCAA
AGTATTTCTAGTAAACCTGAAAACTATACCAATGTTACTGACACGACAAA
AATATTGGAACAGTTGAATCGTTATTTCCACACCATCGTAACTGAAAAGA
AATCAATTGAGAATGGTACGATTACAGATCCGATGGGTGAGTTAATTGAT
TTGCAATTGGGCACAGATGGAAGATTTGATCCAGCAGATTACACTTTAAC
TGCAAACGATGGTAGTCGCTTGGAGAATGGACAAGCTGTAGGTGGTCCAC
AAAATGATGGTGGTTTGTTAAAAAATGCAAAGTGCTCTATGATACGACT
GAGAAAAGGATTCGTGTAACAGGTCTGTACCTTGGAACGGATGAAAAGT
TACGTTGACCTACAATGTTCGTTTGAATGATGAGTTTGTAAGCAATAAAT
TTTATGATACCAATGGTCGAACAACCTTACATCCTAAGGAAGTAGAACAG
AACACAGTGCGCGACTTCCCGATTCCTAAGATTCGTGATGTGCGGAAGTA
TCCAGAAATCACAATTTCAAAAGAGAAAAAACTTGGTGACATTGAGTTTA
TTAAGGTCAATAAAAATGATAAAAAACCACTGAGAGGTGCGGTCTTTAGT
CTTCAAAAACAACATCCGGATTATCCAGATATTTATGGAGCTATTGATCA
```

TABLE 1-continued

AAATGGCACTTATCAAAATGTGAGAACAGGTGAAGATGGTAAGTTGACCT
TTAAAAATCTGTCAGATGGGAAATATCGATTATTTGAAAATTCTGAACCA
GCTGGTTATAAACCCGTTCAAAATAAGCCTATCGTTGCCTTCCAAATAGT
AAATGGAGAAGTCAGAGATGTGACTTCAATCGTTCCACAAGATATACCAG
CGGGTTACGAGTTTACGAATGATAAGCACTATATTACCAATGAACCTATT
CCTCCAAAGAGAGAATATCCTCGAACTGGTGGTATCGGAATGTTGCCATT
CTATCTGATAGGTTGCATGATGATGGGAGGAGTTCTATTATACACACGGA
AACATCCGTAA 4191.3

(SEQ. ID. NO. 339)
ATGAAATCAATCAACAAATTTTTAACAATGCTTGCTGCCTTATTACTGAC
AGCGAGTAGCCTGTTTTCAGCTGCAACAGTTTTTGCGGCTGGGACGACAA
CAACATCTGTTACCGTTCATAAACTATTGGCAACAGATGGGGATATGGAT
AAAATTGCAAATGAGTTAGAAACAGGTAACTATGCTGGTAATAAAGTGGG
TGTTCTACCTGCAAATGCAAAAGAAATTGCCGGTGTTATGTTCGTTTGGA
CAAATACTAATAATGAAATTATTGATGAAAATGGCCAAACTCTAGGAGTG
AATATTGATCCACAAACATTTAAACTCTCAGGGGCAATGCCGGCAACTGC
AATGAAAAAATTAACAGAAGCTGAAGGAGCTAAATTTAACACGGCAAATT
TACCAGCTGCTAAGTATAAAATTTATGAAATTCACAGTTTATCAACTTAT
GTCGGTGAAGATGGAGCAACCTTAACAGGTTCTAAAGCAGTTCCAATTGA
AATTGAATTACCATTGAACGATGTTGTGGATGCGCATGTGTATCCAAAAA
ATACAGAAGCAAAGCCAAAAATTGATAAAGATTTCAAAGGTAAAGCAAAT
CCAGATACACCACGTGTAGATAAAGATACACCTGTGAACCACCAAGTTGG
AGATGTTGTAGAGTACGAAATTGTTACAAAAATTCCAGCACTTGCTAATT
ATGCAACAGCAAACTGGAGCGATAGAATGACTGAAGGTTTGGCATTCAAC
AAAGGTACAGTGAAAGTAACTGTTGATGATGTTGCACTTGAAGCAGGTGA
TTATGCTCTAACAGAAGTAGCAACTGGTTTTGATTTGAAATTAACAGATG
CTGGTTTAGCTAAAGTGAATGACCAAAACGCTGAAAAAACTGTGAAAATC
ACTTATTCGGCAACATTCAATGACAAAGCAATTGTAGAAGTACCAGAATC
TAATGATGTAACATTTAACTATGGTAATAATCCAGATCACGGGAATACTC
CAAAGCCGAATAAGCCAAATGAAAACGGCGATTTGACATTGACCAAGACA
TGGGTTGATGCTACAGGTGCACCAATTCCGGCTGGAGCTGAAGCAACGTT
CGATTTGGTTAATGCTCAGACTGGTAAAGTTGTACAAACTGTAACTTTGA
CAACAGACAAAAATACAGTTACTGTTAACGGATTGGATAAAAATACGAAA
TATAAATTCGTTGAACGTAGTATAAAAGGGTATTCAGCAGATTATCAAGA
AATCACTACAGCTGGAGAAATTGCTGTCAAGAACTGGAAAGACGAAAATC
CAAAACCACTTGATCCAACAGAGCCAAAAGTTGTTACATATGGTAAAAAG
TTTGTCAAAGTTAATGATAAAGATAATCGTTTAGCTGGGCAGAATTTGT
AATTGCAAATGCTGATAATGCTGGTCAATATTTAGCACGTAAAGCAGATA
AAGTGAGTCAAGAAGAGAAGCAGTTGGTTGTTACAACAAAGGATGCTTTA
GATAGAGCAGTTGCTGCTTATAACGCTCTTACTGCACAACAACAAACTCA

TABLE 1-continued

GCAAGAAAAAGAGAAAGTTGACAAAGCTCAAGCTGCTTATAATGCTGCTG
TGATTGCTGCCAACAATGCATTTGAATGGGTGGCAGATAAGGACAATGAA
AATGTTGTGAAATTAGTTTCTGATGCACAAGGTCGCTTTGAAATTACAGG
CCTTCTTGCAGGTACATATTACTTAGAAGAAACAAAACAGCCTGCTGGTT
ATGCATTACTAACTAGCCGTCAGAAATTTGAAGTCACTGCAACTTCTTAT
TCAGCGACTGGACAAGGCATTGAGTATACTGCTGGTTCAGGTAAAGATGA
CGCTACAAAAGTAGTCAACAAAAAAATCACTATCCCACAAACGGGTGGTA
TTGGTACAATTATCTTTGCTGTAGCGGGGGCTGCGATTATGGGTATTGCA
GTGTACGCATATGTTAAAAACAACAAAGATGAGGATCAACTTGCTTAA 4191.4

(SEQ. ID. NO. 340)
ATGACAATGCAGAAAATGCAGAAAATGATTAGTCGTATCTTCTTTGTTAT
GGCTCTGTGTTTTTCTCTTGTATGGGGTGCACATGCAGTCCAAGCGCAAG
AAGATCACACGTTGGTCTTGCAATTGGAGAACTATCAGGAGGTGGTTAGT
CAATTGCCATCTCGTGATGGTCATCGGTTGCAAGTATGGAAGTTGGATGA
TTCGTATTCCTATGATGATCGGGTGCAAATTGTAAGAGACTTGCATTCGT
GGGATGAGAATAAACTTTCTTCTTTCAAAAAGACTTCGTTTGAGATGACC
TTCCTTGAGAATCAGATTGAAGTATCTCATATTCCAAATGGTCTTTACTA
TGTTCGCTCTATTATCCAGACGGATGCGGTTTCTTATCCAGCTGAATTTC
TTTTTGAAATGACAGATCAAACGGTAGAGCCTTTGGTCATTGTAGCGAAA
AAAACAGATACAATGACAACAAAGGTGAAGCTGATAAAGGTGGATCAAGA
CCACAATCGCTTGGAGGGTGTCGGCTTTAAATTGGTATCAGTAGCAAGAG
ATGTTTCTGAAAAAGAGGTTCCCTTGATTGGAGAATACCGTTACAGTTCT
TCTGGTCAAGTAGGGAGAACTCTCTATACTGATAAAAATGGAGAGATTTT
TGTGACAAATCTTCCTCTTGGGAACTATCGTTTCAAGGAGGTGGAGCCAC
TGGCAGGCTATGCTGTTACGACGCTGGATACGGATGTCCAGCTGGTAGAT
CATCAGCTGGTGACGATTACGGTTGTCAATCAGAAATTACCACGTGGCAA
TGTTGACTTTATGAAGGTGGATGGTCGGACCAATACCTCTCTTCAAGGGG
CAATGTTCAAAGTCATGAAAGAAGAAAGCGGACACTATACTCCTGTTCTT
CAAAATGGTAAGGAAGTAGTTGTAACATCAGGGAAAGATGGTCGTTTCCG
AGTGGAAGGTCTAGAGTATGGACATACTATTTATGGGAGCTCCAAGCTC
CAACTGGTTATGTTCAATTAACATCGCCTGTTTCCTTTACAATCGGGAAA
GATACTCGTAAGGAACTGGTAACAGTGGTTAAAAATAACAAGCGACCACG
GATTGATGTGCCAGATACAGGGGAAGAAACCCTTGTATATCTTGATGCTT
GTTGCCATTTTGTTGTTTGGTAG 4191.5

(SEQ. ID. NO. 341)
ATGAGCCACATATACTTATCTATTTTCACAAGTCTCTTGCTGATGCTAGG
ACTTGTCAATGTTGCTCAAGCCGATGAATATTTACGCATCGGTATGGAAG
CAGCATATGCTCCCTTTAACTGGACCCAGGATGATGATAGCAACGGAGCT
GTCAAAATCGATGGGACCAATCAGTATGCCAACGGATACGATGTTCAAAT
CGCCAAGAAAATCGCTAAGGACTTAGGTAAAGAACCTTTGGTTGTTAAAA

TABLE 1-continued

```
CCAAGTGGGAAGGTCTAGTCCCTGCCCTTACTTCTGGTAAGATTGACATG
ATTATCGCAGGTATGAGTCCAACTGCAGAACGCAAACAAGAAATTGCCTT
TTCGAGCAGTTACTATACTAGCGAACCAGTTTTGCTTGTCAAAAAAGATT
CTGCCTACGCAAGTGCTAAATCTTTGGATGACTTTAACGGTGCAAAAATC
ACTTCTCAACAAGGGGTCTACCTTTATAACTTGATTGCACAAATCCCAGG
TGCTAAAAAGAAACAGCCATGGGAGACTTCACTCAAATGCGACAAGCTC
TTGAGGCTGGTGTCATTGATGCTTATGTTTCTGAACGTCCAGAAGCACTG
ACTGCTGAAGCTGCGAACTCTAAGTTCAAGATGATTCAAGTAGAACCTGG
TTTCAAAACTGGGGAAGAAGATACAGCTATCGCTATCGGGCTTCGTAAAA
ATGACAATCGTATTAGCCAAATCAATGCCAGCATTGAAACCATTTCAAAA
GATGACCAAGTTGCCTTGATGGATCGTATGATCAAGGAACAACCTGCCGA
AGCTACAACAACTGAAGAGACTAGCAGTAGTTTCTTTAGCCAAGTTGCTA
AAATTCTTTCTGAAAACTGGCAACAACTCTTGCGTGGTGCTGGTATCACT
CTTTTAATCTCTATCGTCGGAACCATCATAGGTCTCATTATTGGACTTGC
CATTGGTGTCTTCCGTACTGCTCCTCTCTCTGAAAACAAAGTCATTTACG
GCCTACAAAACTAGTCGGCTGGGTTCTCAATGTCTACATTGAAATTTTC
CGTGGTACGCCAATGATTGTTCAATCGATGGTTATCTACTATGGAACTGC
CCAAGCTTTCGGGATCAACCTTGACCGTACACTGGCTGCTATCTTCATCG
TTTCAATCAATACCGGTGCCTACATGACTGAAATCGTCCGTGGTGGTATC
CTAGCAGTTGACAAGGGACAATTTGAAGCTGCGACTGCTCTTGGTATGAC
CCATAACCAGACCATGCGTAAGATTGTCCTACCTCAGGTAGTCCGTAACA
TCCTACCTGCAACTGGTAATGAATTTGTCATCAATATCAAAGATACATCT
GTATTGAACGTTATCTCTGTGTCGAACTTTATTTCTCAGGAAATACCGTG
GCAACACAAACCTATCAATACTTCCAGACATTTACAATCATCGCCGTGAT
TTACTTTGTCCTCACCTTCACCGTAACACGTATCCTACGCTTTATCGAGC
GCAGAATGGACATGGATACCTACACTACAGGTGCTAACCAAATGCAAACG
GAGGATTTGAAATAA
```

4191.6

(SEQ. ID. NO. 342)
```
ATGACACAAGCAATCCTTGAAATTAAACACCTCAAAAAATCCTATGGACA
AAACGAAGTGCTAAAAGACATTTCACTCACTGTCCACAAGGGAGAGGTCA
TCTCTATCATCGGAAGCTCTGGAAGCGGAAAATCGACCTTCCTACGCTCC
ATTAACCTACTTGAAACACCAACTGATGGACAAATCCTTTATCATGGACA
AAACGTCCTCGAAAAAGGCTATGACCTCACGCAATACCGTGAAAGTTGG
GGATGGTTTTCCAATCCTTTAACCTCTTTGAAAATCTCAATGTTCTTGAA
AACACAATCGTCGCTCAGACAACTGTCCTAAAACGCGAACGCACAGAAGC
TGAAAAGATTGCCAAAGAAAACCTGGAAAAGGTCGGCATGGGAGAACGCT
ACTGGCAAGCCAAACCAAAACAACTCTCAGGTGGTCAAAAACAACGTGTG
GCCATCGCTCGTGCCCTCTCCATGAATCCGGACGCTATTCTCTTTGATGA
ACCAACATCAGCTCTCGATCCAGAAATGGTTGGAGAAGTCCTCAAAATCA
TGCAGGACCTGGCTCAGGAAGGCTTGACCATGATTGTCGTAACCCATGAA
ATGGAATTTGCCCGTGATGTCTCTCACCGTGTTATCTTTATGGATAAGGG
CGTGATCGCTGAAGAAGGTAAACCAGAAGACCTCTTCACCAATCCTAAAG
AAGACCGAACAAAAGAGTTCCTTCAACGCTATCTCAAATAA
```

4192.3

(SEQ. ID. NO. 343)
```
ATGAAAAAGTATCAACTTCTATTCAAAATAAGTGCAGTCTTCTCTTACTT
ATTTTTCGTATTTAGTCTTTCTCAGCTGACGCTTATCGTCCAAAACTATT
GGCAATTTCTTCTCAGATAGGCAATTTATTCTGGATTCAAAATATCTTG
AGTTTACTTTTTATTGGAGTCATGATTGTGGTTCTTGTTAAGACAGGCCA
TGGTTATCTCTTCCGCATTCCAAGAAAAAATGGCTTTGGTATTCGATTTT
TGACAGTATTAGTGCTAGTGTTCCAGATCTCTTTTAACGTTCAGACAGCT
AAACATGTTCAGTCAACTGCGGAAGGTTGGGCTGTATTGATTGGTTATAG
TGGGACTAACTTTGCAGAGCTAGGTATTTATATAGCCCTGTTCTTTCTGG
TTCCACTGATGGAAGAATTGATTTATAGAGGATTACTGCAACATGCTTTC
TTTAAGCATTCGCGATTTGGTCTTGATTTGCTTCTTCCTTCTATTTTATT
TGCTCTCCCTCATTTTTCAAGCCTGCCTAGTCTGTTAGATATCTTCGTCT
TTGCAACAGTTGGAATCATCTTTTGCTGGTTTGACCCGCTATACCAAGAG
CATTTATCCATCCTATGCGGTGCATGTGATCAATAATATTGTAGCGACCT
TCCCGTTTTTGCTCACTTTTCTACATAGGGTCTTGGGGTAA
```

4193.1

(SEQ. ID. NO. 344)
```
ATGAACAAGAAACAATGGCTAGGTCTTGGCCTAGTTGCAGTGGCAGCAGT
TGGACTTGCTGCATGTGGTAACCGCTCTTCTCGTAACGCAGCTTCATCTT
CTGATGTGAAGACAAAAGCAGCAATCGTCACTGATACTGGTGGTGTTGAT
GACAAATCATTCAACCAATCAGCTTGGGAAGGTTTGCAGGCTTGGGGTAA
AGAACACAATCTTTCAAAAGATAACGGTTTCACTTACTTCCAATCAACAA
GTGAAGCTGACTACGCTAACAACTTGCAACAAGCGGCTGGAAGTTACAAC
CTAATCTTCGGTGTTGGTTTTGCCCTTAATAATGCAGTTAAAGATGCAGC
AAAAGAACACACTGACTTGAACTATGTCTTGATTGATGATGTGATTAAAG
ACCAAAAGAATGTTGCGAGCGTAACTTTCGCTGATAATGAGTCAGGTTAC
cTTGCAGGTGTGGCTGCAGCAAAAACAACTAAGACAAAACAAGTTGGTTT
TGTAGGTGGTATCGAATCTGAAGTTATCTCTCGTTTTGAAGCAGGATTCA
AGGCTGGTGTTGCGTCAGTAGACCCATCTATCAAAGTCCAAGTTGACTAC
GCTGGTTCATTTGGTGATGCGGCTAAAGGTAAACAATTGCAGCCGCACA
ATACGCAGCCGGTGCAGATATTGTTTACCAAGTAGCTGGTGGTACAGGTG
CAGGTGTCTTTGCAGAGGCAAAATCTCTCAACGAAAGCCGTCCTGAAAAT
GAAAAAGTTTGGGTTATCGGTGTTGATCGTGACCAAGAAGCAGAAGGTAA
ATACACTTCTAAAGATGGCAAAGAATCAAACTTTGTTCTTGTATCTACTT
TGAAACAAGTTGGTACAACTGTAAAAGATATTTCTAACAAGGCAGAAAGA
GGAGAATTCCCTGGCGGTCAAGTGATCGTTTACTCATTGAAGGATAAAGG
GGTTGACTTGGCAGTAACAAACCTTTCAGAAGAAGGTAAAAAAGCTGTCG
```

TABLE 1-continued

```
AAGATGCAAAAGCTAAAATCCTTGATGGAAGCGTAAAAGTTCCTGAAAAA
TAA
4193.3
                                            (SEQ. ID. NO. 345)
ATGTCTAAAAAATTACAACAAATTTCGGTTCCCTTGATTTCTGTATTCCT
AGGAATTTTACTCGGAGCCATTTGTCATGTGGATCTTCGGTTATGATGCT
ATTTGGGGCTACGAAGAATTGTTCTATACAGCCTTTGGCAGTCTGCGTGG
GATTGGAGAAATCTTCCGTGCTATGGGTCCTCTGGTCTTGATTGGTCTTG
GTTTTGCCGTTGCCAGTCGAGCTGGTTTCTTTAACGTCGGACTTCCTGGT
CAGGCTTTGGCAGGTTGGATTCTCAGTGGTTGGTTTGCCCTGTCGCATCC
AGATATGCCCCGTCCCTTGATGATTCTAGCAACCATCGTGATTGCCTTGA
TTGCTGGTGGGATTGTCGGAGCGATTCCAGGTATTCTTAGGGCCTATCTA
GGGACGTCAGAGGTTATTGTAACCATCATGATGAACTACATTGTCTTGTA
TGTAGGGAATGCCTTTATCCATGCTTTCCCTAAAGACTTCATGCAAAGTA
CAGATTCGACCATTCGTGTTGGGGCTAATGCAACCTATCAGACACCTTGG
TTGGCTGAGTTGACTGGTAACTCACGGATGAATATTGGTATTTTCTTTGC
CATCATTGCCGTTCAGTTATTTGGTTCATGCTCAAGAAAACAACTCTTG
GTTTTGAAATCCGTGCAGTTGGTCTTAATCCACATGCTTCAGAATATGCT
GGTATTTCTGCCAAGCGGACTATTATCCTATCTATGATTATTTCAGGTGC
CTTGGCAGGTCTTGGTGGAGCTGTTGAAGGTTTGGGAACCTTCCAGAACG
TCTATGTTCAAGGTTCGTCATTAGCTATCGGATTTAACGGAATGGCGGTT
AGTTTGCTTGCGGCCAACTCACCAATTGGTATACTCTTTGCAGCCTTCCT
ATTTGGCGTTCTCCAAGTTGGGGCTCCTGGTATGAATGCGGCGCAGGTAC
CATCTGAGCTTGTCAGCATTGTAACAGCGTCTATTATCTTCTTTGTCAGT
GTTCATTACCTTATCGAACGCTTTGTCAAACCGAAAAAACAAGTTAAAGG
AGGTAAGTAA
4194.1
                                            (SEQ. ID. NO. 346)
ATGGGAGTGAAAAAGAAACTAAAGTTGACTAGTTTGCTAGGACTGTCTCT
GTTAATCATGACAGCCTGTGCGACTAATGGGGTAACTAGCGATATTACAG
CCGAATCGGCTGATTTTGGAGTAAATTGGTTTACTTCTTTGCGGAAATC
ATTCGCTTTTTATCGTTTGATATTAGTATCGGAGTGGGGATTATTCTCTT
TACGGTCTTGATTCGTACAGTCCTCTTGCCAGTCTTTCAGGTGCAAATGG
TGGCTTCTAGGAAAATGCAGGAAGCTCAGCCACGCATTAAGGCGCTTCGA
GAACAATATCCAGGTCGAGATATGGAAAGCAGAACCCAAACTAGAGCAGGA
AATGCGTAAAGTATTTAAAGAAATGGGTGTCAGACAGTCAGACTCTCTTT
GGCCGATTTTGATTCAGATGCCGGTTATTTTGGCCCTGTTCCAAGCCCTA
TCAAGAGTTGACTTTTTAAAGACAGGTCATTTCTTATGGATTAACCTTGG
TAGTGTGGATACAACCCTTGTTCTTCCGATTTTAGCAGCAGTATTCACCT
TTTTAAGTACTTGGTTGTCCAACAAAGCTTTGTCTGAGCGAAATGGCGCT
ACGACTGCGATGATGTATGGGATTCCAGTCTTGATTTTTATCTTTGCAGT
TTATGCGCCAGGTGGAGTCGCCCTATACTGGACAGTGTCTAATGCTTATC
```

```
AAGTCTTGCAAACCTATTTCTTGAATAATCCATTCAAGATTATCGCAGAG
CGCGAGGCCGTAGTACAGGCACAAAAAGATTTGGAAAATAGAAAAAGAAA
AGCCAAGAAAAAGGCTCAGAAAACGAAATAA
4194.4
                                            (SEQ. ID. NO. 347)
ATGGTTATCGATCCATTTGCTATCAACGAACTAGACTATTACTTAGTTTC
ACACTTCCACAGTGATCATATCGACCCATACACAGCTGCAGCAATTCTCA
ATAATCCTAAGTTAGAGCATGTTAAGTTTATCGGTCCTTACCACTGTGGA
CGAATCTGGGAAGGATGGGGTGTTCCAAAAGAACGTATCATCGTTGTTAA
ACCAGGTGACACTATCGAATTAAAAGATATGAAGATTCATGCAGTAGAAT
CATTTGACCGTACTTGCTTGGTAACTCTCCCAGTGAACGGTGCTGATGAG
ACAGGCGGTGAACTTGCTGGCTTGGCTGTTACAGATGAAGAAATGGCTCA
AAAGGCTGTTAACTATATCTTTGAAACACCAGGTGGAACCATCTATCATG
GTGCAGATTCTCACTTCTCAAACTATTTTGCAAAACATGGTAAAGACTTT
AAAATTGATGTTGCTTTGAATAACTATGGTGAAAATCCGGTAGGTATCCA
AGACAAAATGACATCTATCGACCTTCTTCGTATGGCAGAAAATCTGCGTA
CCAAAGTCATTATCCCAGTTCACTATGATATCTGGTCTAACTTCATGGCT
TCTACTAATGAGATTCTAGAACTTTGGAAAATGCGAAAAGATCGCTTGCA
ATACGATTTCCATCCATTTATCTGGGAAGTTGGCGGTAAGTACACTTATC
CTCAAGATCAACACTTAGTAGAATACCATCATCCACGTGGTTTTGATGAT
TGTTTTGAACAAGACTCTAACATTCAATTTAAAGCTTTGCTATAA
4196.2
                                            (SEQ. ID. NO. 348)
ATGTTCCTTTCAGGCTGGTTGTCTAGTTTTGCTAATACTTATATCCATGA
TTTACTGGGGTTCTTTTCCCAGATAGTCCATTTTTAAATGCCTTTGAAA
GTGCTATTGCGGCTCCTTTGGTAGAAGAACCCTTGAAATTATTGTCACTT
GTTTTTGTTTTGGCTTTGATTCCTGTGCGAAAATTAAAATCTTTGTTTTT
ACTTGGAATTGCTTCCGGTTTGGGATTCCAAATGATTAAGGATATTGGTT
ATATTCGTACGGATTTGCCAGAGGGCTTTGACTTTACTATTTCGCGAATT
TTAGAGCGTATCATCTCAGGAATTGCCTCTCACTGGACTTTTTCAGGTCT
AGCTGTAGTAGGTGTTTACTTGCTTTACAGAGCCTATAAAGGACAGAAGG
TTGGCAAGAAACAGGGCCTTATTTTCTAGGTTTAGCCTTGGGAACTCAC
TTCTTGTTTAACTCTCCTTTTGTGGAGTTGGAAACAGAGTTGCCTTTAGC
GATTCCAGTGGTTACGGCTATTGCTCTCTATGGTTTTTATCATGCTTATT
GCTTTGTTGAGAAACACAATGAGTTGATGACCTAG
4197.1
                                            (SEQ. ID. NO. 349)
ATGAAGGTGGAACCACGTTGCGACGTCCTTTCGAGGATGTCGCATTTTTT
TATTAGGATACTAATTATGGAGTTGCAAGAATTAGTGGAGCGCAGTTGGG
CAATCCGACAAGCTTATCACGAACTGGAAGTTAAGCATCATGATTCCAAG
TGGACGGTAGAAGAAGACCTCTTGGCTTTATCTAATGATATTGGAAATTT
CCAACGACTGGTGATGACAAAGCAAGGACGCTACTATGATGAAACACCCT
ACACACTGGAACAAAAAACTTTCAGAAAATATCTGGTGGCTATTAGAACTT
```

TABLE 1-continued

TCTCAACGTTTGGATATAGACATTCTGACGGAAATGGAAAACTTCCTCTC
TGATAAAGAAAAGCAATTGAACGTTAGGACTTGGAAGTAG 4197.4

(SEQ. ID. NO. 350)
ATGCTTGATTGGAAACAATTTTTTCTAGCCTATCTGCGCTCCCGTAGTCG
TCTTTTTATCTATCTGCTTTCTTTGGCATTTCTTGTCTTACTCTTTCAGT
TTTTTATTTGCCAGTCTAGGAATTTACTTCCTCTACTTTTTCTTCTTGTG
TTGCTTTGTAACCATATTATTTTTCACTTGGGACATATTGGTGGAAACGC
AGGTCTATCGCCAGGAACTTCTCTATGGAGAGAGGGAAGCCAAGTCTCCT
TTGGAAATAGCTTTAGCAGAAAAATTAGAAGCGCGTGAGATGGAACTCTA
TCAGCAGAGGTCAAAAGCAGAAAGAAAACTGACGGATTTGCTGGATTACT
ATACCTTGTGGGTCCATCAGATAAAGACCCCCATTGCAGCCAGTCAACTC
TTAGTTGCAGAAGTGGTCGACCGCCAACTGAAGCAGCAGCTAGAACAGGA
AATTTTCAAAATCGACTCCTATACCAACCTAGTTTTACAGTACCTGCGTT
TAGAAAGTTTCCATGATGATTTGGTCTTAAAGCAGGTTCAAATTGAGGAC
TTGGTCAAGGAAATAATTCGTAAATATGCTCTTTTCTTTATTCAAAAAGG
CTTAAATGTCAATCTACATGACCTTGATAAAGAAATCGTGACGGATAAAA
AGTGGCTGCTAGTGGTTATTGAGCAAATCATCTCAAACAGTCTCAAGTAC
ACCAAGGAAGGTGGTCTGGAGATTTATATGGATGACCAAGAGCTTTGTAT
CAAAGATACGGGAATCGGGATAAAAAACAGTGATGTCCTCCGAGTATTTG
AACGTGGCTTTTCAGGATACAATGGCCGTTTGACCCAGCAGTCCTCTGGA
CTTGGCCTTTATCTATCTAAGAAAATTTCTGAAGAACTGGGGCACCAGAT
TCGTATCGAGTCTGAGGTCGGAAAAGGAACGACAGTGCGGATTCAGTTTG
CTCAAGTGAACTTAGTCCTTGAGTAA 4211.2

(SEQ. ID. NO. 351)
ATGGAACTTAATACACACAATGCTGAAATCTTGCTCAGTGCAGCTAATAA
GTCCCACTATCCGCAGGATGAACTGCCAGAGATTGCCCTAGCAGGGCGTT
CAAATGTTGGTAAATCCAGCTTTATCAACACTATGTTGAACCGTAAGAAT
CTCGCCCGTACATCAGGAAAACCTGGTAAAACCCAGCTCCTGAACTTTTT
TAACATTGATGACAAGATGCGCTTTGTGGATGTGCCTGGTTATGGCTATG
CTCGTGTTTCTAAAAAGGAACGTGAAAAGTGGGGGTGCATGATTGAGGAG
TACTTAACGACTCGGGAAAATCTCCGTGCGGTTGTCAGTCTAGTTGACCT
TCGTCATGACCCGTCAGCAGATGATGTGCAGATGTACGAATTTCTCAAGT
ATTATGAGATTCCAGTCATCATTGTGGCGACCAAGGCGGACAAGATTCCT
CGTGGTAAATGGAACAAGCATGAATCAGCAATCAAAAAGAAATTAAACTT
TGACCCGAGTGACGATTTCATCCTCTTTTCATCTGTCAGTAAGGCAGGGA
TGGATGAGGCTTGGGATGCAATCTTAGAAAAATTGTGA 4211.3

(SEQ. ID. NO. 352)
ATGACAAAGAAACAACTTCACTTGGTGATTGTGACAGGGATGAGTGGCGC
AGGGAAAACTGTAGCCATTCAGTCCTTCGAGGATCTAGGTTATTTCACCA
TTGATAATATGCCGCCAGCTCTCTTGCCTAAGTTTTTGCAGCTGGTTGAA

TABLE 1-continued

ATTAAGGAAGACAATCCTAAGTTGGCCTTGGTAGTGGATATGCGTAGCCG
TTCTTTCTTTTCAGAGATTCAAGCTGTTTTGGATGAGTTGGAAAATCAAG
ATGGTTTGGATTTCAAAATCCTCTTTTTGGATGCGGCTGATAAGGAATTC
CTCGCTCGTTACAAGGAAACCAGACGGAGTCACCCACTAGCAGCAGACGG
TCGTATTTTAGATGGAATCAAGTTGGAACGTGAACTCTTGGCACCTTTGA
AAAATATGAGCCAAAATGTGGTGGATACGACTGAACTCACTCCACGTGAG
CTGCGCAAAACCCTTGCAGAGCAGTTTTCAGACCAAGAACAAGCCCAGTC
TTTCCGTATCGAAGTCATGTCTTTCGGATTTAAGTATGGAATCCCGATTG
ATGCGGACTTGGTCTTTGATGTCCGTTTCTTGCCAAATCCCTATTATTTA
CCAGAACTGAGAAACCAAACGGGTGTGGATGAACCTGTTTATGATTATGT
CATGAACCATCCTGAGTCAGAAGACTTTTATCAACATTTATTGGCCTTGA
TTGAGCCGATTCTGCCAAGTTACCAAAAGGAAGGTAAGTCCGTTTTGACC
ATTGCCATGGGATGTACGGGTGGACAACACCGTAGTGTGGCATTTGCTAA
ACGCTTGGCGCAGGACTTATCCAAGAATTGGTCTGTTAATGAAGGGCATC
GCGACAAAGACCGCAGAAAGGAAACGGTAAACCGTTCATGA 4211.4

(SEQ. ID. NO. 353)
ATGAGAAAACCAAAGATAACGGTGATTGGTGGAGGGACTGGAAGTCCCGT
CATTCTAAAAAGTCTGCGGGAAAAAGATGTGGAAATCGCAGCTATCGTGA
CGGTGGCAGATGATGGTGGTTCTTCAGGTGAACTCCGAAAAAATATGCAA
CAGTTGACACCGCCAGGTGATCTTCGTAATGTCCTTGTGGCCATGTCGGA
TATGCCTAAGTTTTATGAGAAGGTCTTTCAGTATCGGTTCTCTGAGGATG
CCGGAGCCTTTGCTGGCCATCCATTGGGAAATCTCATCATTGCTGGCTTG
TCAGAAATGCAGGGTCAACCTATAATGCCATGCAGTTATTGAGCAAATTT
TTCCATACAACAGGGAAAATTTATCCTTCCAGTGACCATCCTTTGACCCT
TCATGCAGTCTTTCAGGATGGGACAGAAGTGGCTGGAGAGAGTCATATTG
TAGACCATCGAGGCATAATTGACAATGTCTATGTGACCAATGCCCTAAAC
GATGATACGCCTCTGGCCAGCCGTCGAGTAGTGCAGACCATCCTTGAAAG
TGACATGATTGTCCTAGGGCCAGGTTCCCTCTTTACCTCTATTTTGCCCA
ATATCGTGATTAAGGAAATTGGGCGGGCTCTTTTGGAAACCAAGGCAGAA
ATTGCCTATGTCTGCAATATCATGACCCAACGTGGGGAGACGGAACACTT
TACAGATAGCGACCACGTGGAAGTCTTGCATCGTCACCTTGGTCGCCCTT
TTATCGACACTGTCTTGGTGAATATTGAAAAGTGCCTCAGGAATACATG
AATTCCAACCGTTTTGATGAATACTTAGTGCAAGTGGAACACGATTTTGT
AGGTCTTTGTAAGCAAGTTTCGCGCGTGATTTCATCTAACTTCCTTCGTC
TGGAAAATGGCGGTGCCTTCCACGATGGAGATTTGATTGTGGACGAGTTG
ATGCGCATTATACAGGTGAAAAAATGA 4213.1

(SEQ. ID. NO. 354)
ATGAAAAATTTGATAAAGTTGCTAATAATTAGATTGATTGTTAACTTAGC
AGACAGTGTATTTTATATAGTAGCATTGTGGCACGTTAGCAATAATTATT
CTTCGAGCATGTTCTTAGGAATATTTATTGCAGTAAATTATCTACCGGAT

TABLE 1-continued

```
TTGTTACTAATCTTTTTTGGACCAGTTATTGACAGAGTAAATCCGCAAAA
AATTCTTATAATATCAATTTTGGTTCAATTAGCAGTGGCTGTAATATTTT
TATTATTATTAAACCAAATATCATTTTGGGTGATAATGAGTCTAGTGTTT
ATTTCAGTAATGGCTAGCTCCATAAGTTACGTGATAGAAGATGTGTTGAT
TCCTCAAGTGGTAGAATATGATAAGATTGTATTTGCAAATTCTCTTTTTA
GTATTTCGTATAAAGTATTAGATTCTATTTTTAATTCATTCGCATCATTT
TTACAGGTGGCAGTAGGATTTATTTTATTGGTTAAGATAGATATAGGCAT
ATTTTTACTTGCTCTATTTATATTGTTGTTGTTAAAATTTAGAACTAGCA
ATGCGAATATAGAAAACTTCTCTTTCAAATATTACAAGAGAGAAGTGTTG
CAAGGTACAAAGTTTATTTTAAATAATAAATTATTATTTAAAACCAGTAT
TTCTTTAACGCTTATAAACTTTTTTATTCATTTCAGACAGTAGTTGTACC
GATTTTTCTATTCGATATTTTGATGGTCCGATTTTTTATGGTATTTTTT
TAACTATTGCTGGTTTGGGTGGTATATTGGGAAATATGCTAGCGCCAATC
GTAATAAAATATTTAAAATCGAATCAAATTGTTGGTGTATTTCTTTTTTT
GAACGGCTCAAGTTGGTTAGTAGCAATTCTTATAAAAGACTATACTTTAT
CACTTATTTTATTTTTCGTTTGTTTTATGTCTAAAGGAGTCTTCAATATT
ATTTTTAATTCGTTGTACCAACAAATACCTCCACATCAACTTCTTGGTAG
GGTAAATACTACCATTGATTCTATTATTTCTTTTGGAATGCCAATTGGTA
GTTTAGTTTGCAGGAACGCTTATTGATTTGAATATTGAATTAGTGTTAAT
TGCTATTAGCATACCTTATTTTTGTTTTCTTATATTTTTATACGGATA
ATGGATTGAAAGAATTTAGTATATATTAG
```

4213.2
                                      (SEQ. ID. NO. 355)

```
ATGATGTCTAACAAAAATAAGGAAATTCTGATTTTTGCGATTCTCTATAC
AGTCCTCTTTATGTTTGATGGCGTTAAATTGCTGGCTTCTTAATGCCAT
CTGCCATTGCAAATTATCTTGTTTATGTAGTTTTAGCTCTATATGGCTCC
TTCTTGTTCAAGGATAGATTGATCCAACAATGGAAGGAGATTAGAAAGAC
TAAAAGAAAATTCTTCTTTGGAGTCTTAACAGGATGGCTCTTTCTCATTC
TGATGACTGTTGTCTTTGAATTTGTATCAGAGATGTTGAAGCAGTTTGTG
GGACTAGATGGACAAGGTCTAAATCAGTCTAATATTCAAAGTACCTTTCA
AGAACAACCACTACTGATAGCTGTTTTTGCTTGTGTCATTGGACCTCTGG
TAGAAGAATTATTTTTCCGTCAGGTCTTATTGCATTACTTGCAGGAACGG
TTGTCAGGTTTACTAAGCATTATTCTGGTAGGACTTGTTTTTGCTCTGAC
TCATATGCACAGTTTGGCTCTATCAGAGTGGATTGGTGCAGTTGGTTACT
TAGGTGGAGGCCTTGCCTTTTCTATTATTTATGTGAAAGAAAAAGAGAAT
ATCTACTATCCCTACTTGTTCACATGTTAAGCAACAGCCTCTCCTTAAT
CATTTTAGCTATCAGTATAGTAAAATGA
```

4224.1
                                      (SEQ. ID. NO. 356)

```
TTGAAAAAGCCAATTATCGAATTCAAAAACGTCTCTAAAGTTTTTGAAGA
CAGCAACACCAAGGTTCTCAAAGACATCAACTTTGAGTTGGAAGAAGGGA
AATTCTACACCCTTCTAGGTGCATCTGGTTCGGGGAAATCAACTATCCTA
AACATTATTGCAGGTTTACTGGATGCGACGACAGGAGATATCATGCTAGA
CGGTGTTCGTATCAATGATATTCCAACCAACAAGCGCGACGTACATACCG
TCTTCCAATCCTATGCCTTGTTCCCACATATGAATGTGTTTGAAAATGTT
GCCTTTCCACTTCGCTTGCGTAAAATTGATAAGAAAGAAATCGAGCAGCG
TGTAGCGGAAGTTCTCAAGATGGTTCAGTTGGAAGGTTATGAAAAACGTT
CCATCCGCAAACTTTCTGGAGGACAACGTCAGCGTGTGGCCATCGCCCGT
GCTATCATCAACCAACCCCGTGTGGTCTTGTTGGACGAGCCTTTATCAGC
GCTGGACTTGAAATTGAGAACAGACATGCAGTACGAATTGCGTGAATTAC
AACAACGATTGGGCATTACCTTTGTCTTTGTCACTCACGATCAGGAAGAA
GCTCTTGCCATGAGTGACTGGATTTTCGTTATGAATGATGGCGAGATTGT
CCAGTCTGGAACCCCTGTGGACATCTACGATGAGCCAATCAACCACTTTG
TTGCCACCTTTATCGGGGAGTCAAACATCTTGCCAGGTACCATGATTGAG
GACTACTGGTCGAATTTAACGGCAAACGCTTTGAAGCGGTTGATGGTGG
GATGAAGCCAAATGAACCTGTTGAGGTCGTTATTCGTCCAGAGGACTTGC
GCATTACCCTTCCTGAAGAAGGCAAGCTCCAAGTTAAGGTCGATACCCAG
CTTTTCCGTGGAGTTCATTATGAAATTATCGCCTATGACGAACTTGGAAA
TGAATGGATGATCCACTCAACCCGTAAGGCTATCGTGGGTGAGGAAATCG
GTCTGGACTTTGAACCAGAAGACATCCACATCATGCGTCTCAATGAAACC
GAAGAAGAGTTCGATGCTCGTATTGAGGAGTACGTAGAAATCGAAGAGCA
AGAAGCAGGTTTGATCAATGCAATCGAGGAGGAAAGAGATGAAGAAACA
AGCTCTAA
```

4252.1
                                      (SEQ. ID. NO. 357)

```
ATGAAATCAATGAGAATCTTATTTTTGTTAGCTTTAATTCAAATCAGTTT
GAGTAGCTGTTTCCTATGGAAGGAATGCATCTTGTCCTTTAAACAAAGTA
CAGCTTTTTTCATCGGAAGCATGGTTTTCGTTTCAGGAATCTGTGCTGGA
GTAAATTATCTTTATACCCGTAAGCAAGAAGTCCATAGTGTCCTAGCCAG
TAAGAAGTCGGTGAAGCTTTTTTACAGTATGTTACTCTTAATTAATTTGT
TAGGAGCTGTTCTTGTTTTGTCAGATAACTTGTTCATCAAAAATACGCTG
CAGCAAGAATTAGTTGACTTTTTATTGCCATCCTTCTTTTTCCTATTTGG
GCTAGATTTGCTGATTTTTTTACCCTTGAAAAAATACGTGCGCGATTTTC
TTGCTATGCTGGACAGAAAAAGACAGTGTTGGTGACTATTTTAGCAACA
CTTCTTTTCTTAAGAAATCCAATGACCATTGTCTCACTTCTGATTTATAT
TGGACTGGGCTTGTTTTTTGCAGCCTATCTTGTCCCAAATTCGGTTAAGA
AGGAAGTTTCCTTTTATGGTCATATTTTCCGAGATCTTGTATTGGTCAT
TGTTACGCTCATTTTCTTTTAG
```

4252.2
                                      (SEQ. ID. NO. 358)

```
ATGGTTAAAAAAATTATTGGAATGGTGCTAGCTTTACTTTCTGTAACTGT
AGTAGGAGTAGGTGTTTTTGCTTATACTATTTATCAACAAGGGACAGAAA
CCTTAGCTAAAACCTATAAAAAAATCGGTGAAGAAACCAAGGTTATTGAA
GCGACTGAACCTCTAACCATTCTGTTAATGGGAGTGGACACCGGAAATGT
```

TABLE 1-continued

TGAACGAACTGAAACTTGGGTCGGTAGAAGTGATAGCATGATCTTGATGA
CAGTGAATCCTAAAACGAAAAAAACAACAATGATGAGTTTAGAGCGGGAT
ATTCGACGCGCATTGAATCAGGGAATGGTCAGGCTCATGAAGCGAAACTG
AACTCAGCATATGCAGATGGTGGAGCAGAGCTTGCTATAGAAACCATTCA
AAAAATGATGAATATCCATATTGATCGCTATGTGATGGTCAATATGAGAG
GATTGCAAAACTAGTGGATGCAGTAGGAGGTATTACAGTCAATAATATC
CTAGGTTTCCCAATTTCTATCAGTGACCAAGAAGAATTTAATACTATTTC
TATCGGTGTTGGGGAGCAACATATTGGGGAGAAGAAGCCCTAGTCTATG
CACGAATGCGTTACCAAGATCCTGAGGGGATTATGGTCGTCAAAAACGT
CAACGTGAAGTTATTCAAAAAGTCATGGAAAAAGCTCTCAGTTTAAATAG
CATTGGTCATTATCAAGAGATTCTAAAAGCTTTGAGTGACAATATGCAGA
CCAATATTGATTTGTCTGCAAAAAGTATCCCTAACTTGCTAGGCTATAAA
GATTCATTTAAAACCATTGAAACTCAGCAGTTGCAGGGTGAAGGAGAGAT
ACTTCAAGGTGTTTCTTACCAGATTGTTTCGAGAGCACATATGTTGGAAA
TGCAAAATCTACTCCGACGTTCTTTGGGACAAGAAGAAGTTACTCAGCTT
GAAACCAATGCGGTTTTATTTGAAGATTTATTTGGCAGAGCACCTGTTGG
TGATGAAGATAATTAA 4256.2
(SEQ. ID. NO. 359)
ATGAAAAAACAAGCCTATGTCATTATTGCTCTCACCTCCTTCCTATTTGT
CTTTTTTTTCTCCCACAGCTTGCTGGAAATACTTGATTTTGACTGGTCTA
TCTTTTTGCACGATGTCGAAAAAACAGAAAAATTTGTCTTTTTATTGTTG
GTTTTCAGCATGTCCATGACCTGTCTCTTAGCCCTGTTTTGGCGAGGGAT
CGAAGAGCTTTCTCTAAGAAAAATGCAGGCTAATCTCAAGCGTTTATTAG
CAGGGCAAGAAGTGGTTCAGGTTGCAGATCCAGATTTGGATGCCAGTTTC
AAGTCCTTATCAGGTAAACTTAACCTTTTGACAGAGGCTCTTCAAAAAGC
TGAAAATCAGAGCCTTGCTCAGGAAGAGGAAATCATCGAGAAGGAACGGA
AGCGAATTGCTCGGGATTTGCACGATACAGTCAGTCAGGAGTTGTTTGCG
GCCCACATGATTTTATCGGGTATCAGTCAGCAGGCTTTGAAATTGGATAG
AGAAAAGATGCAGACCCAGTTGCAGAGTGTCACAGCTATTTTAGAAACAG
CCCAGAAGGATTTGCGGGTTTTGCTCTTGCATTTGCGACCAGTTGAACTG
GAGCAGAAGAGCTTGATAGAAGGGATTCAAATTCTTTTAAAAGAGCTTGA
GGACAAGAGTGATCTTAGGGTTAGTCTCAAGCAGAATATGACGAAATTGC
CTAAGAAATCGAGGAGCATATCTTCCGTATCCTGCAAGAGTTGATTAGC
AATACCCTCCGCCATGCCCAGGCATCTTGCCTAGATGTCTACCTCTATCA
GACAGATGTTGAATTGCAACTGAAGGTGGTGGACAATGGGATTGGTTTCC
AGTTAGGGAGCTTAGACGACTTGAGTTATGGACTGCGAAATATCAAGGAG
CGGGTTGAAGATATGGCTGGAACAGTTCAACTCTTGACAGCTCCCAAGCA
AGGGCTGGCGGTTGATATCCGTATTCCCCTGTTAGATAAGGAATGA 4263.1
(SEQ. ID. NO. 360)
ATGATTGTTTCCATTATTTCTCAAGGATTTGTCTGGGCTATTCTAGGTCT
GGGAATCTTTATGACATTTAGGATTTTAAACTTTCCAGATATGACGACAG
AAGGTTCCTTCCCTCTTGGGGGAGCTGTTGCTGTCACTTTGATAACCAAA
GGCGTGAACCCATTTTTAGCGACACTTGTTGCTGTAGGAGCAGGTTGTTT
GGCTGGAATGGCAGCAGGCCTTCTTTATACAAAAGGGAAGATCCCAACCT
TGCTCTCAGGGATTTTGGTGATGACTTCTTGTCACTCAATCATGCTCTTG
ATTATGGGACGTGCGAATTTAGGCCTGCTGGAACCAAGCAAATTCAGGAT
GTTTGCCTTTTGATTCGGATTTGAATCAACTCTTGACAGGTCTCATCTTT
GTGAGTATTGTTATTGCTCTCATGCTCTTTTTCTTGGACACTAAACTCGG
ACAAGCCTATATTGCTACAGGGGATAATCCTGATATGGCTAGAAGTTTCG
GGATTCATACTGGACGCATGGAGCTCATGGGCTTGGTCTTATCAAATGGT
GTGATTGCCCTTGCAGGTGCCCTCATTGCTCAGCAAGAAGGTTATGCCGA
TGTGTCTCGAGGGATCGGGGTTATCGTTGTGGGCTTGCAAGTTTGATTA
TTGGAGAAGTTATTTTCAAGAGTTTGAGCTTGGCAGAGCGTTTGGTTACT
ATCGTTGTAGGTTCTATCGCTTATCAATTTTTAGTGTGGGCAGTTATCGC
ACTTGGCTTTAATACAAGTTACCTTCGTTTATACAGTGCCTTGATTTTAG
CAGTCTGCCTCATGATTCCAACATTTAAGCAAACAATCTTGAAAGGAGCC
AAGTTAAGCAAATGA 4346.1
(SEQ. ID. NO. 361)
ATGAAAAAAATGAAAGTTTGGTCTACTGTACTTGCAACGGGAGTTGCTCT
TACTACACTTGCTGCTTGCTCTGGAGGTTCAAATTCTACGACTGCTTCTT
CATCTGAAGAAAAAGCTGATAAAAGTCAAGAATTAGTTATCTATTCGAAC
TCAGTCTCAAATGGTCGTGGTGATTGGTTAACTGCTAAAGCAAAAGAAGC
TGGTTTTAATATAAAAATGGTTGATATCGCTGGCGCTCAATTAGCAGACC
GTGTTATTGCTGAGAAGAATAATGCAGTTGCAGATATGGTATTTGGAATT
GGTGCTGTTGATTCAAATAAAATTAGAGATCAAAAATTACTAGTACAGTA
CAAGCCTAAATGGTTAGATAAAATTGATCAATCTTTATCAGATAAAGATA
ATTATTATAATCCTGTGATTGTTCAACCATTAGTTTTAATTGGGGCGCCT
GATGTAAAAGAAATGCCTAAAGATTGGACTGAATTAGGTAGTAAGTATAA
AGGTAAATATTCAATTTCTGGTCTTCAAGGAGGTACAGGACGGGCAATTC
TAGCAAGTATCTTAGTTCGATACCTTGATGATAAAGGTGAATTAGGTGTT
TCCGAAAAGGTTGGGAAGTAGCAAAAGAATATTTGAAAAATGCATACAC
TCTTCAAAAGGGAGAAAGTTCAATTGTTAAGATGTTAGACAAAGAAGATC
CAATACAATATGGAATGATGTGGGGTTCTGGTGCATTAGTTGGACAAAAA
GAACAAAATGTTGTTTTCAAAGTTATGACTCCTGAGATTGGTGTACCATT
TGTAACTGAACAAACTATGGTTTTAAGCACTAGTAAAAAACAAGCGTTAG
CTAAAGAATTTATTGATTGGTTTGGTCAATCAGAAATTCAAGTAGAATAT
AGTAAGAACTTTGGATCTATTCCTGCAAATAAAGATGCCCTCAAAGATCT
ACCTGAAGATACGAAGAAATTTGTTGATCAAGTGAAACCACAAAATATTG

TABLE 1-continued

ACTGGGAAGCTGTTGGAAAGCATTTGGATGAATGGGTAGAAAAGCTGAA
TTAGAATACGTACAATAA 4346.2

(SEQ. ID. NO. 362)
ATGATTAAATTTGATAATATTCAAATTAAATATGGTGATTTTGTTGCAAT
TGATAATCTGAATTTAGATATACATGAAGGGGAATTTTTTACATTTCTTG
GGCCTTCAGGATGTGGTAAATCAACTACTTTGAGAGCATTGGTAGGTTTT
CTAGATCCATCATCAGGAAGTATTGAAGTTAATGGAACAGATGTCACTCA
TTTGGAACCTGAAAAGCGTGGAATTGGTATTGTATTTCAATCTTATGCGC
TATTTCCAACTATGACTGTTTTTGATAATATTGCATTTGGTTTAAAGTTA
AGAAGGTAGCTCCAGATGTTATTAAAGCTAAAGTATCAGCAGTGGCAGCA
AAAATTAAGATCTCTGATCAACAGTTACAGCGTAATGTATCAGAATTATC
TGGGGGTCAACAACAAAGGGTAGCATTGGCTCGTGCTCTGGTTCTTGAAC
CTAAAATTCTTTGTCTAGATGAACCATTGTCAAACCTTGACGCAAAATTA
CGTGTAGATTTGAGAAAAGAGTTGAAAAGACTTCAAAAAGAGTTAGGTAT
TACTACTTTATATGTTACTCATGATCAAGAGGAAGCCTTGACTTTATCTG
ATAGAATTGCAGTCTTTAACAATGGATACATCGAACAGGTCGGTACACCA
GTAGAGATTTATCATAATTCTCAAACTGAATTTGTATGTGATTTTATTGG
AGATATTAATGTTTTGACCGATGAAACAGTCCACGAAGTATTATTGAAAA
ATACAAGCGTTTTCTTAGAGGATAAAAAGGATACATTCGATTAGAGAAA
GTTCGATTCAATCGTGAAACTGAACAAGATTTTATTCTAAAAGGGACAAT
TATTGATGTTGAGTTTTCTGGAGTTACAATTCACTATACAATAAAAGTTT
CTGAAAGTCAGATTCTTAATGTAACAAGTATTGATAGTCAGGCTGCTATT
AGATCTGTCGGAGAAAGTGTGGAATTATTTATCACACCATCAGACGTTCT
GCAATTTTAA 4346.3

(SEQ. ID. NO. 363)
ATGCGTCATAAAATTAAATTTAAAAGATTGGCTTATTCGTTTAGGGTTAAT
CTGGTTCTTAGTAACATTTATTATTTATCCAAACTTTGATCTAGTAGTGA
ATGTATTTGTAAAAGGAGGAGAATTTTCCCTTGATGCTGTACATCGTGTT
CTAAAATCTCAGAGGGCACTTCAGAGTATTATGAACAGTTTTAAGTTAGC
ATTTTCACTCATTATTACAGTTAATGTCGTAGGTATTCTTTGTGTTCTAT
TTACAGAGTACTTTGATATTAAAGGTGCTAAAATTTAAAATTAGGTTAT
ATGACCTCTTTAATTTATGGAGGAGTGGTTTTAGCGACTGGATATAAATT
TGTCTATGGTCCTTATGGATTGATTACAAAATTTTTACAAAATGTTATCC
CTTCTTTAGACCCTAACTGGTTTATTGGGTATGGTGCAGTCTTATTCATT
ATGACATTTTCAGGAACTGCTAATCATACATTGTTTTAACAAATACAAT
TCGAAGCGTTGACTATCACACTATTGAGGCTGCTCGAAATATGGGAGCAA
AACCATTACTGTTTTCCGAAAAGTAGTGTTACCAACCTTAATTCCAACT
CTATTTGCACTTACTATTATGGTTTTTCTTAGTGGTTTATCTGCAGTAGC
AGCACCCATGATTGTTGGTGGTAAAGAATTTCAAACTATAAATCCAATGA
TTATTACATTTGCAGGGATGGGGAATTCTCGTGATTTAGCTGCCCTACTT

TABLE 1-continued

GCAATTATTTTAGGTATTGCAACTACAATTTTGCTTACTATCATGAATAA
GATAGAAAAGGTGGAAATTATATTTCTATCTCTAAGACTAAAGCGCCTC
TTAAAAAACAAAAAATTGCGTCTAAGCCTTGGAATATCATTGCTCACATT
GTAGCATATGGATTGTTCACAGTTTTCATGCTTCCACTAATTTTTATAGT
ATTATACTCATTTACAGATCCAGTTGCAATTCAAACAGGTAACTTAACAT
TATCAAACTTTACTTTAGAAAATTATCGCTTATTCTTTAGTAATAGTGCG
GCATTCTCTCCATTCTTGGTCAGCTTTATTTATTCTATTATTGCTGCGAC
AACAGCAACAATTCTCGCAGTTGTATTTGCTCGTGTTGTCAGAAAACATA
AATCTCGTTTTGATTTCTTATTTGAATATGGTGCTCTACTTCCTTGGTTA
CTACCAAGTACACTTTTAGCAGTAAGTTTATTATTTACTTTTAATCAGCC
ACAATTTCTTGTCTTGAATCAGATTTTGGTAGGTAGTTTGGTAATTCTAC
TTATTGCATATATAGTTGTAAAAATCCCATTTTCTTATAGAATGGTACGT
GCTATTTTATTTAGTGTTGATGATGAGATGGAAGATGCAGCAAGAAGTAT
GGGTGCTTCACCTTTTTATACTATGATGAAGGTTATCATTCCATTTATTT
TACCGGTTGTTCTCTCTGTTATTGCTTTAAACTTTAACTCTTTATTAACT
GACTTCGACTTATCTGTATTCCTTTACCATCCCCTAGCTCAACCATTAGG
TATTACGATTCGATCTGCAGGTGATGAAACAGCAACATCTAATGCACAAG
CTCTGGTATTTGTTTATACAATTGTTCTGATGATTATTTCTGGAACGGTA
TTATACTTCACACAAAGACCGGGCGTAAAGTAAGGAAATAA

TABLE 2

(SEQ ID. NO. 1)
MEELVTLDCLFIDRTKIEANANKYSFVWKKTTEKFSAKLQEQIQVYFQEE
ITPLLIKYAMFDKKQKRGYKESAKNLANWHYNDKEDSYTHPDGWYYRFHH
TKYQKTQTDFQQEIKVYYADEPESAPQKGLYMNERYQNLKAKECQALLSP
QGRQIFAQRKIDVEPVFGQIKASLGYKRCNLRGKRQVRIDMGLVLMANNL
LKYSKMKZ (SEQ ID. NO. 2)
MGKGHWNRKRVYSIRKFAVGACSVMIGTCAVLLGGNIAGESVVYADETLI
THTAEKPKEEKMIVEEKADKALETKNIVERTEQSEPSSTEAIASEKKEDS
AVTPKEEKVSAKPEEKAPRIESQASNQEKPLKEDAKAVTNEEVNQMIEDR
KVDFNQNWYFKLNANSKIEAKPDADVSTWKKLDLPYDWSIENDFDHESPA
QNEGGQLNGGEAWYRKTFKLDEICDLKKNVRLTFDGVYMDSQVYVNGQLV
GHYPNGYNQFSYDITKYLQKDGRENVIAVHAVNKQPSSRWYSGSGIYRDV
TLQVTDKVHVEKNGTTILTPKLEEQQHGKVETHVTSKIVNTDDKDHELVA
EYQIVERGGHAVTGLVRTASRTLKAHESTSLDAILEVERPKLWTVLNDKP
ALYELITRVYRDGQLVDAKKDLFGYRYYHWTPNEGFSLNGERIKFHGVSL
HHDHGALGAEENYKAEYRRLKQMKEMGVNSIRTTHNPASEQTLQIAAELG
LLVQEEAFDTWYGGKKPYDYGRFFEKDATHPEARKGEKWSDFDLRTMVER
GKNNPAIFMWSIGNEIGEANGDAHSLATVKRLVKVIKDVDKTRYVTMGAD

TABLE 2-continued

KFRFGNGSGGHEKIADELDAVGFNYSEDNYKALRAKHPKWLIYGSETSSA
TRTRGSYYRPERELKHSNGPERNYEQSDYGNDRVGWGKTATASWTFDRDN
AGYAGQRWTGTDYIGEPTPWHNQNQTPVKSSYFGIVDTAGTPKHDFYLYQ
SQWVSVKKKPMVHLLPHWNWENKELASKVADSEGKIPVRAYSNASSVELF
LNGKSLGLKTFNKKQTSDORTYQEGANANELYLEWKVAYQPGTLEAIARD
ESGKEIARDKITTAGKPAAVRLIKEDHAIAADGKDLTYIYYEIVDSQGNV
VPTANNLVRPQLHGQGQLVQVDNGEQASRERYKAQADGSWIRKAFNGKGV
AIVKSTEQAGKETLTAHSDLLKSNQVTVFTGKKEGQEKTVLGTEVPKVQT
IIGEAPEMPTTVPFVYSDGSRAERPVTWSSVDVSKPGIVTVKGMADGREV
EARVEVIALKSELPVVKRIAPNTDLNSVDKSVSYVLIDGSVEEYEVDKWE
IAEEDKAKLAIPGSRIQATGYLEGQPIHATLVVEEGNPAAPAVPTVTVGG
EAVTGLTSQKPMQYPXLAYGAKLPEVTASAKNAAVTVLQASAANGMRASI
IIQPKDGGPLQTYAIQFLEEAPKIAHLSLQVEKADSLKEDQTVKLSVRAH
YQDGTQAVLPADKVTFSTSGEGEVAIRKGMLELHKPGAVTLNAEYEGAKD
QVELTIQANTEKKIAQSIRPVNVVTDLHQEPSLPATVTVEYDKGFPKTHK
VTWQAIPKEKLDSYQTFEVLGKVEGIDLEARAKVSVEGIVSVEEVSTTP
IAEAPQLPESVRTYDSNGHVSSAKVAWDAIRPEQYAKEGVVVNGRLEGTQ
LTTKLHVRVSAQTEQGANISDQWTGSELPLAFASDSNPSDPVSNVNDKLI
SYNNQPANRWTNWNRTNPEASVGVLFGDSGILSKRSVDNLSVGFHEDHGV
GVPKSYVIEYYVGKTVPTAPKNPSFVGNEDHVFNDSANWKPVTNLKAPAQ
LKAGEMNHFSFDKVETYAVRIRMVKADNKRGTSITEVQIFAKQVAAAKQG
QTRIQVDGKDLANFNPDLTDYYLESVDGKVPAVTASVSNNGLATVVPSVR
EGEPVRVLAKAENGDILGEYRLHFTKDKSLLSHKPVAAVKQARLLQVGQA
LELPTKVPVYFTGKDGYETKDLTVEWEEVPAENLTKAGQFTVRGRVLGSN
LVAEITYRVTDKLGETLSDNPNYDENSNQAFASATNDIDKNSHDRVDYLN
DGDHSENRRWTNWSPTPSSNPEVSAGVLFRENGKIVERTVTQGKVQFFAD
SGTDAPSKLVLERYVGPEFEVPTYYSNYQAYDADHPFNNPENWEAVPYRA
DKDIAAGDEINVTFKAIKAKAMRWRMERKADKSGVAMIEMTFLAPSELPQ
ESTQSKILVDGKELADFAENRQDYQITYKGQRPKVSVEENNQVASTVVQS
GEDSFPVLVRLVSESGKQVKEYRLHLTKEKPVSEKTVAAVQEDLPKIEFV
EKDLAYKTVEKKDSTLYLGETRVEQEGKVGKERLEFAINPDGSKEEKLRE
VVEVPTDRIVLVGTKPVAQEAKKPQVSEKADTKPIDSSEASQTNKAQLPS
TGSAASQAAVAAGLTLLGLSAGLVVTKGKKEDZ (SEQ ID. NO. 3)
MKIMKXKYWTLAILFFCLFNNSVTAQEIPKNLDGNITHTQTSESFSESDE
KQVDYSNKNQEEVDQNKFRIQIDKTELPVTTDKHLEKNCCKLELEPQINN
DVNSESNNLLGEDNLDNKIKENVSHLDNRGGNIEHDKDNLESSIVRXYEW
DIDKVTGGGESYKLYSKSNSKVSIAILDSGVDLQNTGLLKNLSNMSKNYV
PNKGYLGKEEGEEGIISDIQDRLGHGTAVVAQIVGDDNINGVNPHVNINV
YRIFGKSSASPDWIVKAWDAVDDGNDHNLSTGQYLMIDGEYEDGTNDFET

FLKYKKAIDYANQKGVIIVAALGNDSLNVSNQSDLLKLISSRIZKVRKPG
LVVDVPSYFSSTISVGGDRIGNLSDFSNKGDSDAIYAPAGSTLSLSELGL
NNFINAEKYKEDWIFSATLGGYTYLYGNSFAAPKVSGAJAMIIDKYKLKD
QPYNYMFVKKFWKKHYQZ (SEQ ID. NO. 4)
MKKTWKVFLTLVTALVAVVLVACGQGTASKDNKEAELKXVDFILDWTPNT
NHTGLYVAKEKGYFKEAGVDVDLKLPPEESSSDLVINGKAPFAVYFQDYM
AKKLEKGAGITAVAAIVEHNTSGILSRKSDNVSSPKDLVGKKYGTWNDPT
ELAMLKTLVESQGGDFEKVEKVPNNDSNSITPIANGVFDTAWIYYGWDGI
LAKSQGVDANFMYLKDYVKEFDYYSPVIIANNDYLKDNKEEARKVIQAIK
KGYQYAMEHPEEAADILIKNAPELKEKRDFVIESQKYLSKEYASDKEKWG
QFDAARWNAPYKWDKENGILKEDLTDKGFTNEFVKZ (SEQ. ID. NO. 5)
MKRTWRNSFVTNLNTPFMIGNIEJPNRTVLAPMAOVTNSAFRTIAKELGA
GLVVMEMVSDKGIQYNNEKTLHMLHIDEGENPVSIQLFGSDEDSLARAAE
FIQENTKTDTVDINMGCPVNKIVKNEAGAMWLKDPDKIYSIINIVQSVLD
IPLTVKMRTGWADPSLAVENALAAEAAGVSALAMHGRTREQMYTGHADLE
TLYKVAQALTICIPPFIANGDIRTVQEAKQRIEEVGADAVMIGRAAMGNPY
LFNQINHYFETGEILPDLTFEDKMKIAYEHLKRLINLKGENVAVRERGLA
PHYLRGTSGTSGAAKLRGAISQASTLAEIETLLQLEKAZ (SEQ. ID. NO. 6)
MIKNPKLLTKSFLRSFAILGGVGLVIHIAIYLTFPPFYYIQLEGEKFNESA
RVFTEYLKTKTSDEIPSLLQSYSKSLTISAHLKRDIVDKRLPLVHDLDIK
DGKLSNYIVMLDMSVSTADGKQVTVQFVHGVDVYKEAKNILLLYLPYTFL
VTIAPSFVFSYFYTKRLLNPLFYISEVTSKMQDLDDNIRFDERJCDEVGE
VGKQINGMYEELLKVIYELESRNEQIVKLQNQKVSFVRGASHELKTPLAS
LRMLENMQHNIGDYKDHPKYIAKSINKIDQMSHLLEEVLESSKFQEWTEC
RETTVKPVLVDILSRYQELAHSIGVTIENQLTDATRVVMSLRALDKVLTN
LISNAIKYSDKNGRVHSEQDGYLSIKNTCAPLSDQELEHLFDFYHSQIVT
DKDESSGLGLY1VNNILESYQMDYSFLPYEHGMEFKISLZ (SEQ. ID. NO. 7)
MYLGDLMEKAECGQFSILLQESQTTVKAVMEETGFSKATLTKYVTLLNDK
ALDSGLELAIHSEDENLRLSIGAATKGRDIRSLFLESAVKYQILVYLLYH
QQFLAHQLAQELVISEATLGRHLAGLNQILSEFDLSIQNGRWRGPEHQIH
YFYFCLFKVWSSQEWEGHMQKPERKQEIANLEEICGASLSAGQKLDLVLW
AHISQQRLRVNACQFQVIEEKMRCYPDNIEYLRLLRKVPSFFAGQHIPLG
VEDGEMMIFFSFLLSHRILPLHTMEYILGFGGQLADLLTQLIQEMKKEEL
LGDYTEDHVTYELSQLCAQVYLYKGYILQDRYKYQLENRHPYLLMEHDFK
ETAEEIFHALPAFQQGTDLDKKILWEWLQLIEYMAEGGQHMRIGLDLTSG
FLVFSRMAAILKRYLEYNRFITTEAYDPSRHYDLLVTNNPIHKKEQTPVY
YLKNDLDMEDLVAIRQLLFTZ

TABLE 2-continued (SEQ. ID. NO. 8)
MEFSKKTRELSIKKMQERTLDLLHGGGITGAGVALQAAASGLETGLIEMQ
DFAEGTSSRSTKLVHGGLRYLKQFDVEVVSDTVSERAVVQQIAPHIPKSD
PMLLPVYDEDGATFSLFRLKVAMDLYDLLAGVSNTPAANKVLSKDQVLER
QPNLKKEGLVGGGVYLDFRNNDARLVIENIKRANQDGALANHKAEGFLFD
ESGKITGVVARDLLTDQVFEIKARLVIINTTGPWSDKVRNLSNKGTQPSQ
MRKGVHLVVDSSKIKVSQPVYFDTGLGDGRMVFVLPRENKTYEGTTDTDY
TGDLEHPKVTQEDVDYLLGIVNNRFPESNITIDDIESSWAGLRPLLAGNS
ASDYNGGNNGTISDESFDNLIATVESYLSKEKTREDVESAVSKLESSTSE
KHLDPSAVSRGSSLDRDDNGLLTLAGGKITDYRKMAEGAMERVVDIICAE
FDRSFKLINSKTYPVSGGELNPANVDSEIEAFAQLGVSRGLDSKEAHYLA
NLYGSNAPKVFALAHSLEQAPLSLADTLSHYAMRNELLTLSPVDFLLRRT
NHMLFMRDSLDSIVEPILDEMGRFYDWTEEEKATYRADVEAALANNDLAE
LKNZ (SEQ. ID. NO. 9)
MMNELFGEFLGTLIILLGNGVVAGVVLPKTKSNSSGWIVITMGWGIAVAV
AVFVSGKLSPAYLNPAVTIGVALKGGLPWASVLPYILAQFAGAMLGQILV
WLQFKPHYEAEENAGNILATFSTGPAIKDTVSNLISEILGTFVLVLTIPA
LGLYDFQAGIGTFAVGTLIVGIGLSLGGTTGYALNPARDLGPRIMHSILP
IPNKGDGDWSYAWIPVVGPVIGAALAVLVFSLFZ (SEQ. ID. NO. 10)
MTKKKERISVIHREKILWLKWYFMRDKEQPKYSVLERKMFDAAKNQDMLA
YQKYATIKQTSEADIRVQTSEADIILEAVKEVYVYNHMNVIGACQRILFI
SQSPAYDKLNKWPNIYSDLYFSVVPLPKMGVYHEMVGIZ (SEQ. ID. NO. 11)
MKNSNEAEMKLLYTDIRTSLTEILTREAEELVAAGKRVFYIAPNSLSFEK
ERAVLEYLSQQASFSITVTRFAQMARYLVLNDLPAKTFITLDDIGLGLAF
YKCLAELDPKDLRVYGAIKQDPQLIQQLIELYHEMTKSQMSFLDLENLTD
EDKRADLLLIFEKVTAYLNQGQLAQESQLSHLIEAIENDKVSSDFNQIAL
VIDGFTRFSAEEERVVDLLHGKGVEWIGAYASKKAYTSPFSEGNLYQAVK
ELHHLASKYQTPAQDCSQTHEKMDSFDKASRLLESSYDFSELALDVDEKD
RENLQIWSCLTQKEELELVARSIRQKLHENSDLSYKHFRJLLGDVASYQL
SLKTIFDQYQIPFYLGRSEAMAHHPLTQFVESILALKRYRPRQEDLINLL
RTDLYTDLSQSDIDAFEQYIRYLGINGLPAFQQTFTKSHHGKFNLERLNV
LRLRILAPLETLFASRKQKAEKLLQKWSVFLKEGAVTKQLQDLTITLEAV
EQERQAEVWKAFCNVLEQFATVFAGSQVSLEDFLALLHSGMSLSQYRTIP
ATVDTVLVQSYDLIAPLTADFVYAIGLTQDNLPKISQNTSLLTDEERQNL
NQATEEGVQLLIASSENLKKNRYTMLSLVNSARKQLFLSAPSLFNESESK
ESAYLQELIHFGFRRREKRMNHKGLSKEDMGSYHSLLSSLVAYHQQGEMS
DTEQDLTFVKVLSRVIGKKLDQQGLENPAIPTSPSSKTLAKDTLQALYPA
KQEFYLSTSGLTEFYRNEYSYFLRYVLGLQEELRLHPDARSHGNFLHRFE
ALQLPNEDSFDQRLEQAIQETSQERBFSAIYQESLEAQITKEVLLDVART
TGHILRHNPAIETIKEEANFGGKDQAFIQLDNGRSVFVRGKVDRIDRLKA
NGAIGVVDYKSSLTQFQFPHFFNGLNSQLPTYLAALKREGEQNFFGAMYL
EMAEPVQSLMAVKSLAGAVVEASKSMKYQGLFLEKESSYLGEFYNKNKAN
QLTDEEFQLLLDYNAYLYKKAAEKILAGRFAINPYTENGRSIAPYVQQHQ
AITGFEANYHLGQARFLEKLDLADGKRLVGEKLKQAWLEKIREELNRZ (SEQ. ID. NO. 12)
MKLIPFLSEEEIQKLQEAEANSSKEQKKTAEQIEAIYTSAQNILVSASAG
SGKTFVMAERLDQLARGVEISQLFISTFTVKAATELKERLEKJCISKKIQ
ETDDVDLKQHLGRQLADLPNAAIGTMDSFTQKFLGKHGYLLLDIAPNFRIL
QNQSEQULENEVFHEVFEAHYQGKQKETFSHLLKNFAGRGKDERGLRQQV
YKIYDFLQSTSNPQKWLSESFLKGFEKADFTSEKEKLTEQIKQALWDLES
FFRYHLDNDAKEIAKAAYLENVQLILDEEGSLNQESDSQAYQAVLARVVA
ISKEKNGRALTNASRKADLKPLADAYNEERKTQFAKLGQISDQIAILDYQ
ERYHGDTWKLAKTFQSFMSDFVEAYRQRKRQENAPEFADISHYTLEILEN
FPQVRESYQERFHEVMVDEYQDTNHIQERMLELLSNGHNRFMVGDIKQSI
YRFRQADPQCFNEKFQRYAQNPQEGRLIILKENFRSSSEVLSATNDVFER
LMDQEVGEINYDNKHQLVFANTKLTPNPDNKAAFLLYDKDDTGEEEESQR
ETKLTGEMRLVIKEILKLHQEKGVAFKRIALLTSSRSRNOQILLALSEYG
EPVKTDGEQNNYLQSLEVQVMLDTLRVIHNPLQDYALVALMKSPMFGFDE
DELARLSLQKAEDGVHENLYEKLVNAQKMASSQKGLIHTALAEKLKQFMD
WASWRLYAKTHSLYDLIWKIYNDRFYYDYVGALPNGPARQANLYALALRA
DQFEKSNFEKGLSRFIRMIDQVLEAQHDLASVAVAPPKDAVELMTIHKSK
GLEFPYVFILNMDQDINKQDSMSEVILSRQNGLGVKYIAKMETGAVEDHY
PKTIKLSIPSLTYRQNEEELQLASYSEQMRLLYVAMTRAEKKLYLVGKGS
REKLESKEYPAAKNGKLNSNTRLQARNFQDWLWAISKVFTKDKLNFSYRF
IGEDQLTREAIGELETKSPLQDSSQADNRQSDTIKEALEMLKEVEVYNTL
HRAAIELPSVQTPSQUCKPYEPVMDMEGVEIAGQGQSVGKKISFDLPDFS
TKEKVTGAEIGSATHELMQRIDLSQQLTLASLTETLKQVQTSQAVRDKIN
LDKILAFFDTVLGQEILANTDHLYREQPFSMLKRDQKSQEDFVVRGILDG
YLLYENKIVLFDYKTDRYDEPSQLVDRYRGQLALYEEALSRAYSIENIEK
YLILLGKDEVQVVKVZ (SEQ. ID. NO. 13)
MELARHAESLGVDALATIPPIYFRLPEYSVAKYWNDISSAAPNTDYVCYN
IPQLAGVALTPSLYTEMLKNPRVIGVKNSSMPVQDIQTFVSLGGEDMIVF
NGPDEQFLGGRLMGARAGIGGTYGAMPELFLKLNQLIADKDLETARELQY
AINAHGKLTSAHGNMYGVIKEVLKINBGLNIGSVRSPLTPVTEEDRPVVE
AAAALIRETKERFLZ (SEQ. ID. NO. 14)
MYKTKCLREKLVLFLKIFFPIUYQFANYSASFVDTAMTGQYNTMDLAGVS
MATSTWNPPFTPLTGIVSALVPIIGHHLGRGKKEEVASDFYQFIYLALGL
SVVLLGMVLPLAPIILNHIGLEAAVAAVARYLWFLSIGIIPLLLFSVIR TABLE 2-continued SLLDSLGLTKLSMYLMLLLLPLNSGFNYLLIYGAFGVPELGGAGAGLTS
LAYWVLLGISVLVLFKQEKLKALHLEKRIPLNMDKIKEGVRLGLPIGGTV
FAEVAIFSVVGLIMAKFSPLIIASHQSAMNFSSLMYAFPMSISSAMAIVV
SYEVGAKRFDDAKTYIGLGRWTALIFAAFTLTFLYIFRGNVASLYGNDPK
FIDLTVRFLTYSLFFQLADTFAAPLQGILRGYKDTVIPFYLGLLGYWGVA
LPVYAIZ (SEQ. ID. NO. 15)
MSTLAKIEALLFVAGEDGLRVRQLAELLSLPPTGIQQSLGKLAQKYEKDP
DSSLALIETSGAYRLVTKPQFAEWKEYSKAPINQSLSRALETLIIAYKQP
ITRIEIDAIRGVNSSGALAKLQAFDLIKEDGKKEVLGRPNLYWITDYFLD
YMGIINHLEELPVIDELEIQAQESQLFGERIEEDENQZ (SEQ. ID. NO. 16)
MDTMISRFFRHLPEALKSLKRNGWMTVAAVSSVMITLTLVAIFASVIFNT
AKLATDIENNVRVVVYIRKDVEDNSQTIEKEGQTVTNNDYHKVYDSLKNM
STVKSVTFSSKEEQYEKLTEIMGDNWKIFEGDANPLYDAYIVEANTPNDV
KTIAEDAKKIEGVSEVQDGGANTERLFKLASFIRVWGLGIAALLIFIAVF
LISNTIRITIISRSREIQIMRLVGAKNSYIRGPFLLEGAFIGLLGAIAPS
VLVFIVYQIVYQSVNKSLVGQNLSMISPDLFSPLMIALLFVIGVFIGSLG
SQGISMRRFLKIZ (SEQ. ID. NO. 17)
MKKVRFIFLALLFFLASPEGAMASDGTWQGGQYLKEDGSQAANEWVFDTH
YQSWFYIKADANYAENEWLKQGDDYFYLKSGGYMAKSEWVEDKGAFYYLD
QDGKMKRNAWVGTSYVGATGAKVLEDWVYDSQYOAWFYIKADGQHAEKEW
LQIKGKDYYFKSGGYLLTSQWINQAYVNASGAKVQQGWLFDKQYQSWFYI
KBNGNYADKEWIFENGFHYYYLKSGGYMAANEWEWDKESWFYLKEDGKMA
EKEWVYDSHSQAWYYFKSGGYMTANEWIWDKESWFYLKSDGKIAEKEWVY
DSHSQAWYYFKSGGYMTANEWIWDKESWFYLKSDGKIAEKEWVYDSHSQA
WYYFKSGGYMAKNETVDGYQLGSDGKWLGGKTTNENAAYYQVVPVTANVY
DSDGEKLSYISQGSVVWLDKDRKSDDKRLAITISGLSGYMKTEDLQALDA
SKDFIPYYESDGHRFYHYVAQNASIPVASHLSDMEVGKKYYSADGLHFDG
FKLENPFLFICDLTEATNYSAEELDKVFSLLNINNSLLENKGATFKEAEE
HYHINALYLLAHSALESNWGRSKIAKDKNNFFGITAYDITPYLSAKTFDD
VDKGILGATKWIKENYIDRGRTFLGNKASGMNVEYASDPYWGEKIASVMM
KTNEKLGGKDZ (SEQ. ID. NO. 18)
MKKVLQKYWAWAFVVIPLLLQAIPFYVPMFQGAFYSFTNWTGLTYNYKFV
GLNNFKLLFMDPKFMNAIGFTAIIAIAMVVEIALCIARVLNSKIKGQTFF
RAWFFFPAVLSGLTVALIFKQVFNYGLPAIGNALHIEFFQTSLLGTKWGA
IFAAVFVLLWQOVAMPEIIFLAGLQSIPTEITEAARIDGATSKQVFWNIE
LPYLLPSVSMVFELALKGGLTAFDQVFAMTGGGPNNATTSLGLLVYNYAF
KNNQFGYANAIAVILFFLIVVISHQLRVSKKFEIZ (SEQ. ID. NO. 19)
MMKQDERKALIGKYILLILGSVLILVPLLATLFSSFKPTKDIVDNFFGFF
TNFTWDNFSRLLADGIGGYYWNSVVITVLSLLAVMIFIPMAAYSIARNMS
KRKAFTIMYTLLILGWVPFQVIMPITVMMSKLGLANTPGLILLYLTYAIP
QTLFLYVGYIKISIPESLDEAAEIDGANQFTTYFRIIFPMMKPMHATTMI
INALWFWNDFMLPLLVLNRDSKMWTLPLFQYNYAGQYFNDYGPSFASYVV
GIISITIVYLFFQRHIHSGMSNGAVKZ (SEQ. ID. NO. 20)
MKSILQKMGEHPMLLLFLSYSTVISILAQNWMGLVASVGMFLFTIFFLHY
QSILSHKFFRLILQFVLFGSVLSAAFASLEHPQIVKKPNYAPLSPNMQVW
HQNRAEVTFFNPNYYGIICCFCIMIAPYLFTLTKLNWLKVFCVIAGPVNL
FGLNFTQNRTAFPAIIAGAIIYLVFTTKNWKAFWLSIGVFAIGLSFLFSS
DLGVRMGTLDSSMEERISIWDAGMALFKQNPFWGEGPLTYMNSYPRLHAP
YHEHAHSLYIDTILSYGIVGTILLVLSSVAPVRLMMDMSQESGKRPIIGL
YLSFLTVVAVHGIFDLALFWIQSGFTFLLVMCSIPLEHRMLVSDMTDZ (SEQ. ID. NO. 21)
MSKMDVQKIIAPMMKFVNMRGIIALIKDGMLAILPLTVVGSLFLIMGQLP
FEGLNKSIASVFGANWTEPPMQVYSGTFAIMGLISCFSIAYSYAKNSGVE
ALPAGVLSVSAFFILLRSSYIPKQGEAIGDAISKVWFGGQGHGAHIGLVV
GSIYTFFIKRKIVIKMPEQVPQAIAKQFEAMIPAVIFLSSMIVYILAKSL
TNGGTFIEMIYSAIQVPLQGLTGSLYGAIGIAFFISFLWWFGVHGQSVVN
GVTALLLSNLDANKAMLASANLSLENGAHIVTQQFLDSFLILSGSGITFG
LVVAMLFAAKSKQYQALGKVAAFPAIFNVNEPVVFGFPEVMNPVMFVPFI
LVPVLAAVIVYGAIATGFMQPFSGVTLPWSTPAILSGFLVGGWQGVETQL
VTLAMSTLVYFPFFKVQDRLAYQNEIKQSZ (SEQ. ID. NO. 22)
MKKKDLVDQLVSEIETGKVRTLGIYGHGASGKSTFAQELYQALDSTTVNL
LETDPYITSGRHLVVPKDAPNQKVTASLPVAHELESLQRDILACRRVWMS
Z (SEQ. ID. NO. 23)
MKKRYLVLTALLALSLAACSQEKTKNEDGETKTEQTAKADGTVGSKSQGA
AQKKAEVVNKGDYYSIQGKYDEIIVANKHYPLSKDYNPGENPTAKAELVK
LIKAMQEAGPPISDHYSGFRSYETQTKLYQDYVNQDGKAAADRYSARPGY
SEHQTGLAFDVIGTDGDLVTEEKAAQWLLDHAADYGFVVRYLKGKEKETG
YMAEEWHLRYVGKEAIKEIAASGLSLEEYYGFEGGDYVDZ (SEQ. ID. NO. 24)
MREPDFLNHFLKKGYFKKHAKAVLALSGGLDSMFLFKVLSTYQKELEEEL
ILAHVNHKQRIESDWEEKELRKLAAEAELPIYISNFSGEFSEARARNFRY
DFFQEVMKKTGATALVTAHHADDQVETLFMRLIRGTRLRYLSGIKEKQVV
GEIEIIRPFLHFQKKDFPSLFHFEDTSNQENHYFRNRLRNSYLPELEKEN
PRFRDAILGIGNELLDYDLAIAELSNNINVEDLQQLPSYSESTQRVLLQT
YLNRFPDLNLTKAQFAEVQQILKSKSQYRHPIKNGYELEKEYQQFQICKI
SPQADEKBDELVLHYQNQVAYQGYLFSFGLPLEGELIQQIPVSRETSIHI TABLE 2-continued

RHRKTGDVLIKNGHRKKLRRLFIDLKIPMEKRNSALIIEQFGEIVSILGI
ATNNLSKKTKNDIMNTVLYIEKIDRZ (SEQ. ID. NO. 25)
MRKPLIILLLPSFLTISKVVSTEKEVVYTSKEIYYLSQSDFGIYFRBKLS
SPMVYGEVPVYANEDLVVESGKLTPKTSFQITEWRLNKQGIPVPKLSNHQ
FIAADKRFLYDQSEVTPTIICKVWLESDFKLYNSPYDLKEVKSSLSAYSQ
VSIDKTMFVEGREFLHIDQAGWVAKESTSEEDNRMSKVQEMLSEKYQKDS
FSIYVKQLYGKSAGINQDEKMYAASVLKISYLYYTQEKINEGLYQLDTTV
KYVSAVNDFPGSYKPEGSGSLPKKEDNKEYSLKDUTKVSKESDNVAHNLL
GYYISNQSDATFKSKMSAIMGDDWDPKEKLISSKMAGKEMEAIYNQNGFV
LESLTKTDFDSQRIAKGVSVKVAHKIGDADEFKHDTGVVYADSPFILSII
ETKNSDYDTISKIAKDVYEVLKZ (SEQ. ID. NO. 26)
MKKQNNGLIKNPFLWLLFIFFLVTGFQYFYSGNNSGGSQQINYTELVQEI
TDGNVKELTYQPNGSVIEWSGVYKNPKSTKEETGIQFFTPSVTKVEKTTS
TILPADITVSELQKLATDHKAEVTVKHBSSSGIWINLLVSWPFGILFFFL
FSNIMGNMGGGNGRNPMSFGRSKAXANKBDIKVRFSDVAGAEEEKQELVE
VVEFLKDPKRFKLGARLPAGVLLEGPPGTGKLLLAKAVAGEAGVPFFSDS
GSDLVEMFVGVGASRVRSLFEDAKKAAPAIIFIDEIDAVGRQRGVGLGGG
NFRTRQTLNQLLIEMDGFEGNEGIIVIAATNSDVLDPALLRPGRFDRKVL
VGRPDVKGEAILKVHAKNKPLAEDVDLKLVAQQTPGFGFVGADLENVLNE
AALVAARRNSIIDASDIDEAEDRVIAGPSKKKDKTVSQKERELVAYHEAG
HIVGLVLSNARVVHKVTIVPRGRAGGYMIALPKEDQMLEDMKEQLAGLMG
GRVAEEIIFNVQITGASNDFEQATQMARAMVTEYGMSEKLGPVQYEGNHA
MLGAQSPQSEQTAYEIDEEVRSLLNEARNKAAEHQSNRETHKLLEALLKY
ETLDSTQIKALYETGKMPEAVEEESHALSYDEVKSKMNDEKZ (SEQ. ID. NO. 27)
MKRSSLLVRMVISIFLVFLILLALVGTFYYQSSSSAIEATIEGNSQSQTS
HFIQSYIKKLETTSGLTQQTDVLAYAENPSQDKVEGIRDLFLTILKSDK
DLKTVVLVTKSGQVISTDDSVQMKTSSDMMAEDWYQKAIHQGAMPVLTPA
RKSDSQWVISVTQELVDAKGANLGVLRLDSYETLEAYLNQLQLGQQGFAF
IINENHEFVYHPQHTVYSSSSKMEAMKPYDTGQGYTPGHKSYVSQEKIAG
TDWTVLGVSSLEKLDQVRSQLLWTLLGASVTSLLVCLCLVWFSLKRWIAP
LKDLRETMLEIASGAQNLRAKEVGAYELREVTRQFNAMLDQIDQLMVAIR
SQEETTRQYQLQALSSQINPHFLYNTLDTIIWMAEFHDSQRVVQVTKSLA
TYFRLALNQGKDLICLSDEINHVRQYLFIQKQRYGDKLEYEINENVAFDN
LVLPKLVLQPLVENALYHGIKEKEGQGHIKLSVQKQDSGLVIREDDGVGF
QDAGDSSQSQLKRGGVGLQNVDQRLKLHPGANYHMKIDSRPQKGTKVEIY
INRIETSZ (SEQ. ID. NO. 28)
MKRSSLLVRMVISIFLVFLILLALVGTIYYQSSSSAIEATIEGNSQTTS
QTSHFIQSYIKKLETTSGLTQQTDVLAYAENPSQDKVEGIRDLFLTILK

SDKDLKTVVLVTKSGQVISTDDSVQMKTSSDMMAEDWYQKAIHQGAMPVL
TPARKSDSQWVISVTQELVDAKGANLGVLRLDISYETLEAYLNQLQLGQQ
GFAFIINENHEFVYHPQHTVYSSSSKMEAMKPYIDTGQGYTPGHKSYVSQ
EKIAGTDWTVLGVSSLEKLDQVRSQLLWTLLGASVTSLLVCLCLVWFSLK
RWIAPLKDLRETMLEIASGAQNLRKEVGAYELREVTRQFNAMLDQIDQLM
VA1RSQEET1RQYQLQALSSQINPHFLYNTLDTUWMAEFHDSQRVVQVTK
SLATYFRLALNQGKDLICLSDENHVRQYLPIQKQRYGDKLEYEINENVAF
DNLVLPKLVLQPLVENALYHGIKEKEGQGHIKLSVQKQDSGLVIRIEDDG
VGFQDAGDSSQSQLKRGGVGLQNVDQRLKLHFGANYHMKIDSRPQKGTKV
EIYINRIETSZ (SEQ. ID. NO. 29)
MFFKLLREALKVKQVRSKILETIFWLVFRIGTSITVPGVNANSLNALSGL
SFLNMLSLVSGNALKNFSIFALGVSPYITASIVVQLLQMDILPKEVEWGK
QGEVGRRKLNQATRYIALVLAFVQSIGITAGFNTLAGAQLIKTALTPQVF
LTIGIILTAGSMIVTWLGEQETDKGYGNGVSMHFAGWSSIPEMIQGIYVD
YFVNVPSSRITSSIIFVHLIITVLLIIYFTTYVQQAEYKIPIQYTKVAQG
APSSSYLPLKVNPAGVIPVIFASSITAAPAAILQFLSATGHDWAWVRVAQ
EMLATTSPTGIAMYALLIILFTFFYTFVQINPEKAAERYKRVVPISMEFV
LVKVQKNICLNFFVVLQLLVPSSLVZ (SEQ. ID. NO. 30)
MDIRQVTETIAMIIEEQNFDIRTITMGISLLDCIDPDENRAAEKIYQKIT
TKAANLVAVGDEIAAELGIPIVNKRVSVTPISLIGAATDATDYVVLAKAL
DKAAKE1GVDFIGGFSALVQKGYQICGDEILINSIPRALAETDKVCSSVN
IGSTKSGINMTAVADMGRIIKETANLSDMGVAKLVVFANAVEDNPFMAGA
FHGVGEADVIINVGVSGPGVVKRALEKVRGQSPDVVAETVKKTAFKITRI
GQLVGQMASERLGVEFGIVDLSLAPTPAVGDSVARVLEEMGLETVGTHGT
TAALALLNDQVKKGGVMACNQVGGLSGAFIPVSEDEGMEAAVQNGSLNLE
KLEAMTAICSVGLDMIAIPEDTPAETIAAMIADEAAIGVINMKTTAVRII
PKGKEGDMIEIGGLLGTAPVMKVNGASSVDFISRGGQIPAPIHSFKNZ (SEQ. ID. NO. 31)
MTQIIDGKALAAKLQGQLAEKTAKLKEETGLVPGLVVILVGDNPASQVYV
RNKERSALAAGFRSEVVRVPETITQEELLDLIAKYNQDPAWHGILVQLPL
PKHIDEEAVLLAIDPEKDVDGFHPLNMGRLWSGHPVMIPSTPAGIMEMFH
EYGIDLEGKNAVVIGRSNIVGKPMAQLLLAKNATVTLTHSRTHNLSKVAA
XADILVVAIGRAKFVTADFVKPGAVVIDVGMNRDENGKLCGDVDYEAVAP
LASHITPVPGGVGPMTITMLMEQTYQAALRTLDRKZ (SEQ. ID. NO. 32)
MSKFNRIHVVLDSVGIGAAPDANNFVNAGVPDGASDTLGHISKTVGLNVP
NMAKIGLGNIPRETPLKTVAAESNPTGYATKLEEVSLGKDTTGHWEIMGL
NITEPFDTFWNGFPEE1LTKIEEFSGRKVIREANKPYSGTAVIYDFGPRQ
MSTGELHYTSADPVLQIAAHEDIIPLDELYRICEYARSITLERPALLGRI
IARPYVGEPGNFTRTANRRDLAVSPFFPTVLDKLNEAGIDTYAVGKINDI

TABLE 2-continued

FNGAGINHDMGHNKSNSHGIDTLLKTMGLAEFEKGFSFTNLVDFDALYGH
RRNAHGYRDCLHEPDERLPEHAAMRENDLLLITADHGNDPTYAGTDHTRE
YIPLLAYSPAFKGNGLIPVGHFADISATVADNFGVETAMIGESFLDKLVZ (SEQ. 1ID. NO. 33)
MFISISAGLVTFLLTLVEPAFIQFYRKAQITGQQMNEDVKQHQAKAGTPT
MGGLVPLITSVLVAFFFALFSSQFSNNVGMILFILVLYGLVGFLDDFLKV
FRKINEGLNPQKLALQLLGGVIFYLFYERGGDILSVPGYPVHLGFFYIP
FALFWLVGFSNAVNLTDGVDGLASISVVISLSAYGVIAYVQGQMDLLLVI
LAMIGGLLGFFIPNHKPAKVFMGDVGSLALGGMLAAISMALHQEWTLLUG
IVYVFEFTSVMMQVSYFKLTGGKPIFRMTPVHHHFELGGLSGKGNPWSEW
KVDFFFWGVGLLASLLTLAILYLMZ (SEQ. ID. NO. 34)
LFKKNKDELNIALPAMGENFLQMLMGMVDSYLVAHLGLIAISGVSVAGNI
MYQAIRALGAAISSVLSKSIGQKDQSKLAYNVTEALKITLLLSILLGFLS
IFAGKSMIGLLGTERDVAESGGLYLSLVGGSIVLLGLMTSLGALIRATHN
PRLPLYVSFLSNALNILFSSLAIFVLDMGIAGVAWGTIVSRLVGLVILWS
QLKLPYGKPTFGLDKELLTLALPAAGERLMMRAGDVVHALVVSFGTEAVA
GNAIGEVLTQFNYMPAFGVATATVMLLARAVGEDDWKRVASLSKQTLFLS
LFMLPLSFSIYVLGVPLTHLYTDSLAVEASVLVTLFSLLGTPMTTGTVIY
TAVWQGLGNARLPFYATSIGMWCIRIGTGYLMGIVLGWGLPGIWAGSLLD
NGFRWLFLRYRYQRYMSLKGZ (SEQ. ID. NO. 35)
MQTQEKRSQAAVLGLQHLAMYSGSILVPIMIATALGYSAEQLTYLISTDI
FMCGVATFLQLQLNKYFGIGLPVVLGVAFQSVAPLIMIGQSHGSGAMFGA
LIASGIYVVLVSGIIFSKVANLFPSIVTGSVITTIGLTLIPVAIGNMGNN
VPEPTGQSLLAAITVLIILINIFTKGFIKSISILIGLVVGTAIAATMGLV
DFSPVAVAPLVHPTPLYFG,PTFEISSIVMMCIIATVSMVESTGVYLALS
DITKDPIDSTRLRNGYREGLAVLLGGIFNTFPYTGFSQNVGLVKLSGIKK
RLPIYYAAGFLVLLGLLPKFGALAQIIPSSVLGGAMLVMFGFVSIQGMQI
LARVDFANNEHNFLIAAVSIAGVGLNNSNLFVSMPTAFQMFFSNGIVVAS
LLAIVLNAVLNHKKKZ (SEQ. ID. NO. 36)
MKDRKEYLQDKGKVTVNDLAQALGKDSSKDFRELIKTLLMERKHQIRFEE
DGSLTLEIKKKHEITLKGLFHAHKNGFGFVSLEGEEDDLFVGKNDVNYAI
DGDTVEVVHCKVADRNKGTAAEAKIIDILEHSLTTVVGQIVLDQEKPKYA
GYISKNQK1SQPIYVKKPALKLEGTEVLKVPEDKYPSKKHDFFVASVLDV
VGHSTDVGIDVLEVLESMDIVSEFPEAVVKEAESVPDAPSQKDMEGRLDL
RDEDGADAKDLDOAVHIKALKNGNLEPGVHADVSYYEGSALDKEALNRTS
VYVTDRVVPMLPERSNGICSLNPQVDRLTQSAIMEIDKHGRVVNTQTVIK
TSFRMTYSDVNDILAGDEEKEYHKIVSSIELMAKLHETLENMRVKRGALN
FDTNEAKILVDKQGKPVDIVLRQRGIAERMIESFMLANETVAEHFSKLD
LPRYIHEBPKAEKVQKFIDYASSFGLRIYGTASELSQEALQDIMRAVEGB
PYADVLSMMLRSMQQARYSEHNHGHYGLAADYYTHFTSPIRRYPDLLVHR
MIRDYGRSKEIAEHFEQVIPEIATQSSNRERRAIEAEREVEAMKKAEYME
EYVGEEYDAVVSSIVKFGLFVELPNTVEGLINTNLPEFYHFNERDLTLRG
EKSGITFRVGQQIRIRVERADKMTGEIDFSFVPSEDFDVIEKGLKQSSRS
GRGRDSNRRSDKKEDKRKSGRSNDKRKHSQKDKKKKGKKPFYKEVAKKGA
KHGKGRGKGRRTKZ (SEQ. ID. NO. 37)
MGTTGFTIIDLIILIVYLLAVLVAGIYFSKKEMKGKEFFKGDGSVPWYVT
SVSIFATMLSPISFLGLAGSSYAGSWLWFAQLGMVVAIPLTHIILPIFAR
DIDTAYDYLDKRFNSKALRISALLFIIYQLGRMSUMYLPSAGLSVLTGID
INILIILMGVVAIVYSYTGGLKSVLWTDFIQGVLLJSGVVLALFVLIANI
KGGFGAVAETLANGKFLAANEKLFDPNLLSNSIFLIVMGSGPTILSSYAS
SQDLVQRFTTTQNIKKLNKMLFTNGVLSLATAVFYLIGTGLYVFYQVQNA
DSAASNIPQDQIFMYFIAYQLPVGITGLILAAIYAASQSTISTGLNSVAT
SWTLDIQDVISKNMSDNRRTKIAQFVSLAVGLPSIGVSIVMAHSDIKSAY
EWFNSFMGLVLGLLGGVRLGVSKKANKQGAYAALPIVMVFICYFLPPTAV
SYWAYSLISISVSVVSGYIVSVLTGNKVSAPKYTTIEDITEIKADSSWEV
RMZ (SEQ. ID. NO. 38)
MKFSKKYAGSAVIVSLSLCAYALNQHRSQENKDNNRVSYVDGSQSSQKSE
NLTPDQVSQKEGIQAEQAEQIVIKITDQGYVTSHGDHYHYYNGKVPYDAL
FSEELLMKDPNYQLKDADIVNEVKGGYUKVDGKYYVYLKDAAHADNVRTK
DEINRQKQEHVKDNEKVNSNVAVARSQGRYTNDGYVPNPADIIEDTGNAY
IVPHGGHYHYIPKSDLSASELAAAKAHLGKNMQPSQLSYSSTASDNNTQS
VAKGSTSKPANKSENLQSLLKELYDSPSAQRYSESDGLVIDPAKIISRTP
NGVAIPHGDHYHPIPYSKLSALEEKTARVPISGTGSTVSTNAKPNEVVSS
LGSLSNPSSLTTSKELSSASDGYIFNPKDIVEETATAYWRHGDHFHYIPK
SNQIGQPTLPNNSLATPSPSLPINPGTSHEKHEEDGYGFDANRIIAEDES
GFVMSHGDHNHYFFKKDLTEEQIKVRKNIZ (SEQ. ID. NO. 39)
MKKRAIVAVIVLLLIGLDQLVKSYIVQQIPLGEVRSWIPNFVSLTYLQNR
GAAPSILQDQQLLFAVITLVVVIGAIWYLHKHMEDSFWMVLGLTLUAGGL
GNFIDRVSQGPVVDMFHLDFINFAIFNVADSYLTVGVIILLIAMLKEEIN
GNZ (SEQ. ID. NO. 40)
MNTNLASFIVGLHDENDRFYFVQKDGQTYALAKEEGQHTVGDTVKGFAYT
DMKQKLRLTTLEVTATQDQFGWGRVTEVRKDLGVFVDTGLPDKEIVVSLD
ILPELKELWPKXGDQLYIRLEVDKKDRIWGLLAYQEDFQRLARPAYNNMQ
NQNWPAIVYRKLSGTFVYLPENNNMLGFIHPSERYAEPRLGQVLDARVIG
FREVDRTNLSLKPRSFEMLENDAQMILTYLSSNGGFMTLNDKSSPDDIKA
TFGISKGQFKKALGGLMKAGKIKQDQFGTELIZ

TABLE 2-continued (SEQ. ID. NO. 41)
MKDVSLFLLKKVFKSRLNWIVLALFVSVLGVTFYLNSQTANSHSLESRLE
SR1AANERAINENEEKLSQMSDTSSEEYQFAXNNLDVQKNLLTRKTEILT
LLKEGRWKEAYYLQWQDEBKNYEFVSNDPTASPGLKMGVDRERKIYQALY
PLNIKAHTLEFPTHGIDQIVWILEVIIPSLFVVAIIFMLTQLFAERYQNH
LDTAHLYPVSKVTFAISSLGVGVGYVTVLFIGICGFSPLVGSLISGFGQL
DYPYNYSLVNQEVTIGKIQDVLFPGLLLAFLAFIVIVEVVYLIAYPFKQK
MPVLFLSLIGIVGLLFGIQTIQPLQRIAHLIPFTYLRSVELLSGRLPKQI
DNVDLNWSMGMVLLPCLIIFLLLGILFISRWGSSQKICEFFNRFZ (SEQ. ID. NO. 42)
MMKFILDIVSTPAILVALIAILGLVLQKKKLPDIIKGGIKTFVGFLVVSG
GAGIVQNSLNPFGTMPEHAPHLSOVVPNNEAIVAVAUITYGSATAMIMFA
GMVFNILIARFTRFKYIFLTGHHTLYMACMIAVILSVAGFTSLPLILLGG
LALGUMSISPAFVQKYMVQLTGNDKVALGHFSSLGYWLSGFTGSLIGDKS
KSTEDIICPPKSLAPLRDSTVSITLSMAVIYUVAIFAGSEYIEKEISSGT
SGLVYALQLAGQFAAGVFVLAGVRLILGEIVPAPKGISERLVPNSKPALD
CPIVYTYAPNAVLIGFTSSFVGGLVSMVIMIASGTVVILPGVVPHFFCGA
TAGVTGNASGGVRGATIGAPLQGILISFLPVFLMPVLGGLGFQGSTFSDA
DFGLSGIILGMLNQFGSQAGIVIGLVLILAVMFGVSPIKKPSATEEZ (SEQ. ID. NO. 43)
MIKTFLSALSVILFSIPIIITYSFPPSSNLNZWLSTQPILAQIYAFPLATA
TMAALLSFLFFFLSFYKKNKQIRFYSGILLLLSLILLLFGTDKTLSSASN
KTKTLKLVTWNVANQIEAQHIERIFSKFDADMAIFPELATNIRGEQENQR
IKLLFPHQVGLSMANYDIFTSPPTNSGIAPVTVIVKXSYGFYTEAKTFHTT
RFGTIVLHSRKQNIPDIIALHTAPPLPGLMEIWKQDLNIIHNQLASKYPK
AIIAGDFNATMRHGALAKISSHRDALNALPPFERGTWNSQSPKLFNATID
HILLPKNHYYVKDLDIVSFQNSDHRCIFTEITFZ (SEQ. ID. NO. 44)
MNPIQRSWAYVSRKRLRSFLILLVLLAGISACLTLMKSNKTVESNLYKSL
NTSPSIKKIENGQTFKLSDLASVSKIKGLENVSPELEVAKLKDKEAVTGE
QSVERDDLSAADNNLVSLTALEDSSKDVTFTSSAFNLKEGRLHLQKGDSK
KILHEELAKKNGSLHDKIGLDAGQSESGKGQTVEFEIIGWSGKKQEKFTG
LSSDFSENQVFTDYESSQTLLGNSEAQVSAARFYVENPKEMDGLMKQVEN
IALENQGYQVEKENKAFEQIKDSVATFQTPLTIFLYGMLIAGAGALILVL
SLWLRERVYEVGILLALGKGKSS1FLQFCLEVVLVSLGALLPAFVAGNAI
TTYLLQTLLASGDQASLQDTLAKASSLTSILSFAESYVFLVLLSCLSVAL
CFLFLFRKSPKEILSSISZ (SEQ. ID. NO. 45)
MLHNAFAYVTRKFFKSIVTFLIILLMASLSLVGLSIKGATAKASQETFKN
ITNSFSMQINRRVNQGTPRGAGNEKGEDIKKITENKAIESYVKIRINAIG
DLTGYDLIETPETKKNLTADRAKRFGSSLMITGVNDSSKEDKFVSGSYKL
VEGEHLTNDDKDKILLHKDLAAKHGWKVGDKVKLDSNIYDADNEKGAKET
VEVTIKGLFDGHNKSAVTYSQELYENTAITDIHTAAKLYGYTEDTAIYGD
ATFFVTADKNLDDVMKELNGISGINWKSYTLVKSSSNYPALEQSISGMYX
MANLLFWGSLSPSVLLLALLLSLWINARRKEVGILLSIGLKQASILGQFI
TESILIAIPALVSAYFLANYTARAIGNTVLANVTSGVAKQASKAAQASNL
GGGAEVDGFSKTLSSLDISIQTSDFIIIFVLALVLVVLVMALASSNLLRK
QPKELLLDGEZ (SEQ. ID. NO. 46)
MSQDKQMKAVSPLLQRVINISSIVGGVGSLIFCIWAYQAGILQSKETLSA
FIQQAGIWGPPLFIFLQILQTVVPIIPGALTSVAGVFIYGHIIGTIYNYI
GIVIGCAIIFYLVRLYGAAFVQSVVSKRTYDKYIDWLDKGNRFDRFFIFM
MIWPISPADFLCMLAALTKMSFKRYMTIIILTKPFTLVVYTYGLTYIIDF
EWQMLZ (SEQ. ID. NO. 47)
MRNMWVIKETYLRHVESWSFFFMVISPFLFLGISVGIGHLQGSSMAKNNK
VAVVTTVPSVAEGLKNVGVNFDYKDEASAKEAIKEEKLKGYLTTDQEDS
VLKAVYHGETSLENGIKFEVTGTLNELQNQLNRSTASLSQEQEKRLAQTI
QFTEKIDEAKENXKFIQTIAAGALGFFLYMILITYAGVTAQEVASEKGTK
IMEVVFSSIRASHYFYARMMALFLVILTHIGIYVVGGLAAVLLFKDLPFL
AQSGILDHLGDAISLNTLLFILISLFMYVVLAAFLGSMVSRPEDSGKALS
PLMILIMGGFFGVTALGAAGDNLLLKIGSYIPFISTFFMPFRTINDYAGG
AEAWISLALTVWAVVATGFIGRMYASLVLQTDDLGIWKTFKRALSYKZ (SEQ. ID. NO. 48)
MTETIKLMIKAHTSVRRFKEQEIPQVDLNEILTAAQMASSWKNFQSYSVI
VVRSQEKKDALYELVPQEAIRQSAVFLLFVGDLNRAEKGARLHTDTFQPQ
GVEGLLISSVDAALAGQNALLAAESLGYGGVHGLVRYKSEEVAELFNLPD
YYTYSVFGMALGVPNQHHDMKPRLPLENVVFEEEYQEQSTEAIQAYDRVQ
ADYAGARATTSWSQRLAEQFGQAEPSSTRKNLEQKKLLZMLKLIAIVGTN
SKRSTNRQLLQYMQKHFTDKAEIELVEIKAIPVFNKPADKQVPAEILEIA
AKIEEADGVHGTPEYDHSIPAVLMSALAWLSYGIYPLLNKPIMITGASYG
TLGSSRAQLQLRQILNAPEIKANVLPDEFLLSHSLQAFNPSGDLVDLDVI
KKLDAIFDDPRIFVKITEKLRNAQELLRKDAEDFDWENLZ (SEQ. ID. NO. 49)
MNTYQLNNGVEIPVLGFGTFICAKDGEEAYRAVLEALKAGYRHIDTAAIY
QNEESVGQAIKDSGVPREEMFVTTKLWNSQQTYSQTRQALEKSIEKLGLD
YLDLYLIHWPNPKPLRENDAWFTRNAEVWRAMEDLYQEGKIRAIGVSNFL
PHHLDALLETATIVPAVNQVRLAPGVYQDQVVAYCREKGILLEAWGPPGQ
GELFDSKQVQEIAANHGKSVAQLALAWSLAEGFLPLPKSVTTSRIQANLD
CFGIELSHEERETLKTIAVQSGAPRVDDVDFZ (SEQ. ID. NO. 50)
MRCKMLDPIAIQLGPLAIRWYALCIVTGLILAVYLTMKEAPRKKIIPDDL
DPILVAFPLAILGARLYYVIFRFDYYSQNLGEIFAIWNGGLAIYGGLITG
ALVLYIFADRKLINTWDFLDIAAPSVMLAQSLGRWGNFFNQEAYGATVDN TABLE 2-continued LDYLPGRRDQMYIEGSYRQPTFLYESLWNLLGFALILIFRRKWKSLRRGH
ITAFYLIWYGFGRMVIEGMRTDSLMFFGFRVSQWLSVVLIGLGIMIVIYQ
NRKKAPYYITEEENZ (SEQ. ID. NO. 51)
MGKLSSILLGTVSGAALALFLTSDKGKQVCSQAQDPLDDLREDPEYAKEQ
VCEKLTEVKEQATDFVLKTKEQVESGEITVDSILAQTKSYAFQATEASKN
QLNNLKEQWQEKAEALDDSEEIVIDITEEZ (SEQ. ID. NO. 52)
MKTKLIFWGSMLFLLSLSILLTIYLAWIFYPMEIQWLNLTNRVYLKPETI
QYNFHILMNYLTNPFSQVLQMPDFRSSAAGLNHFAVVKNLFHLVQLVALV
TLPSFYVFVNRIVKKDFLSLYRKSLLALVVLPVMIGLGGVLIGFDQFFTL
FHQILFVGDDTWLFDPAKDPVIMILPETFFLHAFLLFFALYENFFGYLYL
KSRRKZ (SEQ. ID. NO. 53)
MTYHFTEEYDHVIGAGHAGVEASLAASRMGCKVLLATINIEMLAFMPCNP
SIGGSAKGIVVREVDALGGEMAKTIDKTYIQMKMLNTGKGPAVRALRAQA
DKELYSKEMRKTVENQENLTLRQTMIDEILVEDGKVVGVRTATHQEYAAK
AVNTTGTALRGEIIIGDLKYSSGPNHSLASINLADNLKELGLEIGRFKTG
TPPRVKASSINYDVTEIQPGDEVPNHESYTSRDEDYVKDQVPCWLTYTNG
TSHEUQNNLHRAPMFTGVVKGVGPRYCPSIEDKIVRFADKERHQLFLEPE
GRNTEEVYVQGLSTSLPEDVQRDLVHSIKGLENAEMMRTGYAIEYDMVLP
HQLRATLETKKISGLFTAGQTNGTSGYEEAAGQGUAGINAALKIQGKPEL
ILKRSDGYIGVMIDDLVTKGTIEPYRLLTSRAEYRLILRHDNADMRLTEM
GREIGLVDDERWARFEIKICNQFDNEMKRLDSIKLKPVKETNAKVEEMGF
KPLTDAVTAKEFLRRPEVSYQDVVAFIGPAAEDLDDKIIELIETEIKYEG
YISKAMDQVAKMKRMEEKRTPANIDWDDIDSIATEARQKFKUNPETIGQA
SRISGVNPADISILMVYLEGKNRSISKTLQKSKZ (SEQ. ID. NO. 54)
MTKQVLLVDDEEHILKLLDYHLSKEGFSTQLVTNGRKALALAETEPFDFI
LLDLMLPQLDGMEVCKRLRAKGVKTPIMMVSAKSDEFDKVLALELGADDY
LTKPFSPRELLARVKAVLRRTKGEQEGDDSDNIADDSWLFGTLKVYPERH
EVYKANKLLSLTPKEFESDKNPFFEVFKVSKVTAQZ (SEQ. ID. NO. 55)
MTTFKDGFLWGGAVAAHQLEGGWQEGGKGISVADVMTAGRHGVAREITLG
VLEGKYYPNHEAIDFYHRYKEDIALFAEMGFKCPRTSIAWTRFPKGDELE
PNEEGLQFYDNLPDECLKNGIEPVITLSHFEMPYHLVTEYGGWKNRKLID
FPAREAEVVFKRYKDKVKYWMTFNEINNQANYQEDFAPFTNSGIVYEEGD
NREAIMYQAAHYELVASARAVKIGHEINPDFQIYYMSFAIDSHRENNPYD
YLETEDLVKNNYVKASEWEWQIDPEGLRYALNWFTDHYHLPLFNENGFGM
DQVAADGMVHDDYREYLGAHIREMKKAVVEDGVDLMGYTPWGCIDLVSAG
TGEMRKRYGFIYVDKDDNGKGSYNRSPKKFGWYKEVISSNGESVEZ (SEQ. ID. NO. 56)
MDQQNGLFGFLENHVMGPMGKLAQPKVVLTAAGMAAVPFWGSMFLVFSIL
PQAPSPPWADIFSASFDKFTSLYMVANYATMGSLSLYFVLSLAYELTKIY
AEEEELNMNPLNGALLALMAFVMTVPQUFDGGMMKTSLKEGAVIADGWAM
GNVVARFGTTGIFTAHMAIVTVLIYRMCVKHNWVIKMPEAVPEGVSRGPT
ALVPGFVVAFVVIFINGLLVAMGTDIKVLMPFGFVSNLTNSWIGLMUYLL
TQLLWWGIHGANIVPAFVSPIALANMAENAAGGHFAVAGEFSNMFLVIAG
GSGATLGLCLYIAFASKSEQLKIGRSVVPALFNINEPLILGLPIIYNPAL
AIPFILAPMVTATIYYVANSLNFIKPIIAQVPWPTPVGIGAFLGTADLRA
VLVALVCAFAAPLVYLPFTRVYDQKLVKEEQGIZ (SEQ. ID. NO. 57)
MKKFYVSPIFPILVGLIAFGVLSTFIIFVNNNLLTVLILPLFVGGYVFLF
KKLRVHYTRSDVEQIQYVNHQAEESLTALLEQMPVGVMKLNLSSGEVEWF
NPYAELILTKEGDFDLEAVQTIIKASVGNPSTYAKLGEKRYAVHMDASSG
VLYFVDVSREQAITDELVTSRPVIGVSVDNYDDLEDETSESDISQENSFV
ANFISEFSEKHMMFSRRVSMDRFYLFTDYTVLEGLMNDKFSVIDAFREES
KQRQLPLTLSMGFSYGDGNHDEIGKVALLNLNLAEVRGGDQVVVKENDST
KNPVYFGGGSAASTIKRTRTRTRAMMTASDKIRSVDQVFVVGHKNLDMDA
LGSAVGMQLFASNVIENSYALYDEEQMSPDIERAVSFIEKEGVTKLLSVK
DAMGMVTNRSLLILVDHSKTALTLSKEFYDLFTQTIVIDHHRRPQDFPDN
AVITYIESGASSASELVTELIQPQNSKKNRLSRMQASVLMAOMMLDTKNF
TSRVTSRTFDVASYLRTRGSDSIAIQEIAATDFEEYREVNEULQGRKLGS
DVLIAEAKDMKCYDTVVISKAADAMLAMSGIEASFVLAKNTQOFISLSAR
SRSKLNVQR1MEELGGGGHFNLAAAQIKDVTLSEAGEKLTEIVLNEMKEK
EKEEZ (SEQ. ID. NO. 58)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNTL
GSILLQLSNETITANQSQINDMVQNSSHSSFFLLALLAPICEEILCRGIV
PKKIFRGKENLGFVVGTIVFALLHQPSNLPSLLIYGGMSTVLSVLAYKTQ
RLEMSILLHMIVNGIAFCLLALVVIMSRTLGISVZ (SEQ. ID. NO. 59)
MKEKNMWKELLNRAGWILVFLLAVLLYQVPLVVTSILTLKEVALLQSGLI
VAGLSIVVLALFIMGARKTKLASFNFSFFRAKDLARLGLSYLVIVGSNLG
STLLQLSNETITANQSQINDMVQNSSLISSPFLLALLAPICEEILCRGIV
PKKIPRGKENILGFVVGTWFALLHQPSNLPSLLIYGGMSTVLSWAYKTQR
LEMSILLHMIVNGIAFCLLALVVIMSRTLGISVZ (SEQ. ID. NO. 60)
MDTQKIEAAVKMUEAVGEDANREGLQETPARVARMYQEIFSGLGQTAEEH
LSKSFEIIDDNMVVEKDIFFHTMCEHHFLPFYGRAHIAYIPDGRVAGLSK
LARTVEVYSKKPQIQERLNIEVADALMDYLGAKGAFVVIEAEHMCMSMRG
VRKPGTATUTVARGLFETDKDLRDQAYRLMGLZMKDLFLKRKQAFRKECL TABLE 2-continued GYLRYVLNDHFVLFLLVLLGFLAYQYSQLLQHFPENHWPILLFVGITSVL
LLLWGGTATYMEAPDKLFLLVGEEEIKLHLKRQTGLSLVFWLFVQTLFLL
LFAPLFLAMGYGLPVFLLYVLLLGVGKYFHFCQKASKFFTETGLDWDYVI
SQESKRKQVLLRFFALFTQVKGISNSVKRRAYLDFILKAVQKVPGKIWQN
LYLRSYLRNGDLFALSLRLLLLSLLAQVFIIEQAWIATAVVVLFNYLLLP
QLLALYHAFDYQYLTQLFPLDKGQKEKGLQEVVRGLTSFVLLVELVVGLI
TFQEKLALLALLGAGLVLLVLYLPYQVKRQMDZ (SEQ. ID. NO. 61)
MRKSIVLAADNAYLIPLETTIKSVLYHNRDVDFYILNSDIAPEWFKLLGR
KMEVVNSTIRSVHIDKELFESYKTGPHINYASYFRFFATEVVESDRVLYL
DSDIIVTGELATLFEIDLKGYSIGAVDDVYAYEGRKSGFNTGMLLMDVAK
WKEHSIVNSLLELAAEQNQVVNLGDQSILNIYFEDNWLALDKTYNYMVGI
DEYHLAQECERLDDNPPTIVHYASHDKPWNTYSISRLRELWWVYRDLDWS
EIAFQRSDLNYFERSNQSKKQVMLVTWSADIKHLEYLVQRLPDWHPHLAA
PCDCSEELTSLSQYTNVTVYQNVLHSRIDWLLDDSEVYLDINTGGEVFNV
VTRAQESGKICWAFDITRKSMDDGLYDGWSVERPDDLVDRMKNIEIEZ (SEQ. ID. NO. 62)
MTKIYSSIAVKKGLFTSFLLFIYVLGSRIILPFVDLNTKDFLGGSTAYLA
FSAALTOGNLRSLSIFSVGLSPWMSAMILWQMFSFSKRLGLTSTSIEIQD
RkKMYLTLLIAVIQSLAVSLRLPVQSSYSAILVVLMNTILLIAGTFFLVW
LSDLNASMGIGGSIVILLSSMVLNIPODVLETFQTVHIPTGHVLLALLTL
VFSYLLALMYRARYLVPVNKIGLHNRFKRYSYLEIMLNPAGGMPYMYVMS
FLSVPAYLFILLGFIFPNHSGLAALSKEIMVGKPLWVYVYISVLFLFSII
FAFVTMNGEEIADRMKKSGEYIYGIYPGADTSRFINRLVLRFSVIGGLFN
VIMAGGPMLFVLFDEKLLRLAMIPGLFMMFGGMIFTIRDEVKALRLNETY
RPLIZ (SEQ. ID. NO. 63)
MSSLSDQELVAKTVEFRQRLSEGESLDDILVEAFAVVREADKRILGMFPY
DVQVMGAIVMHYGNVAEMNTGEGKTLTATMPVYLNAPSGEGVMVVTPNEY
LSKRDAEEMGQVYRFLGLTXGVPFTEDPKKEMKASEKKLIYASDWTTINS
NLGPDYLNDNLASNEEGKFLRPFNYVUDEIDDILLDSAQTPLIIAGSPRV
QSNYYAIIDTLVTTLVEGWYIPKEEKEEVWLTTKGAKSAENELGIDNLYK
EEHASFARHLVYAIRAHKLFTKDKDYHRGNEMVLVDKGTGRLMEMTKLQG
GLHQAIEAKEHVKLSPETRAMASITYQSLPKMFNKISGMTGTGKVAEKEF
IETYNMSVVRIPTNRPRQRIDYPDNLYITLPEKVYASLEYIKQYHAKGNP
LLVFVGSVEMSQLYSSLLFREGIAHNVLNANNAAREAQIISESGQMGAVT
VATSMAGRGTDCKLGKGVAELGGUVIGTERMESQRIDLQIRGRSGRQGDP
GMSKFFVSLEDDVIKKFGPSWVHKKYKDYQVQDMTQPEVLKGRKYRKLVE
KAQHASDSAGRSARRQTLEYAESMNIQRDIVYKERNRLIDGSRDLEDVVV
DIIERYTEEVAADHYASRELLFWPIVTNISFHVKEVPDYIDVTDKTAVRS
FMKQVIDKELSEKKELLNQHDLYEQPLRLSLLKAIDDNWVEQVDYLQQLS

MAIGGQSASQKNPEVEYYQEAYAGFEAMKEQIHADMVRNLLMGLVEVTPK
GEIVTHFPZ (SEQ. ID. NO. 64)
MIGTFAAALVAVLANRVPIEITPNSANTELAPPDGIGQVLSNLLLKLVDN
PVNALLTANYIRILSWAVIFGIAMREASKNSQELLKTIADVTSKIVEWII
NLAPFGILGLVFKISDKGVGSLANYGILLVLLVTTMLPVAPVVNPILAPF
FMRRNPYPLVWNCLRVSGVTAPFTRSSATNTPVNMKLCMDLGLNPDTYSV
STPLOSTINMAGVAITINLLTLAAVNTLGTPVDFATAFVLSVVAAISSCD
ASGLAGGSLLUPVACSLFGISNDLAIQIVGVGPVIGVQDSCETALNSSTD
VLFTAVAEYAATRKKZ (SEQ. ID. NO. 65)
MSISQRTITKLILATCLACLLAYFLNLSSAVSAGIIALLSLSDTRRSTLK
LARNRLFSMLLALAIGVLAFHLSGFHIWSLGLYLAVPLAYKMGWEIGITP
STVLVSHLLVQESTSPDLLVNEFLLFAIGTGFALLVNLYMPSREEEIQHY
HTLVEEKDILQRFKYYLSRGDGRNRAQLVAELDTLLKEALRLVYLDHSDH
LFHQTDYHIHYFEMRQRQSRILRNMAQQLNTCHLAASESLILAQLFSKAG
QLSQTNPASDLLDEIERYLEVFRNRSLPKTREEPETRATLLQLLREAKTF
IQVKVDFYQKYRQZ (SEQ. ID. NO. 66)
MEIMSLAIAVFAVIIGLVIGYVSISAKM1SSQEAAELMLLNAEQEATNLR
GQAEREADLLVNEAKRESKSLKKEALLEAKEEARKYREEVDAEFKSERQE
LKQIESRLTERATSLDRXDDNLTSKEQTLEQKEQSISDRAKNLDAREEQL
EEVERQKEAELERIGALSQAEARDIILAQTSENLTREIASRIREAEQEVK
ERSDKMAKDILVQAMQRIAGEYVAESTNSTVHLPDDTMKGRIIGREGRNI
RTFESLTGVDVIIDDTPEVVTLSGFDPIRREIARMTMEMLLKDGRIHPAR
IEELVEKNRQEDNKIREYGEAAAYEIGAPNLHPDLMKIMGRLQPRTSYGQ
NVLRHSIEVAKLAGIMASELGENAALARRAGFLHDIGKAIDHEVEGSHVE
IGMELARKYKEPPVVVNTIASHHGDVEAESVIAVIVAAADALSAARPGAR
SESLESYIKRLHDLEEIANGFEGVQTSFALQAGREIRIMVNPGKIKDDKV
TILAHKVRKKIENNLDYPGNIKVTVIRELRAVDYAKZ (SEQ. ID. NO. 67)
MMLKPSIDTLLDKVPSKYSLVILBAKRAHELEAGAPATQGFKSEKSTLRA
LEEIIESGNVTIHPDPEGKREAVRRRIEEEKRRKEEEEKKIKEQIAKEKE
DGEKIZ (SEQ. ID. NO. 68)
MSAYQLPTVWQDEASNQGAFTGLNRPTAGARFEQNLPKGEQAFQLYSLGT
PNGVKVTILLEELLEAGFKEAAYDLYKIAIMDGDQFGSDPFKLNPNSKIP
ALLDQSGTENVRVFESAHILLYLAEKFGAFLPSNPVEKVEVLNWLFWQAG
AAPFLGGGFGHFFNYAPEKLEYPINRFTMEVKRQLDLLDKELAQKPYIAG
NDYTIADIAIWSWYGQLVQGNLYQGSAKFLDASSYQNLVKWAEKANRPAV
KRGLEVTYTEIKZ

TABLE 2-continued (SEQ. ID. NO. 69)
LASLITSIIMFYVGFDVLRDTIQKWSREETVIDPLGATLGIISAAIMFVV
YLYNTRLSKKSNSNALKAAAKDNLSDAVTSLGTAIAILASSFNYPIVDKL
VAIIITFFILKTAYDLFIESSFSLSDGFDDRLLEDYQKAIMELPKISKVK
SQRGRTYGSNIYLDITLEMNPDLSVFESHEIADQVESMLEERPGVFDTDV
HIEPAPLPEDEILDNVYKKLLMREQLIDQGNQLEELLTDDFVYIRQDGEQ
MDKEAYKTKKELNSAIKDIQITSISQKTKLICYELDGIIHTSIWRRMETW
QNIFHQETKKEZ (SEQ. ID. NO. 70)
MTIKLVATDMDGTFLDGNGRFDMDRLKSLLVSYKEKGIYFAVASGRGFLS
LEKLFAGVRDDIIIFIAENGSLVEYQGQDLYEATMSRDFYLATFEKLKTS
PYVDINKLLLTGKKGSYVLDTVDETYLKVSQHYNENIQKVASLEDITDDI
FKFTTNFTEETLEDGEAWVNENVPGVKAMTTGFESIDIVLDYVDKGVAIV
ELVKKLGITMDQVMAFGDNLNDLHMMQVVGHPVAPENARPEILELAKTVI
GHHKERSVIAYMHGLZ (SEQ. ID. NO. 71)
MADIKLIALDLDGTLLITTDKRLTDRTKETLQAARDRGIKVVLTTGRPLK
AMDFFLHELGTDGQEDEYTITFNGGLVQKNTGEILDKTVFSYDDVARLYE
ETEKLSLPLDAISEGTVYQIQSDQELYAKENPALTFVPVDFEDLSSQMTY
NKCVTAFAQEPLDAAEQKISPELFDQYEIFKSREMLLEWSPKNVHKATGL
AKLISHLGIDQSQVMACGDEANDLSMIEWAGLGVAMQNAVPEVKAAANVV
TPMTNDEEAVAWAIEEYVLKENZ (SEQ. ID. NO. 72)
MESLLILLLIANLAGLFLIWQRQDRQEKHLSKSLEDQADHLSDQLDYRIF
DQARQASQLDQKDLEVVVSDRLQEVRKELHQGLTQVRQEMTDNLLQTRDK
TDQRLQALQESNEQRLEQMRQTVEEKLEKTLQTRLQASFETVSKQLESVN
RGLDEMQTVARDVGALNKVLSGTKTRGALGELQLGQHEDIMTPAQYEREY
ATVENSSERVEYAIKLPGQGDQEYVYLPIDSKFPLADYYRLEEAYETGDK
DEIERCRKSLLASVKRFARDIRNKYIAPPRTTNFGVLFVPTEGLYSEIVR
NPVFFDDLRREEQIWAGPSTLSALLNSLSVGFKTLNIQKSADHISKTLAS
VKTEFGKFGGILVKAQKHLQHASGNIDELLNRRTIAIERTLRHIELSEGE
PALDLLHFQENEEEYEDZ (SEQ. ID. NO. 73)
MKISHMKKDELFEGFYLIKSADLRQTRAGKNYLAFTFQDDSGEIDGKLWD
AQPHNIEAFTAGKVVHMKGRREVYNNTPQVNQITLRLPQAGEPNDPADFK
VKSPVDVIKEIRDYMSQMIFKLENPVWQRIVRNLYTKYDKEFYSYPAAIC
TNHHAFETGLAYHTATMVRLADALSEVYQLNKSLLYAGIMLHDLAKVIEL
TGPDQTEYTVRGNLLGHIALIDSEITKTVMELGIDDTKEEVVLLRHVILS
HHGLLEYGSPVRPRIMEAEIIHMIDNLDASMMMMSTALALVDKGEMTNKI
FAMDNRSFYKPDLDZ (SEQ. ID. NO. 74)
MSEKAKKGFKMPSSKTVLLIIIAIMAVLTFIPAGAPIEGIYETQPQNPQG
IWDVLMAPIRAMLGTHPEEGSLIKBTSAAIIDVAPRLMVGGFLGIVNKTG ALDVGIASIVKKYKGREKMLILVLMPLFALGGTTYGMGEETMAFYPLLVP
VMMAVGFDSLTGVAIILLGSQIGCLASTLNPFATGIASATAGVGTGDGVL
RLIFWVTLTALSTWFVYRYADKIQKDPTKSLVYSTRKEDLKHFNVEESSS
VESTLSSKQKSVLFLPVLTFILMVLSRPWTDLGVTIPDDFNTWLTGLPVI
GNIVGSSTSALGTWYFPEGAMLFAFMGILIGVIYGLKEDKUSSFMNGAAD
LLSVALIVAIARGIQVIMNDGMITDTILNWGKEGLSGISSQVFIVVTYTF
YLPMSFLIPSSSGLASATMGIMAPLGEFVNVRPSLIITAYQSASGVLNLI
APTSGIVMGALALGRINIGTWWKFMGKLVVAIIVVTIALLLLGTPLPFLZ (SEQ. ID. NO. 75)
MSNSFVKLLVSQLFANLADIFFRVTIIANIYUSKSVIATSLVPILIGISS
FVASLLVPLVTKRLALNRVLSLSQFGKTILLAILVGMPTVMQSVAPLVTY
LFVVAISILDGFAAPVSYAIVPRYATDLGKANSALSMTGEAVQLIGWGLG
GLLFATIGLLPTTCINLVLYIISSFLMLFLPNAEVEVLESETNLEILLKG
WKLVARNPRLRLIWSANLLEFSNTIWVSSHLVFTELLNKTESYWGYSNT
AYSIGIIISGLLRISEKFLAAKWEPQLFTPNLIVFIQNPCLSLDPGWFLF
SPNGCFLLDKKEFPLYGISVEKNTKRKETHMNSLPNHHIQNKSFYQLSFD
GGHLTQYGGLWFQELFSQLKLKERISKYLVTNDQRRYCRYSDSDILVQPL
PQLLTGYGTDYACKELSADAYFPKLLEGGQLASQPRFSRTDEETVHSLRC
LNLELVEFFLQPHQLNQLIVDEDSTHFTTYGKQEGVAYNAHYRAHGYHPL
YAFEGKTGYCFNAQLRPGNRYCSEEADSFTTPVLERFNQLLFRMDSGFAT
PKLYDLIEKTGQYYUKLKKTVLSRLGDLSLPCQDEDLTILPHSAYSETLY
QAGSWSHKRRVCQFSERKEONLPYDVISLVTNMTSGTSQDQFQLYRGRGQ
AENFIKEMKBGFFGDKTDSSTLIKNEVRMMMSCIAYNLYLFLKHLAGGDF
QTLTIKRFRMLHVVGKCVRTGRKQLLKLSSLYAYSELFSALYSRIRKVNL
NLPVPYEPPRRKASLMMHZ (SEQ. ID. NO. 76)
MMEFFQQLPHLEPYGNPQYFVYVIAATLPLFIGLFFKKRFAWYEVLVSLF
FIVTMLVGGKTNQLAALGIYLCWEILLLLFYKHYRKDGKWVFYLVSFLSL
LPIIFVKVQPAINGTQSLLGFLGISYLTPRSVGIVIELRDGVIKDPTLWE
FLRFLLFMPTFSSGPIDRFKRFNENYQAIPERDELMDMLDESVRYIMWGF
LYKFILAHVLGETLLPPLKNLALQSGGFFNLYALAVMYTFGLELFFDFAG
YSMPALAISNLMGIRSPINFNKPFLSRDLKEFWNRWHMSLSFWFRDFVPM
RMVMVLTRKKVFKNRNVTSSMAYIVNMLMGFWHGVTWYYIAYGLFHGLGL
VINDAWVRKKKTLNKERKKAGKAALPENRWIQLLGMVVTFPHVVMLSFLLF
SGFLNNLWFKKZ (SEQ. ID. NO. 77)
MLKRLWMIFGPVLIAGLLVFLLIFFYPTEMHHNLGAEKRSAVATTIDSFK
ERSQKVRALSDPNVRFVPFFGSSEWLRFDGAHPAVLAEKYNRSYRYLLGQ
GGAASLNQYFGMQQMLPQLENKQVVYVISPQWFSKNGYDPAAPQQYPNGD
QLTSFLKHQSGDQASQYAATRLLQQPPNVAMKDLVQKLASKEELSTADNE
MIELLARFNERQASFFGQFSVRGYVNYDKHVAKYLKILPDQPSYQAIEDV TABLE 2-continued

VKADAEKTSNNEMGMENYPYNEQIKKDLKKLKDSQKSPTYLKSPEYNDLQ

LVLTQFSKSKVNPIFIIPPVNKKWMNYAGLREDMYQQTVQKIRYQLESQG

FTNIADFSKDGGEPFFMKDTIHLGWLGWLAFDKAVDPFLSNPTPAPTYHL

NERFFSKDWATYDGDVKEFQZ (SEQ. ID. NO. 78)
MEKNLKALKQTTDQEGPAIEPEKAEDTKTVQNGYFEDAAVKDRTLSDYAG

NWQSVYPFLEDGTFDQVFDYKAKLTGKMTQAEYKAYYTKGYHTDVTKINI

TDNTMEFVQGGQSKKYTYKYVGKKILTYKKGNRGVRFLFEATDADAGQFK

YVQFSDHNVAPVKAEHFHIFFGGTSQEALFEEMDNWPTYYPDNLSGQEIA

QEMLAHZ (SEQ. ID. NO. 79)
MKDGHLLAHHIRLLNGRLFQKLLSQDPEALYRGEQGKILAVLWNSETGCA

TATDIALATGLANNTLTTMIKKLEEQKLVIVSPCGKDKRKKYLVLTELGK

SQKEVGHRVSQKLDTIFYKGFSEEEIHQFEGFQERILANLKEKGNEVZ (SEQ. ID. NO. 80)
MTNLIATFQDRFSDWLTALSQHLQLSLLTLLLAILLAIPLAVFLRYHEKL

ADWVLQIAGIFQTIPSLALLGLFIPLMGIGTLPALTALVLYAIFPILQNT

GLKGIDPNLQEAGIAFGMTRWERLKIFEIPLAMPVIMSGIRTAAVLIGTA

TLAALIGAGGLGSPILLGIDRNNASLILIGALSSAVLAIAFNFLLKVMEK

KLRTSGFALVALLLGLSYSPALLVQKEKENLVIAGKIGPEPEILANMYKL

LIEENTSMTATVKPNPGKTSFLYEALKKGDIDIYPEETGTVTESLLQPSP

KVSHEPEQVYQVARDGIAKQDHLAYLICPMSYQNTYAVAVPKKIAQEYGL

KTISDLKKVEGQLKAGFTLEFNDREDGNKGLQSMYGLNLNVATIEPALRY

QAIQSGDIQITDAYSTDAELERYDLQVLEDDKQLFPPYQGAPLMKEALLK

KHPELERVLNTLAGKITESQMSQLNYQVGVEGKSAKQVAKEFLQEQGLLK

KZ (SEQ. ID. NO. 81)
MMHTYLQKKIENIKTTLGEMSGGYRRMVAAMADLGFSGTMKAIWDDLPAH

RSFAQWIYLLVLGSFPLWLELVYEHRIVDWIGMICSLTGIICVIFVSEGR

SNYLFGLINSVIYLILALQKGFYGEVLTTLYFTVMQPIGLLVIYQAQFKK

EKQEFVARKLDGKGWTKYLSISVLWWLAFGFIYQSIGANRPYRDSITDAT

NGVGQILMTAVYREQWIFWAATNVFSIYLWWGESLQIQGKYLIYLINSLV

GWYQWSKAAKQNTDLLNZ (SEQ. ID. NO. 82)
MRNMKAKYAVWVAPFLNLTYAIVEFIAGGVFGSSAVLADSVHDLGDAIAI

GISAFLETISNREEDNQYTLGYKRFSLLGALVTAVILVTGSVLVILENVT

KILHPQPVNDEGILWLGILTINLLSLVVGKGKTKNESILSLHFLEDTLGW

VAVILMAIVLRFTDWYILDPLLSLVISFFLSKALPRFWSTLKIFLDAVPE

GLDIKQVKSGLERDNVASLNQLNLWTMDALEKNAIVHVCLKEMEHMETCK

ESIRIFLKDCGFQNITIEIDADLETHQTHKRKVCDLERSYEHQHZ (SEQ. ID. NO. 83)
MIEYKNVALRYTEKDVLRDVNLQIEDGEFMVLVGPSGSGKTTMLKMINPL

LEPTDGNIYMDGKRIKDYDERELRLSTGYVLQALALIPNLTVAENIALIP (SEQ. ID. NO. 84)
EMKGWSKEEITKKTEELLAKVGLPVAEYGHRLPSELSGGEQQRVGIVLRA

MIGQPICIFLMDEPFSALDAISRKQLQVLTKELIEFGMTFITIFVTHDTD

EALKLADRJAVLQDGEIRQVANPETILKAPATDFVADLPGGSVHDZ (SEQ. ID. NO. 84)
MSAVAISAMTKVMQETHGNPSSIHGHGRQAGKLLREARQELAQLLRTKPQ

HIFFTSGGTEGNNTTIIGYCLRHQEQGKHIITTAIEHHAVLETIDYLVQH

FGFEATIIQPENQEITAQQIQKALRDDTILVSTMFVNNETGNLLPIAEIG

QILKQHPAAYHVDAVQAIGKIPHSEELGIDFLTASAHKFHGPKGIGFLYA

SSMDFDSYLHGGDQEQKRAGTENLPAIVGMVAALKEDLEKQEEHFQHVQN

LETAFLAELEGIQYYLNRGKHHLPYVLNIGFPGQKNDLLLLRLDLAGIST

GSACTAGVVQSSHVLEAMYGANSERLKESLRISLSPQNTVEDLQTLAKTL

KEUGGZ (SEQ. ID. NO. 85)
MLFKLSKEKIELGLSRLSPARRIFLSFALVILLGSLLLSLQFVQVESSRA

TYFDHLFTAVSAVCVTGLSTLPVAHTYNIWGQIICLLLIQIGGLGLMTFI

GVFYIQSKQKLSLRATIQDSFSYGSLRFVYSIFLTTFLVESLGAILLSFR

LIPQLGWGRGLFSSLFLAISAFCNAGPDNLGSTLFAFQTDLLVNLVIAG

LIITGGLGPMVWFDLAGHVGRKKKGRLHFHTKLVLLLTIGLLLFGTATTL

FLEWNNAGTIGNLPVADKVLVSFFQTVTMRTAGFSTIDYTQAHPVTLLIY

ILQMFLGGAPGGTAGGLKITTFFVLLVFARSELLGLPHANVARRTIAPRT

VQKSFSFIIFLMSFLIGLLLGITAKGNPPFIHLVFETISALSTVGVTANL

TPDLGKLALSVIMPLMFMGRIGPLTLFVSLADYXPEKKDMIHYMKADISI

GZ (SEQ. ID. NO. 86)
MSDRTIGILGLGIFGSSVLAALAKQDMNIIAIDDHAERINQFEPVLARGV

IGDITDEELLRSAGIDTCDTVVVATGENLESSVLAVMHCKSLGVPTVIAK

VKSQTAKKVLEKIGADSVISPEYEMGQSLAQTILFHNSVDVFQLDKNVSI

VEMKIPQSWAGQSLSKLDLRGKYNLNILGFREQENSPLDVEFGPDDLLKA

DTYILAVINNQYLDTLVALNSZ (SEQ. ID. NO. 87)
MKLLSIAISSYNAAAYLHYCVESLVIGGEQVGILIINDGSQDQTQEIAEC

LASKYPNIVRAIYQENKCHGGAVNRGLVEASGRYFKVVDSDDWVDPRAYL

KILETLQELESKGQEVDVFVTNFVYEKEGQSRKKSMSYDSVLPVRQIFGW

DQVGNFSKGQYTMMHSLIYRTDLLRASQFZ (SEQ. ID. NO. 88)
MKFNPNQRYTRWSRRLSVGVASVVVASGFFVLVGQPSSVRADGLNPTGQ

VLPEETSGTKEGDLSEKPGDTVLTQAKPEGVTGNTNSLPTPTERTEVSEE

TSPSSLDTLPBKDEEAQKNPELTDVLXETVDTADvDGTQASPAERRPEQV

KGGVKENTKDSIDVPAAYLEKAEGKGPFTAGVNQVIPYELFAGDGMLTRL

LLKASDNAPWSDNGTAKNPALPPLEGLTICGKYFYEVDLNGNTVGKQGQA

UDQLRANGTQTYKATVKVYGNKDGKADLTNLVATKNVDININGLVAKETV

QKAVADNVKDSIIDVPAAYLEKGEGPTAGVNHVIPYELFAGDGMLTRLLL

TABLE 2-continued

LSDKAPWSDNGDAKNPALSPLGENVKTKGQYFYQVALDGNVAGKEKQALI
DQFRANGTQTYSATVNVYGNKDGKPDLDNIVATKKVTLNNGLSKETVQKA
VADNVKDSIDVPAAYLEKAKGEGPFTAGVNHVIPYELFAGDGMLTRLLLK
ASDKAPWSDNGDAKNPALSPLGENVKTKGQYFYQLALDGNVAGKEKQALI
DQFRANGTQTYSATVNVYGNKDGKPDLDNIVATKXVTININGLISKETVQ
KAVADNVKTVSMFQQPTZ (SEQ. ID. NO. 89)
MKLKSYILVGYIISTLLTILVVFWAVQKMLIAKGEIYFLLGMTIVASLVG
AGISLFLLLPVFTSLGKLKEHAKRVAAKDFPSNLEVQGPVEFQQLGQTFN
EMSHDLQVSFDSLEESEREGLMIAQLSHDIKTPITSIQATVEGLLDGIIK
ESEQAHYLATIGRQTERLNKLVEELNFLTLNTARNQVETTSKDSIFLDKL
LIECMSEFQFLIEQERRDVHLQVIPESARIEGDYAKSRJLVNEITVSSQY
GLGSTETLVLNLSGSENKAZ (SEQ. ID. NO. 90)
MFGQTAQHGLTNSLKDFIFLLNIGPQLAFFCQMLRCSRSVEQTGNHRRE
FNMIQQIIFSHFGMTHLGQIKLVYQESIDLELLVNALNHHLLIDRLVLTP
NQITLEDRQIVHGLDLLKGRXDKEIIDIKSMFRQLELASTQQICPNQRVH
HGILAFGEISDLVPAKNLPNRQDZ (SEQ. ID. NO. 91)
MEHLATYPSTYGGAPAALGWLAVGLSGMGSAYGVGKAGQSAAALLKEQPE
KFASALILQLLPGTQOLYGFVIGLIWLQLTPSLPLEKGVAYFVALPIA1V
GYFSAKHQGNVAVAGMQILAKRPKEFMKGAILAAMVETYAILAIWVSFIL
TLRVZ (SEQ. ID. NO. 92)
MLKSEKQSRYQMLNEELSFLLEGETNVLANLSNASALIKSRFPNTVFAGF
YLFDGKELVLGPFQGGVSCIIRIALGKGVCGEAAGHFQETVIVGDVTTYL
NYISCDSLAKSEIVVPMMKNGQLLGVLDLDSSEIEDYDAMDRDYLEQFVA
ILLEKTAWDFTMFEEKSZ (SEQ. ID. NO. 93)
MSVLEKDLHVEIEGKEILKGVNLTLTGEAAIMGPNGTGKSAAIMGNPNYE
VTKGEVLFDGVNILELEVDERARMGLFLAMQYPSEIPGITNAEFLRAAMN
AGKEDDEKISVREFITKLDEKMELLNMKEEMAERYLNEGFSGGEKKRNEI
LQLLMLEPTFALLDEIDSGLDIDALKVVSKGVNAMRGEGFGAMIITTHYQ
RLLNYITPDVVHVMMEGRVVLSGGPELAARLEREGYAKLAEELGYDYKEE
LZ (SEQ. ID. NO. 94)
MPYKRQRSFSMALSKLDSLYMAVVADHSKNPHHQGKLEDAEQISLNNPTC
GDVINLSVKFDAEDRLEDIAFLNGCTISTASASMMTDAVLGKKQEILELA
T1FSEMVQGQKDERQDQLGDAAGVAKFPQPJKCATWNALKIENQEKQZ (SEQ. ID. NO. 95)
MKIQDLLRKDVMLLDLQATEKTAVIDEMIKNLTDHGYVTDEFETFKEGIL
AREALTSTGLGIAMPHSKNAAVKEATVLFAKSNKGVDYESLDGQATDLFF
MIAAPEGANDTHLAALAELSQYLMKDGFADKLRQATSADQVIELFDQASE
KTEELVQAPANDSGDFIVAVTACTTGIAHTYMAQEALQKVAAEMGVGIKV
ETNGASGVGNQLTAEDIRKAKAIIIAADKAVEMDRFDGKPLTNRPVADGI
RKTEELINLALSGDTEVYRANGAJ(AATASNEKQSLGGALYLMSGVSQML
PFVIGGGIMIALAFLIDGALGVPNENLGNLGSYHELASMFMKIGGAAFGL
MLPVFAGYVAYSIAEKPGLVAGFVAGALAKEGFAFGKLPNDFLGGLGGGS
AVLLGIVLGGMMAVDMGGPVNKAAYVFGTGTLAATVSSGGSVAMAAVMAG
GMVPPLAIFVATLLFVLVGAIVSGVVYGYLRKPQAZ (SEQ. ID. NO. 96)
MANKNTSTTRRRPSKAELERKEAIQRMLISLGIAILLIFAAFKLGAAGIT
LYNLIRLLVGSLAYLAIFGLLIYLFFFKWIIRKQEGLLSGFFTIFAGLLL
IFEAYLVWKYGLDKSVLKGTMAQVVTDLTGFRTTSFAGGGLIGVALYPTA
FLFSNIGTYFIGSLILVGSLLVSPWSVYDIAEFSRGFAKWWEGHERRXEE
RFVKQEEKARQKAEKEARLEQEETEKALLDLPPVDMETGEILTEEAVQNL
PPIPEEKWVEPEIILPQAELKFPEQEDDSDDEDVQVDFSAKEALEYKIPS
LQLFAPDKPKDQSKEKKWRENIKILEATFASFGIKVTVERAEIGPSVTKY
EVKPAVGVRVNRISNLSDDLALALAAKDVRIEAPIPGKSUGTEVPNSDIA
TVSFELWEQSQTKAENFLEIPLGKAVNGTARAFDLSKMPHLLVAGSTGSG
KSVAVNGIIASILMKARPDQVKFMMVDPKMVELSVYNDIPILLJPVVTNP
RKASKALQKVVDEMENRYELFAKVGVRNIAGFNAKVEEFNSQSEYKQLPL
PFIVVIVDELADLMMVASKBVEDAIIRLGQKARAAGIHMILATQRPSVDV
ISGUKANVPSRVAFAVSSGTDSRTLDNGAEKLLGRGDMLFKPIDENHPVR
LQGSFISDDDVERIVNPIKTQADADYDESFDPGEVSENEGEFSDGDAGGD
PLFEEAXSLVIETQKASASMIQRRLSVGFNRATRLMEELEIAGVIGPAEG
TKPPJCVLQQZ (SEQ. ID. NO. 97)
MSYFKKYKFDKSQFKLGMRTKTGIAVFLVLLIFGFGWKGLQIGALTAVFS
LRESFDESVHFGTSRTLGNSIGGLYALVFLLNTFFWEAWVTLVVVPICTM
LTLMTNVAMNNCAGVIGGVAAMLHTLSPSGETILYVFVRVLETFMGVFVA
UVNYDIDRIRLFLEKKEKZ (SEQ. ID. NO. 98)
MNKSEHRHQLIRAUTKNKIHTQAELQALLAENDIQVTQATLSRDIKNMNL
SKVREEDSAYYVLNNGSISKWEKRLELYMEDALVWMRPVQHQVLLKTLPG
LAQSFGSHDTLSFPDAATLCGNDVCLIICEDADTAQKCFEELKKFAPPFF
FEEZ (SEQ. ID. NO. 99)
MCSIKLNALSYMGRVLNIFPItTGTYVARVLDRTDYGYFNSVDTILSFFL
PFATYGVYNYGLRAISNVKDNKKDLNRTFSSLFYLCIACTLTRAVYILA
YPLFFTDNPIVKKVYLVMGIQLIAQFSIEWVNBALENYSILFYKTAFRIL
MLVSIFLPVKNEHDEVVYTLVMSLTINYLSYFWKRDIKLVKIHLSDFKP
LFLPLTAMLVANANMLFTTLDRLFLVICTGIDVNVSYAQRJVTVIAGVVT
GAIGVSVPRLSYYLGKGDKEAYVSLVNRCSRIFNPFHPLSFGLMVLGNAI
LLYGSEKYIGGGILTSLFAFRTULALDTILGSQILFTNGYHKRTVYTVFA

TABLE 2-continued

GLLNLGLNSLLFFNHVAPEYYLLTRMLSETSLLVFYIIFEHRKQLIHLGH
IFSYTVRYSLFSLSWAIYFUNFVYPVDMVLNLPFLINTGLIVLLSAISYI
SLLVFRKDStFYEFLNHVLALKNKFKKSZ (SEQ. ID. NO. 100)
MELFMKITNYEIYXLKKSGLTNQQILICVLEYGENVDQELLLGDIADISG
CRNPAVFMERYPQIDDAHLSKEFQKFPSPSILDDCYPWDLSEIYDAPVLL
FYKGNLDLLKFPKVAVVGSRACSKQGAKSVEKVIQGLENELVIVSGLAXG
DTAAHMAALQNGGKTAVIGTGLDVFPKANKRLQDYIGNDHLVLSEYGPGE
QPLKHFPARNRIAGLCRGVIVAEAKMRSGSLTCERAMEEGRDVFALPGSI
LDGLSDGCIIMLIQEGAKLVTSGQDVLAEFEPZ (SEQ. ID. NO. 101)
MKQLTVEDAKQIELEILDYIDTLCKKIININYIINYGTLIGAVRHEGFIP
WDDDDISMPRBDYQRFINIFQKEKSKYKLLSLERDKNYNNFIKTDSTRKI
IDTRNTKTYESGIIDIFPDRFDDPKVIDTCYKESKLLSFSKHKNWYKDSL
LKDWIRTAFWLLLRPVSPRYFANKTEKEIQKYSRENGQYMAFIPSKFKEK
EVFPSGTFDKTIDLPPENLSLPAPEKPDTILTQFYGDYMTLPPEEKRFYS
HEFHAYKLEDZ (SEQ. ID. NO. 102)
MIKINHLTITQNKDLRDLVSDLTMTIQDGEKVAIIGEEGNGKSTLLKLMG
EALSDFTIKGNIQSDYQSLAYPQKVPEDLKKKTLHDYFFLDSIDLDYSIL
YRLAEELHFDSNRFASDQEIGNLSGGEALKIQLIHELAICPFEILFLDEP
SNDLDLETVDWLKGQIQKTRQTVTFISHDEDPLSETADTIVLRLVKHRKE
AETHVEHLDYDSYSEQRKANFAKQSQQAANNQRAYDKTMEKIRRVKQNVE
TALRATKDSTAGRLLAKKMKTVLSQEKRYEKAAQSMTQKPLEEEQIQLFF
SDIQPLPASKVLVQLEKENLSIDDRVLVQKLQLTVRGQEKIGIIGPNGVG
KSTLLAKLQRLLNDKREISLGIMPQDYHXJCLQLDLSPIAYLSKTGEKEE
LQKQSHLASLNFSYPMQHQRSLSGGQQGKLLLLDLVLRKPNFLLLDEPTR
NPSPTSQPQIRKLFATYPGGLITVSHDRRFLKEVCSIIYRMTEHGLKLVN
LEDLZ (SEQ. ID. NO. 103)
MKPKTFYNLLAEQNLPLSDQQKEQFERYFELLVEWNEKINLTAITDKEEV
YLKNFYDSIAPILQGLIPNETIKLLDIGAGAGFPSLPMKLLYPELDVTII
DSLNKRINFLQLLAQELDLNGVHFYHGRAEDFAQDKNFRAQYDFVTARAV
ARMQVLSELTIPYLKVGGKLLALKASNAPEELLEAKNALNLLFSKVEDNL
SYALPNRDPRYITVVEKKKETPNKYPRKAGMPNKRPLZ (SEQ. ID. NO. 104)
MSIKUAVDIDGTLVNSQKEITPEVFSAIQDAKEAGVKVVIATGRPIAGVA
ICLLDDLQLRDEGDYVVTFNGALVQETATGHEIISSLTYEDYLDMEFLSR
KLGVHMHAITKDGIYTANRNIGKYTVHESTLVSMPYRTPEEMAGKJVKCM
FIDEPEIPEIKKIAKYITKTNDESGVAHAIRTWVLZ (SEQ. ID. NO. 105)
MTWIILGVIALIVIIVSYNGLVKNRMQTKEAWSQIDVQLKRRNDLLPNLI
ETVKGYAYEGLEKVAELRN5QVTSPAEAMKASDALTRQVSGIFAVAESYP
DLKASANPVICLQEELTNTENKSYSRQLYNSVVSNYNVKLETFSNIIAGM
FGFKAADFLQTPEEEKSVPKVDPSGLGDZ (SEQ. ID. NO. 106)
MLFDQIASNKRKTWILLLVFFLLLALVGYAVGYLIRSGLGGLVIALIIGF
IYALSMIFQSTEVMSMNGAREVDEQTAPDLYHVVEDMALVAQIPMPRVFI
IDDPALNAFATGSNPQNAAVAATSGLLAIMNREELEAVMGHEVSHIRNYD
IRISTIAVALASAITMLSSMAGRMMWWGGAGRRRSDDDRDGNGLEIIMLV
VSLLAIVLAPLAATLVQLAISRQREFLADASSVELTRNPQGMINALDKLD
NSKPMSRHVDDASSALYINDPKKGGGFQKLFYTHPPtSERIERLKQMZ (SEQ. ID. NO. 107)
MKLNIQEIRKQSEGLNFEQTLDLVDDLRARNQEILDVKDILAVGKVQYED
RMYFLDYQLSYTIVLASSRSMEPVELVESYPVTEVFMEGATNQLDQEVLD
DDLVLPLENGELDLAESVSDNLLNIPIKVLTAEEBAGQCPISGNDWQIMT
EEEYQAQKAVKKEENSPFAGLQGLFDGDEZ (SEQ. ID. NO. 108)
MKRQLALVVPSGGQDSRTCLWVMQHYETVEAVTFAYGQRMHLEQRRREIA
KEQGRHHILDMSLLGQITAQPDFATIHSYIPDKLCVESKSLKLYLFSYRN
HGDFHENCNTIGKDLVNLLDPRYLEVWGKFTPRGGISDPYYNYGKQGTKY
EGLAEQRLFQHDLYPEKIDNRZ (SEQ. ID. NO. 109)
MTETVEDKVSHSn*GLDILKGIVAAGAVISGTVATQTKVFTNESAVLEKT
VEKTDALATNDTVVLGTISTSNSASSTSLSASESASTSASESASTSASTS
ASTSASESASTSASTSISASSTVVGSQTAAATEATAKXVEEDRKKPASDY
VASVTNVNLQSYAgRRKRSVDSIEQLLASIKNAAVSGNTVNGAPAINASL
NLAKSETKVYTGEGVDSVYRVPIYYKLKVTNDGSKLTFTYTVTYVNPKTN
DLGNISSMRPGYSYNSGTSTQTMLTLGSDLGKPSGVKNYITDKNGRQVLS
YNTSTMTRQGSGYTWGNGAQMNGFFAKXGYGLTSSWTVPITGTDTSFTFT
PYAARTDRIGINYFNGGGKVVESSITSQSLSQSKSLSVSASQSASASAST
SASASASTSASASASTSASASASTSASVSASTSASASASTSASASASTSA
SESASTSASASASTSASASASTSASASASTSASESASTSASASASTSASE
SASTSASASASTSASASASTSASGSASTSTSASASTSASASASTSASASA
SISASESASTSASESASTSTSASASTSASASASTSASASASTSASASAST
SASASASTSASASASTSASASASTSASASASTSASASASTSASASASTSA
SASTSASVSASTSASASASTSASESASTSASASASTSASASA
STSASASASTSASESASTSASASASTSASESASTSASASASTSASASAST
SASGSASTSTSASASASTSASASASISASESASTSASESASTST
SASASTSASESASTSASASASTSASASASRQVRRPQPVHLNRM
QPVRQPQQVLVHQLQHQRVHRLQHQPVPRLQRQPVRQLQQVPVLQSQHQQ
VLQPQHRQVPRLQQAHQHLNQRRQAPQLQQVPVRQPQRRQVRQPQQVLVH
QLQHQRVHRLRRQPVHQSQQVPVRQLPHQQVPRLQQAPVRRLQQVLAPQP
QPQPVRQPQQVSQRLNRIIQRVRPLQQVLAPQPQRQQVHRLQRQRVRLNR
HQRVRPLQQVLAPQPQRQQVHRLQHQRVRPLQQVLAPQPQRQQVHLQRQ

TABLE 2-continued

RVRLSQHQRVRQPQQAHQLLNLHQPVRQPQHRQAPQLQQVPVRQPQRRQV
RRLQQVPVRQPQQVPVRQPQRRQVRRPQPVHLNRNQPVRQPQQVLVHQLQ
MQRVHRLQHQPVHQSQQVPVRQPRINKCLGFSKYZ (SEQ. ID. NO. 110)
MGVETWFYSSICWLALGLGSVWKFPYMTAANGGGGFLLIFLLSTILIGPL
LLAEALGRSAGVSAIKTFGKLGKNNKYNIGWIGAFALFLLSFYSVIGGWT
LVYLGIEFGKLFQLGGTGDYAQLFTSfLSNPAIALGAQAAPLLLNIFIVS
RGVQKGLERASKVMMPLLFIVFVFIIGRSLSLPNAMEGVLYPDSKLTSTG
LLYALGQSFALSLGVTVMLTYASYLDKXTNLVQSGISIVAMNISISIMAG
LAFQARSPFNQSEGGPSLLVLPQLIDKMPFGTUYVLFLLLFLFATVTFSV
VMLEINVDNITQDNSKRAXWSVILGLTFVFGTPSALSYGVMADVHIFGK
TFFDAMDFLVSNLLMPFGALYLSLTGYTFKKALAMEELHLDERAWKQGLF
QVWLFLLRFFVSSFQSSSLWSSLPNLCNQKGLEZ (SEQ. ID. NO. 111)
MLKKWQLKDVILLAFLSLFFC3GVFVGSGYVVYNELSLLLTPLGLQAFANE
ILFGLWCMAAPIAAIFVPRVGSATIGEVLAALAEVLYGSQFGLGALLSGF
VQGLGSEFGFIVTKNRYESWLSLTANSIGITLVSFVYEYIKLGYYAFSLP
FVLSLLVVRFISVYFFCTILVRAIVKLYHQFATGGKAZ (SEQ. ID. NO. 112)
MVKVATQTPHSLLLILSLETSFIPSIALTLSVVAPCILFMLYYRRFKMLA
WMLLLAILPSFANYWAVQLHGDASQAVMLGTRAFVTVCIGLVFVSSVSLK
ELLLYLAQKGLSRSWSYALIVVFNSFPLQQEIKSLKEACLLRGQELHFWS
PLIYSKVLMTVFRWRHLYLRALSAHGYDEHAQLKNSYRTFYPKKTKLIYL
LFFLLLQTSLLZ (SEQ. ID. NO. 113)
MRKHQLQVHKLTLSMMALDVVLTPRIEGMAPMSSVVNLAGIMMGPVYALA
MATVRAFXRNfFRQGIPPLALTGATFGALLAGLFYKYGRKFHYSALGEIL
GTGUGSIVSYPVMVLFTGSAAKLSWFEYTPREFGATLIGTALSFIAFRFL
KQEFFKKVQGYFFSERIDZ (SEQ. ID. NO. 114)
MQETNPFPIGSSSLIHCFLNEISCEMLANGILALGCKPVMADDSREVLDF
IKQSQALNLGHLSAEKEKJJRMAASYANQSSLPMVVDAVGVRSSIRKSLV
KDLLDYRPRVLKGNMSEIRSLVGLKHHGVGVDASAJCDQETEDLLQVLKD
WCQTYPGMSFLVTGPKDLVVSKNQVAVLGNGCTELDWLTGTGDLVGALTA
VFLSQGKTGPEASCLAVSYLNIAAEKIVVQOMGLEEFRYQVLNQLSLLRR
DENWLDTIKGEVYEZ (SEQ. ID. NO. 115)
MNHKAILSDVMGNATALEAVL&DAXNQGASEYWLLGDIFLPGPGANDLVA
LLKDLPPASVRGNWDDRVLEALDGQYGLEDPQEVQLLRMTQYLMERMDPA
TIVWLRSLPLLEKKEIDGLRFSISHNLPDKNYGGDLLVENDTEKEDQLLD
AETDVAVYGHVHKQLLRYGSQGQQIINPGSIGMPYFNWEALKNHRSQYAV
IEVEDGELLNIQFRKVAYDYEAELELAKSKGLPFIEMYEELRRDDNYQGH
NLELLASLIEKHGYVEDVKNFFDFLZ (SEQ. ID. NO. 116)
MNVQIVRIIPTLKANNRKLNETFYIETLGMKALLEESAFLSLGDQTGLEK
LVLEEAPSMRTRKVEGRKKLARLIVKVENPLEIEGTTDSIHRLYKGQNGY
AFEIPSPEDDLILIHAEDDIASLVEVGEKPEQTDLASKEISMELHLDIFL
ESSEIGASLDFIPAQGQDLTVDNTVTWDLSMLKFLVNELDLSRQKEEST
EYIPKSEKGKDNVELWEVZ (SEQ. ID. NO. 117)
MKWTKHIIKKIEEQIEAGIYPGASFAYFKDNQWTEFYLGQSDPEHGLQTE
AGLVYDLASVSKVVGVGTVCTFLWEIGQLDIDRLVIDFLPESDYPDTIRQ
LLTRATDLDPPIPNRDLLTAPELKEAMFHLNRSQPAFLYSDVHPLLLGFL
EFNQDLDVILKDQVWKPWGMTETKFGPVELAVPTVRGVEAGIVHDPKARL
LGREAGSAGLFSTIKDLQIFLEHYLADDFALNQNFSPLDDKERSLAWNLE
GDWLDHTGYTGTFIMWNRQKQEATFLSNRTYEKDERAQWILDRNQVMNLI
EEZ (SEQ. ID. NO. 118)
MMKKTYNHILVWGVIFYSICIVCFCFTPQEQSTVGVGTPGIQHLGRLVFL
LTPFNSLWKLGEVSDIGQLCWIFLQNILNVFLFFPLIFQLLYLFPNLRKT
KKVLLFSFLVSLGIECTQLILDFFFDFNRVFEIDDLWTNTLGGYLAWLLY
KRLHKVRNZ (SEQ. ID. NO. 119)
MKIPLLTFLARHKFVYVLLTLLFLALVYRDVLMYFFDIHAPDLAKFDGQA
IKNDLLKSALDFRILQNLGQSFILPHIVLLGFQYIELKNXVLRLSRBVSY
QGLKRKLTLQVASIPCLIYLVTVLUAHTYFFGTFSPLGWNSLSDGSGLQR
LLDGEIKSYLFFTCVLLIGIFINAIYFLQIVDYVGNVTRSAITYLMFLWL
GSMLLYSALPYYMVPMTSLMQASYGDVSLMKLPYILYIVPYMVLEICYED
NVZ (SEQ. ID. NO. 120)
MFKVLQKVGKAFMLPIAILPAAGLLLGLGGALSNPRTIATYPILDNSIFQ
SWQVMSSAGEVVFSNLSLLLCVGLCIGLAKRDKGTAALAGVTGYLVMTAT
UALVKLFMAEGSAIDTGVIGALVVGIVAVYLHNRYNNIQLPSALGGGSPP
ISFSSILIGFVFFVWPPFQQLLVSTGGYSQAGPIGTLYGFLMRLSGAVGL
HHIIYPMTYTELGGVETVAGQTVGAQKIPAQLADLAHSGLFREGTREAGR
FSTMMFGLPAACLAMYHSVPKNRRRKKYAGLFGVALTSFITGITEPIEFMF
LPVSPVLYVHAFLDGVSPFIADVLNISIGNTFSGGVIDRLFGILQGNAK
TNWVLQIPGLIWSVLYYIIFRWFTQNVLTRGEEVDSKEISESADSTSNTA
DYLKQDSLQIIRALGGSNNIEDVDACVTRLRVAVEVNQVDKALLKQIGAV
DVIEVKGGIQAIYGAKAILYKNSINEILGVDDZ (SEQ. ID. NO. 121)
MKFRKLACVLAGAAVLGLAACGNSGGSKDAAKSGGDGAKTEITWWAPVF
TQEKTGDGVGTYEKSUEAFEKANPDIKVKLETDFKSGPEKNTAIEAGTAP
DVLFDAPGRHQYGKNGKLAELNDLFTDEFVKDVNNENRVQASKAGDKAYM
YPISSAPFYMAMNKKMLEDAGVANLVKEGWITDDFEKVLKALKDKGYTPG
SLFSSGQGGDQGTRAFISNLYSGSVTDEKVSKYTRDDPKFVKGLEKATSW

TABLE 2-continued

IKDNLINNGSQFDGGADIQNFANGQTSYTILWAPAQNGIQAKLLEASKVE
VVEVPFPSDEGKPALEYLVNGFAVNNKDDKKVAASKKIQFIADDKEWGPK
DVVRTGAFPVRTSFGKLYEDKRMETSGWTQSPYYNTIDGFAEMRTLWPML
QSVSNGDEKPADALKAFTEKANETIKKAMKQZ (SEQ. ID. NO. 122)
MQSTEKKPLTAFTVISTIILLLLTVLFIPPFYWILTGAFKSQPDTIVIPP
QWFPKMPTMENFQQLMVQNPALQWMWNSVFISLVTMFLVCATSSLAGYVL
AKKRFYGQRILFAIFIAAMALPKQVVLVPLVRIVNFMGHDTLWAVILPLI
GWPFGVFLMKQFSENIPTELLESAKIDGCGEIRTFWSVAPPVKPGFAALA
IPTFINTWNDYFMQLVMLTSRNNLTISLGVATMQAEMATNYGLMAGAALA
AVPIVTVFLVFQKSTQGITMGAVKGZ (SEQ. ID. NO. 123)
MKLMFKNFNNILLNRCIVLLLRIVLMMILINHLLSTAVQKQDAVIFFKRE
LSFSYNDYSEANLELPICLLLNLSIFMVGWLSVILLESDLADHYHHLIRY
QSSSFFDYTRKRLVVISKFFTQDLFVWFLGLLPLGIHFKTVALFFLLAQL
MMLYLLLSYUALISAGAGFSFFLYPLAFVGQEWMMDHIVTVYLVLLSLLV
MLVSRLESKEKKGZ (SEQ. ID. NO. 124)
MGKGEMGKGVIGLEFDSEVLVNKAPTLQLANGKTATFLTQYDSICTLLPA
VDKEDIGQEIIGIAKGSIESMHNLPVNLAGARVPGVNGSKAAVHEVPEFT
GGVNGTEPAVHEIAEYKGSDSLVTLTTGKDYTYKAPLAQQALPETGNKES
DLLASLGLTAFLGLFTLGKXREQZ (SEQ. ID. NO. 125)
MKKTFFLLVLGLFCLLPLSVIAIDFKINSYQGDLYIHADNTAEFRQKIVY
QFEEDFKGQIVGLGRAGKMPSGFDIDPHPKIQAAKNGAELADVTSEVTEA
DGYTVRVYNPGQEGDIVEVDLVWNL,KNLLPLYDDIAELNWQPLTDSSES
IEKFEFHVRGDKGAEKLFFTGKLBGTIEKSNLDYTIRLDNLPAKRGVELH
AYWPRTDFASARDQGLKGNRLEENKIEDSIVREKDQSKQLVTWVLPSILS
ISLLLSVCYFIYRRKTRPSVKYAKNHRLYEPPMELEPMVLSEAVY5TSLE
EVSPLVKGAGKFTFDQLIQATLLDVIDRGNVSIISEGDAVGLRLVKEDGL
SSFEKDCLNLAFSGKICEETLSNLFADYKVSDSLYRRAKVSDEKRIQARG
LQLKSSPEEVLNQMQEGVRKRVSFWGLPDYYRPLTGGEKALQVGMGALTL
PLFIGFGLFLYSLDVNGYLYLPLPILGFLGLVLSVFYYWKLRLDNRDGVL
NBAGAEVYYLWTSFENMLRIARLDQAELESVVWNRLLVYATLFGYADKVS
HLMKVNQIQVENPDINLYVAYGWHSTYHSTAQMSHYASVANTASTYSVSS
GSGSSGGGFSGGGGGGSIGAFZ (SEQ. ID. NO. 126)
MKKVRKIFQKAVAGLCCISQLTASSIVALAETPETSPAIGKVVIKBTOEG
GALLGDAVFELKNNTDGTTVSQRTEAQTGEAIFSNIKPGTYTLTEAQPPV
GYKPSTKQWTVEVEKNGRTTVQGEQVENREEALSDQYPQTGTYPDVQTPY
QUCVDGSEKNGQHKALNPNPYERVPEGTLSKRIYQVNNLDDNQYGIELTV
SGKTVYEQKDKSVPLDVVILLDNSNSMSNIRNKNARRAERAGEATRSLID

KTSDSENRVALVTYASTIFDGTEFTVBKGVADKNGKRLNDSLFwNYDQTS
VITNTKDYSYLKLTNDKNDIVELKNKVPTEAEDHDGNRLMYQFGATFTQK
ALMKADEILTQQARQNSQKVLFHITDGVPTMSYPTNFNHATFAPSYQNQL
NAFFSKSPNKDGLLSDRTQATSGEITIVRGDGQSYQMFTDKTVYEKGAPA
AFPVKPEKYSEMKAAGYAVGDPNGGYWLNWRESILAYPFNSNTAKITNHG
DPTRWYYNGNIAPDGYDVFTVGIGINGDPGTDEATATSFMQSISSKPENY
TNVTDTRKILEQLNRYFHTIVTEKKSENGTITDPMGELIDLQLGTDGRFD
PADYTLTANDGSRLENGQAVGGPQNDGGLLKNAKVLYDRREKRIRVTGLY
LGTDEKVTLTYNVRLNDEFVSNKFYDTNGIfLRLHPKEVEQNTVRDFPIP
KIRDVRKYPEITSKEKKLGDIBFIKVNKNDKKPLRGAVFSLQKQHPDYPD
IYGAIDQNGTYQNVRTGEDGKLTFKNLSDGKYRLFENSEPAGYKPVQNKP
IVAFQIVNGEVRDVTSVPQDIPAGYEFTNDKHYRRNEPIPPKREYPRTGG
IGMLPFYLIGCMMMGGVLLYRRKHPZ (SEQ. ID. NO. 127)
MKSIINKFLTMLAALLLTASSLFSAATVFAAGTTTTSVTVHKLLATDGDM
DKIANELETGNYAGNKVGVLPANAKEIAGTLTGSKAVPIEIELPLNDVVD
AHVYPKNTEAKPKIDKDFKGKANPDTPRVDKDTPVNHQVGDVVEYEIVTK
IPALANYATANWSDRMTEGLAFNKGTVVTVDDVALEAGDYALTEVATGFD
LKLTDAGLAKVNDQNAEKTVKITYSATLNDKAIVEVPESNDVTINYGNNP
DHGNTPKPNKPNENGDLTLTKTWVDATGAPIPAGAEATFDLVNAQTGKVV
QTVTLDKNTVTVNGLDKNTEYKFVERSIKGYSADYQEITAGEIAVKNWKD
ENPKPLDTEPKVVTYGKKFVKVNDKDNRIAGAEFEWVADKDNENVVKLVS
DAQGRFEITGLLAGTYYLEETKQPAGYALLTSRQKFEVTATSYSATGQGI
EYTAGSGKDDATKVVNKKITIPQTGGIGTIIFAVAGAAIMGIAVYAYVKN
NKDEDQLAZ (SEQ. ID. NO. 128)
MTMQKMQKMSRJFFVMALCPSLVWGAHAVQAQEDHTLVLQLENYQEVVSQ
LPSRDGHRLQVWKLDDSYSYDDRVQIVRDLHSWDENKLSSFKKTSFEMTF
LENQLEVSHIPNGLYYVRSUQTDAVSYPAEPLFEMTDQTVEPLVIVAKJC
TDTMVKLIKVDQDHNRLEGVGFKLVSVARDVSEKEVPLIGEYRYSSSGQV
GRTLYTDKGEIPVRNLPLGNYRYKEVELAGYAVTTLDTDVQLVDHQLVTI
TVVNQKLPRGNVDFMKVDORTNTSLQGAMFKVMKEESGHYTPVLQNGKEV
VVTSGKDGRFRVEGLEYGTYYLWELQAPTGYVQLTSPVSFTIGKDTRKEL
VTVVKNNKRRJDVPDTGEETLVYLDACCHVVWZ (SEQ. ID. NO. 129)
MSHIYLSLFTSLLLMLGLVNVAQADEYLRIGMEAAYAPFNWTQDDDSNGA
VKIDGTNQYANGYDVQIAKKAKDLGKEPLVVKTKWEGLVPALTSGKIDMI
IAGMSAERICQEIAFSSSYYTSEPVLLVKKDSAYAS&YLDDPNGAKITSQ
QGVYLYNLL4QIPGAKICITAMGDFAQMRQALEAGVDAYVSERPEALTAE
AANSKFKMIQVEPGFKGEEDTAIAIGLRKNDNRISQINASLETSKDDQVA
LMDRMIKEQPAEATITEETSSSFFSQVAKILSENWQQLLRGAGITLLISV

TABLE 2-continued

GTIIGLIIGLAIGVFRTAPLSENKVIYGLQKLVGWVLNVYIEIRGTPMVQ
SMVIYYGTAQAFGINLDRTLAAIFIVSINTGAYMTEVRGGILAVDKGQFE
AATALGMTHNQTMRKWLPQVVRNILPATGNEFVINIKDTSVLNVISVVEL
YFSGNTVATQTYQYFQTFRIIAVIYFVLTFTVTRILRFIERRMDMDTYTR
OANQMQTEDLKZ (SEQ. ID. NO. 130)
MTQAILEIKHLKKSYGQNEVLKDSLTHKGEVISIIGSSGSGKSTFLRINL
LETPTDGQYHGQNVLEKGYDLTQYREKLGMVFQSFNLFENLNVLENTIVA
QTRVLKRIERTEAEKIAKENLEKVGMGERYWQAKPKQLSGGQKQRVALAR
ALSMNPDAILFDETSALDPEMVGEVLKIMQDLAQEGLTMIVVTHEMEFAR
DVSHRVFMDKGVLAEEGKPEDLFTNPKEDRTKEFLQRYLKZ (SEQ. ID. NO. 131)
MKKYQLLFSAVFSYLFFVFSLSQLTLIVQNYWQFSSQGNLPWIQNILSLL
FIGVMIVVLVQGHGYLFPJPPJCKWLWYSLTVLVLVQISFNVQTAKHVQS
TAEGWAVLIGYSGTNFAELGIYALFFLVPLMEELYRGLLQHAFFKRFGLD
LLLPSILFALPHFSSLPSLLDIFVFATVGIIFAGLTRYTKSIYPSYAVHV
INNIVATFPFLLTFLHRVLGZ (SEQ. ID. NO. 132)
MNKKQWLGLGLVAVAAVGLAACGNRSSRNAASSSDVKTKIVTDTGGVDDK
SFNQSAWEGLQAWGKEHNKDNGFTYFQSTSEADYANNLQQAAGSYNLIEG
VGFALNNAVKDAAKEHTDLNYYLIDDVIKDQKNVASVTFADNESGYLAGV
AAAKTTKTKQVGFVGGIESEVISRFEAGFKAGVASVDPISKVQVDYAGSF
GDAAKGKTIAAQYAAGADIVYQVAGGTGAGVFAEAKSLNESRPENEKVWI
GVDRDQEAEGKYTSKDGKESNFVLVSTLKQVGTTVKDISNKAERGEFPGG
QVIVYSLKDKGVDLAVTNLEEGKKAVEDAKAKIILDGSVKPEKZ (SEQ. ID. NO. 133)
MSKKLQQISVPLISVFLGILLGAIVMWIFGYDAIWGYEELPYTAFGSLRG
IGEIFRAMGPLVLIGLGFAVASRAGFPNVGLPGQALAGWILSGWFALSHP
DMPRPLMILATIVIALIAGGIVGAIPGILRAYLGTS2VIVTIMMNYIVLY
VGNAPIHAPPKDFMQSTDSTIRVGANATYQTPWLAELTGNSRMNIGLFFA
IIAVAVIWFMLKKTRLGFEIRAVGLNPMASEYAGISAKRTHLSMIISGAL
AGLGGAVEGLGTFQNVYVQGSSLAIGFNGMAVSLLAANSPIGILPAAFLF
GVLQVGAPGMNAAQVPSELVSIVTASIIFFVSVEYLIERPVKPKKQVKGG
KZ (SEQ. ID. NO. 134)
MGVKKLKLTSLLGSLLITACATNGVTSDITAESADWSKLVYFFAEIIRFL
SFDISIGVGUuLFRVLIRTVLLPVQVQMVASRKMQEAQPRIKALREQYPGR
DMESRTKLEQEMRKVFKEMGVRQSDSLWPILIQMPVILALFQALSRVDFL
KTGHFLWINLGSVDTRLVLPILAAVFTFLSTWLSNKALSERNGATTAMMY
GIPVLIRPAVYAPGGVALYWTVSNAYQVLQTYFLNNPFKIIAEREAVVQA
QKDLENRKRKAKKKAQKTKZ (SEQ. ID. NO. 135)
MVIDPFANELDYYLVSHFHSDHIDPYTAAAILNNPKLEHVKFIGPYHCGR
IWEGWGVKERFLVVKPGDTIELKDMKIHAVESFDRTCLVTLPVNGADETG
GELAGLAVTDEEMAQKAVNYIPETPGGTIYHGADSHFSNYFAJCHGKDFK
IDVALNNYGENPVGIQDKMTSIDLLRMAENLRTKVIIPVHYDIWSNFMAS
TNEILELwKMRKDRLQYDFHPFIwEVGGKYTYPQDQHLVEYHHPRGFDDC
FEQDSNIQFKALLZ (SEQ. ID. NO. 136)
MFLSGWLSFANYIHDLLVLFPDSPFLNAFESAIAAPLVEELSCVFVTM4P
VRXKSTLTGIASOLCFQMIKNGYIRTDLPEGFDFTISRILERJISGIASH
WTFSGLAVVGVYLLYRAYKC3QKVGKKQGLLFLGLALGTHFLFNSPFVEL
ETEIPLAIPVVTAIALYGFYMAYCFVEKHNELMTZ (SEQ. ID. NO. 137)
MKVEPRCDVLSRMSHFFIRILIMLQELVERSWAIRQAYHELEVKHHDSKV
RRVEEDLLALSNDIGNPQRLVMTKQGRYYDETPYTLEQKLSENIWWLLEL
SQRLDIDILTEMENFLSDKEKQLNVRTWKZ (SEQ. ID. NO. 138)
MLDWKQFFLAYLRSRSRLFIYLLSLAFLVLLFQFLASLGIYFLYFPPLCC
FVTLFRWDILVETQVYRQELLYGEREAKSPLEIALAEKLEAREMELYQQR
SKAERKLTDLLDYYTLWVHQIKTPIAASQLLVAEVVDRQLKQQLEQEIFI
CIDSYTNLVLQYLRLESPHDDLVLKQVQIEDLVKEIIRKYALFRQKGLNV
NLHDLDKEIVTDKJCwLLVVIIEQIISNSLKYTKEGGLEIYMDDQELCIK
DTGIGIKNSDVLRVFERGFSGYNGRLTQQSSGLGLYLSKKISEELGHQIR
IESEVGKGTRVRIQFAQVNLVLEZ (SEQ. ID. NO. 139)
MELNTHNAEILLSAANKSHYPQDELPEIALAGRSNVGKSSFINTMLNRXN
LARTSGKPGQLLNFFNIIDDKMRFVDVPGYGYARVSKKEREKWGCMIEEY
LTRRENLAVVSLVDLRHDPSADDVQMYEFLKYYEIPVRVATKADKIPRGK
WNKHESAIKKKLNFDPSDDFIILFSSVSKAGMDEAWDAILEKLZ (SEQ. ID. NO. 140)
MTKKQLHLVVTGMSGAGKTVAIQSFBDLGYFEDNMPPALLPKFLQLVEIK
EDNPKLALVVDMRSRSFFSEIQAVLDELENQDGLDPKILLDAADKELVAR
YKETRRSHPLAADGRLDGIgLRELLAPLKNMSQNVVDRRELTPRELRITL
AEQFSDQEQAQSFPJEVMSFGIKYGIPIDADLVFDVRFLPNPYYLPELRN
QTGVDEPVYDYVMNHPESEDFYQHLLALIEPILPSYQKEGKSVLTIAMGC
TGGQMRSVAFAKRLAQDLSKNWSVNEGHPDKDRRKETVNRSZ (SEQ. ID. NO. 141)
MRKPKITVIGGGTGSPVTLKSLREKDVEAAIVTVADDGGSSGELRKNMQQ
LTPPGDLRNVLVAMSDMPKFYEKVFQYRFSEDAGAFAGHPLGNLUAGLEM
QGSTYNAMQLLSKFPHRGKYPSSDHPLTLVFQTEVAGHIVDMRGIIDNEV
LHRLRPFIDTVLVNEKVPEYMNSRNRPDEYLVQVEHDFVGLCKQVSRVISS
NPLPENGGAIDLIVDELMRIQVKKZ

TABLE 2-continued (SEQ. ID. NO. 142)
MKNLIKLLIUVNLADSVFYIVALWHVSNNYSSSMFLGFIAVNYLPDLLLI
GPVDRVNPQKLLIILVQLAVAVIFTLLLNQISFWVIMSLVFSVMASSISY
VIEDVLIQVVEYDKIVFANSLFSISYKVLDSFNSFFLQVAVGILLVKIDI
GIPLLALFILLLLKRTSNANIENFSFKYYKREVLQGTHFILNNGLLFTSI
SLTLINFFYSFQTVVVPFSIRYGPIJYGIPLTGLGGILGNMLAPIVIKYL
KSNQVGVFLFLNGSSWLVAIVIKDYThSLILFFVCFMSKGVNIINSLYQQ
IPPHQLLGRVNTTIDSIISFGMPIGSLVAGTLIDLNIELVLIAISIPYFL
FSYLFYTDNGLKEFSIYZ (SEQ. ID. NO. 143)
MMSNKNKEILIFAILYTVLPMFDGVKLLASLMPSAIANYLVYVVLALYGS
FLFKDRLIQQWKEIRKTKRKFFFGVLTGWLFLILMTVVFEFVSEMLKQFV
GLDGQGLNQSNIQSTFQEQPLLIAVFACVIGPLVEELFFRQVLLHYLQER
LSGLLSIILVGLVFALTHMHSLALSEWIGAVGYLGGGLAFSIIYVKEKEN
IYYPLLVITIMLSNSLSLIILAISIVKZ (SEQ. ID. NO. 144)
LKKPIIEFKNVSKVFEDSNTCVLKDNFELEEGICYTLLGASGSGKSTILN
HAGLLDATRGDIMLDGVRINDPTIKRDVHTVFQSYALFPHMNVFENVAFP
LRLRKIDKKEIEQRVAEVLKMVQLEGYEKRSLRKLSGGQRQRVAIARAII
NQPRVVLLDEPLSALDLKLRTDMQYELRELQQRLGITFVFVTHDQEALAM
SDWTVMNDGETVQSGTPVDIYDEPINHFVATFGBSNILPGTMIEDYLVEF
NGKREAVDGGMKPNEPVEVVIRPEDLRTLPEEGKLQVKVDTQLFRGVHYE
UAYDELGNEWMIHSTRKAVGEEGLDFBPEDIHIMRLNETEEEFDAPJEEY
VEIEEQEAGLINALEEERDEENKLZ (SEQ. ID. NO. 145)
MKSMRILFLLALIQISLSSCFLWKECILSFKQSTAFFIGSMVFVSGJCAG
VNYLYTRKQEVHSVLASKKSVKLFYSMLLLNLLGAVLVLSDNLFKNLQQE
LVDFLLPSFFLFGLDLLIFLPLKXYVRDFLAMLDRXTVLVTILATLLFLR
NPMTVSLLIYIGLGLFFAAYLVPNSVKKEVSFYGHIRDLVLVIVTLIFFZ (SEQ. ID. NO. 146)
MVKKIIGMVLALLSVTVVGVGVFAYTIYQQGTETLAIZTYKKIGEETKVI
EATEPLTILLMGVURGNVERTETWVGRSDSMILMTVNPKTKRITMMSLER
DILTRIESGNGQAHEAKLNSAYADGGAELAIETIQKMMNIHIDRYVMVNM
RGLQKLVDAVGGRRVNNLGFPISSDQEENTSIGVGEQHIGGEEALVYARM
RYQDPEGDYGRQKRQREVIQKVMEKALSLNSIGHYQEILKALSDNMQTNI
DLSAKSPNLLGYPZDSFKTIETQQLQGEGEILQGVSYQIVSRAHMLEMQN
LLRRSLGQEEVTQLETNAVLFEDLFGRAPVGDEDNZ (SEQ. ID. NO. 147)
MKKQAYVUALTSFLFVFFFSHSLLEILDFDWSIFLHDVEKTEKFVFLLLV
FSMSMTCLLALFwRGIEELSLRKMQANLKRLLAGQEVVQVADPDLDASFK
SLSGKLNLLTEALQKAENQSLAQEEEIIEKERKRIARDLHDTVSQELFAA
HMILSGISQQALKLDREKMQTQLQSVTAILETAQKDLRVLLLHLRPVELE
QKSLIEGIQILLKELEDKSDLRVSLKQNMTKLPKKLEEHIFRJLQELSNT
LRHAQASCLDVYLYQTDVELQLKVVDR4GIGFQLGSLDDLSYGLRNIKER
VEDMAGTVQLLTAPKQGLAVDLRIPLLDKEZ (SEQ. ID. NO. 148)
MIVSIISQGFVWAILGLGIFMTFRILNFPDMTTEGSLPLGGAVAVTLITK
GVNPFLATLVAVGAGCLAGMAAGLLYTKGKIPTLLSGILVMTSCHSIMLL
IMGRANLGLLGTKQIQDVLPFDSDLNQLLTGLRFVSRVXALMLPLLDTKL
GQAYIATGDNPDMARSFGHTGRMELMGLVLSNGVIALAOALAQQEGYADV
SRGGVIVVGLASLIIGEVISLAEPVTIVVGSLAYQFLVWAVIAIOFNTSY
LRLYSALILAVCLMUTFKQTILKGAJCLSKZ (SEQ. ID. NO. 149)
MKKMKVWSTVLATGVALTRLAACSGGSNSTTASSSEEKADKSQELVIYSN
SVSNGRGDWLTAXAEAGFNIKMVDIAGAQLADRVLAEKNNAVADMVFGIG
AVDSNKIRDQKLLVQYKPKWLDKIDQSLSDKDNYYNPVIVQPLVLIGAPD
VKEMPKDWTELGSKYKGKYSISGLQGGTGRALASILVRYLDDKGELGVSE
KGWEVAICEYLKNAYTLQKOESSIVKMLDKEDPIQYGMMWGSGALVGQKE
QNVVPKVMTPEIGVPFVTEQTMVLSTSKKQALAKEFIDWFGQSEIQVEYS
KNFGSIPANKDALKDLPEDTKKFVDQVKPQNIDWEAVGKHLDEWVEKAEL
EYVQZ (SEQ. ID. NO. 150)
MIKFDNIQIKYGDFVAIDNLNLDHEGEFTFLGPSGCGKSTLRALVGFLDP
SSGSIEVNGTDVTHLEPEKRGIGVFQSYALFPTMTVDNIAFGLKVKKVAP
DVIKAKVSAVAAKIKISDQQLQRNVSELSGGQQQRVALARLVLEPKILCL
DEPLSNLDAKLRVDLRKELKRLQKELGRITLYVTHDQEEALTLSDRIAVF
NNGYIEQVGTPVEIYHNSQTEVCDPIGDNVLTDETVHEVLLKNTSVFLED
KKGYIRLEKVRFNRETEQDFLKGTUDVEFSGVTEHYTIKVSESQILNVTS
IDSQAARSVGESVELFITPSDVLQFZ (SEQ. ID. NO. 151)
MRHKLNLKDWLRLGLRWFLVTRIYPNFDLVVNVFVKGGESLDAVHRVLKQ
PALQSMNSPSLIVNVVGILCVLFTEYFDIKGAKZLKLGYMTSLIYGGVVL
ATGYKFVYGPYGLITKFLQNVIPSLDPNWPIGYGAVLFIMTFSGTANHTL
FLTNTHSVDYTIEARNMGKPVFRICVVLPTITLFALTIMVFLSGLSAVA
APMIVGGKEFQTINPMIITFAGMGNSRDLAALLAIILGIATTILLTIMNK
IEKGGNYISISKTKAPLKKQKIASKPWNIIAHIVAYGLFTVFMLPLIFIV
LYSPTDPVVIALNFNSLLTDFDLSVFLYHPLAQPLGITIPSAGDETATSN
AQALVF\RYTIVLMIISGTVLYPTQPJGPJVPJ CZ

TABLE 3

ID201-4106.4

(SEQ. ID. NO. 168)
ATGATAAAAAATCCTAAATTATTAACCAAGTCTTTTTTAAGAAGTTTTGC
AATTCTAGGTGGTTGGTCTAGTCATTCATATAGCTATTTATTTGACCTTT
CCTTTTTTATTATATTCAACTGGAGGGGGAAAAGTTTAATGAGAGCGCAAG

TABLE 3-continued

```
AGTGTTTACGGAGTATTTAAAGACTAAGACATCTGATGAAATTCCAAGCT
TACTCCAGTCTTATTCAAAGTCCTTGACCATATCTGCTCACCTTAAAGA
GATATTGTAGATAAGCGGCTCCCTCTTTGTGCATGACTTGGATATTAAAG
ATGGAAAGCTATCAAATTATATCGTGATGTTAGATATGTCTGTTAGTACA
GCAGATGGTAAACAOGTAACCGTGCAATTTGTTTCACGGGGTGGATGTCT
ACAAAGAAGCAAAGAATATTTTGCTTTTGTATCTCCCATATACATTTTTG
GTTACAATTGCTTTTTCCTTTGTTTTTCTTATTTTTATACTAACGCTTG
CTCAATCCTCTTTTTTACATTTCAGAAGTGACTAGTAAAATGCAAGATTT
GGATGACAATATTCGTTTTGATGAAAGTAGGAAAGATGAAGTTGGTGAAG
TTGGAAAACAGTTAATGGTATGTATGAGCACTTGTTGAAGGTTATTTATG
AGTTGGAAAGTCGTAATGAGCAAATTGTAAAATTGCAAAATCAAAGGTT
TCCTTTGTCCGCGGAGCATCACATGAGTTGAAAACCCCTTTAGCCAGTCT
TAGAATTATCCTAGAGAATATGCAGCATAATATTGGAGATTACAAAGATC
ATCCAAAATATATTGCAAAGAGTATAAATAAGATTGACCAGATGAGCCAC
TTATTAGAAGAAGTACTGGAGTCTTCTAAATTCCAAGAGTGGACAGAGTG
TCGTGAGACCTTGACTGTTAAGCCAGTTTTAGTAGATATTTTATCACGTT
ATCAAGAATTAGCTCATTCAATAGGTGTTACAATTGAAAATCAATTGACA
GATGCTACCAGGGTCGTCATGAGTCTTAGGGCATTGGATAAGGTTTTGAC
AAACCTGATTAGTAATGCAATTAAATATTCAGATAAAAATGGGCGTGTAA
TCATATCCCAGCAAGATGGCTATCTCTCTATCAAAAATACATGTGCGCCT
CTAAGTGACCAAGAACTAGAACATTTATTTGATATATTCTATCATTCTCA
AATCGTGACAGATAAGGATGAAAGTTCCGGTTTGGGTCTTTACATTGTGA
ATAATATTTTAGAAAGCTATCAAATGGATTATAGTTTTCTCCCTTATGAA
CACGGTATCGAATTTAAGATTACCTTATAG
```

(SEQ. ID. NO. 152)
MIKNPKLLTKSFLRSFAILGGVGLVIHIAIYLTFPFYYIQLEGEKFNESA
RVFTEYLKTKTSDEIPSLLQSYSKSLTISAHLKRDIVDKRLPLVHDLDIK
DGKLSNYIVMLDMSVSTADGKQVTVQFVHGVDVYKEAKNLLLLYLPYTFL
VTIAFSFVFSYFYTKRLLNPLFYISEVTSKMQDLDDNIRFDESRKDEVGE
VGKQINGMYEHLLKVIYELESRNEQIVKLQNQKVSFVRGASHELKTPLAS
LRIILENMQHNIGDYKDHPKYIAKSINKIDQMSHLLEEVLESSKFQEWTE
CRETLTVKPVLVDILSRYQELAHSTGVTTENGLTDATRVVMSLRALDKVL
TNLTSNATTCYSDJGRVIISEQDGYLSIKNTCAPLSDQELEHLFDIFYHS
QIVTDKDESSGLGLYIVNNILESYQMDYSFLPYEHGMEFKLSLZ

ID202-41069

(SEQ. ID. NO. 169)
ATGGATAAAATTATTAAAACTATATCAGAAAGCGGAGCCTTTCGTGCTTT
TGTCCTTGATAGCACTGAAACCGTCCGCACTGCTCAAGAAAAACATCAAA
CCCAAGCTAGCTCAACTGTAGCGCTTGGTCGAACTCTTATCGCTAGCCAG
ATTCTCGCAGCCAATGAAAAGGAAATACCAAACTTACAGTTAAGGTGTT
GGGATCTAGCTCTCTAGGTGCTATTATCACCGTCGCTGATACCAAGGGGA

ACGTCAAAGGCTATGTTCAAAATCCTGGTGTTGACATCAAAAAGACTGCG
ACTGGTGAAGTCCTAGTCGGACCTTTTGTTGGAAATGGTCAATTCCTCGT
TATCACAGACTACGGTACTGGAAATCCTTACAACTCTATAACTCCCCTCA
TCTCTGGAGAAATCGGTGAAGACCTTGCCTTTTACCTTACTGAAAGCCAA
CAAACGCCTTCAGCGGTCGGCCTCAATGTCCTTTTGGACGAGGAAGACAA
GGTCAAGGTTGCAGGTGGTTTCCTAGTTCAAGTCTTGCCAGGAGCCAAGA
AAGAAGAGATTGCTCGCTTTGAAAAACGCATCCAAGAAATGCCAGCTATC
TCTACTCTTCTCGAAACGTTTCCAATGTGACTGTAGCCATGAACGCTTTA
TGAACGCTCTTGCCAGCCTTCCAAGCTCAGACTTACAGGAAATGAAAGAG
GAAGACCACGGGGCAGAAATCACTTGTCAATTCTGCCAAACTACTTACAA
CTTTGATGAAAAGGACCTGGAGGAACTCATTCGTGACAAATCTTAA (SEQ. ID. NO. 153)
MDKIIKTISESGAFRAFVLDSTETVRTAQEKHQTQASSTVALGRTLIASQ
ILAANEKGNTKLTVKVLGSSSLGAIITVADTKCNV1CGYVQPCVDTKKTA
TGEVLVGPFVGNGQFLVTTDYGTG&PYNSTTPLTSGETGEDLAFYLTES
QQTPSAVGLNLLDEEDKVKVAGGFLVQVLPGAKKEETARFETCRTQEMPA
TSTLLESDDHIEALLKATYGDEAYKRLSEEEIRFQCDCSHERFMNALASL
PSSDLQEMKEEDHGAEITCQFCQTTYNFDEKDLEELLRDKSZ

ID203-4115

(SEQ. ID. NO. 170)
ATGAAATCAATAACTAAAAAGATTAAAGCAACTCTTGCAGGAGTAGCTGC
CTTGTTTGCAGTATTTGCTCCATCATTTGTATCTGCTCAAGAATCATCAA
CTTACACTGTTAAAGAAGGTGATACACTTTCAGAAATCGCTGAAACTCAC
AACACACAACAGTTGAAAAATTGGCAGAAAACAACCACATTGATAACATTCA
TTTGATTTATGTTGATCAAGAGTTGGTTATCGATGGCCCTGTAGCGCCTG
TTGCAACACCAGCGCCAGCTACTTATGCGGCACCAGCCGCTCAAGATGAA
ACTGTTTCAGCTCCAGTAGCAGAAACTCCAGTAGTAAGTGAAACAGTTGT
TTCAACTGTAAGCGGATCTGAAGCAGAAGCCAAAGAATGGATCGCTCAAA
AAGAATCAGGTGGTAGTATACAGCTACAAATGGACGTTATATCGGACGTT
ACCAATTAA (SEQ. ID. NO. 154)
MKSITKKIKATLAGVAALFAVFAPSFVSAQESSTYTVKEGDTLSEIAETH
NTTVEKLAENNHTDNTHLTYVDQELVIDGPVAPVATPAPATYAAPAAQDE
TVSAPVAETPVVSETVVSTVSGSEAEAKEWIAQKESGGSIQLQMDVISDV
TNZ

ID204-4111.7

(SEQ. ID. NO. 171)
ATGAATTTAGGAGAATTTTGGTACAATAAAATAAATAAGAACAGAGGAAG
AAGGTTAATGAAGAAAGTAAGATTTATTTTTTTAGCTCTGCTATTTTTCT
TAGCTAATCCAGAGGGTGCAATGGCTAGTGATGGTACTTGGCAAGGAAAA
CAGTATCTGAAAGAAGATGGCAGTCAAGCAGCAAATGAGTGGGTTTTGA
TACTCATTATCAATCTTGGTTCTATATAAAAGCAGATGCTAACTATGCTG
AAAATGAATGGCTAAAGCAAGGTGACGACTATTTTTACCTCAAATCTGGT
```

TABLE 3-continued

```
GGCTATATGGCCAAATCAGAATGGGTAGAAGACAAGGGAGCCTTTTATTA
TCTTGACCAAGATGGAAAGATGAAAAGAAATGCTTGGGTAGGAACTTCCT
ATGTTGGTGCAACAGGTGCCAAAGTAATAGAAGACTGGGTCTATGATTCT
CAATACGATGCTTGGTTTTATATCAAAGCAGATGGACAGCACGCAGAGAA
AGAATGGCTCCAAATTAAAGGGAAGGACTATTATTTCAAATCCGGTGGTT
ATCTACTGACAAGTCAGTGGATTAATCAAGCTTATGTGAATGCTAGTGGT
GCCAAAGTACAGCAAGGTTGGCTTTTTGACAAACAATACCAATCTTGGTT
TTACATCAAAGAAAATGGAAACTATGCTGATAAAGAATGGATTTTCGAGA
ATGGTCACTATTATTATCTAAAATCCGGTGGCTACATGGCAGCCAATGAA
TGGATTTGGGATAAGGAATCTTGGTTTTATCTCAAATTTGATGGGAAAAT
GGCTGAAAAGAATGGGTCTACGATTCTCATAGTCAAGCTTGGTACTACT
TCAAATCCGGTGGTTACATGACAGCCAATGAATGGATTTGGGATAAGGAA
TCTTGGTTTTATCTCAAATCTGATGGGAAAATAGCTGAAAAGAATGGGT
CTACGATTCTCATAGTCAAGCTTGGTACTACTTCAAATCCGGTGGTTACA
TGACAGCCAATGAATGGATTTGGGATAAGGAATCTTGGTTTTACCTCAAA
TCTGATGGGAAAATAGCTGAAAAGAATGGGTCTACGATTCTCATAGTCA
AGCTTGGTACTACTTCAAATCTGGTGGCTACATGGCGAAAAATGAGACAG
TAGATGGTTATCAGCTTGGAAGCGATGGTAAATGGCTTGGAGGAAAAACT
ACAAATGAAAATGCTGCTTACTATCAAGTAGTGCCTGTTACAGCCAATGT
TTATGATTCAGATGGTGAAAAGCTTTCCTATATATCGCAAGGTAGTGTCG
TATGGCTAGATAAGGATAGAAAAGTGATGACAAGCGCTTGGCTATTACT
ATTTCTGGTTTGTCAGGCTATATGAAAACAGAAGATTTACAAGCGCTAGA
TGCTAGTAAGGACTTTATCCCTTATTATGAGAGTGATGGCCACCGTTTTT
ATCACTATGTGGCTCAGAATGCTAGTATCCCAGTAGCTTCTCATCTTTCT
GATATGGAAGTAGGCAAGAAATATTATTCGGCAGATGGCCTGCATTTTGA
TGGTTTTAAGCZTGAGAATCCCTTCCTTTTCAAAGATTTAACAGAGGCTA
CAAACTACAGTGCTGAAGAATTGGATAAGGTATTTAGTTTGCTAAACATT
AACAATAGCCTTTTGGAGAACAAGGGCGCTACTTTTAAGGAAGCCGAAGA
ACATTACCATATCAATGCTCTTTATCTCCTTGCCCATAGTGCCCTAGAAA
GTAACTGGGGAAGAAGTAAAATTGCCAAAGATAAGAATAATTTCTTTGGC
ATTACAGCCTATGATACGACCCCTTACCTTTCTGCTAAGACATTTGATGA
TGTGGATAAGGGAATTTTAGGTGCAACCAAGTGGATTAAGGAAAATTATA
TCGATAGGGGAAGAACTTTCCTTGGAAACAAGGCTTCTGGTATGAATGTG
GAATATGCTTCAGACCCTTATTGGGCGAAAAAATTGCTAGTGTGATGAT
GAAAATCAATGAAAGCTAGGTGGCAAAGATTAG
```

(SEQ. ID. NO. 155)
MNLGEFWYNKINKNRGRRLMKKVRFIFLALLFFLASPEGAMASDGTWQGK
QYLKEDGSQAANEWVFDTHYQSWFYIKADANYAENEWLKQGDDYFYLKSG
GYMAKSEWVEDKGAFYYLDQDGKMKRNAWVGTSYVGATGAKVIEDWVYDS
QYDAWFYIKADGQHAEKEWLQIKGKDYYFKSGGYLLTSQWINQAYVNASG

AKVQQGWLFDKQYQSWFYTKFNGNYADKEWIFENGHYYYLKSGGYMAANE
WIWDKESWFYLKEDGKMAEKEWVYDSHSQAWYYFKSGGYMTANEWTWDKE
SWFYLKSDGKIAEKEWVYDSHSQAWYYFKSGGYMTANEWIWDKESWFYLK
SDGKIAEKEWVYDSHSQAWYYFKSGGYMAKNETVDGYQLGSDGKWLGGKT
TNENAAYYQVVPVTANVYDSDGEKLSYISQGSVVWLDKDRKSDDKRLAIT
ISGLSGYMKTEDLQALDASKDFIPYYESDGHRFYHYVAQNASIPVASHLS
DMEVGKKYYSADGLHFDGFKLENPFLFKDLTEATNYSAEELDKVFSLLNI
NNSLLENKGATFKEAEEHYHINALYLLAHSALESNWGRSKIAKDKNNFFG
ITAYDTTPYLSAKTFDDVDKGILGATKWIKENYIDRGRTFLGNKASGMNV
EYASDPYWGEKIASVMMKINEKLGGKDZ

ID205-41181.1
(SEQ. ID. NO. 172)
```
ATGAAAAAATTAGGTACATTACTCGTTCTCTTTCTTTCTGCAATCATTCT
TGTAGCATGTGCTAGCGGAAAAAAAGATACAACTTCTGGTCAAAAACTAA
AAGTTGTTGCTACAAACTCAATCATCGCTGATATTACTAAAAATATTGCT
GGTGCAAAATTGACCTTCATAGTATCGTTCCGATTGGGCAAGACCCACAC
GAATACGAACCACTTCCTGAAGACGTTAAGAAAACTTCTGAGGCTAAATT
TGATTTTCTATAACGGTATCAACCTTGAAACAGGTGGCAATGCTTGGTTT
ACAAAATTGGTAGAAAATGCCAAGAAAACTGAAAACAAAGACTACTTCGC
AGTCAGCGACGGCGTTGATGTTATCTACCTTGAAGGTCAAAATGAAAAAG
GAAAAGAAGACCCACACGCTTGGCTTAACCTTGAAAACGGTATTATTTTT
GCTAAAAATATCGCCAAACAATTGAGCGCCAAAGACCCTAACAATAAAGA
ATTCTCATGAAAAAAATCTCAAAGAATATACTGATAAGTTAGACAAACTT
GATAAAGAAAGTAAGGATAAATTTAATAAGATCCCTGCTGAAAAGAAACT
CCATTGTAACCAGCGAAAGGAGCATTCAAATACTTCTCTAAAGCCTATGG
TGTCCCAAGTGCTTTACATCTGGGAAATCAATACTGAAGAAGAAGGAACT
CCTGAACAAATCAAGACCTTGGTTGAAAAACTTCGCCAAACAAAACTTCC
ATCACTCTTTGTAGAATCAAGTGTGGATGACCGTCCAATGAAAACTGTTT
CTCAAGACACAAACATCCCAATCTACGCTCAAATCTTTACTGACTCTATC
GCAGAACAAGGTCCCGAAGGCGACAGCTACTACAGCATGATGAAATACAA
CCTTGACAAGATTGCTGAAGGATTGGCAAAATAA
```

(SEQ. ID. NO. 156)
MKKLGTLLVLFLSAIILVACASGKKDTTSGQKLKVVATNSIIADITKNIA
GDKIDLHSIVPIGQDPHEYEPLPEDVKKTSEANLIFYNGINLETGGNAWF
TKLVENAKKTENKDYFAVSDGVDVIYLEGQNEKGKEDPHAWLNLENGIIF
AKNIAKQLSAKDPNNKEFYEKNLKEYTDKLDKLDKESKDKENKIPAEKKL
IVTSEGAFKYFSKAYGVPSAYIWEINTEEEGTPEQIKTLVEKLRQTKVPS
LFVESSVDDRPMKTVSQDTNIPIYAQIFTDSIAEQGKEGDSYYSMMKYNL
DKIAEGLAKZ

TABLE 3-continued

ID206-41191.1
(SEQ. ID. NO. 173)
ATGGAATGGTATAAAAAAATCGGACTTCTTGCAACTACAGGTTTAGCTTT
GTTTGGGCTCGGCGCTTGCTCCAACTATGGTAAATCTGCGGATGGCACAG
TGACCATCGAGTATTTCAACCAGAAAAAAGAAATGACCAAAACCTTGGAA
GAAATCACTCGTGATTTTGAGAAGGAAAACCCTAAGATCAAGGTCAAAGT
CGTCAATGTACCAAATGCTGGTGAAGTATTGAAGACACGCGTTCTCGCAG
GAGATGTGCCTGATGTGGTCAATATTTACCCACAGTCCATCGAACTGCAA
GAATGGGCAAAAGCAGGTGTTTTTGAAGATTGACCAACAAAGACTACCTG
AAACGCGTGAAAATGGCTACGCTGAAAAATATGCTGTAAACGAAAAAGTT
TACAACGTTCCTTTTACAGCTAATGCTTATGGAATTTACTACAACAAAGA
TAAATTCGAAGAACTGGGCTTGAAGGTTCCTGAAACCTGGGATGAATTTG
AACAGTTAGTCAAAGATATCGTTGCTAAAGGACAAACACCATTTGGAATT
GCAGGTGCAGATGCTTGGACACTCAATGGTTACAATCAATTAGCCTTTGC
GACAGCAACAGGTGGAGGAAAAGAAGCAAATCAATACCTTCGTTATTCTC
AACCAAATGCCATTAAATTGTCGGATCCGATTATGAAAGATGATATCAAG
GTCATGGACATCCTTCGCATCAATGGATCTAAGCAAAAGAACTGGGAAGG
TGCTGGCTATACCGATGTTATCGGAGCCTTCGCACGTGGGGATGTCCTCA
TGACACCAATGGGTCTTGGCGATCACAGCGATTAATGAACAAAAACCGA
ACTTTAAGATTGGGACCTTCATGATTCCAGGAAAAGAAAAAGGACAAAGC
TTAACCGTTGGTGCGGGAGACTTGGCATGGTCTATCTCAGCCACCACCAA
ACATCCAAAAGAAGCCAATGCCTTTGTGGAATATATGACCCGTCCAGAAG
TCATGCAAAATACTACGATGTGGACGGATCTCCAACAGCGATCGAAGGG
GTCAAACAAGCAGGAGAAGATTCACCGCCTTGCTGGTATGACCGAATATG
CCTTTACGGATCGTCACTTGGTCTGGTTGCAACAATACTGGACCAGTGAA
GCAGACTTCCATACCTTGACCATGAACTATGTCTTGACCGGTGATAAACA
AGGCATGGTCAATGATTTGAATGCCTTCTTTAACCCGATGAAAGCGGATG
TGGATTAG (SEQ. ID. NO. 157)
MEWYKKIGLLATTGLALFGLGACSNYGKSADGTVTIEYFNQKKEMTKTLE
EITRDFEKENPKIKVKVVNVPNAGEVLKTRVLAGDVPDVVNIYPQSIELQ
EWAKAGVFEDLSNKDYLKRVKNGYAEKYAVNEKVYNVPFTANAYGIYYNK
DKFEELGLKVPETWDEFEQLVKDIVAKGQTPFGIAGADAWTLNGYNQLAF
ATATGGGKEANQYLRYSQPNAIKLSDPIMKDDIKVMDILRTNGSKQKNWE
GAGYTDVIGAFARGDVLMTPNGSWAITAINEQKPNFKIGTFMIPGKEKGQ
SLTVGAGDLAWSISATTKHPKEANAFVEYMTRPEVMQKYYDVDGSPTAIE
GVKQAGEDSPLAGMTEYAFTDRHLVWLQOYWTSEADFHTLTMNYVLTGDK
QGMVNDLNAFFNPMKADVDZ

ID207-4123.1
(SEQ. ID. NO. 174)
ATGAAGAAAATCAAACCGCATTGGACCGTTACCAAGTCAGACTCAGCTAG
CTTATCTGGGAGATGAACTAGCAGCTTTTATCCACTTCGGTCCTAATACC

TABLE 3-continued

TTTTATGACCAAGAATGGGGGACTGGACAGGAGGATCCTGAGCGCTTTAA
CCCGAGTCAGTTGGATGCGCGTGAGTGGGTTCGTGTGCTCAAGGAAACGG
GCTTCAAAAAGTTGATTTTGGTGGTCAAGCACCACGATGGCTTTGTCCTT
TATCCGACAGCTCACACAGATTATTCGGTTAAGGTCAGTCCTTGGAGGAG
AGGAAAGGGCGAGTTGCTCCTTGAAGTATCCCAAGCTGCCACAGAGTTTG
ATATGGATATGGGGGTCTACCTGTCACCGTGGGATGCCCATAGTCCCCTC
TATCATGTGGACCGAGAAGCGGACTACAATGCCTATTATCTGGCTCAGTT
GAAGGAAATCTTATCAAATCCTAACTATGGGAATGCTGGTAAGTTCGCTG
AGGTTTGGATGGATGTGCCAGAGGAGAGGGCGCGCAAAAGGTTAATTAT
GAATTTGAAAATGGTTTGAAACCATTCGTGACCTGCAGGGCGATTGCTT
GATTTTTTCAACAGAAGGCACCAGTATCCGCTGGATTGGCAATGAACGAG
GGTATGCAGGTGATCCACTGTGGCAAAAGGTGAATCCTGATAAACTAGGA
ACAGAAGCAGAGCTGAACTATCTTCAGCACGGGGATCCCTCGGGCACGAT
TTTTTCAATCGGAGAGGCAGATGTTTCCATCCGTCCAGGCTGGTTCTACC
ATGAGGATCAGGATCCTAAGTCTCTCGAGGAGTTGGTCGAAATCTACTTT
CACTCAGTAGGGCGAGGAACTCCACTCTTGCTTAATATTCCGCCGAATCA
AGCTGGGCTCTTTGATGCAAAGGATATTGAACGACTTTATGAATTTGCGA
CCTATCGCAATGAGCTCTATAAAGAAGATTTGGCTCGGGAGCTGAGGTA
TCTGGTCCAGCTCTTTCCGCAGACTTTGCTTGTCGCCATTTGACAGACGG
CCTTGAGACCAGCTCTTGGGCAAGCGATGCAGACTTGCCCATCCAGTTAG
AACTCGACTTAGGTTCTCCTAAAACTTTTGATGTAATTGAGTTAAGAGAA
GATTTGAAGCTAGGGCCCGAATCGCTGCTTTTCATGTGCAAGTAGAGGTG
GATGGTGTCTGGCAGGAGTTTGGTTCGGGTCATACTGTTGGTTACAAACG
TCTCTTACGAGGAGCAGTTGTTGAGGCACAGAAGATACGTGTAGTCATTA
CAGAATCACAGGCCTTTGCCTTTGTTGACCAAGATTTCCCTTTATAAAAC
TCCTGGATTATCAAAAAAAGAAGTTGTTCAGGAACTAGCATTTGCAGAAA
AAAGCCTAGCTGTGGCAAAGGGAGAAAATGCCTATTTTACAGTTAAGCGC
AGAGAATGTAGTGGTCCTTTAGAAGCTAAGATTTCGATTCAACCGGGGAC
AGGTGTCCATGGTGTCGCCTATCAGGATGAGATTCAAGTCCTTGCGTTTC
AAACTGGTGAGACTGAAAAAAGTCTGACGCTACCAACCTTGTATTTCGCA
GGAGATAAAACCTTGGATTTCTATCTGAACCTAACGGTGGATGGTCAGCT
TGTGGATCAACTTCAAGTCCAAGTTTCATAA (SEQ. ID. NO. 158)
MKKIKPHGPLPSQTQLAYLGDELAAFIHFGPNTFYDQEWGTGQEDPERFN
PSQLDAREWVRVLKETGFKKLILVVKHHDGFVLYPTAHTDYSVKVSPWRR
GKGDLLLEVSQAATEFDMDMGVYLSPWDAHSPLYHVDREADYNAYYLAQL
KEILSNPNYGNAGKFAEVWMDGARGEGAQKVNYEFEKWFETIRDLQGDCL
IFSTEGTSTRWIGNERGYAGDPLWQKVNPDKLGTEAELNYLQHGDPSGTL
FSIGEADVSIRPGWFYHEDQDPKSLEELVEIYFHSVGRGTPLLLNIPPNQ
AGLFDAKDIERLYEFATYRNELYKEDLALGAEVSGPALSADFACRHLTDG

TABLE 3-continued

LETSSWASDADLPIQLELDLGSPKTFDVIELREDLKLGQRIAAFHVQVEV
DGVWQEFGSGHTVGYKRLLRGAVVEAQKTRVVTTESQALPLLTKTSLYKT
PGLSKKEVVQELAFAEKSLAVAKGENAYFTVKRRECSGPLEAKISIQPGT
GVHGVAYQDEIQVLAFQTGETEKSLTLPTLYFAGDKTLDFYLNLTVDGQL
VDQLQVQVSZ

ID208-4125.12
(SEQ. ID. NO. 175)
ATGCTTGAAAGACTGAAAAGAATACATTATATGTTTTGGATCAGTTTAAT
TTTTATGATTTTCCCCATCCTGTCTGTAGTGACTGGGTGGCTTTCTGCCT
GGCATTTATTGATTGATATTCTATTTGTAGTGGCATATTTGGGTGTTTTA
ACAACTAAGAGCCAGCGCCTATCTTGGCTATATTGGGGCCTCATGCTGAC
TTATGTAGTTGGGAATACTGCCTTTGTTGCTGTTAATTATATCTGGTTTT
TCTTTTTCCTATCCAATCTCTTAAGTTATCATTTCAGCGTACGTAGTTTA
AAGTCTTTACATGTCTGGACTTTTCTTCTTGCTCAAGTCCTTGTTGTGGG
GCAACTGTTGATTTTTCAGAGAATCGAAGTTGAGTTTCTATTCTATCTAC
TTGTAATTCTTACTTTTGTCGATTTAATGACTTTTGGATTGGTTCGGATT
CGTATTGTCGAGGATTTGAAAGAAGCTCAGGTCAAGCAAAATGCTCAGAT
AAATCTATTGCTTGCTGAAAATGAACGTAGTCGTATCGGTCAGGATTTGC
ATGATAGTCTGGACATACCTTTGCTATGCTGAGTGTCAAGACAGATTTA
GCCTTGCAGTTATTTCAGATGGAGCTTATCCACAGGTGGAAAGGAATTAA
AGAAATTCACCAGATAGCAGGATCCATGA (SEQ. ID. NO. 159)
MLERLKRTHYMFWTSLTFMTFPTLSVVTGWLSAWHLLTDTLFVVAYLGVL
TTKSQRLSWLYWGLMLTYVVGNTAFVAVNYIWFFFFLSNLLSYHFSVRSL
KSLHVWTFLLAQVLVVGQLLIFQRIEVEFLFYLLVILTFVOLMTFGLVRI
RIVEDLKEAQVKQNAQINLLLAENERSRIGQDLHDSLGHTFAMLSVKTDL
ALQLFQMEAYPQVEKELKEIHQISKDPZ

ID209-4126.3
(SEQ. ID. NO. 176)
ATGAATGATAAGTTAAAAATCTTCTTGTTGCTAGGAGTATTTTTTCTAGC
CATAACCGGTTTCTATGTTCTATTGATACGAAATGCAGGGCAGACAGATG
CCTCGCAAATTGAAAAGGCGGCAGTTAGCCAAGGAGGAAAAGCAGTGAAA
AAAACAGAAATTAGTAAAGACGCAGACTTGCACGAAATTTATCTAGCTGG
AGGTTGTTTCTGGGGAGTGGAGGAATATTTCTCACGTGTTTCCGGGGTG
ACGGATGCCGTTTCAGGCTATGCAAATGGTAGAGGAGAAACAACCAAGTA
CGAATTGATTAACCAAACAGGTCATGCAGAAACCGTCCATGTCACCTATG
ATGCCAAGCAAATTTCTCTCAAGGAAATCCTGCTTCACTATTTCCGCATT
ATCAATCCAACCAGCAAA)*ATAAACAAGGAAATGATGTGGGGACCCAGT
ACCGTACTGGTGTTTATTACACAGATGACAAGGATTTGGAAGTGATTAAC
CAAGTCTTTGATGAGGTGGCTAAGAAATACGATCAACCTCTAGCAGTTGA
AAAGGAAAACTTGAAGAATTTTGTGGTGGCTGAGGATTACCATCAAGACT
ATCTAAAGAAAAATCCAAATGGCTACTGCCATATCAATGTTAATCAGGCG

TABLE 3-continued

GCCTATCCTGTCATTGATGCCAGCAAATATCCAAAACCAAGTGATGAGGA
ATTGAAAAAGACCCTGTCACCTGAGGAGTATGCAGTTACCCAGGAAAATC
AAACAGAACGAGCTTTCTCAAACCGTTACTGGGATAAATTTGAATCCGGT
ATCTATGTGGATATAGCAACTGGGGAACCTCTCTTTTCATCAAAAGACAA
ATTTGAGTCTGGTTGTGGCTGGCCTAGTTTTACCCAACCCATCAGTCCAG
ATGTTGTCACCTACAAGGAAGATAAGTCCTACAATATGACGCGTATGGAA
GTGCGGAGCCGAGTAGGAGATTCTCACCTTGGGCATGTCTTTACGGATGG
TCCACAGGACAAGGGCGGCTTACGTTACTGTATCAATAGCCTCTCTATCC
GCTTTATTCCCAAAGACCAAATGGAAGAAAAAGgcTACGCTTATTTACTA
GATTATGTTGATTAA (SEQ. ID. NO. 160)
MNDKLKIFLLLGVFFLALTGFYVLLIRNAGQTDASQLEKAAVSQGGKAVK
KTEISKDADLHETYTAGGCFWGVEEYFSRVPGVTDAVSGYANGRGETTKY
ELINQTGHAETVHVTYDAKQISLKEILLHYFRIINPTSKNKQGNDVGTQY
RTGVYYTDDKDLEVINQVFDEVAKKYDQPLAVEKENLKNFVVAEDYHQDY
LKKNPNGYCHINVNQAAYPVIDASKYPKPSDEELKKTLSPEEYAVTQENQ
TERAFSNRYWDKFESGIYVDIATGEPLFSSKDKFESGCGWPSFTQPISPD
VVTYKEDKSYNMTRMEVRSRVGDSHLGMVFTDGPQDKGGLRYCINSLSIR
FIPKDQMEEKGYAYLLDYVDZ

ID210-4127.1
(SEQ. 1ID. NO. 177)
ATGAAAAAGAAATGGATGTATTATGCTGCTTGTTCTTCTAATGAATCTGC
CGATGACAGTTCATCTGATAAAGGAGACGGCGGTTCGCTAGTCGTTTATT
CACCAAACTCAGAGGGCTTAATTGGAGCAACTATTCCTGCCTTTGAAGAA
AAATATGGTATCAAAGTAGAACTGATTCAAGCTGGTACTGGAGAACTTTT
CAAAA)ACTAGAGTCAGAAAAAGAAGTTCCTGTAGCTGATGTTATCTTTG
GTGGTTCTTATACACAATATACTACCCACGGAGAACTCTTTGAAAACTAT
ACTTCAAAAGAAAATGATAATGTTATCAAAGAATATCAAAACACAACTCG
CTACTCTACTCCTTATACACTAGATGGTAGTGTTTTAATCGTCAACCCTG
ATTTAACTAAAGGCATGAACATCGAAGGATATAACGATCTTTTCAAACCT
GAACTAAAGGAAAATCGCAACTGCTGACCCAGCAAACTCTTCTAGCGC
CTTTGCTCAATTAACAAATATGCTACAAGCTCAAGGTGGTTAACAAAGAT
GATAAGGCTTGGTCTTATGTAAAAGATCTTTTCACACTTATTGATGGTAA
AATCGGTTCAGTTCATCTAGTGTCTATAAAGTAGTCGCTGATGGAGAAAT
GGCTGTTGGTCTCTCTTATGAAGATCCAGCAGTTAAACTCTTAAATGACG
GAGCTAACATTAAGGTAGTCTATCCAAAAGAAGGAACCGTCTTCCTACCT
GCTAGTGCTGCTATCGTTAAAAAATCTAAAAATATGGAAAATGCCAAGAA
ATTTATCGATTTTATTATCTCTCAAGAAGTACAAGATACACTTGGTACAA
CCACTACTAACCGTCCTGTTCGTAAAAATGCTAAAACAAGCGAAAACATG
AAACCAATTGACAAAATCAAAACACTCACTGAAGATTATGATTATGTCAT

TABLE 3-continued

```
CAAGAATAAATCAGATATCGTTAAGAAATACAACGAAGTCTTTACAGATA
TCCAATCTAAACAGTAA
```

(SEQ. ID. NO. 161)
MKKKWMYYAACSSNESADDSSSDKGDGGSLVVYSPNSEGLIGATIPAFEE
KYGIKVELIQAGTGELFKKLESEKEVPVADVIFGGSYTQYTTHGELFENY
TSKENDNVIKEYQNTTGYSTPYTLDGSVLTVNPDLTKGMNIEGYNDLFKP
ELKGKIATADPANSSSAFAQLTNMLQAQGGYKDDKAWSYVKDLFTLIDGK
IGSSSSSVYKVVADGEMAVGLSYEDPAVKLLNDGANIKVVYPKEGTVFLP
ASAAIVKKSKNMENAKKFIDFIISQEVQDTLGTTTTNRPVRKNAKTSENM
KPIDKIKTLTEDYDYVIKNKSDIVKKYNEVFTDIQSKQZ

ID211-4127.2

(SEQ. ID. NO. 178)
```
ATGAGTGAGATCAAAATTATTAACGCCAAAAAAATCTACCACGATGTCCC
TGTTATTGAGAATTTGAACATTACAATTCCAAAAGGAAGTCTCTTTACCC
TTCTTGGAGCTTCAGGATGTGGGAAAACGACCCTTCTTCGTATGATTGCA
GGTTTCAACAGTATCGAAGGTGGAGAATTTTACTTCGATGATACAAAAAT
CAATAATATGGAACCCAGCAAACGCAATATCGGGATGGTTTTCCAAAACT
ACGCTATTTTCCCACATTTGACTGTCCGAGACAACGTTGCTTTTGGTCTT
ATGCAAAAGAAGGTTCCAAAAGAAGAATTGATTCAACAGACCAACAAGTA
TCTTGAACTCATGCAAATTGCTCAATATGCGGATCGAAAGCCCGATAAAC
TCAGTGGTGGACAACAACAACGTGTCACCTTGGCATGCGCCTTAGCGGTT
AATCCAAGTGTTCTCCTCATGGACGAGCCACTTAGTAATCTGGAGGCCAA
ACTTCGCTTGGATATGCGTCAAGCCATCCGAGAAATCCAACACGAAGTGG
GAATTACAACTGTTTATGTAACCCACGACCAAGAAGAAGCCATGGCTATT
TCAGACCAAATTGCTGTTATGAAAGATGGGGTGATCCAACAAATCGGCCG
ACCAAAAGAACTCTATCATAAACCAGCTAATGAGTTTGTGGCAACCTTTA
TCGGACGCACAAATATTATCCCTGCCAATCTTGAAAAACGGAGCGACGGC
GCTTATATCGTCTTTTCAGATGGCTATGCCCTTCGAATGCCAGCTCTTGA
TCAGGTTGAGGAGCAAGCTATTCATGTAAGCATTCGTCCCGAAGAGTTTA
TCAAAGATGAATCTGGAGATATTGAAGGAACTATTAGAGATAGCGTCTAT
CTTGGACTAAATACGGATTATTTCATTGAGACAGGTTTTGCCTCAAAAAT
TCAAGTTAGTGAAGAATCAACTTTTGAAGAAGATCTACAAAAAGGCAATC
GTATTCGTCTACGAATCAATACGCAAAAATTAAACATCTTTTCTGCAGAT
GGTTCCCAAAACCTGATAAAAGGAGTCAACCATGAACGTAA
```

(SEQ. ID. NO. 162)
MSEIKIINAKKIYHDVPVLENLNITIPKGSLFTLLGASGCGKTTLLRMIA
GFNSIEGGEFYFDDTKINNMEPSKRNIGMVFQNYAIFPHLTVRDNVAFGL
MQKKVPKEELIQQTNKYLELMQIAQYADRKPDKLSGGQQQRVTLACALAV
NPSVLLMDEPLSNLEAKLRLDMRQAIREIQHEVGITTVYVTHDQEEAMAI
SDQIAVMKDGVIQQIGRPKELYHKPANEFVATFIGRTNIIPANLEKRSDG
AYWFSDGYALRMPALDQVEEQAIHVSIRPEEFIKDESGDIEGTRDSVYLG
LNTDYFIETGFASKIQVSEESTFEEDLQKGNRIRLRINTQKLNIFSADGS
QNLIKGVNHGTZ

ID212-4136.1

(SEQ. ID. NO. 179)
```
ATGAAGAAAAAATTATTGGCAGGTGCCATCACACTATTATCAGTAGCAAC
TTTAGCACGTTGTTCGAAAGGGTCAGAAGGTGCAGACCTTATCAGCATGA
AAGGGGATGTCATTACAGAACATCAATTTTATGAGCAAGTGAAAACGAAC
CCTTCAGCCCAACAAGTCTTGTTAAATATGACCATCCAAAAAGTTTTTGA
AAAACAATATGGCTCAGAGCTTGATGATAAAGAGGTTGATGATACTATTG
CCGAAGAAAAAAAACAATATGGCGAAAACTACCAACGTGTCTTGTCACAA
GCAGGTATGACTCTTGAAAACACGTAAAGCTCAAATTCGTACAAGTAAATT
AGTTGAGTTGGCAGTTAAGAAGGTAGCAGAAGCTGAATTGACAGATGAAG
CCTATAAGAAAGCCTTTGATGAGTACACTCCAGATGTAACGGCTCAAATC
ATCCGTCTTAATAATGAAGATAAGGCCAAAGAAGTTCTCGAAAAAGCCAA
GGCAGAAGGTGCTGATTTTGCTCAATTAGCCAAAGATAATTCAACTGATG
AAAAAACAAAAGAAAATGGTGGAGAAATTACCTTTGATTCTGCTTCAACA
GAAGTACCTGAGCAAGTCAAAAAAGCCGCTTTCGCTTTAGATGTGGATGG
TGTTTGTGATGTGATTACAGCAACTGGCACACAAGCCTACAGTAGCCAAT
ATTACATTGTAAAACTCACTAAGAAAACAGAAAAATCATCTAATATTGAT
GACTACAAAGAAAAATTAAAAACTGTTATCTTGACTCAAAAACAAAATGA
TTCAACATTTGTTCAAAGCATTATCGGAAAAGAATTGCAAGCAGCCAATA
TCAAGGTTAAGGACCAAGCCTTCCAAAATATCTTTACCCAATATATCGGT
GGTGGAGATTCAAGCTCAAGCAGTAGTACATCAAACGAATAG
```

(SEQ. ID. NO. 163)
MKKKLLAGAITLLSVATLAACSKGSEGADLISMKGDVITEHQFYEQVKSN
PSAQQVLLNMTIQKVFEKQYGSELDDKEVDDTIAEEKKQYGENYQRVLSQ
AGMTLETRKAQIRTSKLVELAVKKVAEAELTDEAYKKAFDEYTPDVTAQI
IRLNNEDKAKEVLEKAKAEGADGAQLAKDNATDEKTKENGGEITFDSAST
EVPEQVKKAAFALDVDGVSDVITATGTQAYSSQYYIVKLTKKTEKSSNID
DYKEKLKTVILTQKQNDSTFVQSIIGKELQAANIKVKDQAFQNWTQYIGG
GDSSSSSSTSNEZ

ID213-4137.3

(SEQ. ID. NO. 180)
```
ATGAAAAAAAATATTAAACAATATGTAACCTTAGGTACTGTAGTGGTATT
ATCAGCATTTGTTGCTAACTCAGTTGCAGCTCAGGAGACTGAAACTTCTG
AAGTATCAACACCAAAGTTGGTGCAACCTGTTGCACCAACGACTCCGATT
TCGGAAGTACAACCTACATCGGATAACTCTTCGGAAGTTACTGTACAACC
TCGAACAGTTGAAACTACTGTTAAGGATCCATCTTCTACAGCGGAAGAAA
CTCCTGTCTTAGAAAAAAATAATGTTACTTTAACAGGGGCGGAGAAAAT
GTTACTAAAGAGTTAAAGGATAAATTTACTAGCGGTGACTTTACTGTAGT
GATTAAGTACAATCAGTCAAGTGAGAAAGGCTTACAAGCTCTGTTTGGAA
TATCTAATTCCAAACCCGGTCAACAAAATAGTTATGTAGATGTGTTCCTT
```

TABLE 3-continued

```
AGAGACAATGGTGAGTTGGGGATGGAAGCGCGTGATACTTCTTCCAATAA
AAATAACCTAGTATCCAGACCTGCTTCAGTTTGGGGTAAGTACAAACAAG
AGGCTGTGACTAACACTGTTGCAGTAGTAGCAGATTCAGTCAAAAAACA
TATTCTTTATACGCAAATGGTACAAAAGTAGTAGAAAAGAAAGTGGATAA
TTTCCTAAACATCAAGGATATTAAAGGTATTGATTACTATATGCTTGGGG
GAGTGAAACGTGCAGGAAAAACGGCGTTTGGTTTTAACGGAACACTAGAA
AATATCAAATTCTTTAATAGTGCATTGGATGAAGAAACTGTTAAAAAGAT
GACAACAAACGCTGTTACTGGACATTTAATTTATACGGCTAATGATACAA
CAGGTTCTAACTATTTCCGTATTCCAGTTCTGTATACTTTTAGCAATGGT
CGGGTATTTTCAACGATTGACGCTCGTTACGGTGGAACTCATGATTTCTT
GAATAAATTAATATTGCTACAAGTTATAGTGATGATAATGGTAAGACATG
GACTAAACCAAAATTAACATTGGCATTCGATGATTTTGCGCCAGTACCAT
TAGAATGGCCTCGTGAAGTTGGTGGACGTGACTTACAAATCAGCGGTGGT
GCAACCTATATTGACTCTGTTATTGTTGAAAAAAGAACAAACAAGTACT
CATGTTTGCTGATGTGATGCCTGCTGGAGTAAGTTTTAGAGAAGCAACTA
GAAAAGATTCAGGTTATAAACAAATTGATGGTAATTATTACCTTAAATTA
AGGAAACAAGGTGATACTGATTACAATTATACTATTCGTGAAATGGTAC
TGTATACGACGATCGTACCAACAGACCAACTGAATTTTCAGTAGATAAAA
ATTTCGGTATTAAACAAATGGTAATTTATTTGACGGTAGAGCGG
```

(SEQ. ID. NO. 164)
MKKNIKQYVTLGTVVVLSAFVANSVAAQETETSEVSTPKLVQPVAPTTPI
SEVQPTSDNSSEVTVQPRTVETTVKDPSSTAEETPVLEKNNVTLTGGGEN
VTKELKDKETSGDFTVVIKYNQSSEKGLQALFGISNSKPGQQNSYVDVFL
RDNGELGMEARDTSSNKNNLVSRPASVWGKYKQEAVTNTVAVVADSVKKT
YSLYANGTKVVEKKVDNFLNIKDIKGDYYMLGGVKRAGKTAFGFNGTLEN
IKFFNSALDEETVKKMTTNAVTGHLIYTANDTTGSNYFRIPVLYTFSNGR
VFSSIDARYGGTHDFLNKINIATSYSDDNGKTWTKPKLTLAFDDFAPVPL
EWPREVGGRDLQISGGATYIDSVIVEKKNKQVLMFADVMPAGVSFREATR
KDSGYKQIDGNYYLKLRKQGDTDYNYTIRENGTVYDDRTNRPTEFSVDKN
FGIKQNGNYLTVER

ID214-4185
(SEQ. ID. NO. 181)
ATGAAAAAATTTAGCCTATTACTAGCTATCCTACCATTTTTGGTTGCCTG
TGAGAATCAAGCTACACCCAAAGAGACTAGCGCTCAAAAGACAATCGTCC
TTGCTACAGCTGGCGACGTGCCACCATTTGACTACGAAGACAAGGGCAAT
CTGACAGGCTTTGATATCGAAGTTTTAAAGGCAGTAGATGAAAAACTCAG
CGACTACGAGATTCAATTCCAAAGAACCGCCTGGGAGAGCATCTTCCCAG
GACTTGATTCTGGTCACTATCAGGCTGCGGCCAATAACTTGAGTTACACA
AAAGAGCGTGCTGAAAATACCTTTACTCGCTTCCAATTTCAACAATCC
CCTCGTCCTTGTCAGCAACAAGAAAATCCTTTGACTTCTCTTGACCAGA
TCGCTGGTAAAACAACACAAGAGGATACCGGAACTTCTAACGCTCAATTC

```
ATCAATAACTGGAATCAGAAACACACTGATAATCCCGCTACAATTAATTT
TTCTGGTGAGGATATTGGTAAACGAATCCTAGACCTTGCTAACGGAGAGT
TTGATTTCCTAGTTTTTGACAAGGTATCCGTTCAAAAGATTATCAAGGAC
CGTGGTTTAGACCTCTCAGTCGTTGATTTACCTTCTGCAGATACGGGGAG
CAATTATATCATTTTCTCAAGCGACCAAAAAGAGTTTAAAGAGCAATTTG
ATAAAGCGCTCAAAGAACTCTATCAAGACGGAACCCTTGAAAAACTCAGC
AATACCTATCTAGGTGGTTCTTACCTCCCAGATCAATCTCAGTTACAATA
A
```

(SEQ. ID. NO. 165)
MKKFSLLLAILPFLVACENQATPKETSAQKTIVLATAGDVPPFDYEDKGN
LTGFDIEVLKAVDEKLSDYEIQFQRTAWESIFPGLDSGHYQAAANNLSYT
KERAEKYLYSLPISNNPLVLVSNKKNPLTSLDQIAGKTTQEDTGTSNAQF
INNWNQKHTDNPATINFSGEDIGKRILDLANGEFDFLVFDKVSVQKHKDR
GLDLSVVDLPSADSPSNYIIFSSDQKEFKEQFDKALKELYQDGTLEKLSN
TYLGGSYLPDQSQLQZ

ID215-4211.1
(SEQ. ID. NO. 182)
```
ATGAAAAAAATAGTTTATATATCATATCCTCACTCTTTTTTGCTTGTGT
CTTATTTGTCTATGCTACGGCGACGAATTTTCAAAACAGTACCAGTGCTA
GGCAGGTAAAAACGGAAACCTATACTAATACAGTAACAAATGTCCCTATT
GACATACGCTATAATAGTGATAAGTATTTTATTAGCGGTTTTGCTTCAGA
AGTATCAGTGGTCTTGACTGGTGCAAATCGCCTATCGCTAGCTAGTGAAA
TGCAAGAAAGTACACGTAAATTCAAGGTTACTGCTGACCTAACAGATGCC
GGTGTTGGAACGATTGAAGTTCCTTTGAGCATTGAAGATTTACCCAATGG
GCTGACCGCTGTGGCGACTCCGCAAAAAATTACAGTCAAGATTGGTAAGA
AGGCTCAGAAGGATAAGGTAAAGATTGTACCAGAGATTGACCCTAGTCAA
ATTGATAGTCGGGTACAAATTGAAAATGTCATGGTGTCAGATAAAGAAGT
GTCTATTACGAGTGACCAAGAGACATTGGATAGAATTGATAAGATTATCG
CTGTTTTGCCAACTAGCGAACGTATAACAGGTAATTACAGTGGTTCAGTA
CCTTTGCAGGCAATCGACCGCAATGGTGTTGTCTTACCGGCAGTTATCAC
TCCGTTTGATACAATAATGAAGGTGACTACAAAACCAGTAGCACCAAGTT
CAAGCACATCAAATTCAAGTACAAGCAGTTCATCGGAGACATCTTCGTCA
ACGAAACGAACTAGTTCAAAAACGAATTAA
```

(SEQ. ID. NO. 166)
MKKNSLYIISSLFFACVLFVYATATNFQNSTARQVKTETYTNTVTNVPI
DIRYNSDKYFISGFASEVSVVLTGANRLSLASEMQESTRKFKVTADLTDA
GVGTIEVPLSIEDLPNGLTAVATPQKITVKIGKKAQKDKVKIVPEIDPSQ
IDSRVQIENVMVSDKEVSITSDQETLDRIDKIIAVLPTSERITGNYSGSV
PLQAIDRNGVVLPAVITPFDTIMKVTTKPVAPSSSTSNSSTSSSSETSSS
TKATSSKTNZ

TABLE 3-continued

ID216-4127.3
(SEQ. ID. NO. 183)
ATGTTGATTGGCGAAGGGTATCGGACTTTCCCTGTCCTGATTTATACCCA
ATTTATTAGCGAGGTTGGAGGAAATTCTGCTTTTGCAATTATGGCGATTA
TCATTGCCTTGGCAATTTTCCTTATCCAAAAACACATTGCAAACCGCTAC
AGTTTCAGCATGAATCTGCTCCATCCAATTGAGCCTAAAAAAACTACAAA
AGGAAAAATGGCTGCCATTTATGCAACAGTCTACGGAATTATCTTTATCT
CTGTTTTACCTCAAATCTACTTAATTTATACCTCTTTCCTAAAAACATCA
GGTATGGTATCTGTTAAAGGTTATTCTCCAAACAGTTACAAGGTAGCTTT
CCATCGTATGGGATCTGCTATTTTCAATACCATTCGTATCCCTTTGATTG
CCTTAGTTCTAGTTGTTCTATTTGCGACATTTATCTCCTACCTAGCCGTT
AGAAAACGGAATTTGTTTACAAACTTAATTGACAGCCTCAGTATGGTACC
TTATATTGTACCAGGAACCGTTCTAGGGATTGCCTTCATTTCTTCCTTCA
ATACTGGTCTATTTGGAAGTGGATTTCTTATGATTACAGGGACTGCTTTC
ATCTTGATTATGTCTCTATCTGCCAGAAGATTACCTTATACTATTCGCTC
ATCTGTTGCTAGCTTACAACAAATAGCACCAAGTATTGAAGAAGCTGCTG
AAAGCTTAGGAAGTAGTCGTCTCAATACCTTTGCTAAGATTACAACTCCA
ATGATGCTATCTGGTATCATTTCTGGAGCCATCTTATCTTGA (SEQ. ID. NO. 167)
MLIGEGYRTFPVLIYTQFISEVGGNSAFAIMAIIALAIFLIQKHLANRY
SFSMNLLHPIEPKKTTKGKMAAIYATVYGIIFISVLPQIYLIYTSFLKTS
GMVSVKGYSPNSYKVAFHRMGSAIFNTIRIPLIALVLVVLFATFISYLAV
RKRNLFTNLIDSLSMVPYIVPGTVLGIAFISSFNTGLFGSGFLMITGTAF
ILIMSLSARRLPYTIRSSVASLQQIAPSIEEAAESLGSSRLNTFAKITTP
MMLSGIISGAILSZ

TABLE 4

ID301
(SEQ. ID. NO. 196)
ATGAATAAGAAAAAAATGATTTTAACAAGTCTAGCCAGCGTCGATATCTT
AGGGGCTGGTTTTGTTACGTCTCAGCCTACTTTTGTAAGAGCAGAAGAAT
CTCCACAAGTTGTCGAAAAATCTTCATTAGAGAAGAAATATGAGGAAGCA
AAAGCAAAAGCTGATACTGCCAAGAAAGATTACGAAACGGCTAAAAAGAA
AGCAGAAGACGCTCAGAAAAAGTATGAAGATGATCAGAAGAGAACTGAGG
AGAAAGCTCGAAAAGAAGCAGAAGCATCTCAAAAATTGAATGATGTGGCG
CTTGTTGTTCAAAATGCATATAAAGAGTACCGAGAAGTTCAAAATCAACG
TAGTAAAATAAATCTGACGCTGAATATCAGAAAAAATTAACAGAGGTCG
ACTCTAAAATAGAGAAGGCTAGGAAAGAGCAACAGGACTTGCAAAATAAA
TTTAATGAAGTAAGAGCAGTTGTAGTTCCTGAACCAAATGCGTTGGCTGA
GACTAAGAAAAAAGCAGAAGAAGCTAAAGCAGAAGAAAAGTAGCTAAGA
GAAAATATGATTATGCAACTCTAAAGGTAGCACTAGCGAAGAAAGAAGTA
GAGGCTAAGGAACTTGAAATTGAAAAACTTCAATATGAAATTTCTACTTT

GGAACAAGAAGTTGCTACTGCTCAACATCAAGTAGATAATTTGAAAAAAC
TTCTTGCTGGTGCGGATCCTGATGATGGCACAGAAGTTATAGAAGCTAAA
TTAAAAAAAGGAGAAGCTGAGCTAAACGCTAAACAAGCTGAGTTAGCAAA
AAAACAAACAGAACTTGAAAAACTTCTTGACAGCCTTGATCCTGAAGGTA
AGACTCAGGATGAATTAGATAAAGAAGCAGAAGAAGCTGAGTTGGATAAA
AAAGCTGATGAACTTCAAAATAAAGTTGCTGATTTAGAAAAAGAAATTAG
TAACCTTGAAATATTACTTGGAGGGGCTGATCCTGAAGATGATACTGCTG
CTCTTCAAAATAAATTAGCTGCTAAAAAAGCTGAGTTAGCAAAAAAACAA
ACAGAACTTGAAAAACTTCTTGACAGCCTTGATCCTGAAGGTAAGACTCA
GGATGAATTAGATAAAGAAGCAGAAGAAGCTGAGTTGGATAAAAAAGCTG
ATGAACTTCAAAATAAAGTTGCTGATTTAGAAAAAGAAATTAGTAACCTT
GAAATATTACTTGGAGGGGCTGATTCTGAAGATGATACTGCTGCTCTTCA
AAATAAATTAGCTACTAAAAAAGCTGAATTGGAAAAAACTCAAAAGAAT
TAGATGCAGCTCTTAATGAGTTAGGCCCTGATGGAGATGAAGAAGAAACT
CCAGCGCCGGCTCCTCAACCAGAGCAACCAGCTCCTGCACCAAAACCAGA
GCAACCAGCTCCAGCTCCAAAACCAGAGCAACCAGCTCCTGCACCAAAAC
CAGAGCAACCAGCTCCAGCTCCAAAACCAGAGCAACCAGCTCCAGCTCCA
AAACCAGAGCAACCAGCTAAGCCGGAGAAACCAGCTGAAGAGCCTACTCA
ACCAGAAAAACCAGCCACTCCAAAAACAGGCTGGAAACAAGAAAACGGTA
TGTGGTATTTCTACAATACTGATGGTTCAATGGCAATAGGTTGGCTCCAA
AACAACGGTTCATGGTACTACCTAAACGCTAACGGCGCTATGGCAACAGG
TTGGGTGAAAGATGGAGATACCTGGTACTATCTTGAAGCATCAGGTGCTA
TGAAAGCAAGCCAATGGTTCAAAGTATCAGATAAATGGTACTATGTCAAC
AGCAATGGCGCTATGGCGACAGGCTGGCTCCAATACAATGGCTCATGGTA
CTACCTCAACGCTAATGGTGATATGGCGACAGGATGGCTCCAATACAACG
GTTCATGGTATTACCTCAACGCTAATGGTGATATGGCGACAGGATGGGCT
AAAGTCAACGGTTCATGGTACTACCTAAACGCTAACGGTGCTATGGCTAC
AGGTTGGGCTAAAGTCAACGGTTCATGGTACTACCTAAACGCTAACGGTT
CAATGGCAACAGGTTGGGTGAAAGATGGAGATACCTGGTACTATCTTGAA
GCATCAGGTGCTATGAAAGCAAGCCAATGGTTCAAAGTATCAGATAAATG
GTACTATGTCAATGGCTTAGGTGCCCTTGCAGTCAACACAACTGTAGATG
GCTATAAAGTCAATGCCAATGGTGAATGGGTTTAA (SEQ. ID. NO. 184)
MNKKKMILTSLASVAILGAGFVTSQPTFVRAEESPQVVEKSSLEKKYEEA
KAKADTAKKDYETAKKKAEDAQKKYEDDQKRTEEKARKEAEASQKLNDVA
LVVQNAYKEYREVQNQRSKYKSDAEYQKKLTEVDSKIEKARKEQQDLQNK
FNEVRAVVVPEPNALAETKKKAEEAKAEEKVAKRKYDYATLKVALAKKEV
EAKELEIEKLQYEISTLEQEVATAQHQVDNLKKLLAGADPDDGTEVIEAK
LKKGEAELNAKQAELAKKQTELEKLLDSLDPEGKTQDELDKEAEEAELDK
KADELQNKVADLEKEISNLEILLGGADPEDDTAALQNKLAAKKAELAKKQ

TABLE 4-continued

TELEKLLDSLDPEGKTQDELDKEAEEAELDKKADELQNKVADLEKEISNL
EILLGGADSEDDTAALQNKLATKKAELEKTQKELDAALNELGPDGDEEET
PAPAPQPEQPAPAPKPEQPAPAPKPEQPAPAPKPEQPAPAPKPEQPAPAP
KPEQPAKPEKPAEEPTQPEKPATPKTGWKQENGMWYFYNTDGSMAIGWLQ
NNGSWYYLNANGAMATGWVKDGDTWYYLEASGAMKASQWFKVSDKWYYVN
SNGAMATGWLQYNGSWYYLNANGDMATGWLQYNGSWYYLNANGDMATGWA
KVNGSWYYLNANGAMATGWAKVNGSWYYLNANGSMATGWVKDGDTWYYLE
ASGAMKASQWFKVSDKWYYVNGLGALAVNTTVDGYKVNANGEWVZ

ID302
(SEQ. ID. NO. 197)
ATGTTTGCATCAAAAAGCGAAAGAAAAGTACATTATTCAATTCGTAAATT
TAGTGTTGGAGTAGCTAGTGTAGTTGTTGCCAGTCTTGTTATGGGAAGTG
TGGTCATGCGACAGAGAACGAGGGAGCTACCCAAGTACCCACTTCTTCTA
ATAGGGCAAATGAAAGTCAGGCAGAACAAGGAGAACAACCTAAAAAACTC
GATTCAGAACGAGATAAGGCAAGGAAAGAGGTCCAGGAATATGTAAAAAA
AATAGTGGGTGAGAGCTATGCAAAATCAACTAAAAAGCGACATACAATTA
CTGTAGCTGCCAGTCTTGTTATGGGAAGTGTGGTTCATGCGACAGAGAAC
GAGGGAGCTACCCAAGTACCCACTTCTTCTAATAAGATACTGATGATGGA
GAGTCGATCAAAAGTAGATGAAGCTGTGTCTAAGTTTGAAAAGGACTCAT
CTTCTTCGTCAAGTTCAGACTCTTCCACTAAACCGGAAGCTTCAGATACA
GCGAAGCCAAACAAGCCGACAGAACCAGGAGAAAAGGTAGCAGAAGCTAA
GAAGAAGGTTGAAGAAGCTGAGAAAAAAGCCAAGGATCAAAAAGAAGAAG
ATCGTCGTAACTACCCAACCATTACTTACAAAACGCTTGAACTTGAAATT
GCTGAGTCCGATGTGGAAGTTAAAAAAGCGGAGCTTGAACTAGTAAAAGT
GAAAGCTAACGAACCTCGAGACGAGCAAAAAATTAAGCAAGCAGAAGCGG
AAGTTGAGAGTAAACAAGCTGAGGCTACAAGGTTAAAAAAAATCAAGACA
GATCGTGAAGAAGCAGAAGAAGAAGCTAAACGAAGAGCAGATGCTAGATG
CGAAGTCTTCAGATTCTAGCGTAGGTGAAGAAACTCTTCCAAGCCCATCC
CTGAAACCAGAAAAAAAGGTAGCAGAAGCTGAGAAGAAGGTTGAAGAAGC
TAAGAAAAAGCCGAGGATCAAAAAGAAGAAGATCGCCGTAACTACCCAA
CCAATACTTAGAAAACGCTTGAACTTGAAATTGCTGAGTCCGATGTGGAA
GTTAAAAAAGCGGAGCTTGAACTAGTAAAAGAGGAAGCTAAGGAACCTCG
AAACGAGGAAAAGTTAAGCAAGCAAAAGCGGAAGTTGAGAGTAAAAAAG
CTGAGGCTACAAGGTTAGAAAAAATCAAGACAGATCGTAAAAAAGCAGAA
GAAGAAGCTAAACGAAAAGCAGCAGAAGAAGATAAAGTTAAAGAAAAACC
AGCTGAACAACCACAACCAGCGCCGGCTCCAAAAGCAGAAAAACCAGCTC
CAGCTCCAAAACCAGAGAATCCAGCTGAACAACCAAAAGCAGAAAAACCA
GCTGATCAACAAGCTGAAGAAGACTATGCTCGTAGATCAGAAGAAGAATA
TAATCGCTTGACTCAACAGCAACCGCCAAAAACTGAAAAACCAGCACAAC
CATCTACTCCAAAAACAGGCTGGAAACAAGAAAACGGTATGTGGTACTTC
TACAATACTGATGGTTCAATGGCGACAGGATGGCTCCAAAACAATGGCTC

ATGGTACTACCTCAACAGCAATGGCGCTATGGCGACAGGATGGCTCCAAA
ACAATGGTCATGGTACTATCTAAACGCTAATGGTTCAATGGCAACAGGAT
GGCTCCAAAACAATGGTTCATGGTACTACCTAAACGCTAATGGTTCAATG
GCGACAGGATGGCTCCAATACAATGGCTCATGGTACTACCTAAACGCTAA
TGGTTCAATGGCGACAGGATGGCTCCAATACAATGGCTCATGGTACTACC
TAAACGCTAATGGTGATATGGCGACAGGTTGGGTGAAAGATGGAGATACC
TGGTACTATCTTGAAGCATCAGGTGCTATGAAAGCAAGCCAATGGTTCAA
AGTATCAGATAAATGGTACTATGTCAATGGCTCAGGTGCCCTTGCAGTCA
ACACAACTGTAGATGGCTATGGAGTCAATGCCAATGGTGAATGGGTAAAC
TAA (SEQ. ID. NO. 185)
MFASKSERKVHYSIRKFSVGVASVVVASLVMGSVVHATENEGATQVPTSS
NRANESQAEQGEQPKKLDSERDKARKEVEEYVKKIVGESYAKSTKKRHTI
TVALVENELNNIKNEYLNKIVESTSESQLQILMMESRSKVDEAVSGEKDS
SSSSSSDSSTKPEASDTAKPNKPTEPGEKVAEAKKKVEEAEKKAKDQKEE
DRRNYPTITYKTLELEIAESDVEVKKAELELVKVKANEPRDEQKIKQAEA
EVESKQAEATRLKKIKTDREEAEEEAKRRADAKEQGKPKGRAKRGVPGEL
ATPDKKENDAKSSDSSVGEETLPSPSLKPEKKVAEAEKKVEEAKKKAEDQ
KEEDRRNYPTNTYKTLELEIAESDVEVKKAELELVKEEAKEPRNEEKVKQ
AKAEVESKKAEATRLEKIKTDRKKAEEEEAKRKAAEEDKVKEKPAEQPQPA
PAPKAEKPAPAPKPENPAEQPKAEKPADQQAEEDYARRSEEEYNRLTQQQ
PPKTEKPAQPSTPKTGWKQENGMWYFYNTDGSMATGWLQNNGSWYYLNSN
GAMATGWLQNNGSWYYLNANGSMATGWLQNNGSWYYLNANGSMATGWLQY
NGSWYYLNANGSMATGWLQYNGSWYYLNANGDMATGWVKDGDTWYYLEAS
GAMKASQWFKVSDKWYYVNGSGALAVNTTVDGYGVNANGEWVNZ

ID303
(SEQ. ID. NO. 198)
ATGGTAAAAAGACGTATAAGGAGAGGGACGAGAGAACCTGAAAAAGTTGT
TGTTCCTGAGCAATCATCTATTCCTTCGTATCCTGTATCTGTTACATCTA
ACCAAGGAACAGATGTAGCAGTAGAACCAGCTAAAGCAGTTGCTCCAACA
ACAGACTGGAAACAAGAAAATGGTATGTGGTATTTTTATAATACTGATGG
TTCCATGGCAACAGGTTGGGTACAAGTTAATAGTTCATGGTACTACCTCA
ACAGCAACGGTTCTATGAAAGTCAATCAATGGTTCCAAGTTGGTGGTAAA
TGGTATTATGTAAATACATCGGGTGAGTTAGCGGTCAATACAAGTATAGA
TGGCTATAGAGTCAATGATAATGGTGAATGGGTGCGTTAA (SEQ. ID. NO. 186)
MVKRRIRRGTREPEKVVVPEQSSIPSYPVSVTSNQGTDVAVEPAKAVAPT
TDWKQENGMWYFYNTDGSMATGWVQVNSSWYYLNSNGSMKVNQWFQVGGK
WYYVNTSGELAVNTSIDGYRVNDNGEWVRZ

ID304
(SEQ. ID. NO. 199)
CTGAATACAAGTTTTGTTCATGCTGCTGATGGGATTCAATATGTCAFAGA
TGATACTAGAGATAAAGAAGAGGGAATAGAGTATGATGACGCTGACAATG

TABLE 4-continued

```
GGGATATTATTGTAAAAGTAGCGACTAAACCTAAGGTAGTAACCAAGAAA
ATTTCAAGTACGCGAATTCGTTATGAAAAAGATGAAACAAAAGACCGTAG
TGAAAATCCTGTTACAATTGATGGAGAGGATGGCTATGTAACTACGACAA
GGACCTACGATGTTAATCCAGAGACTGGTTATGTTACCGAACAGGTTACT
GTTGATAGAAAAGAAGCCACGGATACAGTTATCAAAGTTCCAGCTAAAAG
CAAGGTTGAAGAAGTCTTGTTCCATTTGCTACTAAATATGAAGCAGACAA
TGACCTTTCTGCAGGACAGGAGCAAGAGATTACTCTAGGAAAGAATGGGA
AAACAGTTACAACGATAACTTATAATGTAGATGGAAAGAGTGGACAAGTA
ACTGAGAGTACTTTAAGTCAAAAAAAAGACTCTCAAACAAGAGTTGTTAA
AAAAAGAACCAAGCCCCAAGTTCTGTCCAAGAAATTCCAATCGAAACAGA
ATATCTCGATGGCCCAACTCTTGATAAAAGTCAAGAAGTAGAAGAAGTAG
GAGAAATTGGTAAATTACTCTTACTACAATCTATACTGTAG
                                              (SEQ. ID. NO. 187)
LNTSFVHAADGIQYVRDDTRDKEEGIEYDDADNGDIIVKVATKPKVVTKK
ISSTRIRYEKDETKDRSENPVTIDGEDGYVTTTRTYDVNPETGYVTEQVT
VDRKEATDTVIKVPAKSKVEEVLVPFATKYEADNDLSAGQEQEITLGKNG
KTVTTITYNVDGKSGQVTESTLSQKKDSQTRVVKKRTKPQVLVQETPIET
EYLDGPTLDKSQEVEEVGEIGKLLLLQSILZ

ID305
                                              (SEQ. ID. NO. 200)
ATGAAGCTTTTGAAAAAATGATGCAAATCGCACTAGCCACATTTTTCTT
CGGTTTGTTAGCGACAAATACAGTATTTGCAGATGATTCTGAAGGATGGC
AGTTTGTCCAAGAAAATGGTAGAACCTACTACAAAAAGGGGGATCTAAAA
GAAACCTACTGGAGAGTGATAGATGGGAAGTACTATTATTTTGATCCTTT
ATCCGGAGAGATGGTTGTCGGCTGGCAATATATACCTGCTCCACACAAGG
GGGTTACGATTGGTCCTTCTCCAAGAATAGAGATTGCTCTTAGACCAGAT
TGGTTTTATTTTGGTCAAGATGGTGTATTACAAGAATTTGTTGGCAAGCA
AGTTTTAGAAGCAAAAACTGCTACGAATACCAACAAACATCATGGGGAAG
AATATGATAGCCAAGCAGAGAAACGAGTCTATTATTTTGAAGATCAGCGT
AGTTATCATACTTTAAAAACTGGTTGGATTTATGAAGAGGGTCATTGGTA
TTATTTACAGAAGGATGGTGGCTTTGATTCGCGCATCAACAGATTCACGG
TTGGAGAGCTAGCACGTGGTTGGGTTAAGGATTACCCTCTTACGTATGAT
GAAGAGAAGCTAAAAGCAGCTCCATGGTACTATCTAAATCCAGCAACTGG
CATTATGCAAACAGGTTGGCAATATCTAGGTAATAGATGGTACTACCTCC
ATTCGTCAGGAGCTATGGCAACTGGCTGGTATAAGGAAGGCTCAACTTGG
TACTATCTAGATGCTGAAAATGGTGATATGAGAACTGGCTGGCAAAACCT
TGGGAACAAATGGTACTATCTCCGTTCATCAGGAGCTATGGCAACTGGTT
GGTATCAGGAAAGTTCGACTTGGTACTATCTAAATGCAAGTAATGGAGAT
ATGAAAACAGGCTGGTTCCAAGTCAATGGTAACTGGTACTATGCCTATGA
TTCAGGTGCTTTAGCTGTTAATACCACAGTAGGTGGTTACTACTTAAACT
ATAATGGTGAATGGGTTAAGTAA
```

```
                                              (SEQ. ID. NO. 188)
MKLLKKMMQIALATFFFGLLATNTVFADDSEGWQFVQENGRTYYKKGDLK
ETYWRVIDGKYYYFDPLSGEMVVGWQYIPAPHKGVTIGPSPRIEIALRPD
WFYFGQDGVLQEFVGKQVLEAKTATNTNKHHGEEYDSQAEKRVYYFEDQR
SYHTYLHSSGAMATGWYKEGSTWYYLDAENGDMRTGWQNLGNKWYYLRSS
GAMATGWYQESSTWYYLNASNGDMKTGWFQVNGNWYYAYDSGALAVNTTV
GGYYLNYNGEWVKZ

ID306
                                              (SEQ. ID. NO. 201)
TTGGCTGGTAGATATGGTTCTGCTGTTCAGTGTACAGAAGTGACTGCCTC
AAACCTTTCAACAGTTAAAACTAAAGCTACGGTTGTAGAAAAACCACTGA
AAGATTTTAGAGCGTCTACGTCTGATCAGTCTGGTTGGGTGGAATCTAAT
GGTAAATGGTATTTCTATGAGTCTGGTGATGTGAAGACAGGTTGGGTGAA
AACAGATGGTAAATGGTACTATTTGAATGACTTAGGTGTCATGCAGACTG
GATTTGTAAAATTTTCTGGTAGCTGGTATTACTTGAGCAATTCAGGTGCT
ATGTTTACAGGCTGGGGAACAGATGGTAGCAGATGGTTCTACTTTGACGG
CTCAGGAGCTATGAAGACAGGCTGGTACAAGGAAAATGGCACTTGGTATT
ACCTTGACGAAGCAGGTATCATGAAGACAGGTTGGTTTAAAGTCGGACCA
CACTGGTACTATGCCTACGGTTCAGGAGCTTTGGCTGTGAGCACAACAAC
ACCAGATGGTTACCGTGTAAATGGTAATGGTGAATGGGTAAACTAG
                                              (SEQ. ID. NO. 189)
LAGRYGSAVQCTEVTASNLSTVKTKATVVEKPLKDFRASTSDQSGWVESN
GKWYFYESGDVKTGWVKTDGKWYYLNDLGVMQTGFVKFSGSWYYLSNSGA
MFTGWGTDGSRWFYFDGSGAMKTGWYKENGTWYYLDEAGIMKTGWFKVGP
HWYYAYGSGALAVSTTTPDGYRVNGNGEWVNZ

ID307
                                              (SEQ. ID. NO. 200)
ATGAAAATTTTGAAAAAAACTATGCAAGTTGGACTGACAGTATTTTCTT
TGGTTTGCTAGGGACCAGTACAGTATTTGCAGATGATTCTGAAGGATGGC
AGTTTGTCCAAGAAAACGGAAGAACCTACTACAAAAAGGGGGACCTCAAA
GAAACCTACTGGCGAGTGATTGATGGTAAGTACTATTATTTTGATTCTCT
ATCTGGAGAGATGGTTGTCGGCTGGCAATATATCCCGTTTCCATCTAAAG
GTAGTACAATTGGTCCTTTACCCAAATGGTATCAGATTAGAAGGTTTTCC
AAAGTCAGAGTGGTACTACTTCGATAAAAATGGAGTGCTACAAGAGTTTG
TTGGTTGGAAAACATTAGAGATTAAAACTAAAGACAGTGTTGGAAGAAAG
TACGGGAAAAACGTGAAGATTCAGAAGATAAAGAAGAGAAGCGTTATTA
TACGAACTATTACTTTAATCAAAATCATTCTTTAGACACACGTTCGCTTT
ATGATCAGTCTAACTCGTATTATCTAGCTAAGACGGAAATTAATGGAGAA
AACTACCTTGGTGGTGAAAGACGTGCGGGGTGGATAAACGATGATTCGAC
TTGGTACTACCTAGATCCAACAACTGGTATTATGCAAACAGGTTGGCAAT
ATCTAGGTAATAAGTGGTACTACCTCCGTTCCTCAGGAGCAATGGCCACT
GGCTGGTATCAGGAAGGTACCACTTGGTATTATTTAGACCACCCAAATGG
CGATATGAAAACAGGTTGGCAAAACCTTGGGAACAAATGGTACTATCTCC
```

TABLE 4-continued

```
GTTCATCAGGAGCTATGGCAACTGGTTGGTATCAAGATGGTTCAACTTGG
TACTACCTAAATGCAGGTAATGGAGACATGAAGACAGGTTGGTTCCAGGT
CAATGGCAACTGGTACTATGCTTAT
```

(SEQ. ID. NO. 190)
```
MKILKKTMQVGLTVFFFGLLGTSTVFADDSEGWQFVQENGRTYYKKGDLK
ETYWRVIDGKYYYFDSLSGEMVVGWQYIPFPSKGSTIGPYPRGIRLEGFP
KSEWYYFDIOGVLQEFVGWKTLEILKTISVGRKYGEKREDSEDKEEKRYY
TNYYFNQNHSLETGWLYDQSNWYYLAKTEINGENYLGGERRAGWINDDST
WYYLDPTTGIMQTGWQYLGNKWYYLRSSGAMATGWYQEGTTWYYLDHPNG
DMKTGWQNLGNKWYYLRSSGAMATGWYQDGSTWYYLNAGNGDMKTGWFQV
NGNWYYAYSSGALAVNTTVDGYSVNYNGEWVRZ
```

ID308

(SEQ. ID. NO. 203)
```
ATGAAAAAGAAATTAACTAGTTTAGCACTTGTAGGCGCTTTTTTAGGTTT
GTCATGGTATGGGAATGTTCAGGCTGAAGAAAGTTCAGGAAATAAAATCC
ACTTTATCAATGTTCAAGAAGGTGGCAGTGATGCGATTATTCTTGAAAGC
AATGGACATTTTGCCATGGTGGATACAGGAGAAGATTATGATTTCCCAGA
TGGAAGTGATTCTCGCTATCCATGGAGAGAAGGAATTGAAACGTCTTATA
AGCATGTTCTAACAGACCGTGTCTTTCGTCGTTTGAAGGAATTGGGTGTC
CAAAAACTTGATTTTATTTTGGTGACCCATACCCACAGTGATCATATTGG
AAATGTTGATGAATTACTGTCTACCTATCCAGTTGACCGAGTCTATCTTA
AGAAATATAGTGATAGTCGTATTACTAATTCTGAACGTCTATGGGATAAT
CTGTATGGCTATGATAAGGTTTTACAGACTGCTGCAGAAAAAGGTGTTTC
AGTATTCAAAATATCACACAAGGGGATGCTCATTTTCAGTTTGGGGACAT
GGATATTCAGCTCTATAATTATGAAAATGAAACTGATTCATCGGGTGAAT
TAAAGAAAATTTGGGATGACAATTCCAATTCCTTGATThGCGTGGTGAAA
GTCAATGGCAAGAAAATTTACCTTGGGGGCGATTTAGATAATGTTCATGG
AGCAGAAGACAAGTATGGTCCTCTCATTGAAAAGTTGATTTGATGAAGT
TTAATCATCACCATGATACCAACAAATCAAATACCAAGGATTTCATTAAA
AATTTGAGTCCGAGTTTGATTGTTCAAACTTCGGATAGTCTACCTTGGAA
AAATGGTGTTTGATAGTGAGTATGTTAATTGGCTCAAAGAACGAGGAATT
GAGAGAATCACGCAGCCAGCAAAGACTATGATGCAACAGTTTTTGATATT
CGAAAAGACGGTTTTGTCAATATTTCAACATCCTACAAGCCGATTCCAAG
TTTTCAAGCTGGTTGGCATAAGAGTGCATATGGGAACTGGTGGTATCAAG
CGCCTGATTCTACAGGAGAGTATGCTGTCGGTTGGAATGAAATCGAAGGT
GAATGGTATACTTTAACCAAACGGGTATCTTGTTACAGAATCAATGGAAA
AAATGGAACAATCATTGGTTCTATTGACAGACTCTGGTGCTTCTGCTAA
AAATTGGAAGAAAATCGCTGGAATCTGGTATTATTTTAACAAAGAAAACC
AGATGGAAATTGGTGGATTCAAGATA)*AGAGCAGTGGTATTATTTGGA
TGTTGATGGTTCTATGAAGACAGGATGGCTTCAATATATGGGGCAATGGT
ATACTTTGCTCCATCAGGGGAAATGAAAATGGGCTGGGTAAAAGATAAAG
```

```
AAACCTGGTACTATATGGATTCTACTGGTGTCATGAAGACAGGTGAGATA
GAAGTTGCTGGTCAACATTATTATCTGGAAGATTCAGGAGCTATGAAGCA
AGGCTGGCATAAAAAGGCAAATGATTGGTATTTCTACAAGACAGACGGTT
CACGAGCTGTGGGTTGGATCAAGGACAAGGATAAATGGTACTTCTTGAAA
GAAAATGGTCAATTACTTGTGAACGGTAAGACACCAGAAGGTTATACTGT
GGATTCAAGTGGTGCCTGGTTAGTGGATGTTTCGATCGAGAAATCTGCTA
CAATTAAAACTACAAGTCATTCAGAAATAAAAGAATCCAAAGAAGTAGTG
AAAAAGGATCTTGAAAATAAAGAAACGAGTCAACATGAAAGTGTTACAAA
TTTTTCAACTAGTCAAGATTTGACATCCTCAACTTCACAAAGCTCTGAAA
CGAGTGTAAACAAATCGGAATCAGAACAGTAG
```

(SEQ. ID. NO. 191)
```
MKKKLTSLALVGAFLGLSWYGNVQAQESSGNKIHFINVQEGGSDAIILES
NGHFAMVDTGEDYDFPDGSDSRYPWREGIETSYKHVLTDRVFRRLKELGV
QKLDFILVTHTHSDHIGNVDELLSTYPVDRVYLKKYSDSRITNSERLWDN
LYGYDKVLQTAAEKGVSVIQNITQGDAHFQFGDMDIQLYNYENETDSSGE
LKKIWDDNSNSLISVVKVNGKKIYLGGDLDNVHGAEDKYGPLIGKVDLMK
FNHHHDTNKSNTKDFIKNLSPSLIVQTSDSLPWJGVDSRYVNWLKERGIL
ERINAASKDYDATVFDIRKDGFVNISTSYKPIPSFQAGWHKSAYGNWWYQ
APDSTGEYAVGWNEIEGEWYYFNQTGILLQNQWKKWNNHWFYLTDSGASA
KNWKKIAGIWYYFNKENQMEIGWIQDKEQWYYLDVDGSMKTGWLQYMGQW
YYFAPSGEMKMGWVKDKETWYYMDSTGVMKTGEIEVAGQHYYLEDSGAMK
QGWHKKANDWYFYKTDGSRAVGWIKDKDKWYFLKENGQLLVNGKTPEGYT
VDSSGAWLVDVSIEKSATIKTTSHSEIKESKEVVKKDLENKETSQHESVT
MFSTSQDLTSSTSQSSETSVNKSESEQZ
```

ID309

(SEQ. ID. NO. 204)
```
ATGGAAATTAATGTGAGTAAATTAAGAACAGATTTGCCTCAAGTCGGCGT
GCAACCATATAGGCAAGTACACGCACACTCAACTGGGAATCCGCATTCAA
CCGTACAGAATGAAGCGGATTATCACTGGCGGAAAGACCCAGAATTAGGT
TTTTTCTCGCACATTGTTGGGAACGGTTGCATCATGCAGGTAGGACCTGT
TGATAATGGTGCCTGGGACGTTGGGGGCGGTTGGAATGCTGAGACCTATG
CAGCGGTTGAACTGATTGAAAGCCATTCAACCAAAGAAGAGTTCATGACG
GACTACCGCCTTTATATCGAACTCTTACGCAATCTAGCAGATGAAGCAGG
TTTGCCGAAAACGCTTGATACAGGGAGTTTAGCTGGAATTAAAACGCACG
AGTATTGCACGAATAACCAACCAAACAACCACTCAGACCACGTTGACCCT
TATCCATATCTTGCTAAATGGGGCATTAGCCGTGAGCAGTTTAAGCATGA
TATTGAGAACGGCTTGACGATTGAAACAGGCTGGCAGAAGAATGACACTG
GCTACTGGTACGTACATTCAGACGGCTCTATCCAAAAGACAAGTTTGAGA
AAATCAATGGCACTTGGTACTACTTTGACAGTTCAGGCTATATGCTTGCA
GACCGCTGGAGGAAGCACACAGACGGCAACTGGTACTGGTTCGACAACTC
AGGCGAAATGGCTACAGGCTGGAAGAAAATCGCTGATAAGTGGTACTATT
```

TABLE 4-continued

TCAACGAAGAAGGTGCCATGAAGACAGGCTGGGTCAAGTACAAGGACACT
TGGTACTACTTAGACGCTAAAGAAGGCGCCATGGTATCAAATGCCTTTAT
CCAGTCAGCGGACGGAACAGGCTGGTACTACCTCAAACCAGACGGAACAC
TGGCAGACAAGCCAGAATTCACAGTAGAGCCAGATGGCTTGATTACAGTA
AAATAA (SEQ. ID. NO. 192)
MEINVSKLRTDLPQVGVQPYRQVHAHSTGNPHSTVQNEADYHWRKDPELG
FFSHIVGNGCIMQVGPVDNGAWDVGGGWNAETYAAVELIESHSTKEEFMT
DYRLYIELLRNLADEAGLPKTLDTGSLAGIKTHEYCTNNQPNNHSDHVDP
YPYLAKWGISREQFKHDIENGLTIETGWQKNDTGYWYVHSDGSYPKDKFE
KINGTWYYFDSSGYMLADRWRKHTDGNWYWFDNSGEMATGWKKIADKWYY
FNEEGAMKTGWVKYKDTWYYLDAKEGAMVSNAFIQSADGTGWYYLKPDGT
LADKPEFTVEPDGLITVKZ

ID310
(SEQ. ID. NO. 205)
ATGGGCACAACAGGATTTACAATAATTGACTTAATTATCTTGATTGTTTA
TTTACTTGCGGTGTTGGTTGCAGGTATCTATTTCTCTAAAAAAGAGATGA
AAGGAAAAGAGTTCTTTAAAGGAGATGGTTCGGTTCTTCGGTATGTTACT
TCGGTATCCATTTTTGCCACAATGCTCAGTCCGATTTCCTTCTTGGGACT
CGCTGGTAGCTCTTATGCAGGTAGCTGGATTTTATGGTTTGCTCAATTAG
GGATGGTAGTAGCTATTCCACTGACAATTCGTTTTATCTTACCTATCTTT
GCACGGATAGACATCGATACGGCATATGATTACTTGGATAAACGTTTTAA
TTCTAAAGCACTTCGTATTATTTCAGCACTCTTGTTTATTATTTATCAAT
TGGGACGTATGTCTATCATTATGTACCTCCCATCAGCTGGTTTATCAGTA
TTCAGAGGAATTGACATCAATATTTTGATTATTTGATGGGTGTAGTGCAA
TTGTTTATTCTTATACTGGTGGTCTAAAATCCGTATTATGGACAGACTTT
ATTCAAGGTGTGATTCTGATTAGTGGTGTCGTTTTAGCTTTATTTGTACT
GATTGCTAATATTAAAGGTGGCTTTGGTCAGTAGCAGAAACATTAGCAA
ACGGGAAATTCCTTGCTGCAAATGAAAAACTTTTCGATCCTAACTTGCTT
TCAAACTCCATCTTTTTAATTGTGATGGGTTCAGGCTTTACAATCTTGTC
TTCCTATGCTTCATCTCAAGATTTGGTTCAACGTTTTACTACAACACAAA
ATATTAAGAAACTTAATAAGATGTTGTTCACAAAGCCTGTTTTGTCACTT
GCAACTGCAACAGTCTTTTACTTGATTGGTACAGGCTTGTACGTATTCTA
TCAAGTACAAAATGCAGATAGTGCAGCTAGCAATATCCCTCAAGACCAAA
TCTTTATGTACTTTATTGCATACCAGTTACCAGTAGGTATCACAGGTTTG
ATCTTGGCAGCGATTTATGCAGCATCTCAATCAACTATTTCAACAGGTTT
GAACTCTGRTGCAACTTCATGGACATTGGATATTCAAGATGTCATTTCTA
AAAATATGTCAGACAATCGTCGTACGAAAATTGCACAATTCGTATCTCTA
GCAGTAGGTTTATTCTCAATTGGTGTTTCCATTGTCATGGCTCACTCAGA
TATTAAATCTGCATACGAATGGTTCAATAGTTTCATGGGACTTGTACTTG
GTCTACTTGGTGGTGTATTTATTCTTGGATTTGTTTCTAAAAAAGCAAAT

AAACAAGGTGCTTATGCAGCGCTGATTGTATCAACCATCGTCATGGTATT
TATTAAATACTTCCTTCCTCCAACAGCTGTTAGCTACTGGGCATATTCAT
TGATTTCAATCTCTGTATCAGTAGTTTCAGGTTATATTGTATCTGTTCTT
ACTGGAAATAAAGTATCTGCACCTAAATATACAACGATRCATGATATTAC
AGAAATTAAAGCGGATTCAAGTTGGGAAGTTCGTCACTAA (SEQ. ID. NO. 193)
MGTTGFTIIDLIILIVYLLAVLVAGIYFSKKEMKGKEFFKGDGSVPWYVT
SVSIFATMLSPISFLGLAGSSYAGSWILWFAQLGMVVAIPLTIRFILPIF
ARIDIDTAYDYLDKRFNSKALRIISALLFIIYQLGRMSIIMYLPSAGLSV
LTGIDINILIILMGVVAIVYSYTGGLKSVLWTDFIQGVILISGVVLALFV
LIANIKGGFGAVAETLANGKFLAANEKLFDPNLLSNSIFLIVMGSGFTIL
SSYASSQDLVQRFTTTQNIKKLN14LFTNGVLSLATAIVFYLIGTGLYVF
YQVQNADSAASNIPQDQIFMYFIAYQLPVGITGLILAAIYAASQSTISTG
LNSVATSWTLDIQDVISKNMSDNRRTKIAQFVSLAVGLFSIGVSIVMAHS
DIKSAYEWFNSFMGLVLGLLGGVFILGFVSKKANKQGAYAALIVSTIVMV
FIKYFLPPTAVSYWAYSLISISVSVVSGYIVSVLTGNKVSAPKYTTIHDI
TEIKADSSWEVRHZ

ID311
(SEQ. ID. NO. 206)
ATGAAAATTAATAAAAAATATCTAGCAGGTTCAGTGGCAGTCCTTGCCCT
AAGTGTTTGTTCCTATGAGCTTGGTCGTCACCAAGCTGGTCAGGATAAGA
AAGAGTCTAATCGAGTTGCTTATATAGATGGTGATCAGGCTCGTCAAAAG
GCAGAAACTTGACACCAGATGAAGTCAGTAAGAGGGAGGGGATCAACGC
CGAACAAATCCTCATCAAGATTACGGATCAAGGTTATGTGACCTCTCATG
GAGACCATTATCATTACTATAATGGCAAGCTCCCTTATGATGCCATCATC
AGTGAAGAGCTCCTCATGAAAGATCCGAATTATCAGTTGAAGGATTCAGA
CATTGTCAATGAAATCAAGGGTGGTTATGTCATCAAGGTAGACGGAAAAT
ACTATGTTThCCTTAAGGATGCAGCTCATGCGGATAATATTCGGACAAAA
GAAGAGATTAAACGTCAGAAGCAGGAACGCAGTCATAATCACGGGTCAGG
AGCTAACGATCATGCAGTAGCTGCAGCCAGAGCCCAAGGACGCTATACAA
CGGATGATGGGTATATCTTCAATGCATCTGATATCATTGAGGACACGGGT
GATGCTATATCGTTCCTCACGGCGACCATTACCATACATTCCTAAGAAT
GAGTTATCAGCTAGCGAGTTAGCTGCTGCAGAAOCCTATTGGAATGGGAA
GCAGGGATCTCGTCCTTCTTCAAGTTCTAGTTATAATGCAAATCCAGCTC
AACCAAGATTGTCAGAGAACCACAATCTGACTGTCACTCAAACTTATCAT
CAAAATCAAGGGGAAAACATTICAAGCCTTTTACGTGAATHGTATGCTAA
ACCCTTATCAGAACGCCCATTGGAATCTGATGGCCTATTTTCGACCCAG
CGCAAATCACAAGTCGAACCCCCAGAGGTGTAGCTGTCCCTCATGGTAAC
CATTACCACTTTATCCCTTATGAACAAATCTCTGAATTGGAAAAACGAAT
TGCTCGTATTATTCCCCTTCGTTATCGTTCAAACCATTGGGTACCAGATT
CAAGACCAGAACAACCAAGTCCACAATCGACTCCGGAACCTAGTCCAAGT

TABLE 4-continued

```
CCGCAACCTGCACCAAATCCTCAACCAGCTCCAAGCAATCCAATTGATGA
GAAATTGGTCAAAGAAGCTGTTCGAAAAGTAGGCGATGGTTATGTCTTTG
AGGAGAATGGAGTTTCTCGTTATATCCCAGCCAAGGATCTTTCAGCAGAA
ACAGCAGCAGGCATTGATAGCAAACTGGCCAAGCAGGAAAGTTTATCTCA
TAAGCTAGGAGCTAAGAAAACTGACCTCCCATCTAGTGATCGAGAATTTT
ACAATAAGGCTTATGACTTACTAGCAAGAATTCACCAAGATTTACTTGAT
AATAAAGGTCGACAAGTTGATTTYGAGGCTTTGGATAACCTGTTGGAACG
ACTCAAGGATGTCCCAAGTGATAAAGTCAAGTTAGTGGATGATATTCTTG
CCTTCTTAGCTCCGATTCGTCATCCAGAACGTTTAGGAAAACCAAATGCG
CAAATTACCTACACTGATGATGAGATTCAAGTAGCCAAGTTGGCAGGCAA
GTACACAACAGAAGACGGTTATATCTTTGATCCTCGTGATATAACCAGTG
ATGAGGGGATGCCTATGTAACTCCACATATGACCCATAGCCACTGGATT
AAAAAGATAGTTTGTCTGAAGCTGAGAGAGCGGCAGCCCAGGCTTATGC
TAAAGAGAAAGGTTTGACCCCTCCTTCGACAGACCATCAGGATTCAGGAA
ATACTGAGGCAAAAGGAGCAGAAGCTATCTACAACCGCGTGAAAGCAGCT
AAGAAGGTGCCACTTGATCGTATGCCTTACAATCTTCAATATACTGTAGA
AGTCAAAAACGGTAGTTTAATCATACCTCATTATGACCATTACCATAACA
TCAAATTTGAGTGGTTTGACGAAGGCCTTTATGAGGCACCTAAGGGGTAT
ACTCTTGAGGATCTTTTGGCGACTGTCAAGTACTATGTCGAACATCCAAA
CGAACGTCCGCATTCAGATAATGGTTTTGGTAACGCTAGCGACCATGTTC
AAAGAAACAAAAATGGTCAAGCTGATACCAATCAAACGGAAAAACCAAGC
GAGGAGAAACCTCAGACAGAAAAACCTGAGGAAGAAACCCCTCGAGAAGA
GAAACCGCAAAGCGAGAAACCAGAGTCTCCAAAACCAACAGAGGAACCAG
AAGAATCACCAGAGGAATCAGAAGAACCTCAGGTCGAGACTGAAAAGGTT
GAAGAAAAACTGAGAGAGGCTGAAGATTTACTTGGAAAAATCCAGGATCC
AATTATCAAGTCCAATGCCAAAGAGACTCTCACAGGATTAAAAAATAATT
TACTATTTGGCACCCAGGACAACAATACTATTATGGCAGAAGCTGAAAAA
CTATTGGCTTTATTAAAGGAGAGTAAGTAA
```

(SEQ. ID. NO. 194)
MKINKKYLAGSVAVLALSVCSYELGRHQAGQDKKESNRVAYIDGDQAGQK
AENLTPDEVSKREGINAEQIVIKITDQGYVTSHGDHYHYYNGKVPYDAII
SEELLMKDPNYQLKDSDIVNEIKGGYVIKVDGKYYVLKDAAHADNIRTK
EEIKRQKQERSHNHGSGANDHAVAAARAQGRYTTDDGYIFNASDIIEDTG
DAYIVPHGDHYHYIPKNELSASELAAAEAYWNGKQGSRPSSSSSYNANPA
QPRLSENWNTTVTPTYHQNQGENISSLLRELYAKPLSERJVESDGLIFDP
AOITSRTARGVAVPHGNHYHFIPYEQMSELEKRIARIIPLRYRSNHWVPD
SRPEQPSPQSTPEPSPSPQPAP4PQPAPSNPIDEKLVKEAVRKVGDGYVF
EENGVSRYIPAKDLSAETAAGIDSKLAKQESLSHKLGAKKTDLPSSDREF
YNKAYDLLARIHQDLLDNKGRQVDFEALDNLLERLKDVPSDKVKLVDDIL
AFLAPIRHPERLGKPNAQITYTDDEIQVAKLAGKYTTEDGYIFDPRDITS

DEGDAYVTPHMTHSHWIKKDSLSEAERAAAQAYAKEKGLTPPSTDHQDSG
NTEAKGAEAIYNRNKAAKKVPLDRMPYNLQYTVEVKNGSLIIPHYDHYHN
IKFEWFDEGLYEAPKGYTLEDLLATVKYYVEHPNERPHSDNGFGNASDHV
QRNKNGQADTNQTEKPSEEKPQTEKPEEETPREEKPQSEKPESPKPTEEP
EESPEESEEPQVETEKVEEKLREAEDLLGKIQDPIIKSNAKETLTGLKNN
LLFGTQDNNTIMAEAEKLLALLKESKZ

ID312

(SEQ. ID. NO. 307)
```
ATGGAGGGATTGGTTAGAGTGCATTTATTGCCTGTATTTGGCGATTACAA
GCTATCTAAACTTACTACGCCTATTCTTCAACAGCAAGTAAACAAATGGG
CTGACAAGGCAAATAAAGGCGAAAAAGGGGCATTTGCTAACTACTCTTTG
CTCCATAACATGAATAAGCGTATTTTGAAATATGGCGTAGCTATCCAGGT
AATACAATACAACCCAGCTAATGATGTCATCGTTCCACGCAAACAGCAAA
AAGAAAAGGCTGCTGTCAAATACTTAGACAACAAAGAATTAAAACAGTTT
CTTGATTATTTAGATGCTCTGGATCAATCAAATTATGAGAACTTATTTGA
TGTTGTTCTGTATAAGACTTTATTGGCCACTGGTTGCCGTATTAGTGAGG
CTCTGGCTCTTGAATGGTCTGATATTGACCTAGAAAGCGGTGTTATCAGC
ATCAATAAGACACTAAACCGCTATCAGGAAATAAACTCACCTAAATCAAG
CGCTGGTTATCGTGATATACCAATAGACAAAGCCACATTACTTTTTACTGA
AACAATACAAAACCGTCAACAAATTCAGTCTTGGAAATTAGGCCGATCT
GAAACAGTTGTATTCTCTGTATTTACGGAGAAATATGCTATGCTTGTAAC
TTACGCAAACGCCTAAATAAGCATTTTGATGCTGCTGGAGTAACTAACGT
ATCATTTCATGGTTTCCGCCATACACATACTACTATGATGCTCTATGCTC
AGGTTAGCCCGAAAGATGTTCAGTATAGATTAGGCCACTCTAATTTAATG
ATCACTGAAAATACTTACTGGCATACTAACCAAGAGAATGCAAAAAAAGC
CGTCTCAAATTATGAAACAGCTATCAACAATTTATAA
```

(SEQ. ID. NO. 195)
MEGLVRVHLLPVFGDYKLSKLTTPILQQQVNKWADKANKGEKGAFANYSL
LHNMNKRILKYGVAIQVIQYNPANDVIVPRKQQKEKAAVKYLDNKELKQF
LDYLDALDQSNYQNLFDVVLYKTLLATGCRISEALALEWSDIDLESGVIS
INKTLNRYQEINSPKSSAGYRDIPIDKATLLLLKQYKNRQQIQSWKLGRS
ETVVFSVFTEKYAYACNLRKRLNKHFDAAGVTNVSFHGFRHTHTTMMLYA
QVSPKDVQYRLGHSNLMITENTYWHTNQENAKKAVSNYETAINNLZ

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07632515B2). An electronic copy of the "Sequence Listing" will also be available from the USPTO upon request and payment of the fee set forth in 37 CFR 1.19(b)(3).

What is claimed is:

1. An isolated *Streptococcus pneumoniae* polypeptide comprising:
   (a) the amino acid sequence of SEQ ID NO: 163; or
   (b) a purified polypeptide comprising an amino acid sequence at least 95% sequence identical to SEQ ID NO: 163.

2. A fusion protein comprising
   an isolated *Streptococcus pneumoniae* polypeptide comprising:
   (a) the amino acid sequence of SEQ ID NO: 163; or
   (b) a purified polypeptide comprising an amino acid sequence at least 95% sequence identical to SEQ ID NO: 163.

3. An immunogenic and/or antigenic composition comprising the polypeptide of claim 1 and one or more excipients, diluents, or adjuvants.

4. The composition of claim 3, wherein said composition is an antigenic composition.

5. The composition of claim 3, wherein said composition is an immunogenic composition.

* * * * *